(12) United States Patent
Han et al.

(10) Patent No.: US 10,005,731 B2
(45) Date of Patent: Jun. 26, 2018

(54) MODULATORS OF THE RETINOID-RELATED ORPHAN RECEPTOR GAMMA (ROR-GAMMA) FOR USE IN THE TREATMENT OF AUTOIMMUNE AND INFLAMMATORY DISEASES

(71) Applicant: Glaxo Group Limited, Brentford, Middlesex (GB)

(72) Inventors: Fangbin Han, Shanghai (CN); Hui Lei, Shanghai (CN); Xichen Lin, Shanghai (CN); Qinghua Meng, Shanghai (CN); Yonghui Wang, Shanghai (CN)

(73) Assignee: Glaxo Group Limited (GB)

( * ) Notice: Subject to any disclaimer, the term of this patent is extended or adjusted under 35 U.S.C. 154(b) by 0 days. days.

(21) Appl. No.: 14/649,585

(22) PCT Filed: Dec. 5, 2013

(86) PCT No.: PCT/EP2013/075594
§ 371 (c)(1),
(2) Date: Jun. 4, 2015

(87) PCT Pub. No.: WO2014/086894
PCT Pub. Date: Jun. 12, 2014

(65) Prior Publication Data
US 2015/0299121 A1    Oct. 22, 2015

(30) Foreign Application Priority Data

Dec. 6, 2012   (WO) ............... PCT/CN2012/001636
Feb. 25, 2013  (WO) ............... PCT/CN2013/000182
Jul. 1, 2013   (WO) ............... PCT/CN2013/000803

(51) Int. Cl.
| | |
|---|---|
| C07D 211/16 | (2006.01) |
| C07D 403/12 | (2006.01) |
| C07D 401/14 | (2006.01) |
| C07D 413/14 | (2006.01) |
| C07D 401/12 | (2006.01) |
| C07D 407/12 | (2006.01) |
| C07D 241/04 | (2006.01) |
| C07D 413/12 | (2006.01) |
| C07D 417/12 | (2006.01) |
| C07D 417/14 | (2006.01) |
| C07D 471/04 | (2006.01) |
| C07D 405/12 | (2006.01) |

(52) U.S. Cl.
CPC .......... *C07D 211/16* (2013.01); *C07D 241/04* (2013.01); *C07D 401/12* (2013.01); *C07D 401/14* (2013.01); *C07D 403/12* (2013.01); *C07D 405/12* (2013.01); *C07D 407/12* (2013.01); *C07D 413/12* (2013.01); *C07D 413/14* (2013.01); *C07D 417/12* (2013.01); *C07D 417/14* (2013.01); *C07D 471/04* (2013.01)

(58) Field of Classification Search
None
See application file for complete search history.

(56) References Cited

U.S. PATENT DOCUMENTS

| | | |
|---|---|---|
| 8,604,069 B2 | 12/2013 | Maeba et al. |
| 9,242,972 B2 | 1/2016 | Birault et al. |
| 2016/0257664 A1 | 9/2016 | Birault et al. |
| 2016/0304478 A1 | 10/2016 | Birault et al. |
| 2017/0081278 A1 | 3/2017 | Birault et al. |
| 2017/0101399 A1 | 4/2017 | Lei et al. |
| 2017/0121313 A1 | 5/2017 | Deng et al. |
| 2017/0197978 A1 | 7/2017 | Deng et al. |

FOREIGN PATENT DOCUMENTS

| | | | |
|---|---|---|---|
| WO | WO 2007/022257 | 2/2007 | |
| WO | 2007070626 | * 6/2007 | ............ A61K 31/54 |
| WO | 2007078839 | * 7/2007 | .......... A61K 31/496 |
| WO | 2007089336 | * 8/2007 | .......... A61K 31/551 |
| WO | WO 2012/147916 A1 | 1/2012 | |
| WO | WO 2012/027965 A1 | 3/2012 | |
| WO | WO 2012/028100 A1 | 3/2012 | |
| WO | WO 2012/100732 A1 | 8/2012 | |
| WO | WO 2012/100734 A1 | 8/2012 | |
| WO | WO 2012/139775 A1 | 10/2012 | |
| WO | WO 2012/145254 A2 | 10/2012 | |
| WO | WO 2012/158784 A2 | 11/2012 | |

(Continued)

OTHER PUBLICATIONS

Silverman. The Organic Chemistry of Drug Design and Action, 2004, pp. 25-34.*

(Continued)

*Primary Examiner* — Noble Jarrell
(74) *Attorney, Agent, or Firm* — Fang Qian

(57) ABSTRACT

The present invention relates to novel retinoid-related orphan receptor gamma (RORγ) modulators and their use in the treatment of diseases mediated by RORγ.

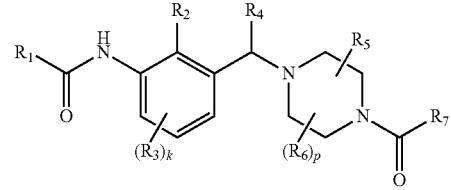

Formula I

19 Claims, No Drawings

(56) References Cited

FOREIGN PATENT DOCUMENTS

| WO | WO 2013/036912 A2 | 3/2013 |
| WO | WO 2013/045431 A1 | 4/2013 |
| WO | WO 2013/160418 A1 | 10/2013 |
| WO | WO 2013/160419 A1 | 10/2013 |
| WO | WO 2013/171729 A2 | 11/2013 |
| WO | WO 2015/061515 A1 | 4/2015 |
| WO | WO 2015/061686 A2 | 4/2015 |
| WO | WO 2015/180612 A1 | 12/2015 |
| WO | WO 2015/180613 A1 | 12/2015 |
| WO | WO 2015/180614 A1 | 12/2015 |

OTHER PUBLICATIONS

Leipe, et al. Arthritis & Rheumatism, 62(10): 2876-2885 (Oct., 2010).
Rutz, et al. Cytokine & Growth Factor Reviews, 30: 1-17 (2016).
Xue, et al. Scientific Reports, 1-17 (2016). Available online at www.nature.com/scientificreports/.

* cited by examiner

MODULATORS OF THE RETINOID-RELATED ORPHAN RECEPTOR GAMMA (ROR-GAMMA) FOR USE IN THE TREATMENT OF AUTOIMMUNE AND INFLAMMATORY DISEASES

This application is a 371 of International Application No. PCT/EP2013/075594, filed 05 Dec. 2013, which claims priority of PCT/CN2013/000803, filed 01 Jul. 2013, PCT/CN2013/000182, filed 25 Feb. 2013, and PCT/CN2012/001636, filed 06 Dec. 2012.

The present invention relates to novel retinoid-related orphan receptor gamma (RORγ) modulators and their use in the treatment of diseases mediated by RORγ.

BACKGROUND OF THE INVENTION

Retinoid-related orphan receptors (RORs) are transcription factors which belong to the steroid hormone nuclear receptor superfamily (Jetten & Joo (2006) *Adv. Dev. Biol.* 16:313-355). The ROR family consists of three members, ROR alpha (RORα), ROR beta (RORβ) and ROR gamma (RORγ), each encoded by a separate gene (RORA, RORB and RORC, respectively). RORs contain four principal domains shared by the majority of nuclear receptors: an N-terminal A/B domain, a DNA-binding domain, a hinge domain, and a ligand binding domain. Each ROR gene generates several isoforms which differ only in their N-terminal A/B domain. Two isoforms of RORγ have been identified: RORγ1 and RORγt (also known as RORγ2). RORγ is a term used to describe both RORγ1 and/or RORγt.

While RORγ1 is expressed in a variety of tissues including thymus, muscle, kidney and liver, RORγt is exclusively expressed in the cells of the immune system. RORγt has been identified as a key regulator of Th17 cell differentiation. Th17 cells are a subset of T helper cells which produce IL-17 and other proinflammatory cytokines. Th17 cells have been shown to have key functions in several mouse autoimmune disease models including experimental autoimmune encephalomyelitis (EAE) and collagen-induced arthritis (CIA). In addition, Th17 cells or their products have been shown to be associated with the pathology of a variety of human inflammatory and autoimmune disorders including multiple sclerosis, rheumatoid arthritis, psoriasis, Crohn's disease and asthma (Jetten (2009) *Nucl. Recept. Signal.* 7: e003; Manel et al. (2008) *Nat. Immunol.* 9:641-649). The pathogenesis of chronic autoimmune diseases including multiple sclerosis and rheumatoid arthritis arises from the break in tolerance towards self-antigens and the development of auto-aggressive effector T cells infiltrating the target tissues. Studies have shown that Th17 cells are one of the important drivers of the inflammatory process in tissue-specific autoimmunity (Steinman (2008) *J. Exp. Med.* 205: 1517-1522; Leung et al. (2010) *Cell. Mol. Immunol.* 7:182-189). There is evidence that Th17 cells are activated during the disease process and are responsible for recruiting other inflammatory cells types, especially neutrophils, to mediate pathology in the target tissues (Korn et al. (2009) *Annu. Rev. Immunol.* 27:485-517).

RORγt plays a critical role in the pathogenic responses of Th17 cells (Ivanov et al. (2006) *Cell* 126:1121-1133). RORγt deficient mice show very little Th17 cells. In addition, RORγt deficiency resulted in amelioration of EAE. Further support for the role of RORγt in the pathogensis of autoimmune or inflammatory diseases can be found in the following references: Jetten & Joo (2006) *Adv. Dev. Biol.* 16:313-355; Meier et al. (2007) *Immunity* 26:643-654; Aloisi & Pujol-Borrell (2006) *Nat. Rev. Immunol.* 6:205-217; Jager et al. (2009) *J. Immunol.* 183:7169-7177; Serafini et al. (2004) *Brain Pathol.*14:164-174; Magliozzi et al. (2007) *Brain* 130:1089-1104; Barnes (2008) *Nat. Rev. Immunol.* 8:183-192.

In light of the role RORγ plays in the pathogenesis of diseases, it is desirable to prepare compounds that modulate RORγ activity, which can be used in the treatment of diseases mediated by RORγ.

SUMMARY OF THE INVENTION

The invention is directed to novel RORγ modulators and their use in the treatment of diseases mediated by RORγ. Specifically, the invention is directed to compounds according to Formula I.

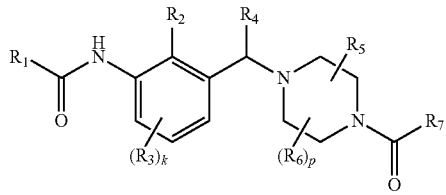

Formula I wherein $R_1$, $R_2$, $R_3$, $R_4$, $R_5$, $R_6$, $R_7$, k and p are defined below, and to pharmaceutically-acceptable salts thereof.

In another aspect, this invention provides for the use of the compounds of Formula (I) for the treatment of diseases mediated by RORγ. Examples of such diseases include autoimmune or inflammatory diseases such as multiple sclerosis, rheumatoid arthritis, psoriasis, Crohn's disease and asthma. In yet another aspect, the invention is directed to methods of treating such diseases.

DETAILED DESCRIPTION OF THE INVENTION

Terms and Definitions

"Alkyl" refers to a monovalent saturated hydrocarbon chain having the specified number of member atoms. For example, C1-C6 alkyl refers to an alkyl group having from 1 to 6 member atoms. Alkyl groups may be optionally substituted with one or more substituent as defined herein. Alkyl groups may be straight or branched. Representative branched alkyl groups have one, two, or three branches. Alkyl includes methyl, ethyl, propyl (n-propyl and isopropyl), butyl (n-butyl, isobutyl, and t-butyl), pentyl (n-pentyl, isopentyl, and neopentyl), and hexyl.

"Alkoxy" refers to the group —O—R where R is alkyl having the specified number of carbon atoms. Alkoxy includes methoxy, ethoxy and propoxy.

"Cycloalkyl" refers to a saturated hydrocarbon ring having the specified number of member atoms. Cycloalkyl groups are monocyclic ring systems or are fused or bridged bicyclic ring systems. For example, C3-C7 cycloalkyl refers to a cycloalkyl group having from 3 to 7 member atoms. Cycloalkyl groups may be optionally substituted with one or more substituent as defined herein. Cycloalkyl includes cyclopropyl, cyclobutyl, cyclopentyl, and cyclohexyl.

"Enantiomeric excess" or "ee" is the excess of one enantiomer over the other expressed as a percentage. As a result, since both enantiomers are present in equal amounts in a racemic mixture, the enantiomeric excess is zero (0% ee). However, if one enantiomer was enriched such that it constitutes 95% of the product, then the enantiomeric excess would be 90% ee (the amount of the enriched enantiomer, 95%, minus the amount of the other enantiomer, 5%).

"Enantiomerically pure" refers to products whose enantiomeric excess is 99% ee or greater.

"Half-life" refers to the time required for half of a quantity of a substance to be converted to another chemically distinct species in vitro or in vivo.

"Halo" refers to the halogen radicals fluoro, chloro, bromo, and iodo.

"Heteroaryl" refers to an aromatic ring containing from 1 to 4 heteroatoms as member atoms in the ring. Heteroaryl groups containing more than one heteroatom may contain different heteroatoms. Heteroaryl groups may be optionally substituted with one or more substituent as defined herein. Heteroaryl groups are monocyclic ring systems or are fused or bridged bicyclic ring systems.

Monocyclic heteroaryl rings have from 5 to 7 member atoms. Bicyclic heteroaryl rings have from 7 to 11 member atoms. Bicyclic heteroaryl rings include those rings wherein phenyl and a monocyclic heterocycloalkyl ring are attached forming a fused, spiro, or bridged bicyclic ring system, and those rings wherein a monocyclic heteroaryl ring and a monocyclic cycloalkyl, cycloalkenyl, heterocycloalkyl, or heteroaryl ring are attached forming a fused, spiro, or bridged bicyclic ring system. Heteroaryl includes pyrrolyl, pyrazolyl, imidazolyl, oxazolyl, isoxazolyl, oxadiazolyl, thiazolyl, isothiazolyl, thiadiazolyl, furanyl, furazanyl, thienyl, triazolyl, pyridinyl, pyrimidinyl, pyridazinyl, pyrazinyl, triazinyl, tetrazinyl, tetrazolyl, indolyl, isoindolyl, indolizinyl, indazolyl, purinyl, quinolinyl, isoquinolinyl, quinoxalinyl, quinazolinyl, pteridinyl, cinnolinyl, benzimidazolyl, benzopyranyl, benzoxazolyl, benzisoxazolyl, benzofuranyl, isobenzofuranyl, benzothiazolyl, benzisothiazolyl, benzothienyl, furopyridinyl, and naphthyridinyl.

"Heteroatom" refers to a nitrogen, sulphur, or oxygen atom.

"Heterocycloalkyl" refers to a saturated or unsaturated ring containing from 1 to 4 heteroatoms as member atoms in the ring. However, heterocycloalkyl rings are not aromatic. Heterocycloalkyl groups containing more than one heteroatom may contain different heteroatoms. Heterocycloalkyl groups may be optionally substituted with one or more substituent as defined herein. Heterocycloalkyl groups are monocyclic ring systems or are fused, spiro, or bridged bicyclic ring systems. Monocyclic heterocycloalkyl rings have from 5 to 7 member atoms. Bicyclic heterocycloalkyl rings have from 7 to 11 member atoms. In certain embodiments, heterocycloalkyl is saturated. In other embodiments, heterocycloalkyl is unsaturated but not aromatic. Heterocycloalkyl includes pyrrolidinyl, tetrahydrofuranyl, dihydrofuranyl, pyranyl, tetrahydropyranyl, dihydropyranyl, tetrahydrothienyl, pyrazolidinyl, oxazolidinyl, thiazolidinyl, piperidinyl, homopiperidinyl, piperazinyl, morpholinyl, thiamorpholinyl, azepinyl, 1,3-dioxolanyl, 1,3-dioxanyl, 1,4-dioxanyl, 1,3-oxathiolanyl, 1,3-oxathianyl, 1,3-dithianyl, azetidinyl, azabicylo[3.2.1]octyl, azabicylo[3.3.1]nonyl, azabicylo[4.3.0]nonyl, and oxabicylo[2.2.1]heptyl.

"Member atoms" refers to the atom or atoms that form a chain or ring. Where more than one member atom is present in a chain and within a ring, each member atom is covalently bound to an adjacent member atom in the chain or ring. Atoms that make up a substituent group on a chain or ring are not member atoms in the chain or ring.

"Optionally substituted" indicates that a group, such as alkyl, alkenyl, alkynyl, aryl, cycloalkyl, cycloalkenyl, heterocycloalkyl, or heteroaryl, may be unsubstituted, or the group may be substituted with one or more substituent as defined.

"RORγ" refers to all isoforms encoded by the RORC gene which include RORγ1 and RORγt.

"RORγ modulator" refers to a chemical compound that inhibits, either directly or indirectly, the activity of RORγ. RORγ modulators include antagonists and inverse agonists of RORγ.

"Pharmaceutically acceptable" refers to those compounds, materials, compositions, and dosage forms which are, within the scope of sound medical judgment, suitable for use in contact with the tissues of human beings and animals without excessive toxicity, irritation, or other problem or complication, commensurate with a reasonable benefit/risk ratio.

"Substituted" in reference to a group indicates that one or more hydrogen atom attached to a member atom within the group is replaced with a substituent selected from the group of defined substituents. It should be understood that the term "substituted" includes the implicit provision that such substitution be in accordance with the permitted valence of the substituted atom and the substituent and that the substitution results in a stable compound (i.e. one that does not spontaneously undergo transformation such as by rearrangement, cyclization, or elimination and that is sufficiently robust to survive isolation from a reaction mixture). When it is stated that a group may contain one or more substituent, one or more (as appropriate) member atom within the group may be substituted. In addition, a single member atom within the group may be substituted with more than one substituent as long as such substitution is in accordance with the permitted valence of the atom.

Compounds

The present invention provides, in a first aspect, a compound of Formula I or a pharmaceutically acceptable salt thereof.

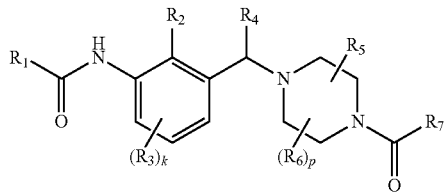

Formula I wherein:
R1 is:
C1-C6 alkyl optionally substituted with one or two substituents selected from the group consisting of: i) phenyl, said phenyl is optionally substituted with halo, methoxy or $SO_2CH_2CH_3$; ii) C3 cycloalkyl; iii) methoxy; iv) halo; v) phenoxy; and vi) heteroaryl;
C2 alkenyl optionally substituted with one F and one phenyl;
C3-C7 cycloalkyl, said cycloalkyl is optionally substituted with one or two substituents selected from the group consisting of phenyl, methyl and F; or said cycloalkyl is optionally fused to a phenyl ring;
heterocycloalkyl optionally substituted with one or two C1-C3 alkyl;
heteroaryl optionally substituted with one to two substituents selected from the group consisting of: C1-C3 alkyl, C1-C3 alkoxy and $CF_3$; and phenyl optionally substituted with one to three substituents selected from the group consisting of:
i) halo;
ii) CN;
iii) C1-C3 alkyl optionally substituted with one to three F;
iv) C1-C3 alkoxy;
v) (CH2)$_n$NRaRb;
vi) C(O)CH$_3$; and
vii) CH$_2$OCH$_3$;
R2 is selected from the group consisting of H, halo and C1-C3 alkyl;
R3 is halo or methyl;
R4 is H or methyl; wherein when R2 and R4 are each methyl, R2 and R4 may optionally be joined together to form a bicyclic ring with the phenyl group to which R2 is attached, or when R3 and R4 are each methyl, R3 and R4 may optionally be joined together to form a bicyclic ring with the phenyl group to which R3 is attached;
R5 is C1-C3 alkyl;
R6 is C1-C3 alkyl;
R7 is selected from the group consisting of:
C1-C7 alkyl optionally substituted with one or more substituents selected from the group consisting of methoxy, halo, C3-C5 cycloalkyl and CF3;
C3-C7 cycloalkyl optionally substituted with one or two substituents selected from the group consisting of F, CH$_2$F, CHF$_2$, methyl and methoxy,
phenyl optionally substituted with halo, and
heteroaryl optionally substituted with methyl;
each k is 0 or 1; each p is 0 or 1; each n is 0, 1 or 2;
each Ra is H or C1-C3 alkyl; each Rb is H or C1-C3 alkyl;
provided that: (i) R7 is not phenyl when R1 is piperazinyl; and ii) R7 is not chlorophenyl when R1 is phenyl.

In one embodiment, the invention relates to the compounds of Formula I, wherein R1 is heteroaryl substituted with C1-C3 alkyl. In one embodiment, this invention also relates to compounds of any of the above embodiments, wherein R1 is heteroaryl substituted with methyl. In one embodiment, this invention also relates to compounds of any of the above embodiments, wherein R1 is pyridinyl substituted with methyl.

In one embodiment, the invention relates to the compounds of Formula I, wherein R1 is phenyl substituted with one to two substituents selected from the group consisting of halo, CN and C1-C3 alkyl. In one embodiment, this invention also relates to compounds of any of the above embodiments, wherein R1 is phenyl substituted with CN, F or Cl. In one embodiment, this invention also relates to compounds of any of the above embodiments, wherein R1 is phenyl substituted with CN. In one embodiment, this invention also relates to compounds of any of the above embodiments, wherein R1 is phenyl substituted with two subtitutents selected from the group consisting of F, methyl and CN.

In one embodiment, this invention also relates to compounds of any of the above embodiments, wherein R2 is methyl.

In one embodiment, this invention also relates to compounds of any of the above embodiments, wherein R3 is halo. In one embodiment, this invention also relates to compounds of any of the above embodiments, wherein R3 is F or Cl.

In one embodiment, this invention also relates to compounds of any of the above embodiments, wherein k is 1.

In one embodiment, this invention also relates to compounds of any of the above embodiments, wherein R4 is H.

In one embodiment, this invention also relates to compounds of any of the above embodiments, wherein R5 is methyl.

In one embodiment, this invention also relates to compounds of any of the above embodiments, wherein p is 0.

In one embodiment, this invention also relates to compounds of any of the above embodiments, wherein R7 is C3-C6 cycloalkyl optionally substituted with one or two F. In one embodiment, this invention also relates to compounds of any of the above embodiments, wherein R7 is C3-C6 cycloalkyl optionally substituted with one or two methyl. In one embodiment, this invention also relates to compounds of any of the above embodiments, wherein R7 is cyclopentyl.

In one embodiment, this invention also relates to compounds of any of the above embodiments, wherein R7 is C1-C2 alkyl substituted with C3-C5 cycloalkyl. In one embodiment, this invention also relates to compounds of any of the above embodiments, wherein R7 is methyl substituted with C3-C5 cycloalkyl.

The present invention provides, in a second aspect, a compound of Formula I or a pharmaceutically acceptable salt thereof.

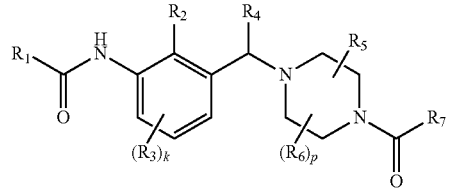

Formula I wherein:
R1 is:
C1-C6 alkyl;
methyl substituted with i) C3-C5 cycloalkyl; ii) phenoxy; or iii) a phenyl and a second substituent selected from the group consisting of methyl, halo and methoxy;
ethyl substituted with i) phenyl, said phenyl is optionally substituted with halo or methoxy, or ii) heteroaryl;
benzyl, wherein the phenyl group of said benzyl is optionally substituted with halo, methoxy or SO$_2$CH$_2$CH$_3$;
C2 alkenyl optionally substituted with one F and one phenyl;
C3-C7 cycloalkyl, said cycloalkyl is optionally substituted with one or two substituents selected from the group consisting of phenyl, methyl and F; or said cycloalkyl is optionally fused to a phenyl ring;
heterocycloalkyl optionally substituted with one or two C1-C3 alkyl;
heteroaryl optionally substituted with one to two substituents selected from the group consisting of: C1-C3 alkyl, C1-C3 alkoxy and CF$_3$; and
phenyl substituted with one to three substituents selected from the group consisting of:
i) halo;
ii) CN;
iii) C1-C3 alkyl optionally substituted with one to three F;
iv) C1-C3 alkoxy;
v) (CH2)$_n$NRaRb;

vi) C(O)CH$_3$; and
vii) CH$_2$OCH$_3$;
R2 is selected from the group consisting of H, halo and C1-C3 alkyl;
R3 is halo or methyl;
R4 is H or methyl;
R5 is C1-C3 alkyl;
R6 is C1-C3 alkyl;
R7 is selected from the group consisting of:
C1-C7 alkyl optionally substituted with one or more substituents selected from the group consisting of halo, C3-C5 cycloalkyl and CF3;
C3-C7 cycloalkyl optionally substituted with one or two substituents selected from the group consisting of F, CH$_2$F, CHF$_2$, methyl and methoxy,
each k is 0 or 1; each p is 0 or 1; each n is 0, 1 or 2;
each Ra is H or C1-C3 alkyl; each Rb is H or C1-C3 alkyl;

In one embodiment of the second aspect, the invention relates to the compounds of Formula I, wherein R1 is heteroaryl substituted with C1-C3 alkyl. In one embodiment, this invention also relates to compounds of any of the above embodiments, wherein R1 is pyridinyl substituted with methyl. In one embodiment, this invention also relates to compounds of any of the above embodiments, wherein R1 is pyrimidinyl substituted with methyl.

In one embodiment, the invention relates to the compounds of Formula I, wherein R1 is phenyl substituted with one to two substituents selected from the group consisting of halo, CN and C1-C3 alkyl. In one embodiment, this invention also relates to compounds of any of the above embodiments, wherein R1 is phenyl substituted with CN, F or Cl. In one embodiment, this invention also relates to compounds of any of the above embodiments, wherein R1 is phenyl substituted with CN.

In one embodiment, this invention also relates to compounds of any of the above embodiments, wherein R2 is halo or C1-C3 alkyl. In one embodiment, this invention also relates to compounds of any of the above embodiments, wherein R2 is methyl.

In one embodiment, this invention also relates to compounds of any of the above embodiments, wherein R3 is halo. In one embodiment, this invention also relates to compounds of any of the above embodiments, wherein R3 is F. In one embodiment, this invention also relates to compounds of any of the above embodiments, wherein R3 is Cl.

In one embodiment, this invention also relates to compounds of any of the above embodiments, wherein k is 1.

In one embodiment, this invention also relates to compounds of any of the above embodiments, wherein R4 is H.

In one embodiment, this invention also relates to compounds of any of the above embodiments, wherein R5 is methyl.

In one embodiment, this invention also relates to compounds of any of the above embodiments, wherein p is 0.

In one embodiment, this invention also relates to compounds of any of the above embodiments, wherein R7 is C3-C6 cycloalkyl optionally substituted with one or two F. In one embodiment, this invention also relates to compounds of any of the above embodiments, wherein R7 is cyclobutyl substituted with two F. In one embodiment, this invention also relates to compounds of any of the above embodiments, wherein R7 is C3-C6 cycloalkyl optionally substituted with one or two methyl. In one embodiment, this invention also relates to compounds of any of the above embodiments, wherein R7 is cyclobutyl substituted with methyl. In one embodiment, this invention also relates to compounds of any of the above embodiments, wherein R7 is cyclopentyl.

In one embodiment, this invention also relates to compounds of any of the above embodiments, wherein R7 is C1-C2 alkyl substituted with C3-C5 cycloalkyl. In one embodiment, this invention also relates to compounds of any of the above embodiments, wherein R7 is methyl substituted with cyclopropyl.

In one embodiment, the invention relates to compounds of Formula (I), wherein R1 is pyridinyl substituted with methyl, R2 is methyl, R3 is Cl, k is 1, R4 is H, R5 is methyl, p is 0, R7 is i) methyl substituted with cyclopropyl, ii) cyclopentyl, or iii) cyclobutyl substituted with methyl.

In another embodiment, the invention relates to compounds of Formula (I), wherein R1 is phenyl substituted with CN, R2 is methyl, R3 is F, k is 1, R4 is H, R5 is methyl, p is 0, R7 is cyclopentyl or difluorocyclobutyl.

In yet another embodiment, the invention relates to compounds of Formula (I), wherein R1 is pyrimidinyl substituted with methyl, R2 is methyl, R3 is Cl or F, k is 1, R4 is H, R5 is methyl, p is 0, R7 is i) cyclopentyl or ii) cyclobutyl substituted with methyl.

In one embodiment, the compound of Formula I is selected from:
(S)-N-(3-((4-(cyclopentanecarbonyl)-3-methylpiperazin-1-yl)methyl)-5-fluoro-2-methylphenyl)-2-methylpyrimidine-5-carboxamide (E20);
(S)-N-(5-chloro-3-((4-(cyclopentanecarbonyl)-3-methylpiperazin-1-yl)methyl)-2-methylphenyl)-6-methylnicotinamide (E62);
(S)-3-cyano-N-(3-((4-(3,3-difluorocyclobutanecarbonyl)-3-methylpiperazin-1-yl)methyl)-5-fluoro-2-methylphenyl)benzamide, trifluoroacetic acid salt (E175);
(S)-N-(5-chloro-3-((4-(2-cyclopropylacetyl)-3-methylpiperazin-1-yl)methyl)-2-methylphenyl)-6-methylnicotinamide (E184);
N-(5-fluoro-2-methyl-3-(((S)-3-methyl-4-((cis)-3-methylcyclobutanecarbonyl)piperazin-1-yl)methyl)phenyl)-6-methylnicotinamide (E185);
N-(5-fluoro-2-methyl-3-(((S)-3-methyl-4-((trans)-3-methylcyclobutanecarbonyl)piperazin-1-yl)methyl)phenyl)-6-methylnicotinamide (E186);
N-(5-chloro-2-methyl-3-(((S)-3-methyl-4-((trans)-3-methylcyclobutanecarbonyl)piperazin-1-yl)methyl)phenyl)-6-methylnicotinamide (E188);
N-(5-chloro-2-methyl-3-(((S)-3-methyl-4-((cis)-3-methylcyclobutanecarbonyl)piperazin-1-yl)methyl)phenyl)-6-methylnicotinamide (E189);
N-(5-chloro-2-methyl-3-(((S)-3-methyl-4-((cis)-3-methylcyclobutanecarbonyl)piperazin-1-yl)methyl)phenyl)-2-methylpyrimidine-5-carboxamide, trifluoroacetic acid salt (E190);
N-(5-chloro-2-methyl-3-(((S)-3-methyl-4-((trans)-3-methylcyclobutanecarbonyl)piperazin-1-yl)methyl)phenyl)-2-methylpyrimidine-5-carboxamide, trifluoroacetic acid salt (E191);
(S)-N-(5-chloro-3-((4-(cyclopentanecarbonyl)-3-methylpiperazin-1-yl)methyl)-2-methylphenyl)-2-methylpyrimidine-5-carboxamide (E192); and
(S)-N-(5-chloro-3-((4-(cyclopentanecarbonyl)-3-methylpiperazin-1-yl)methyl)-2-methylphenyl)-3-cyanobenzamide, trifluoroacetic acid salt (E193).

In one embodiment, the compound of Formula I is (S)-N-(5-chloro-3-((4-(2-cyclopropylacetyl)-3-methylpiperazin-1-yl)methyl)-2-methylphenyl)-6-methylnicotinamide (E184).

In one embodiment, the compound of Formula I is (S)-3-cyano-N-(3-((4-(cyclopentanecarbonyl)-3-methylpiperazin-1-yl)methyl)-5-fluoro-2-methylphenyl)benzamide (E66).

The compounds according to Formula I may contain one or more asymmetric center (also referred to as a chiral center) and may, therefore, exist as individual enantiomers, diastereomers, or other stereoisomeric forms, or as mixtures thereof. Chiral centers, such as chiral carbon atoms, may also be present in a substituent such as an alkyl group. Where the stereochemistry of a chiral center present in Formula I, or in any chemical structure illustrated herein, is not specified the structure is intended to encompass all individual stereoisomers and all mixtures thereof. Thus, compounds according to Formula I containing one or more chiral center may be used as racemic mixtures, enantiomerically enriched mixtures, or as enantiomerically pure individual stereoisomers.

Individual stereoisomers of a compound according to Formula I which contain one or more asymmetric center may be resolved by methods known to those skilled in the art. For example, such resolution may be carried out (1) by formation of diastereoisomeric salts, complexes or other derivatives; (2) by selective reaction with a stereoisomer-specific reagent, for example by enzamatic oxidation or reduction; or (3) by gas-liquid or liquid chromatography in a chiral environment, for example, on a chiral support such as silica with a bound chiral ligand or in the presence of a chiral solvent. The skilled artisan will appreciate that where the desired stereoisomer is converted into another chemical entity by one of the separation procedures described above, a further step is required to liberate the desired form. Alternatively, specific stereoisomers may be synthesized by asymmetric synthesis using optically active reagents, substrates, catalysts or solvents, or by converting one enantiomer to the other by asymmetric transformation.

The compounds according to Formula I may also contain double bonds or other centers of geometric asymmetry. Where the stereochemistry of a center of geometric asymmetry present in Formula I, or in any chemical structure illustrated herein, is not specified, the structure is intended to encompass the trans (E) geometric isomer, the cis (Z) geometric isomer, and all mixtures thereof. Likewise, all tautomeric forms are also included in Formula I whether such tautomers exist in equilibrium or predominately in one form.

In certain embodiments, compounds according to Formula I may contain an acidic functional group. In certain other embodiments, compounds according to Formula I may contain a basic functional group. Thus, the skilled artisan will appreciate that pharmaceutically-acceptable salts of the compounds according to Formula I may be prepared. Indeed, in certain embodiments of the invention, pharmaceutically-acceptable salts of the compounds according to Formula I may be preferred over the respective free base or free acid because such salts may impart greater stability or solubility to the molecule thereby facilitating formulation into a dosage form. Accordingly, the invention is further directed to the use of pharmaceutically-acceptable salts of the compounds according to Formula I.

As used herein, the term "pharmaceutically-acceptable salts" refers to salts that retain the desired biological activity of the subject compound and exhibit minimal undesired toxicological effects. These pharmaceutically-acceptable salts may be prepared in situ during the final isolation and purification of the compound, or by separately reacting the purified compound in its free acid or free base form with a suitable base or acid, respectively.

As used herein, the term "compounds of the invention" means both the compounds according to Formula I and the pharmaceutically-acceptable salts thereof. The term "a compound of the invention" also appears herein and refers to both a compound according to Formula I and its pharmaceutically-acceptable salts.

The invention also includes various deuterated forms of the compounds of Formula (I). Each available hydrogen atom attached to a carbon atom may be independently replaced with a deuterium atom. A person of ordinary skill in the art will know how to synthesize deuterated forms of the compounds of Formula (I). Commercially available deuterated starting materials may be employed in the preparation of deuterated forms of the compounds of Formula (I), or they may be synthesized using conventional techniques employing deuterated reagents (e.g. lithium aluminum deuteride).

The compounds of the invention may exist in solid or liquid form. In the solid state, the compounds of the invention may exist in crystalline or noncrystalline form, or as a mixture thereof. For compounds of the invention that are in crystalline form, the skilled artisan will appreciate that pharmaceutically-acceptable solvates may be formed wherein solvent molecules are incorporated into the crystalline lattice during crystallization. Solvates may involve nonaqueous solvents such as ethanol, isopropanol, DMSO, acetic acid, ethanolamine, and ethyl acetate, or they may involve water as the solvent that is incorporated into the crystalline lattice. Solvates wherein water is the solvent that is incorporated into the crystalline lattice are typically referred to as "hydrates." Hydrates include stoichiometric hydrates as well as compositions containing variable amounts of water. The invention includes all such solvates.

The skilled artisan will further appreciate that certain compounds of the invention that exist in crystalline form, including the various solvates thereof, may exhibit polymorphism (i.e. the capacity to occur in different crystalline structures). These different crystalline forms are typically known as "polymorphs." The invention includes all such polymorphs. Polymorphs have the same chemical composition but differ in packing, geometrical arrangement, and other descriptive properties of the crystalline solid state. Polymorphs, therefore, may have different physical properties such as shape, density, hardness, deformability, stability, and dissolution properties. Polymorphs typically exhibit different melting points, IR spectra, and X-ray powder diffraction patterns, which may be used for identification. The skilled artisan will appreciate that different polymorphs may be produced, for example, by changing or adjusting the reaction conditions or reagents, used in making the compound. For example, changes in temperature, pressure, or solvent may result in polymorphs. In addition, one polymorph may spontaneously convert to another polymorph under certain conditions.

Compound Preparation

The compounds according to Formula I may be prepared using conventional organic syntheses. Suitable synthetic routes are depicted below in the following general reaction scheme.

The skilled artisan will appreciate that if a substituent described herein is not compatible with the synthetic methods described herein, the substituent may be protected with a suitable protecting group that is stable to the reaction conditions. The protecting group may be removed at a suitable point in the reaction sequence to provide a desired intermediate or target compound. Suitable protecting groups and the methods for protecting and de-protecting different substituents using such suitable protecting groups are well known to those skilled in the art; examples of which may be found in T. Greene and P. Wuts, *Protecting Groups in Chemical Synthesis* (3rd ed.), John Wiley & Sons, NY (1999). In some instances, a substituent may be specifically selected to be reactive under the reaction conditions used. Under these circumstances, the reaction conditions convert the selected substituent into another substituent that is either useful as an intermediate compound or is a desired substituent in a target compound.

able or is made from commercially available starting materials using methods known to those skilled in the art.

Benzoic acids 1 may be reduced by $BH_3.THF$ to provide benzyl alcohol 2. Benzyl alcohol 2 can also be obtained by reduction of corresponding benzoic ester by $NaBH_4$. Alcohol 2 may be oxidized by PCC to the corresponding aldehyde followed by reductive amination with 3 to provide nitro compound 4. Nitro compound 4 may be reduced to amine 5 which is then reacted with various acids to give final compounds of Formula I.

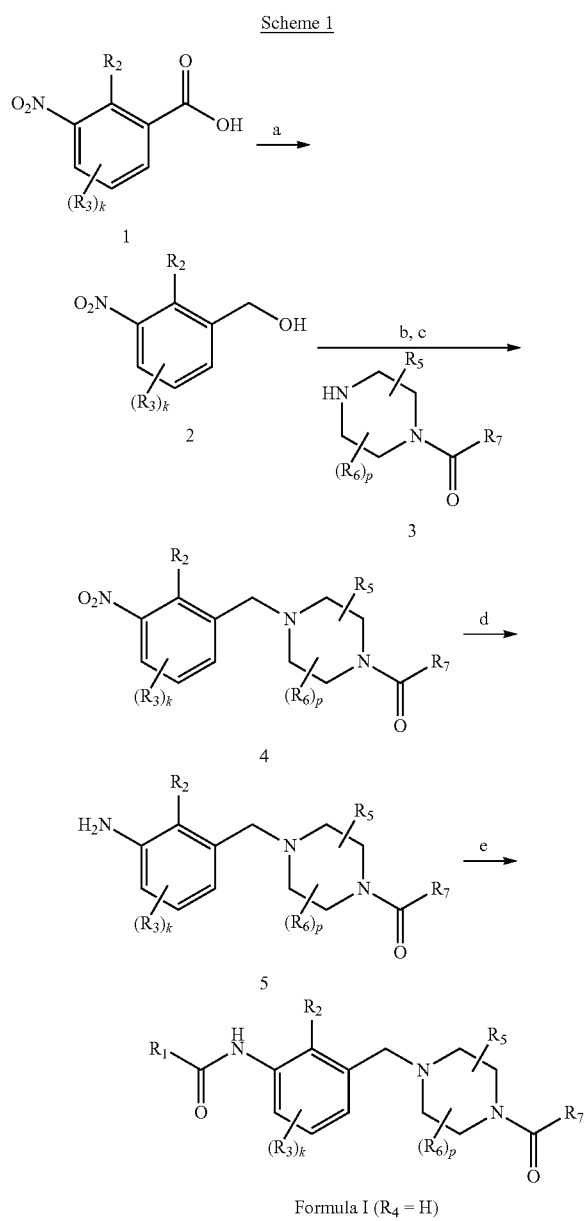

Formula I ($R_4$ = H)

[Exemplary conditions: a) $BH_3\cdot THF$, THF, 0° C.-r.t; b) PCC, $CH_2Cl_2$; c) $NaBH(OAc)_3$, $CH_2Cl_2$, 3; d) Fe, HOAc, 60° C.; e) $R_1CO_2H$, HOBt, EDCI, $CH_2Cl_2$].

Scheme 1 represents a general reaction scheme for preparing compounds of Formula I where R4 is H, and R1, R2, R3, R5, R6 and R7 are as defined above. The starting material or reagents described are either commercially avail-

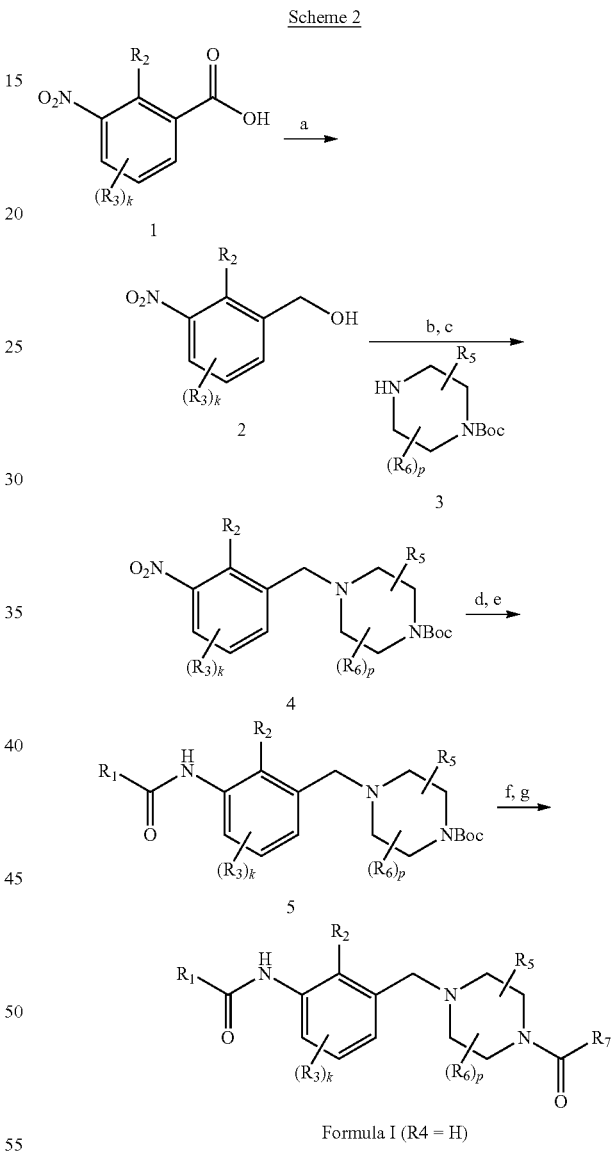

Formula I ($R_4$ = H)

[Exemplary conditions: a) $BH_3\cdot THF$, THF, 0° C.-r.t; b) PCC, $CH_2Cl_2$; c) $NaBH(OAc)_3$, $CH_2Cl_2$, 3; d) Pd/C, MeOH, $H_2$; e) $R_1CO_2H$, HOBt, EDCI, $CH_2Cl_2$; f) TFA, DCM; g) $R_7CO_2H$, HOBt, EDCI, $CH_2Cl_2$].

Scheme 2 represents another reaction scheme for preparing compounds of Formula I where R4 is H, and R1, R2, R3, R5, R6 and R7 are as defined above. The starting material or reagents described are either commercially available or is made from commercially available starting materials using methods known to those skilled in the art.

Benzoic acids 1 may be reduced by $BH_3.THF$ to provide benzyl alcohol 2. Benzyl alcohol 2 can also be obtained by reduction of corresponding benzoic ester by NaBH$_4$. Alcohol 2 may be oxidized by PCC to corresponding aldehyde followed by reductive amination with 3 to provide nitro compound 4. Reduction of nitro compound 4 with Pd/C in the presence of H$_2$ afforded the amine which may be reacted with various acids to give amide 5. The Boc protection of 5 may be removed by treatment with TFA and the resulting amine reacted with various acids to provide final compounds of Formula I.

EXAMPLES

Abbreviations
conc. concentrated
DCE 1,2-Dichloroethane
DCM dichloromethane
DIB Iodobenzene diacetate
DIPEA N,N-diisopropylethylamine
DME 1,2-dimethoxyethane
DMF N,N-dimethylformamide
DMSO dimethylsulphoxide
EDC N-(3-Dimethylaminopropyl)-N'-ethylcarbodiimide hydrochloride
HATU O-(7-Azabenzotriazol-1-yl)-N,N,N',N'-tetramethyluronium hexafluorophosphate
HOBt Hydroxybenzotriazole
LCMS Liquid Chromatography Mass Spectrometry
MDAP mass directed automated preparative liquid chromatography.
MS mass spectrometry
NBS n-bromosuccinamide
NIS N-iodosuccinimide
NMP N-methyl-2-pyrrolidone
PE petroleum ether
PCC pyridinium chlorochromate
PG protecting group
RT room temperature
sat. saturated
SM starting material
TEA triethylamine
TFA trifluoroacetic acid
THF tetrahydrofuran
Chromatography
Unless stated otherwise, all chromatography was carried out using silica columns.
LCMS Conditions:
1) Acidic conditions:
    Mobile phase: water containing 0.05% TFA/acetonitrile
    Column: Agilent SB-C18 4.6×30 mm 1.8 m
    Detection: MS and photodiode array detector (PDA)
2) Basic conditions:
    Mobile phase: 10mM NH$_4$HCO$_3$ aqueous/acetonitrile
    Column: Waters XBridge C18 4.6×50 mm 3.5 m;
    Detection: MS and photodiode array detector (PDA)
MDAP Conditions:
1) Acidic conditions:
    Instrument: Waters Mass Directed Auto-purification System
    Column: Waters Sunfire Prep C18 column (5 um, 19×50 mm)
    Mobile phase: water containing 0.05% TFA/acetonitrile.
2) Basic conditions:
    Instrument: Mass Directed Auto-purification System
    Column: Xbridge Prep C18 column (5 um, 19×50 mm)
    Mobile phase: water containing 0.05% ammonia/ acetonitrile.

In the procedures that follow, after each starting material, reference to an intermediate is typically provided. This is provided merely for assistance to the skilled chemist. The starting material may not necessarily have been prepared from the batch referred to.

Description 1

(2-chloro-3-nitrophenyl)methanol (D1)

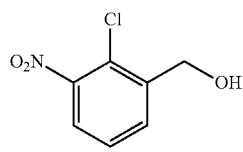 [SMILES: O=[N+]([O-])c1cccc(CO)c1Cl]

To a solution of methyl 2-chloro-3-nitrobenzoate (1.509 g, 7 mmol) in THF (15 mL) was added NaBH$_4$ (1.589 g, 42.0 mmol) in one portion. The mixture was refluxed for 30 mins. Methanol (6 mL) was added into the mixture dropwise slowly, and continued stirring for overnight. Water was added into the mixture, and extracted with AcOEt, the organic phase was washed with brine, dried over anhydrous sodium sulfate, then filtered and the filtrate was concentrated in vacuo to give the title compound (1 g). MS (ES): C$_7$H$_6$ClNO$_3$ requires 187, found 188 (M+H$^+$).

Description 2

2-chloro-3-nitrobenzaldehyde (D2)

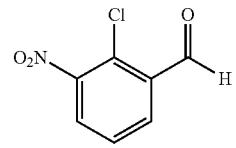

To a mixture of (2-chloro-3-nitrophenyl)methanol (D1) (8.7 g) in DCM (300mL) was added PCC (12.35 g) and the mixture was stirred at room temperature overnight. The mixture was concentrated in vacuo. The residue was purified by column chromatography to afford the title compound (6.9 g) as white solid. MS (ES): C$_7$H$_4$ClNO$_3$ requires 185, found 186 (M+H$^+$).

Description 3

6-fluoro-2-methyl-3-nitrobenzoic acid (D3)

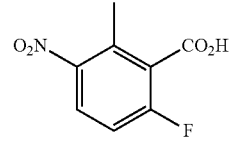

To a solution of nitric acid (4.35 ml) in conc. sulfuric acid (10 ml) was added a solution of 2-fluoro-6-methylbenzoic acid (10 g, 65 mmol) in conc. sulfuric acid (40 ml) at −15° C., and the mixture was stirred at 0° C. for 30 mins. The reaction mixture was poured into ice water and the mixture was extracted with ethyl acetate (100 ml×2). The combined organic were dried over anhydrous Na$_2$SO$_4$, filtered and concentrated in vacuo to afford the title compound (13.44 g) as a light yellow solid. MS (ES): $C_8H_6FNO_4$ requires 199; found no mass.

Description 4

(6-fluoro-2-methyl-3-nitrophenyl)methanol (D4)

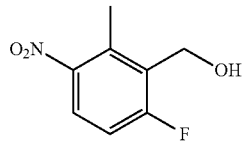

To a solution of 6-fluoro-2-methyl-3-nitrobenzoic acid (D3) (12.936 g, 65 mmol) in THF (200 mL) was added $BH_3$.THF (1M, 97 Ml, 97 mmol) dropwise at 0° C. in 10 mins. The reaction mixture was heated to 60° C. for 4 hr. The reaction mixture was cooled to 0° C., and quenched with $NH_4Cl$ (200 ml ). The organic layer was separated, and the aqueous layer was extracted with ethyl acetate (100 ml×2). The combined organic phase was dried over sodium sulphate, filtered and concentrated to afford the crude title compound (10.951 g) as a yellow solid. MS (ES): $C_8H_8FNO_3$ requires 185; found 186 (M+H+).

Description 5

6-fluoro-2-methyl-3-nitrobenzaldehyde (D5)

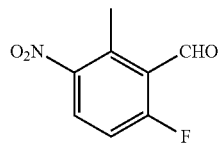

To the solution of (6-fluoro-2-methyl-3-nitrophenyl) methanol (D4) (13.293 g, 71.8 mmol) in DCM (200 mL) was added pyridinium chlorochromate (18.57 g, 86 mmol) in portionwise. Then the mixture was stirred at RT overnight. To the mixture was added water (100 ml), the organic phase was separate and the aqueous was extracted again with DCM (100 ml). The combined organic was dried and concentrated to afford a crude product, which was purified by column chromatography (silica gel, eluting with petroleum ether: EtOAc=10:1) to afford the title compound (10 g) as a light yellow solid. δH (CDCl$_3$, 400 MHz):10.54(1H, s), 8.01(1H, q), 7.20(1H, t), 2.73(3H, s).

Description 6

5-fluoro-2-methyl-3-nitrobenzoic acid (D6)

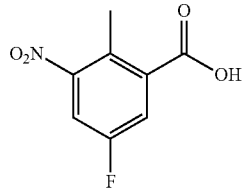

5-Fluoro-2-methylbenzoic acid (20 g) was added portion-wise to ice-cooled conc. sulfuric acid (98%, 80 mL), the mixture was stirred at 0° C. until all solid dissolved, and then the mixture of nitric acid (65%, 6mL) and $H_2SO_4$ (98%, 12 mL) was added portion-wise, the mixture was warmed gradually to rt and stirred at rt for 6hr. The mixture was poured into ice (500 mL), the resulting solid was collected and washed with water (100 mL), re-dissolved in ethyl acetate (200 mL) and washed with brine. The organic layer was dried over anhydrous $Na_2SO_4$ and concentrated in vacuo to afford the title compound (11 g) as brown solid. MS (ES): $C_8H_6FNO_4$ requires 199; found 197.9 (M−H+).

Description 7

5-chloro-2-methyl-3-nitrobenzoic acid (D7)

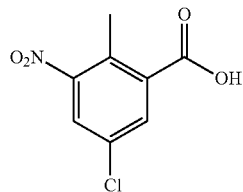

5-Chloro-2-methylbenzoic acid (8.5 g) was added portion-wise to ice-cooled conc. sulfuric acid (98%, 150 mL) and the mixture was stirred at 0° C. until all solid dissolved. Nitric acid (65%, 17.1 mL) was added portion wise and the mixture was warmed gradually to rt and stirred at rt for 5 h. The mixture was poured into ice (500 mL), the resulting solid was collected and washed with water (100 mL) to afford title compound (10.7g). δH (CDCl$_3$, 400 MHz): 2.47(3H, s), 8.01 (1H, s), 8.17(1H, s).

Description 8

(5-fluoro-2-methyl-3-nitrophenyl) methanol (D8)

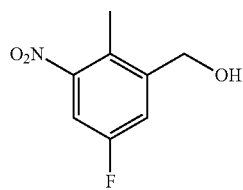

A mixture of 5-fluoro-2-methyl-3-nitrobenzoic acid (D6) (11 g) and $BH_3$.THF (1N, 72 mL) was heated to 80° C. for 2hr. MeOH (20 ml) was added slowly to the mixture to quench the reaction, then concentrated in vacuo to remove the solvents. The residue was dissolved in DCM (50 ml) and washed with saturated $NaHCO_3$ solution (50 ml×2) and brine (50 ml×2). The organic phase was dried over $Na_2SO_4$, filtered and concentrated to afford the title compound (9 g)

as yellow solid. MS (ES): $C_8H_8FNO_3$ requires 185; found no mass.

Description 9

(5-chloro1-2-methyl-3-nitrophenyl) methanol (D9)

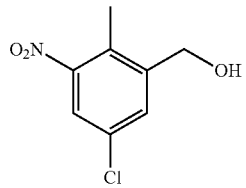

To a mixture of 5-chloro1-2-methyl-3-nitrobenzoic acid (D7) (10.7 g) in THF (60 ml) was added $BH_3$.THF (1N, 99 mL) portion wise at 0° C. The mixture was warmed gradually to rt and stirred at rt for 5hr. MeOH (50 ml) was added slowly to the mixture to quench the reaction, then concentrated in vacuo to remove the solvents and to afford the title compound (8.5 g). δH (CDCl$_3$, 400 MHz): 2.33(3H, s), 4.73 (2H, d), 7.65 (1H, s), 7.67(1H, s).

Description 10

5-fluoro-2-methyl-3-nitrobenzaldehyde (D10)

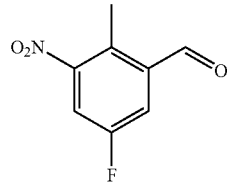

To a mixture of (5-fluoro-2-methyl-3-nitrophenyl)methanol (D8) (9 g) in DCM(100 ml) was added PCC(14 g) portion-wise. The mixture was stirred at rt overnight. The solvent was removed in vacuo to give a crude product, which was purified by column chromatography (silica gel, ethyl acetate/petroleum ether=1:20) to afford the title compound (5 g) as pale yellow solid. MS (ES): $C_8H_6FNO_3$ requires 185; found no mass.

Description 11

5-chloro-2-methyl-3-nitrobenzaldehyde (D11)

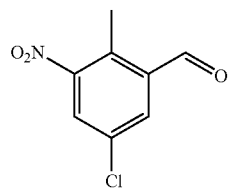

To a mixture of (5-chloro1-2-methyl-3-nitrophenyl) methanol (D9) (8.5 g) in DCM (150 ml) was added PCC (10.9 g) portion wise at 0° C., the mixture was warmed gradually to rt and stirred at rt overnight. The solvent was removed in vacuo to give the crude product, which was purified by column chromatography (silica gel, ethyl acetate/petroleum ether=1:20) to afford the title compound (4.8 g). δH (CDCl$_3$, 400 MHz): 2.74(3H, s), 7.96 (1H, d), 8.01(1H, d), 10.34(1H, s).

Descriptions 12 and 13 were prepared using a similar procedure to that described for D10.

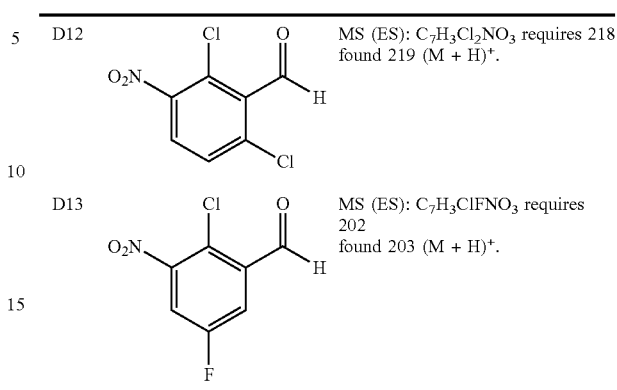

Description 14

(3R, 5S)-1-(2-chloro-3-nitrobenzyl)-3,5-dimethyl-piperazine (D14)

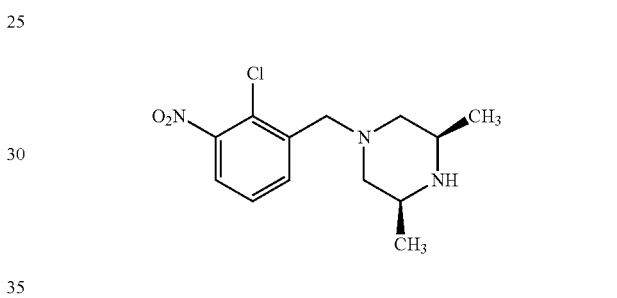

To a mixture of (2R,6S)-2,6-dimethylpiperazine (4 g, 35 mmol) and 2-chloro-3-nitrobenzaldehyde (D2) (6.50 g, 35 mmol) in DCM (150 mL) at 0° C. was added sodium triacetoxyborohydride (14.85 g, 70.1 mmol) portionwise, and then stirred at RT overnight. The mixture was washed with water (50 ml×2) and then sat. NaCl solution (50 ml). The organic phase was dried over anhydrous $Na_2SO_4$, filtered and concentrated to leave the crude product as light yellow solid, which was purified by column chromatography (silica gel, eluting with petroleum ether:EtOAc:DCM=1:1:1) to afford the title compound (8.6 g). MS (ES): $C_{13}H_{18}ClN_3O_2$ requires 283, found 284 (M+H$^+$).

Description 15

((2R,6S)-4-(2-chloro-3-nitrobenzyl)-2,6-dimethyl-piperazin-1-yl)(cyclopentyl)methanone (D15)

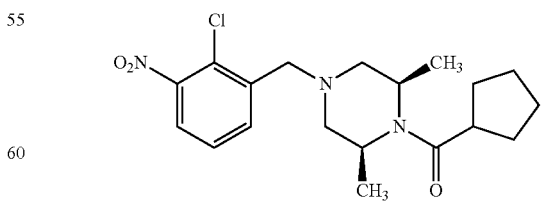

To a mixture of (3R,5S)-1-(2-chloro-3-nitrobenzyl)-3,5-dimethylpiperazine (D14) (8.6 g) and Et$_3$N (12.67 mL) in DCM (150 mL) was added cyclopentanecarbonyl chloride (4.82 g), then stirred at 5° C. overnight. The mixture was washed with water (50 ml×3) and then sat. NaCl solution (50 ml). The organic phase was dried over Na₂SO₄, filtered and concentrated in vacuo to afford the title compound (11.5 g) as a light yellow oil, MS (ES): $C_{19}H_{26}ClN_3O_3$ requires 379; found 380 (M+H⁺).

Description 16

((2R,6S)-4-(3-amino-2-chlorobenzyl)-2,6-dimethyl-piperazin-1-yl)(cyclopentyl)methanone (D16)

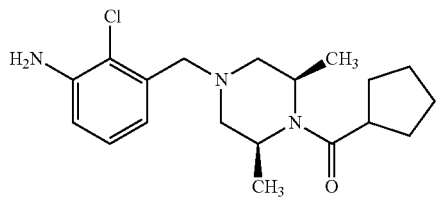 [SMILES: C[C@@H]1CN(Cc2cccc([N+](=O)[O-])c2Cl)C[C@H](C)N1C(=O)C1CCCC1]

The mixture of ((2R,6S)-4-(2-chloro-3-nitrobenzyl)-2,6-dimethylpiperazin-1-yl)(cyclopentyl)methanone (D15) (9 g), ammonium formate (8.60 g) and zinc (4.46 g) in methanol (75 mL) and water (75 mL) was heated to 80° C. for 2hr. The solid was filtered off and the filtrate was extracted with DCM (100 ml×3). The combined organics were washed with sat. NaCl solution (50 ml×2), dried over Na₂SO₄ and concentrated in vacuo. The residue was purified by column chromatography to afford the title compound (5.3 g) as a white solid. δH (CDCl₃, 400 MHz): 1.33 (d, 6H), 1.40 (s, 2H), 1.75 (m, 6H), 2.22 (s, 2H), 2.72 (m, 2H), 2.85 (m, 1H), 3.56 (s, 2H), 4.12 (s, 3H), 4.64 (s, 1H), 6.73 (d, 1H), 6.92 (d, 1H), 7.06 (m, 1H). MS (ES): $C_{19}H_{28}ClN_3O$ requires 349; found 350 (M+H⁺).

Description 17

(R)-tert-butyl 3-methylpiperazine-1-carboxylate (D17)

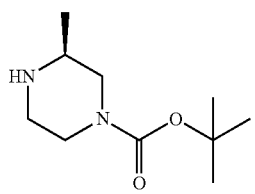

To a solution of (S)-2-methylpiperazine (500 mg, 4 99 mmol) in DCM (5 ml) was added Et₃N (1010 mg, 9 98 mmol) and (Boc)₂O (1198 mg, 5.49 mmol) in DCM (3 ml) dropwise. The mixture was stirred at 0° C. for 2 hr. DCM (10 mL), H₂O (5 mL) and 30% NaHSO₄ (10 mL) were added to the reaction mixture. The resulted mixture was stirred for 10 min, and to the aqueous layer was added sat. Na₂CO₃ solution until a pH of 8 was obtained, whereupon the mixture was extracted with isopropyl alcohol:chloroform=1:3 (20 ml×5). The combined organic layers were washed with sat. NaCl (5 mL×1), dried over Na₂SO₄, filtered and concentrated to give the title compound (562 mg) as a light yellow oil. MS (ES): $C_{10}H_{20}N_2O_2$ requires 200, found 201 (M+H⁺).

Description 18

(S)-tert-butyl 4-(cyclopentanecarbonyl)-3-methyl-piperazine-1-carboxylate (D18)

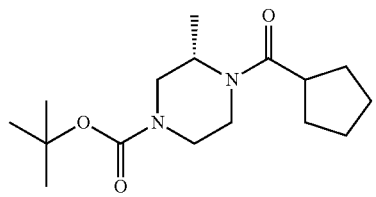 [SMILES: C[C@H]1CN(C(=O)OC(C)(C)C)CCN1C(=O)C1CCCC1]

To a solution of (S)-tert-butyl 3-methylpiperazine-1-carboxylate (D17) (15 g, 74.9 mmol) and triethylamine (31.3 mL, 225 mmol) in DCM (300 mL) stirred at room temperature under nitrogen was added cyclopentanecarbonyl chloride (12.91 g, 97 mmol) dropwise. The reaction mixture was stirred at room temperature overnight. The mixture was concentrated to give the title compound (24 g) as a yellow oil. MS (ES): $C_{16}H_{28}N_2O_3$ requires 296, found 297 (M+H⁺).

Description 19

(S)-cyclopentyl(2-methylpiperazin-1-yl)methanone (D19)

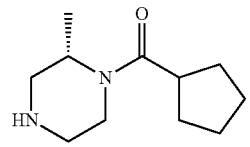

To a solution of (5)-tert-butyl 4-(cyclopentanecarbonyl)-3-methylpiperazine-1- carboxylate (D18) (24 g, 81 mmol) in DCM (300 mL) stirred at RT was added TFA (31.2 mL, 405 mmol) slowly. The mixture was stirred at RT overnight. The reaction mixture was evaporated. Sat. KHCO₃ solution (100 mL) was added and extracted with EtOAc (50 ml×3). The organic layer was evaporated to give the title compound (15 g) as a yellow oil. MS (ES): $C_{11}H_{20}N_2O$ requires 196, found 197 (M+H⁺).

Description 20

(S)-(4-(2-chloro-3-nitrobenzyl)-2-methylpiperazin-1-yl)(cyclopentyl)methanone (D20)

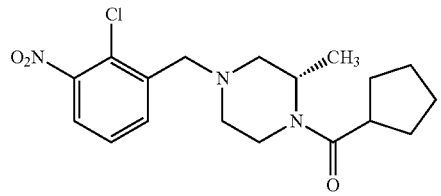 [SMILES: C[C@H]1CN(Cc2cccc([N+](=O)[O-])c2Cl)CCN1C(=O)C1CCCC1]

To a stirred solution of 2-chloro-3-nitrobenzaldehyde (D2) (10 g, 53.9 mmol) and (S)-cyclopentyl(2-methylpiperazin-1-yl)methanone (D19) (12.69 g, 64.7 mmol) in DCM (200 mL) at rt under nitrogen was added sodium triacetoxyborohydride (14.85 g, 70.1 mmol) in portion-wise. The reaction mixture was stirred at rt overnight. The mixture was concentrated to give a crude product, which was purified by column chromatography (silica gel, elution with ethyl acetate:petroleum ether=1:3) to obtain the title compound (5 g) as a yellow oil. MS (ES): $C_{18}H_{24}ClN_3O_3$ requires 365, found 366 (M+H$^+$).

Description 21

(S)-(4-(3-amino-2-chlorobenzyl)-2-methylpiperazin-1-yl)(cyclopentyl)methanone (D21)

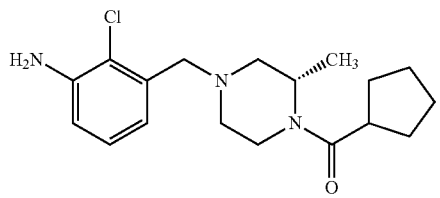

To a solution of (S)-(4-(2-chloro-3-nitrobenzyl)-2-methylpiperazin-1-yl)(cyclopentyl)methanone (D20) (5.0 g, 13.67 mmol) and ammonium formate (6.89 g, 109 mmol) in methanol (50 mL) and water (50 mL) under nitrogen atmosphere at rt was added zinc (3.57 g, 54.7 mmol) in one portion. The solution was stirred at 80° C. for 2 hr. The reaction mixture was cooled to RT and filtered off. The organic layer was evaporated and the residue dissolved in ethyl acetate (100 ml) and washed with saturated NaCl (100 ml) to remove ammonium formate. The organic layer was evaporated to afford the title compound (4.0 g) as a brown oil. MS (ES): $C_{18}H_{26}ClN_3O$ requires 335, found 336 (M+H$^+$).

Description 22

(S)-cyclopentyl(4-(6-fluoro-2-methyl-3-nitrobenzyl)-2-methylpiperazin-1-yl)methanone (D22)

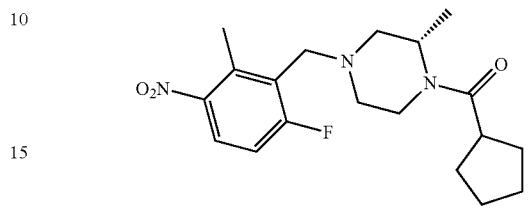

A mixture of 6-fluoro-2-methyl-3-nitrobenzaldehyde (D5) (2 g) and (S)-cyclopentyl (2-methylpiperazin-1-yl)methanone (D19) (2.358 g) in DCM (30 mL) with several drops of acetic acid was stirred at rt for 1 hr. Then sodium triacetoxyborohydride (6.94 g) was added and the resulting mixture was stirred overnight. The reaction was quenched with saturated NaHCO3 aqueous solution and then extracted with DCM. The organic phase was collected, dried over Na2SO4, filtered and then concentrated to afford the title compound (3.6 g). MS (ES): $C_{19}H_{26}FN_3O_3$ requires 363; found 364(M+H$^+$).

Descriptions 23-25 (D23-D25) were prepared using a similar procedure to that described for D22.

D23 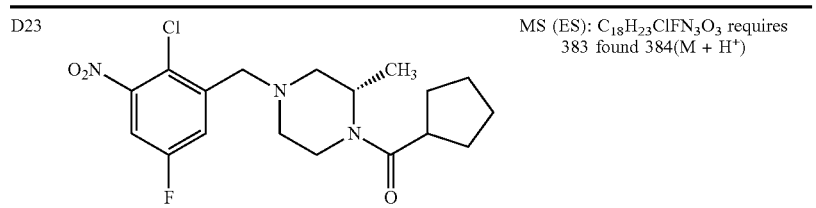

MS (ES): $C_{18}H_{23}ClFN_3O_3$ requires 383 found 384(M + H$^+$)

D24 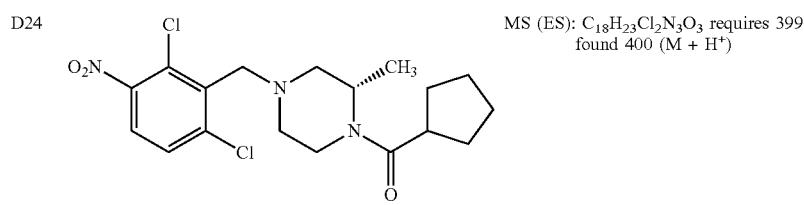

MS (ES): $C_{18}H_{23}Cl_2N_3O_3$ requires 399 found 400 (M + H$^+$)

D25 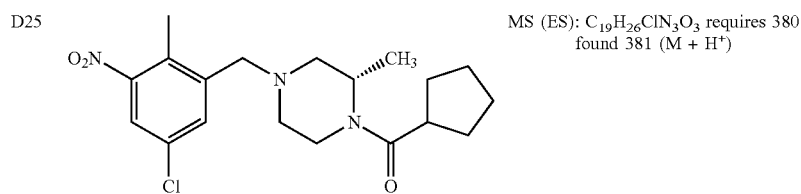

MS (ES): $C_{19}H_{26}ClN_3O_3$ requires 380 found 381 (M + H$^+$)

Description 26

(S)-(4-(3-amino-6-fluoro-2-methylbenzyl)-2-methyl-piperazin-1-yl)(cyclopentyl)methanone (D26)

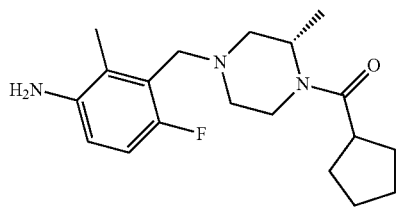 [SMILES: Cc1c([N+](=O)[O-])ccc(F)c1CN1CCN(C(=O)C2CCCC2)[C@@H](C)C1]

The mixture of (S)-cyclopentyl(4-(6-fluoro-2-methyl-3-nitrobenzyl)-2-methylpiperazin-1-yl)methanone (D22) (2.1 g) and Pd/C (0.061 g) in Ethanol (30 mL) was stirred overnight under a hydrogen balloon. The Pd/C was filtered off and the filtrate concentrated to afford the title compound (1.5 g), which was used directly in the next step without further purification. MS (ES): $C_{19}H_{28}FN_3O$ requires 333; found 334(M+H$^+$).

Description 27

(S)-(4-(3-amino-5-chloro-2-methylbenzyl)-2-methyl-piperazin-1-yl)(cyclopentyl)methanone (D27)

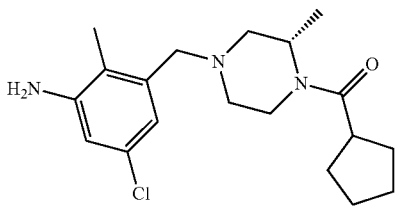

To a solution of (S)-(4-(5-chloro-2-methyl-3-nitrobenzyl)-2-methylpiperazin-1-yl)(cyclopentyl)methanone (D25) (2.4 g, 6.32 mmol) in acetic Acid (40 mL) was added iron (3.53 g, 63.2 mmol) portion-wise under vigorous stirring. After addition, the resulting mixture was stirred for another 4 hr. The solid was filtered off and the cake was washed three times with EA. The filtrate was collected and the solvent was removed in vacuo. The residue was dissolved in EA and washed with aqueous Na2CO3 solution and brine. The organic layer was separated, dried over Na2SO4, giltered and solvent removed to afford the title compound (1.8 g). MS (ES): $C_{19}H_{28}ClN_3O$ requires 349; found 350(M+H$^+$).

Descriptions 28 and 29 were prepared using a similar procedure to that described for D27.

D28

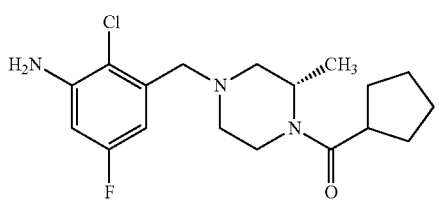 [SMILES: C[C@H]1CN(Cc2cc(F)cc([N+](=O)[O-])c2Cl)CCN1C(=O)C1CCCC1]

MS (ES): $C_{18}H_{25}ClFN_3O$ requires 353; found 354 (M + H$^+$)

D29

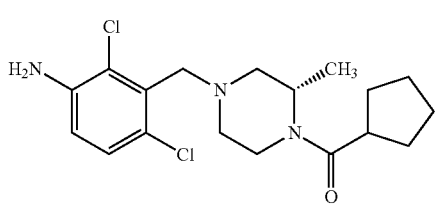 [SMILES: C[C@H]1CN(Cc2c(Cl)ccc([N+](=O)[O-])c2Cl)CCN1C(=O)C1CCCC1]

MS (ES): $C_{18}H_{25}Cl_2N_3O_3$ requires 369; found 370 (M + H$^+$)

Description 30

(S)-cyclopentyl(4-(5-fluoro-2-methyl-3-nitrobenzyl)-2-methylpiperazin-1-yl)methanone (D30)

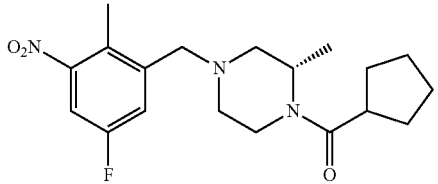 [SMILES: Cc1c(CN2CCN(C(=O)C3CCCC3)[C@@H](C)C2)cc(F)cc1[N+](=O)[O-]]

A mixture of 5-fluoro-2-methyl-3-nitrobenzaldehyde (D10) (4.4 g) and (S)-cyclopentyl(2-methylpiperazin-1-yl)methanone (D19) (4.6 g) in anhydrous DCM(50 mL) was stirred at RT for 10 min. NaBH(OAc)$_3$ (4.9 g) was added portion-wise and the reaction mixture was stirred at 20° C. overnight. After the reaction completed, MeOH was added dropwise to quench the reaction. When the gaseous evaluation had ceased, the solvents was removed in vacuo to give a crude product, which was purified by column chromatography (silica gel, ethyl acetate/petroleum ether=1:100) to afford the title compound (7 g) as yellow oil. MS (ES): $C_{19}H_{26}FN_3O_3$ requires 363; found 364 (M+H$^+$).

Description 31

(S)-(4-(3-amino-5-fluoro-2-methylbenzyl)-2-methyl-piperazin-1-yl)(cyclopentyl)methanone (D31)

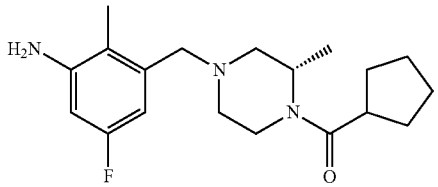

A mixture of (S)-cyclopentyl(4-(5-fluoro-2-methyl-3-nitrobenzyl)-2- methylpiperazin-1-yl)methanone (D30) (7 g), HCOONH$_4$ (1.8 g) and zinc (1.439 g, 22.01 mmol) in methanol (60 mL) and water (60 mL) was stirred at 80° C. for 4 hr. After the reaction completed, the solvent was removed in vacuo, the residue was extracted with ethyl acetate (50 ml×4). The combined organic extract was washed with brine (100 ml), dried over anhydrous sodium sulfate and concentrated to afford the title compound (5.1 g) as pale yellow oil. MS (ES): $C_{19}H_{28}FN_3O$ requires 333; found 334(M+H$^+$).

Description 32

(S)-tert-butyl 4-(5-fluoro-2-methyl-3-nitrobenzyl)-2-methylpiperazine-1-carboxylate (D29)

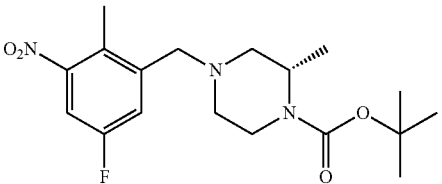 [SMILES: Cc1c(CN2CCN(C(=O)OC(C)(C)C)[C@@H](C)C2)cc(F)cc1[N+](=O)[O-]]

To a solution of 5-fluoro-2-methyl-3-nitrobenzaldehyde (D10) (10 g, 54.6 mmol) and (S)-tert-butyl 2-methylpiperazine-1-carboxylate (12.03 g, 60.1 mmol) in DCM (120 mL) was added drops of acetic acid (3.28 g, 54.6 mmol) and the mixture was stirred at rt for an hour. Sodium triacetoxyhydroborate (23.15 g, 109 mmol) was added to the mixture in ice-bath and the mixture was stirred at rt overnight and quenched with sat. NaHCO3 solution. The organic layer was dried with anhydrous Na2SO4, filtered and the filtrate evaporated in vacuo to give the title compound (22.17 g) as a syrup. MS (ES): $C_{18}H_{26}FN_3O_4$ requires 367; found 368 (M+H$^+$).

Description 33

(S)-tert-butyl 4-(5-fluoro-2-methyl-3-nitrobenzyl)-2-methylpiperazine-1-carboxylate (D33)

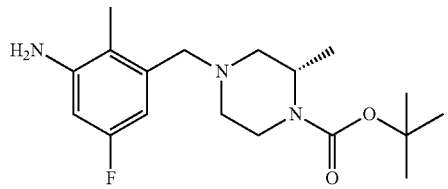

To a solution of (5)-tert-butyl 4-(5-fluoro-2-methyl-3-nitrobenzyl)-2-methylpiperazine-1-carboxylate (D32) (5 g, 13.61 mmol) in ethanol (65 mL) was added palladium (0.145 g, 1.361 mmol) under H$_2$ and the mixture was stirred at RT for 24 hr. The mixture was filtered and the filtrate evaporated in vacuo to give the title compound (4.5 g). MS (ES): $C_{18}H_{28}FN_3O_2$ requires 337; found 338(M+H$^+$).

Description 34

(S)-1-(5-fluoro-2-methyl-3-nitrobenzyl)-3-methylpiperazine (D34)

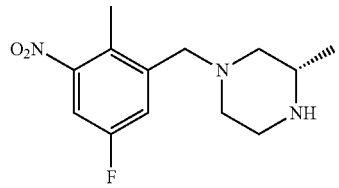 [SMILES: Cc1c(CN2CCN[C@@H](C)C2)cc(F)cc1[N+](=O)[O-]]

To a solution of (5)-tert-butyl 4-(5-fluoro-2-methyl-3-nitrobenzyl)-2-methylpiperazine-1-carboxylate (D32) (4 g, 10.89 mmol) in DCM (15 mL) was added hydrogen chloride/MeOH (27.2 mL, 109 mmol). The mixture was degassed and reacted under nitrogen at rt for 12 hr. The mixture was conc. to afford the title compound (3.1 g). MS (ES): $C_{13}H_{18}FN_3O_2$ requires 267; found 268 (M+H$^+$).

Description 35

(S)-(4-(5-fluoro-2-methyl-3-nitrobenzyl)-2-methyl-piperazin-1-yl) (3-fluorophenyl) methanone (D35)

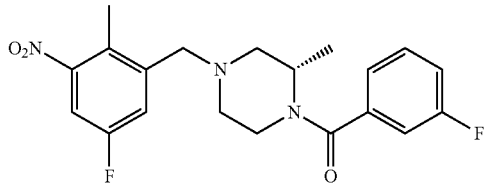

To a solution of (S)-1-(5-fluoro-2-methyl-3-nitrobenzyl)-3-methylpiperazine (D34) (1.7 g, 6.36 mmol) and triethylamine (0.886 mL, 6.36 mmol) in DCM (50 mL) stirred under nitrogen at RT was added 3-fluorobenzoyl chloride (1.109 g, 7 mmol) dropwise and the reaction mixture was stirred at rt overnight. The reaction mixture was partitioned between ethyl acetate and saturated brine and the organic phase was dried over sodium sulphate, evaporated in vacuo and purified by column chromatography to give the title compound (2.4 g). MS (ES): $C_{20}H_{21}F_2N_3O_3$ requires 389, found 390 (M+H$^-$).

Description 36

(S)-(4-(3-amino-5-fluoro-2-methylbenzyl)-2-methyl-piperazin-1-yl)(3-fluorophenyl)methanone (D36)

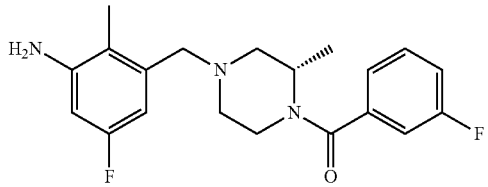 [SMILES: Cc1c(CN2CCN(C(=O)c3cccc(F)c3)[C@@H](C)C2)cc(F)cc1[N+](=O)[O-]]

The mixture of (S)-(4-(5-fluoro-2-methyl-3-nitrobenzyl)-2-methylpiperazin-1-yl)(3-fluorophenyl)methanone (D35) (2.4 g, 6.16 mmol) and Pd—C (0.066 g, 0.616 mmol) in Methanol (40 mL) stirred under hydrogen was stirred at rt overnight. The reaction mixture was evaporated in vacuo to give the title compound (2 g). MS (ES): $C_{20}H_{23}F_2N_3O$ requires 359, found 360 (M+H$^+$).

Description 37

4-nitro-2,3-dihydro-1H-inden-1-one (D37)

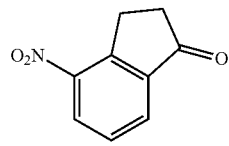 [SMILES: O=C1CCc2c1cccc2[N+](=O)[O-]]

To a solution of 2,3-dihydro-1H-inden-1-one (3.96 g, 30 mmol) in conc. sulfuric acid (25 ml, 469 mmol) stirred in air at 0° C. was added potassium nitroperoxous acid (3.06 g, 30.3 mmol) in several portions over 15 mins and the reaction mixture was stirred for 1 hr at this temperature. After reaction was completed, the mixture was poured into ice-water, and extracted with AcOEt. The organic phase was washed with water and saturated NaHCO3, dried over anhydrous sodium sulfate, filtered and the filtrate was concentrated under reduced pressure to afford a crude product, which was purified by column chromatography (silica gel, eluent: AcOEt/Pet 0~25%, v/v) to give the title compound. MS (ES): $C_9H_7NO_3$ requires 177, found 178 (M+H$^+$).

Description 38

6-nitro-2,3-dihydro-1H-inden-1-one (D38)

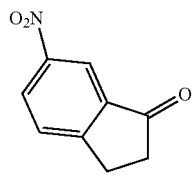 [SMILES: O=C1CCc2ccc([N+](=O)[O-])cc21]

The title compound was prepared using a similar procedure to that described for D37 MS (ES): $C_9H_7NO_3$ requires 177, found 178(M+H$^+$).

Description 39

4-nitro-2,3-dihydro-1H-inden-1-ol (D39)

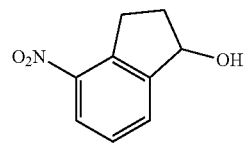 [SMILES: O=[N+]([O-])c1cccc2c1CCC2O]

To the solution of 4-nitro-2,3-dihydro-1H-inden-1-one (D37) (0.4 g, 2.258 mmol) in ethanol (10 mL), was added sodium boronhydride (0.171 g, 4.52 mmol) and the mixture was stirred at RT for 2 hr. The mixture was quenched with aqueous NH4Cl, extracted with ethyl acetate (50 ml×2) and the organic layer was concentrated to afford the title compound (0.4 g). MS (ES): $C_9H_9NO_3$ 179.2 found 162 (M−OH).

Description 40

6-nitro-2,3-dihydro-1H-inden-1-ol (D40)

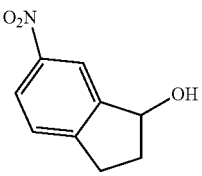 [SMILES: O=[N+]([O-])c1ccc2c(c1)C(O)CC2]

The title compound was prepared using a similar procedure to that described for D36 MS (ES): C₉H₉NO₃ requires 179 found 162 (M−OH).

Description 41

1-chloro-4-nitro-2,3-dihydro-1H-indene (D41)

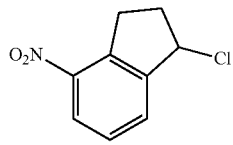 [SMILES: O=[N+]([O-])c1cccc2c1CCC2Cl]

To an ice-cold solution of 4-nitro-2,3-dihydro-1H-inden-1-ol (D39) (0.4 g, 2.232 mmol) in toluene (10 mL), was added SOCl₂ (0.244 mL, 3.35 mmol) dropwise and the mixture was stirred at this temperature for 30 min followed by heating at 55° C. for 1 hr. The reaction mixture was quenched with water (50 mL), extracted with ethyl acetate (50 mL×2), washed and dried. The organic layer was concentrated to afford the title compound (0.45 g). MS (ES): C₉H₈ClNO₂ requires 197, found 198 (M+H⁺).

Description 42

1-chloro-6-nitro-2,3-dihydro-1H-indene (D42)

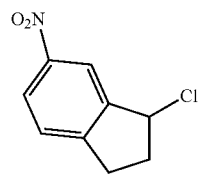 [SMILES: O=[N+]([O-])c1ccc2c(c1)C(Cl)CC2]

The title compound was prepared using a similar procedure to that described for D41. MS (ES): C₉H, 8; ClNO₂ requires 197 found 198 (M+H⁺).

Description 43

Cyclopentyl((2S)-2-methyl-4-(4-nitro-2,3-dihydro-1H-inden-1-yl)piperazin-1-yl)methanone (D43

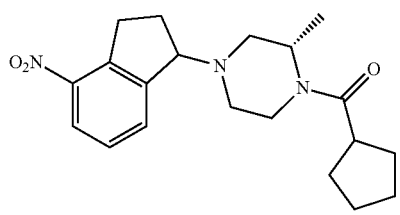

A mixture of 1-chloro-4-nitro-2,3-dihydro-1H-indene (D41) (0.45 g, 1.822 mmol), (S)-cyclopentyl(2-methylpiperazin-1-yl)methanone (D19) (0.715 g, 3.64 mmol) and DIPEA (0.795 mL, 4.55 mmol) in Acetonitrile (10 mL) was heated at 80° C. overnight. The reaction mixture was concentrated under reduced pressure, the residue purified with column chromatography (acidic condition) to afford the title compound (0.4 g). MS (ES): C₂₀H₂₇N₃O₃ requires 357, found 358 (M+H⁺).

Description 44

Cyclopentyl((2S)-2-methyl-4-(6-nitro-2,3-dihydro-1H-inden-1-yl)piperazin-1-yl)methanone (D44)

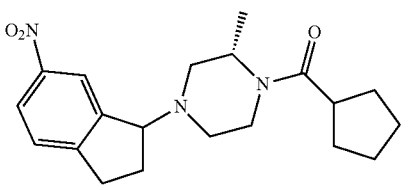

The title compound was prepared using a similar procedure to that described for D43. MS (ES): C₂₀H₂₇N₃O₃ requires 357, found 358 (M+H⁺).

Description 45

((2S)-4-(4-amino-2,3-dihydro-1H-inden-1-yl)-2-methylpiperazin-1-yl)(cyclopentyl) methanone (D45)

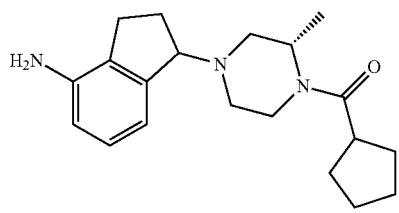 [SMILES: C[C@H]1CN(C2CCc3c2cccc3[N+](=O)[O-])CCN1C(=O)C1CCCC1]

The mixture of cyclopentyl((2S)-2-methyl-4-(4-nitro-2,3-dihydro-1H-inden-1-yl)piperazin-1-yl)methanone (D43) (0.4 g, 1.119 mmol) and nickel (0.066 g, 1.119 mmol) in ethanol (20 mL), was stirred under hydrogen balloon at rt for 4 hr. The reaction mixture was filtrated and the filtrate was concentrated to afford the title compound (0.35 g). MS (ESI) C₂₀H₂₉N₃O requires: 327, found 328 (M+H⁺).

Description 46

((2S)-4-(6-amino-2,3-dihydro-1H-inden-1-yl)-2-methylpiperazin-1-yl)(cyclopentyl) methanone (D46)

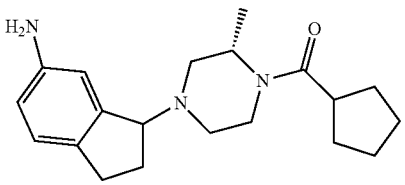 [SMILES: C[C@H]1CN(C2CCc3ccc([N+](=O)[O-])cc32)CCN1C(=O)C1CCCC1]

The title compound was prepared using a similar procedure to that described for D45. MS (ESI) $C_{20}H_{20}N_3O$ requires: 327, found 328 (M+H$^+$).

Description 47

(S)-tert-butyl 4-(2-chloro-3-nitrobenzyl)-2-methylpiperazine-1-carboxylate (D47)

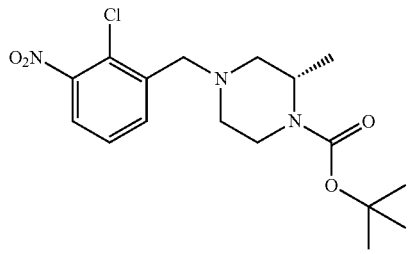 [SMILES: C[C@H]1CN(Cc2cccc([N+](=O)[O-])c2Cl)CCN1C(=O)OC(C)(C)C]

Sodium triacetoxyborohydride (6.85g, 32.3mmol) was added into a mixture of 2-chloro-3-nitrobenzaldehyde (D2) (3 g, 16.17 mmol), (S)-tert-butyl 2-methylpiperazine-1-carboxylate (3.40 g, 16.98 mmol) and AcOH (0.463 mL, 8.08 mmol) in DCM (300 mL) at rt and stirred for 2 hr. LCMS confirmed that the reaction was completed and sat. NaHCO$_3$ aqueous solution was added to the reaction mixture carefully with stirring until pH reached approximately 8 (note: gaseous evaluation). The organic phase was separated, dried over Na$_2$SO$_4$, filtered and the solvent was removed. The residue was purified via column chromatography (10% EA in PE) to afford the title compound (5 g) as brown oil. MS (ESI) $C_{17}H_{24}ClN_3O_4$ requires: 369, found 370 (M+H$^+$).

Description 48

(S)-tert-butyl 4-(3-amino-2-chlorobenzyl)-2-methylpiperazine-1-carboxylate (D48)

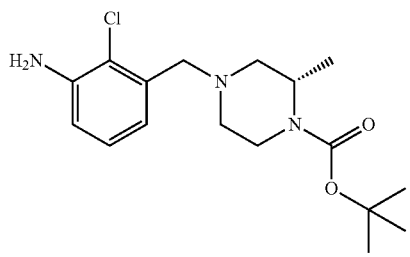

Pd/C (0.144 g, 1.352 mmol) was added into a mixture of (S)-tert-butyl 4-(2-chloro-3-nitrobenzyl)-2-methylpiperazine-1-carboxylate (D47) (5 g, 13.52 mmol) in ethanol (50 mL) at rt and the reaction was stirred under hydrogen overnight. The mixture was filtered through Celite and the filtrate was concentrated to give the title compound (4.5 g) as brown oil. MS (ESI) $C_{17}H_{26}ClN_3O_2$ requires: 339, found 340 (M+H$^+$).

Description 49

(S)-tert-butyl 4-(5-fluoro-2-methyl-3-(6-methylnicotinamido)benzyl)-2-methylpiperazine-1-carboxylate (D49)

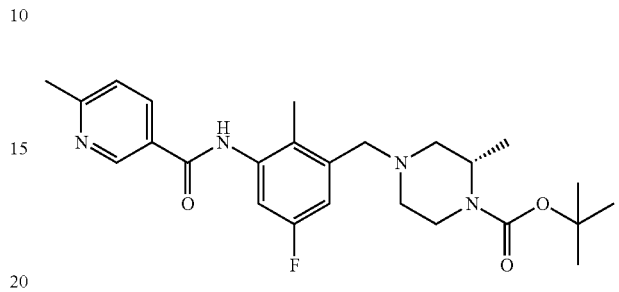

Oxalyl dichloride (1.505 mL, 17.78 mmol) was added into a solution of 6-methylnicotinic acid (1.301 g, 9.48 mmol) and cat. DMF (0.043 g, 0.593 mmol) in DCM (15 mL) at 0° C. and the mixture was stirred at 0° C. for 1 hr. The mixture was concentrated to give the acid chloride which was added into a solution of (S)-tert-butyl 4-(3-amino-5-fluoro-2-methylbenzyl)-2-methylpiperazine-1-carboxylate (D33) (2 g, 5.93 mmol) and pyridine (2 mL) in DCM (10 mL). The reaction was stirred at rt overnight and the mixture was purified by MDAP to give the title compound (3.18 g) as white solid. MS (ES): $C_{25}H_{33}FN_4O_3$ requires 456; found 457(M+H$^+$).

Description 50

(S)-N-(5-fluoro-2-methyl-3-((3-methylpiperazin-1-yl)methyl)phenyl)-6-methylnicotinamide (D50)

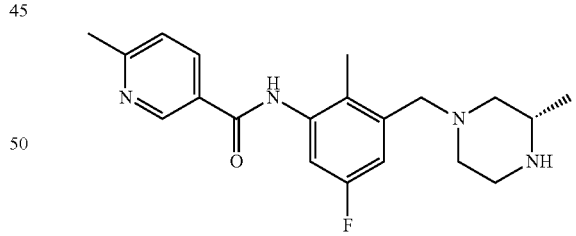

To a solution of (S)-tert-butyl 4-(5-fluoro-2-methyl-3-(6-methylnicotinamido)benzyl)-2-methylpiperazine-1-carboxylate (D49) (3.18 g, 6.97 mmol) in methanol (4 mL) and DCM (30 mL), 2,2,2-trifluoroacetic acid (20 mL, 269 mmol) was added and the reaction was stirred at 40° C. overnight. The reaction was neutralized with solid NaHCO$_3$. After filtration, the residue was washed with EA, the solvent was evaporated and the residue was purified by column chromatography (MeOH:DCM=1:20)) to give the title compound (1.4 g). MS (ES): $C_{20}H_{25}FN_4O$ requires 356; found 357 (M+H$^+$).

Description 51

(S)-3-cyano-N-(5-fluoro-2-methyl-3-((3-methylpiperazin-1-yl)methyl)phenyl)benzamide (D51)

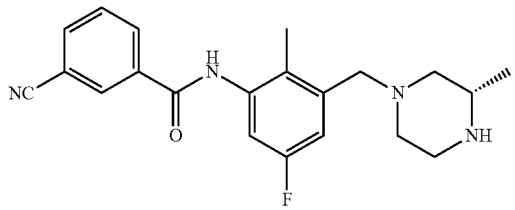 [SMILES: Cc1c(CN2CCN[C@@H](C)C2)cc(F)cc1NC(=O)c1cccc(C#N)c1]

To the solution of (S)-tert-butyl 4-(3-amino-5-fluoro-2-methylbenzyl)-2-methylpiperazine-1-carboxylate D33 (3.2 g, 9.48 mmol) in DCM (20 mL) was added the solution of 3-cyanobenzoyl chloride (1.727 g, 10.43 mmol) in DCM (20 mL) dropwise at rt with stirring followed by the dropwise addition of DIPEA (4.97 mL, 28.5 mmol). The resulted reaction mixture was stirred for another 2 hr. The reaction mixture was washed with water and brine, the organic phase separated and then solvent was evaporated in vacuo to afford (S)-tert-butyl 4-(3-(3-cyanobenzamido)-5-fluoro-2-methylbenzyl)-2-methylpiperazine-1-carboxylate (4.2 g). MS (ESI) $C_{26}H_{31}FN_4O_3$, requires: 466, found 467 (M+H$^+$). To a solution of (S)-tert-butyl 4-(3-(3-cyanobenzamido)-5-fluoro-2-methylbenzyl)-2-methylpiperazine-1-carboxylate (4.2 g, 9 mmol) in DCM (60 mL) was added TFA (20.81 mL, 270 mmol) at rt with stirring. The resulting reaction mixture was heated overnight under reflux at 50° C. The reaction was cooled to RT and quenched with saturated $Na_2CO_3$ aqueous solution carefully, adjusting the pH to around 10. The aqueous phase was separated and extracted five times with THF/ethyl acetate. All organic phases were combined and concentrated in vacuo to a volume of approximately 100 mL by rotavap, the mixture was dried over $Na_2SO_4$, filtered and the filtrate concentrated to afford the title compound (2.8 g). MS (ESI) $C_{21}H_{23}FN_4O$ requires: 366, found 367 (M+H$^+$).

Description 52

(S)-tert-butyl 4-(2-chloro-3-(3-cyanobenzamido)benzyl)-2-methylpiperazine-1-carboxylate (D52)

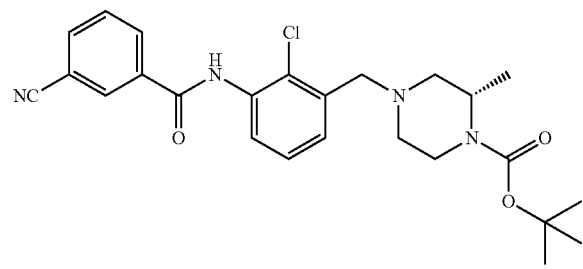 [SMILES: C[C@H]1CN(Cc2cccc(NC(=O)c3cccc(C#N)c3)c2Cl)CCN1C(=O)OC(C)(C)C]

3-cyanobenzoyl chloride (1.267 g, 7.65 mmol) was added to a mixture of (S)-tert-butyl 4-(3-amino-2-chlorobenzyl)-2-methylpiperazine-1-carboxylate (D48) (2 g, 5.88 mmol) and pyridine (0.952 mL, 11.77 mmol) in DCM (20 mL) at 0° C. The reaction mixture was warmed to RT and stirred overnight. The mixture was filtered through Celite and the filtrate concentrated to give a residue that was purified using column chromatography (17% EA in PE) to give the title compound (0.8 g) as brown oil. MS (ESI) $C_{25}H_{29}ClN_4O_3$ requires: 468, found 469 (M+H$^+$).

Description 53

(S)-N-(2-chloro-3-((3-methylpiperazin-1-yl)methyl)phenyl)-3-cyanobenzamide (D53)

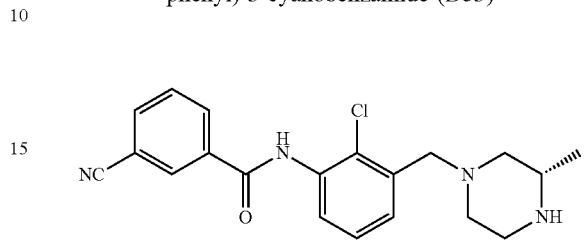

TFA (3.94 mL, 51.2 mmol) was added into a mixture of (S)-tert-butyl 4-(2-chloro-3-(3-cyanobenzamido)benzyl)-2-methylpiperazine-1-carboxylate (D52) (2.4 g, 5.12 mmol) in DCM (8 mL) at RT and stirred overnight. The mixture was filtered through celite and the filterate was concentrated and purified by column chromatography (40% MeOH in DCM) to give the title compound (1.8 g) as brown solid. MS (ESI) $C_{20}H_{21}ClN_4O$ requires: 368, found 369 (M+H$^+$).

Description 54

Benzyl cyclopent-3-enecarboxylate (D54)

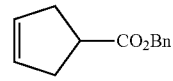

To an ice-cold solution of cyclopent-3-enecarboxylic acid (2g, 17.84 mmol) in THF (50 mL) was added sodium hydride (0.642 g, 26.8 mmol) and stirred for 30 mins, bromomethyl benzene (4.58 g, 26.8 mmol) was added drop-wise and the mixture was allowed to warm to rt and stirring continued for 14 hr. The mixture was diluted with water, extracted with EtOAc, dried and concentrated. The resulting residue was purified by chromatography to give the title compound (1.8 g) as a colorless oil. MS (ES): $C_{13}H_{14}O_2$ requires 202; found 203(M+H$^+$).

Description 55

Benzyl 3-hydroxycyclopentanecarboxylate (D55)

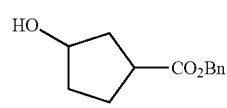

To a solution of benzyl cyclopent-3-enecarboxylate (D54) (1200 mg, 5.93 mmol) in THF (60 mL) was added $BH_3$.THF (6.53 mL, 6.53 mmol) at 0° C. and the solution stirred for 30 mins. Sodium 1,2,3-dioxaboriran-3-olate tetrahydrate (3652 mg, 23.73 mmol) in water was added and stirred for 1 h. The mixture was diluted with water, extracted with EtOAc, dried and concentrated to give a residue that was purified by Description 56 benzyl 3-fluorocyclopentanecarboxylate (D56)

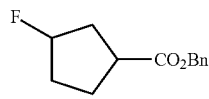

To a solution of benzyl 3-hydroxycyclopentanecarboxylate (D55) (1 g, 4.54 mmol) in DCM (20 mL) was added DAST (1.464 g, 9.08 mmol) at −78° C., after 6 hr, the mixture was diluted with ice water, extracted EtOAc(20 mL×2), dried, concentrated to afford the title compound D56 (800 mg) as a colorless oil. MS (ES): $C_{13}H_{15}FO_3$ requires 222; found 223(M+H+).

Description 57

3-fluorocyclopentanecarboxylic acid (D57)

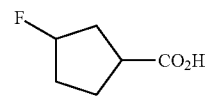

To a solution of benzyl 3-fluorocyclopentanecarboxylate (D56) (500 mg, 2.250 mmol) in Methanol (15 mL) was added Pd/C (120 mg, 0.112 mmol) and the mixture stirred for 5 hr under hydrogen (30 psi) at rt. The mixture was filtered and the filtrate was concentrated to give the title compound (187 mg) as a yellow oil. δH (CDCl$_3$, 400 MHz): 1.62-1.75 (m, 1H), 1.98-2.31 (m, 5H), 2.869 (s, 1H), 5.06-5.21 (m, 1H), 6.30-6.31 (s, 1H). δF (MeOD-d$_4$, 376 MHz): −170.039. MS (ES): $C_6H_9FO_2$ requires 132.1; found 113.1 (M−F).

Description 58

Methyl 3-hydroxy-3-methylcyclobutanecarboxylate (D58)

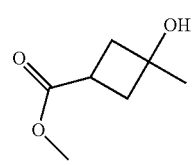

To a stirred solution of methyl 3-oxocyclobutanecarboxylate (1.28 g, 9.99 mmol) in THF (20 mL) stirred under nitrogen at −78° C. was slowly added methylmagnesium bromide (1.430 g, 11.99 mmol). After complete addition, the cold bath was removed, and the reaction mixture was warmed to rt over 1 hr. Aqueous saturated sodium sulfate was added and the aqueous layer was extracted with DCM. The combined organic phases were dried over sodium sulphate and evaporated in vacuo to give the title compound (1.2 g).

Description 59

Methyl 3-fluoro-3-methylcyclobutanecarboxylate (D59)

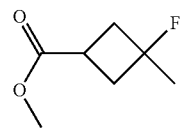

To a solution of methyl 3-hydroxy-3-methylcyclobutanecarboxylate (D58) (1 g, 6.94 mmol) in DCM (20 mL) stirred under nitrogen at −70° C. was added DAST (1.833 mL, 13.87 mmol) dropwise over 5 min. And the reaction mixture was stirred at RT for 12 hr. Water was added and the aqueous phase extracted. The organic layer were washed with brine, dried over Na2SO4, flitered and concentrated to afford the title compound (700 mg).

Description 60

Methyl 3-fluoro-3-methylcyclobutanecarboxylate (D60)

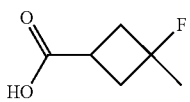

To a solution of methyl 3-fluoro-3-methylcyclobutanecarboxylate (D59) (700 mg, 4.79 mmol) in THF (4 mL), methanol (1 mL) and water (4 mL) stirred under nitrogen at RT was added LiOH (172 mg, 7.18 mmol), the reaction mixture was stirred at rt for 2 hr. The solvent was removed, the residue was treated with conc. HCl to pH 1, extracted with DCM (5 ml×3), and the combined organic phase was washed with saturated brine 10 mL, dried over sodium sulphate and evaporated in vacuo to give the title compound (300 mg).

Description 61

Methyl 2-cyclopropyl-2-hydroxyacetate (D61)

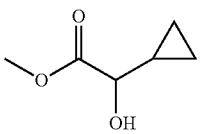

To a solution of methyl 2-oxoacetate (2 g, 11.36 mmol) in THF (20 mL) stirred under nitrogen at −70° C. was added a solution of cyclopropylmagnesium bromide (24.98 ml, 12.49 mmol) dropwise over 15 min. The reaction mixture was stirred at −20° C. for 2 hr. The reaction mixture was quenched with water and extracted with ethyl acetate. The organic layer was washed with brine, dried over Na2SO4, filtered, and concentrated to give the title compound (1 g).

Description 62

Methyl 2-cyclopropyl-2-fluoroacetate (D62)

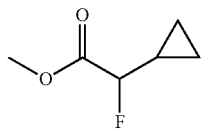

To a solution of methyl 2-cyclopropyl-2-hydroxyacetate (D62) (1 g, 7.68 mmol) in DCM (20 mL) stirred under nitrogen at −70° C. was added DAST (2.030 mL, 15.37 mmol) dropwise over 5 min and the reaction mixture was stirred at rt for 12 hr. Then water was added and the mixture was extracted. The organic layer was washed with brine, dried over Na2SO4, flitered and the filtrate concentrated to afford the title compound (1 g).

Description 63

2-cyclopropyl-2-fluoroacetic acid (D63)

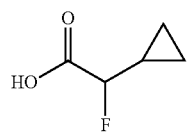

To a solution of methyl 2-cyclopropyl-2-fluoroacetate (D62) (1 g, 7.57 mmol) in THF (9 mL), methanol (3 mL) and water (9 mL) stirred under nitrogen at RT was added LiOH (0.725 g, 30.3 mmol) and the reaction mixture was stirred at rt for 2 hr. The solvent was removed, the residue was treated with conc. HCl to pH 1 and extracted with DCM (5 mL×3). The combined organic phases were washed with saturated brine 10 mL, dried over sodium sulphate and evaporated in vacuo to give the title compound (500 mg).

Description 64

2-cyclopropylacetyl chloride (D64)

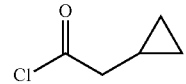

To a solution of 2-cyclopropylacetic acid (2.14 g, 21.38 mmol) in DCM (20 mL) stirred at 20° C. was added SOCl₂ (2.340 mL, 32.1 mmol) and a drop of DMF as catalyst and the reaction mixture was stirred at 20° C. for 2 hr. The solvent and excess SOCl₂ were removed in vacuo to give the title compound (2.1 g).

Description 65

Methyl 2-cyclopropylacetate (D65)

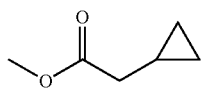

2-cyclopropylacetyl chloride (D64) (2 g, 16.87 mmol) in methanol (15 mL) was stirred at 25° C. for 1 hr. The reaction mixture was concentrated to give the title compound (1 g).

Description 66

Methyl 2-cyclopropylpropanoate (D66)

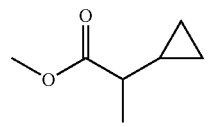

To a solution of methyl 2-cyclopropylacetate (D62) (400 mg, 3.50 mmol) in THF (5 mL) stirred under nitrogen at −70° C. was added LDA (1.752 mL, 3.50 mmol) over 5 min. MeI (0.437 mL, 7 mmol) was added and the reaction mixture was stirred at rt for 12 hr. The reaction mixture was quenched with water, extracted with DCM, dried over Na₂SO₄, filtered and concentrated to give the title compound (360 mg).

Description 67

2-cyclopropylpropanoic acid (D67)

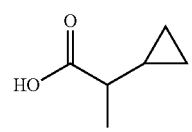

To a solution of methyl 2-cyclopropylpropanoate (D66) (540 mg, 4.21 mmol) in THF (4 mL) and water (1 mL) stirred at RT was added LiOH (404 mg, 16.85 mmol) and the reaction mixture was stirred at rt for 16 hr. The solvent was removed, the residue was treated with conc. HCl to pH 1 and extracted with DCM (5 ml×3). The combined organic phases were washed with saturated brine 10 mL, dried over sodium sulphate and evaporated in vacuo to give the title compound (300 mg).

Description 68

2-cyclobutylacetyl chloride (D68)

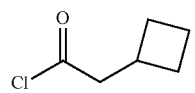

To a solution of 2-cyclobutylacetic acid (1 g, 8.76 mmol) in DCM (20 mL) stirred at 20° C. was added SOCl₂ (0.959 mL, 13.14 mmol) and a drop of DMF as catalyst. The reaction mixture was stirred at 20° C. for 2 hr. The solvent and excess SOCl$_2$ were removed in vacuo to give the title compound (300 mg).

Description 69

Methyl 2-cyclobutylacetate (D69)

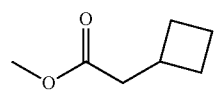

2-cyclobutylacetyl chloride (D68) (300 mg, 2.263 mmol) in methanol (3 mL) was stirred at 25° C. for 1 hr. The reaction mixture was concentrated to give the title compound (200 mg).

Description 70

Methyl 2-cyclobutylpropanoate (D70)

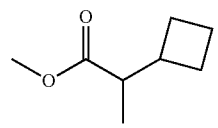

To a solution of methyl 2-cyclobutylacetate (D35) (200 mg, 1.560 mmol) in THF (5 mL) stirred under nitrogen at −70° C. was added LDA (0.780 mL, 1.560 mmol). MeI (0.195 mL, 3.120 mmol) was then added over 5 min and then the reaction mixture was stirred at RT for 12 hr. The reaction mixture was quenched with water, extracted with DCM, dried over Na2SO4, filtered and concentrated to give the title compound (120 mg).

Description 71

2-cyclobutylpropanoic acid (D71)

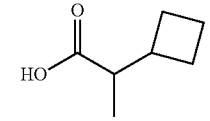

To a solution of methyl 2-cyclobutylpropanoate (D67) (80 mg, 0.563 mmol) in THF (3 mL) and water (1 mL) stirred in air at RT was added solid lithium hydroxide (53.9 mg, 2.250 mmol). The reaction mixture was stirred at 26° C. for 16 hr. The reaction mixture was extracted with EA, dried over Na2SO4, filtered and concentrated to give the title compound (26 mg).

Description 72

Ethyl 2-hydroxycyclopentanecarboxylate (D72)

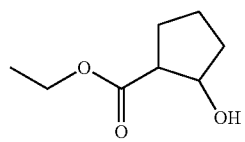

To a solution of ethyl 2-oxocyclopentanecarboxylate (3 g, 19.21 mmol) in methanol (30 mL) stirred in air at 0° C. was added sodium borohydride (2.180 g, 57.6 mmol) portionwise and the reaction mixture was stirred at 0° C. for 30 min. To this mixture was added water (10 mL) and the mixture was extracted with DCM (10 ml×3). The organic layer was dried over Na$_2$SO$_4$, filtered and evaporated to give the title compound (2.9 g) as colourless oil. δH (CDCl3-d$_1$, 400 MHz): 1.26 (m, 3H), 1.65 (m, 1H), 1.75 (m, 2H), 1.95 (m, 3H), 2.65 (m, 1H), 3.08 (m, 1H), 4.18 (m, 2H), 4.42 (m, 1H).

Description 73

Ethyl 2-fluorocyclopentanecarboxylate (D73)

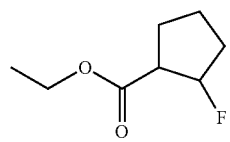

To a solution of ethyl 2-hydroxycyclopentanecarboxylate (D70) (2.9 g, 18.33 mmol) in DCM (30 mL) stirred under nitrogen at 0° C. was added DAST (5.91 g, 36.7 mmol) dropwise and the reaction mixture was stirred at 0° C. for 1 hr. This mixture was queched with sat NaHCO3, extracted with DCM (10 ml×3), dried over sodium sulphate and evaporated in vacuo to give crude product that was purified by silica gel chromatography (PE:EA=100:1) to afford the title compound (450 mg). δH (CDCl3-d$_1$, 400 MHz): 1.21 (m, 3H), 1.89 (m, 4H), 2.06 (m, 1H), 2.45 (m, 1H), 2.95 (m, 1H), 4.10 (m, 2H), 5.29 (m, 1H).

Description 74

2-fluorocyclopentanecarboxylic acid (D74)

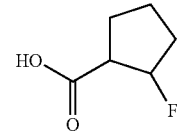

To a solution of ethyl 2-fluorocyclopentanecarboxylate (D73) (400 mg, 2.497 mmol) and lithium hydroxide (524 mg, 12.49 mmol) in methanol (5 mL) stirred in air at rt was added water (5 mL) and the reaction mixture was stirred at rt for 48 hr. This mixture was adjusted pH=5 with 2 N HCl and extracted with DCM (20 ml×3). The organic layer was dried over Na$_2$SO$_4$, filtered and evaporated to afford the title compound (280 mg) as white solid. δH (CDCl3-d$_1$, 400 MHz): 1.76 (m, 3H), 2.15 (m, 1H), 2.50 (m, 2H), 3.00 (m, 1H), 5.25 (m, 1H).

Description 75

3-methylenecyclobutane carboxylic acid (D75)

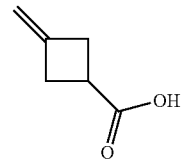

To a solution of 3-methylenecyclobutanecarbonitrile (5 g, 53.7 mmol) in ethanol (25 mL) and water (25 mL) was added KOH (15.06 g, 268 mmol) and the reaction mixture was stirred at rt for 15 hr. The solvent was removed, the residue was treated with conc. HCl to pH 1, extracted with DCM (20 mL×3), and the combined organic phases were washed with sat. brine 25 mL, dried over sodium sulphate and evaporated in vacuo to give the title compound (5.6 g) as a colorless oil. δH (CDCl3-$d_1$, 400 MHz): 3.03 (m, 4H), 3.16 (m, 1H), 4.82 (s, 2H), 11.00 (brs, 1H).

Description 76

3-methylcyclobutanecarboxylic acid (D76)

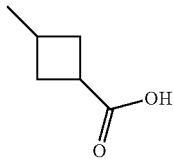

To a solution of 3-methylenecyclobutanecarboxylic acid (D75) (2 g, 17.84 mmol) in ethanol (30 mL) was added Pd/C (1 g, 9.40 mmol), the reaction mixture was stirred at rt under hydrogen for 4 hr. The reaction mixture was filtered and the filtrate was concentrated to give the title compound (1.8 g). δH (CDCl3-$d_1$, 400 MHz): 1.10 (m, 3H), 1.85 (m, 2H), 2.30 (m, 3H), 3.00 (m, 1H), 9.50 (brs, 1H).

Description 77

Bicyclo[2.2.1]heptane-2-carboxylic acid (D77)

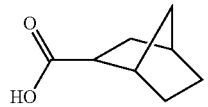

To a solution of bicyclo[2.2.1]hept-5-ene-2-carboxylic acid (300 mg, 2.171 mmol) in MeOH (40 mL) was added Pd/C (23.11 mg, 0.022 mmol) and the mixture was reacted for 16 hr under hydrogen (20 psi) at rt. The reaction mixture was filtered and the filtrate was concentrated to obtain the title compound (180 mg) as a white oil. LCMS $C_8H_{12}O_2$ requires: 140.18, found 141.0 (M+H$^+$).

Description 78

Benzyl 3-formylcyclobutanecarboxylate (D78)

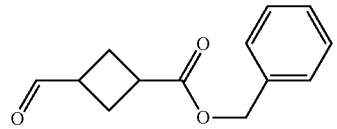 [SMILES: O=CC1CC(C(=O)OCc2ccccc2)C1]

To a solution of benzyl 3-(hydroxymethyl)cyclobutanecarboxylate (2 g, 9.08 mmol) in DCM (20 mL) was added PCC (2.94 g, 13.62 mmol) and stirred at 26° C. for 16 hr. The reaction mixture was filtered and the filtrate was concentrated to give a residue. The residue was diluted with a mixture of PE:EA=15:1 and filtered. The filtrate was concentrated to give the title compound (1.22 g). LCMS (ES): C, 13; H, 14; O, 3; requires 218; found 219(M+H$^+$).

Description 79

Benzyl 3-(difluoromethyl)cyclobutanecarboxylate (D79)

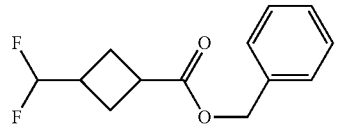 [SMILES: O=C(OCc1ccccc1)C1CC(C(F)F)C1]

To a solution of benzyl 3-formylcyclobutanecarboxylate D78 (1 g, 4.58 mmol) in DCM (20 mL) stirred under nitrogen at −70° C. was added DAST (1.211 mL, 9.16 mmol) dropwise over 5 min and the reaction mixture was stirred at rt for 12 hr. Then water was added and the reaction mixture extracted. The organic extracts were washed with brine, dried over Na$_2$SO$_4$, flitered and concentrated. The residue was purified by chromatography (PE:EA=20:1) to afford the title compound. MS (ES): C, 13; H, 14; F, 2; O, 2; requires 240; found 257(M+17).

Description 80

3-(difluoromethyl)cyclobutanecarboxylic acid (D80)

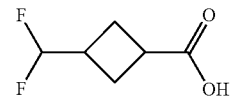

To a solution of benzyl 3-(difluoromethyl)cyclobutanecarboxylate (D79) (210 mg, 0.874 mmol) in methanol (10 mL) stirred at rt was added nickel(II) chloride, 6H$_2$O (623 mg, 2.62 mmol) and NaBH$_4$ (298 mg, 7.87 mmol) and the reaction mixture was stirred at rt for 20 min. Then water was added and the pH adjusted to pH=2 with HCl. The mixture was extracted with ethyl acetate, dried over Na$_2$SO$_4$, filtered and concentrated to give the title compound (100 mg).

Description 81

Benzyl 3-methylenecyclobutanecarboxylate (D81)

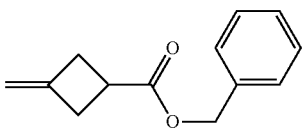

To a solution of 3-methylenecyclobutanecarboxylic acid (D75) (2 g, 17.84 mmol) in ethyl acetate (10 mL) stirred at RT was added a suspension of CDI (3.18 g, 19.62 mmol) in ethyl acetate (10 mL) portionwise over 5 min and the reaction mixture was stirred at RT for about 1.5 hr. Phenylmethanol (2.315 g, 21.40 mmol) was added and stirring continued overnight. The solution was diluted with PE(20 mL), washed with water (20 mL), dried over Na$_2$SO$_4$ and evaporated in vacuo. The residue was purified by chroma tography (PE:EA=20:1) to afford the title compound (3.4 g). MS (ES): $C_{13}H_{14}O_2$ requires 202; found 203 (M+H).

Description 82

Benzyl 3-(hydroxymethyl)cyclobutanecarboxylate (D82)

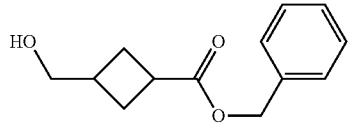 [SMILES: O=C(OCc1ccccc1)C1CC(CO)C1]

To a solution of benzyl 3-methylenecyclobutanecarboxylate (D81) (3.2 g, 15.82 mmol) in THF (20 mL) stirred under nitrogen at RT was added $BH_3$.DMS (0.751 mL, 7.91 mmol). After 1 hr, sodium perborate tetrahydrate (2.92 g, 18.99 mmol) in water was added and the reaction mixture was stirred at RT for 30 min. Then the mixture was warmed to 60° C. for another 1 hr. The reaction mixture was washed with sat.$NH_4Cl$ 5 mL, extracted with DCM (5 ml×3), then washed with saturated brine 10 mL, dried over sodium sulphate and evaporated in vacuo to give the title compound (3 g). (ES): $C_{13}H_{16}O_3$ requires 220; found 221 $(M+H^+)$.

Description 83

Benzyl 3-(fluoromethyl)cyclobutanecarboxylate (D83)

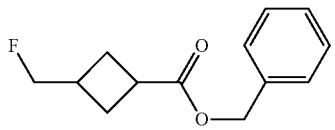 [SMILES: O=C(OCc1ccccc1)C1CC(CF)C1]

To a solution of benzyl 3-(hydroxymethyl)cyclobutanecarboxylate (D82) (1 g, 4.54 mmol) in DCM (20 mL) stirred under nitrogen at −70° C. was added DAST (1.2 mL, 9.08 mmol) dropwise over 5 mins. and the reaction mixture was stirred at rt for 12 hr. Water was added and the mixture was extracted. The organic extracts were washed with brine, dried over $Na_2SO_4$, flitered and concentrated. The residue was purified by chromatography (PE:EA=20:1) to give the title compound (210 mg). MS (ES): $C_{13}H_{15}FO_2$ requires 222; found 203 $(M-19^-)$.

Description 84

3-(fluoromethyl)cyclobutanecarboxylic acid (D84)

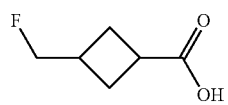

To a solution of benzyl 3-(fluoromethyl)cyclobutanecarboxylate (D80) (200 mg, 0.900 mmol) in methanol (10 mL) stirred at rt was added nickel(II) chloride, $6H_2O$ (642 mg, 2.70 mmol) and $NaBH_4$ (306 mg, 8.10 mmol) and the reaction mixture was stirred at rt for 20 min. Water was added and the pH was adjusted to pH=2 with HCl. The mixture was extracted with ethyl acetate, dried over $Na_2SO_4$, filtered and concentrated to afford the title compound (100 mg).

Description 85

Methyl 3-oxocyclobutanecarboxylate (D85)

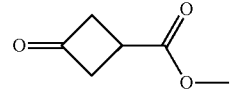

To a solution of 3-oxocyclobutanecarboxylic acid (16 g, 140 mmol), methanol (4.94 g, 154 mmol) and N1-((ethylimino)methylene)-N3,N3-dimethylpropane-1,3-diamine hydrochloride (40.3 g, 210 mmol) in DCM (200 mL) stirred under nitrogen at 0° C. was added N,N-dimethylpyridin-4-amine (1.713 g, 14.02 mmol) slowly, and the reaction mixture was stirred at RT for 15 hr. The organic phase was washed with water 50 mL, extracted with DCM (50 ml×3). The organic phase was washed with 0.5 M HCl, saturated sodium bicarbonate solution and brine, dried over sodium sulphate and evaporated in vacuo to give the title compound as a colorless oil. δH (CDCL3-$d_1$, 400 MHz): 3.28 (m, 3H), 3.43 (m, 2H), 3.74 (s, 3H).

Description 86

Methyl 3-hydroxycyclobutanecarboxylate (D86)

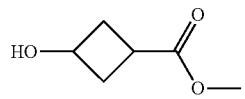

To a solution of methyl 3-oxocyclobutanecarboxylate D85 (7 g, 54.6 mmol) in methanol (100 mL) stirred under nitrogen at 0° C. was added sodium tetrahydroborate (2.480 g, 65.6 mmol) slowly and the reaction mixture was stirred at 0° C. for 4 hr. The organic phase was washed with saturated $NH_4Cl$ (100 mL), extracted with DCM (50 ml×3), and the combined organic phase was washed with sat. sodium bicarbonate solution (50 mL) and brine (50 mL), dried over sodium sulphate and evaporated in vacuo to give the title compound as a colorless oil. δH (CDCL3-$d_1$, 400 MHz): 2.13 (m, 2H), 2.54 (m, 4H), 3.62 (s, 3H), 4.13 (m, 1H).

Description 87

Methyl 3-methoxycyclobutanecarboxylate (D87)

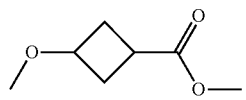

To a solution of methyl 3-hydroxycyclobutanecarboxylate (1.2 g, 9.22 mmol) and N1,N1,N8,N8-tetramethylnaphthalene-1,8-diamine (7.90 g, 36 9 mmol) in DCM (20 mL) stirred under nitrogen at 0° C. was added trimethyloxonium tetrafluoroborate (2.73 g, 18.44 mmol) and the reaction mixture was stirred at RT for 4 hr. The reaction mixture was quenched with water and extracted with DCM (5 ml×3). The combined organic phases were washed with 1N HCl (10 ml×3), saturated sodium bicarbonate solution 10 mL and saturated sodium bicarbonate solution (10 mL), dried over sodium sulphate and evaporated in vacuo to give the title compound as a colorless oil. δH (CDCL3-d$_1$, 400 MHz): 2.18 (m, 2H), 2.50 (m, 2H), 2.63 (m, 1H), 3.23 (s, 3H), 3.68 (s, 3H), 3.80 (m, 1H).

Description 88

3-methoxycyclobutanecarboxylic acid (D88)

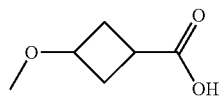

To a solution of methyl 3-methoxycyclobutanecarboxylate (860 mg, 5 97 mmol) in THF (6 mL), methanol (2 mL) and water (6 mL) stirred under nitrogen at rt was added LiOH (214 mg, 8.95 mmol) and the reaction mixture was stirred at RT for 2 hr. The solvent was removed and the residue was treated with conc. HCl to pH 1, extracted with DCM (5 ml×3), and the combined organic phase was washed with saturated brine 10 mL, dried over sodium sulphate and evaporated in vacuo to give the title compound (400 mg). δH (CDCL3-d$_1$, 400 MHz): 2.23 (m, 2H), 2.52 (m, 2H), 2.68 (m, 1H), 3.23 (s , 3H), 3.81 (m, 1H).

Description 89

Bicyclo[3.1.0]hexane-6-carboxylic acid ethyl ester (D89)

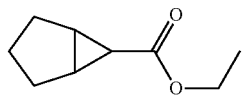

To a suspension of cyclopentene (3.4 g, 49.9 mmol) and rhodium(II) acetate dimer (0.044 g, 0.100 mmol) stirred under nitrogen at rt was added ethyl 2-diazoacetate (5.70 g, 49.9 mmol) dropwise over 2 hr and the reaction mixture was stirred at rt for 16 hr. The reaction mixture was diluted with DCM (100 ml), filtered, the filtrated was concentrated to give the title compound.

Description 90

Bicyclo[3.1.0]hexane-6-carboxylic acid (D90)

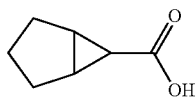

To a suspension of crude ethyl bicyclo[3.1.0]hexane-6-carboxylate (D89) (5 g, 32.4 mmol) in methanol (30 mL) stirred in air at rt was added NaOH (3.89 g, 97 mmol) in water in one portion and the reaction mixture was stirred at rt for 3 hr. The resulting mixture was concentrated and treated with water (30 ml). The aqueous phase was washed with DCM (50 ml) and then brought to pH=3 with HCl solution. The product was then extracted with DCM (50 ml×2) and the combined organic layers were dried, concentrated to give the title compound (1.5 g). $^1$H NMR (400 MHz, DMSO) δ: 1.85 (m, 6H), 1.62 (m, 1H), 1.39 (t, J=3.2 Hz, 1H), 1.10 (m, 1H).

Description 91

Cyclobutane-1,1-diyldimethanol (D91)

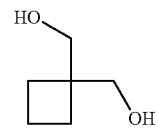

To a suspension of aluminum (III) lithium hydride (5.7 g, 150 mmol) in dry THF (300 ml) at ca. −5° was added dropwise a solution of diethyl cyclobutane-1,1-dicarboxylate (10 g, 49.9 mmol) in dry THF (100 ml) and the mixture was stirred at rt overnight. The reaction was quenched with sat. Na$_2$SO$_4$, filtered through Celite and evaporated, the residue was purified by column chromatography (PE: EtOAc=1:1) to afford the title compound (4 g) as oil.

Description 92

Cyclobutane-1, 1-diylbis(methylene)bis (4-methylbenzenesulfonate) (D92)

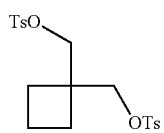

Cyclobutane-1,1-diyldimethanol (D91) (2 g, 17.22 mmol) in pyridine (10 ml) was added to a cooled) (−5°) solution of 4-methylbenzene-1-sulfonyl chloride (10 g, 52.5 mmol) in pyridine (10 ml). The mixture was stirred for 3hr (<0°) and then poured into ice-water and filtered. The filtered cake was washed with water (50 ml), 5% H$_2$SO$_4$ (50 ml), 5% Na$_2$CO$_3$ (100 ml), again with water (50 ml) and finally with aqueous acetone (50 ml×2). The resulting pale solid was dissolved in DCM (100 ml) and dried over anhydrous Na$_2$SO$_4$, filtered and evaporated to give a residue that was dried under vacuum at 50-6° C. for 5 hr to give the title compound (12 g) as a white solid.

Description 93

Diethyl spiro[3.3]heptane-2,2-dicarboxylate (D93)

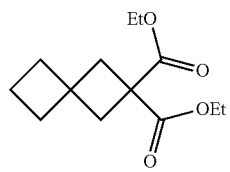 [SMILES: CCOC(=O)C1(C(=O)OCC)CC2(CCC2)C1]

To a solution of cyclobutane-1,1-diylbis (methylene) bis (4-methylbenzenesulfonate) (D90) (6 g, 14.13 mmol) and diethyl malonate (9 g, 56.2 mmol) in driedp-xylene (35 mL) was added sodium (0.75 g, 32.6 mmol) and the mixture was heated to 140° and stirred overnight. After cooled to rt, the mixture was quenched with saturated NH$_4$Cl (100 ml). Ether (50 ml) was added and filtered to remove sodium p-methylbenzene-sulfonate salt and the filtered cake was washed with ether (50 ml). The aqueous layer was extracted with ether (50 ml×2). The combined organic layers were washed with brine (100 ml), dried over anhydrous Na$_2$SO$_4$, filtered and evaporated to leave the crude product, which was distilled under reduced pressure (1 mmHg, 85° C.-95° C.) to give the title compound as colorless oil.

Description 94

Spiro[3.3]heptane-2,2-dicarboxylic acid (D94)

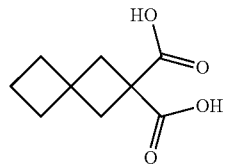 [SMILES: O=C(O)C1(C(=O)O)CC2(CCC2)C1]

To a solution of diethyl spiro[3.3]heptane-2,2-dicarboxylate (D93) (1.134 g, 4.72 mmol) in anhydrous ethanol (20 mL) was added potassium hydroxide (1.18 g, 21.03 mmol) and the mixture was heated to reflux for 1hr. On cooling to rt, the mixture was filtered and the cake was washed with EtOH (20 ml). The cake was dissolved in water (2 ml) and cooled to ca. −5° C. and 50% aqueous H$_2$SO$_4$ (3 ml) was added dropwise. The resulting white precipitate was filtered to give the title compound (600 mg) as white solid.

Description 95

Spiro[3.3]heptane-2-carboxylic acid (D95)

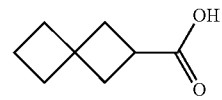

Spiro[3.3]heptane-2,2-dicarboxylic acid (D94) (590 mg, 3.20 mmol) was dissolved in pyridine (25 mL) and the resulting solution was refluxed for 5 hr. On cooling to RT, the reaction mixture was concentrated to dryness and to the residue was added 6N HCl solution with ice cooling and stirring. The mixture was concentrated to remove HCl gas at RT. The residue was extracted with ether (20 ml) and the organic layer was washed with water (30 ml) and dried over anhydrous MgSO$_4$. The mixture was filtered and the filtrate was concentrated to give a residue which was purified by column chromatography (PE: EtOAc=4:1) to afford the title compound (480 mg) as a yellow oil. $^1$H NMR Spectrum (DMSO-d6) δ(ppm): 1.74(2H, m), 1.86 (2H, m), 1.98(2H, m), 2.08(2H, m), 2.13(2H, m), 2.87(1H, m), 11.94(1H, br).

Description 96

Cyclopentanecarboxylic acid ethyl ester (D96)

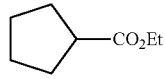

A solution of cyclopentanecarboxylic acid (50 g, 438 mmol), ethanol (1614 g, 35087 mmol) and sulfuric acid (859 g, 8761 mmol) was stirred at 120° C. for 10 hr. The mixture was poured into water (2 L). The upper layer was collected, then distilled at 125° C. to give the title compound as colourless oil (34.0 g). $^1$H-NMR (400 MHz, CDCl$_3$) δ ppm 1.22-1.25(t, 3H), 1.25-1.87 (m, 8H), 2.67-1.71(m,1H), 4.08-4.14 (q, 2H).

Description 97

1-Fluoro-cyclopentanecarboxylic acid ethyl ester (D97)

To a solution of diisopropylamine (17.08 g, 169 mmol) in THF (300 ml) was added n-BuLi (62 mL, 155 mmol) at −60° C. The reaction mixture was stirred for 1 hr and ethyl cyclopentanecarboxylate (D93) (20 g, 141 mmol) was added. The reaction was stirred for 2 hr, then added to a soluion of N-fluoro-N-(phenylsulfonyl)benzenesulfonamide (53.2 g, 169 mmol) in THF (300 mL). The reaction mixture was stirred at −60° C. overnight. The solvent was concentrated, and extracted with DCM (3×80 mL). The organic extracts were concentrated and distillled under reduced pressure to give the title compound (14.0 g). $^1$H-NMR (400 MHz, CDCl$_3$) δ ppm 1.29-1.33 (t, 3H), 1.72-2.22 (m, 8H), 4.24-4.26 (q,2H).

Description 98

1-Fluoro-cyclopentanecarboxylic acid (D98)

A suspension of ethyl 1-fluorocyclopentanecarboxylate (D97) (4 g, 24.97 mmol) and lithium hydroxide (0.598 g, 24.97 mmol) in THF (50 mL) and water (50 mL) was stirred at 80° C. for 6 hr. The solvent was concentrated, and acidified to pH=6, then extracted with DCM (3×40 mL). The organic layer was dried over Na$_2$SO$_4$, and concentrated to give the title compound (2.0 g). $^1$H-NMR (400 MHz, CDCl$_3$) δ ppm 1.82-1.93 (m, 4H), 2.11-2.23 (m,4H).

Description 99

Methyl 3-(methoxymethyl)benzoate (D99)

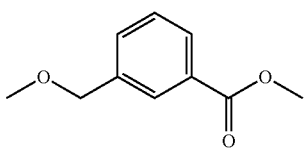

To a solution of sodium methoxide (0.731 g, 13.53 mmol) in anhydrous MeOH (10 ml), an anhydrous MeOH solution (10 ml) of methyl 3-(bromomethyl)benzoate (2 g, 8.73 mmol) was added dropwise under N$_2$. After addition, the reaction mixture was heated at 60° C. for 2 hr. When LCMS indicated that the reaction was completed, the reaction mixture was cooled down to rt and the solvent was evaporated. The residue was suspended in DCM (20 ml), poured into 1 M HCl (20 ml) and stirred vigorously. The organic layer was separated and the solvent evaporated to give a crude product, which was purified by column chromatography (24 g column, petro ether/EtOAc, 5%-40% EtOAc, 30 min) to give the title compound as pale yellow oil. $^1$H NMR showed some solvent. $C_{10}H_{12}O_3$ 180.2 found 181.1.

Description 100

3-(methoxymethyl)benzoic acid (D100)

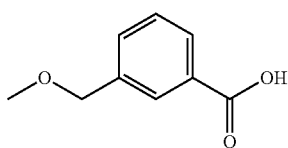

To a solution of methyl 3-(methoxymethyl)benzoate (D99) (1.2 g, 6.66 mmol) in THF (10 mL), sodium hydroxide (0.666 g, 16.65 mmol) aqueous solution (10 mL) was added and the reaction mixture was heated for 3 hr at 50° C. LCMS showed the reaction completed. The mixture was cooled down to rt, most of the solvent was evaporated and water (15 ml) was added. The mixture was washed with DCM (5 ml) and the aqueous layer was acidified with 3M HCl to pH=1. The aqueous layer was extracted with EtOAc (20 ml×2), dried over $Na_2SO_4$ and the solvent was evaporated. The residue was dried under vacuum for 1 hr, to give the title compound (965 mg) as white solid. $C_9H_{10}O_3$ 166.2 found 167.1.

Description 101

(S)-N-(3-(((S)-4-(cyclopentanecarbonyl)-3-methyl-piperazin-1-yl)methyl)-5-fluoro-2-methylphenyl) pyrrolidine-3-carboxamide (D101)

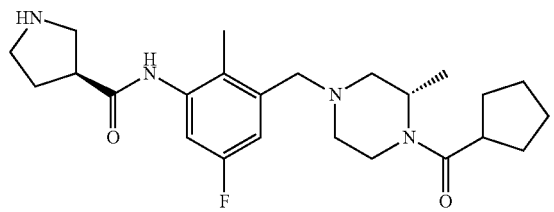 [SMILES: Cc1c(CN2CCN(C(=O)C3CCCC3)[C@@H](C)C2)cc(F)cc1NC(=O)[C@H]1CCNC1]

A mixture of (S)-(4-(3-amino-5-fluoro-2-methylbenzyl)-2-methylpiperazin-1-yl)(cyclopentyl)methanone (D31) (200 mg, 0.6 mmol), HATU (251 mg, 0 66 mmol), (S)-1-(tert-butoxycarbonyl)pyrrolidine-3-carboxylic acid (142 mg, 0.66 mmol) and DIPEA (233 mg, 1.799 mmol) in DCM (3 mL) was stirred at RT for 80 hr. TFA (0.924 mL, 12 mmol) was added and the mixture was heated at 40° C. for 3 hr. The reaction mixture was concentrated in vacuo and the residue dissolved in EA, washed with aqueous NaHCO3 and brine. The organic phase was separated, dried over Na2SO4, filtered and the solvent evaporated to give the title compound (250 mg). $C_{24}H_{35}FN_4O_2 \cdot C_2HF_3O_2$ 430 found 431.

Description 102

(R)-N-(3-(((S)-4-(cyclopentanecarbonyl)-3-methyl-piperazin-1-yl)methyl)-5-fluoro-2-methylphenyl) pyrrolidine-2-carboxamide (D102)

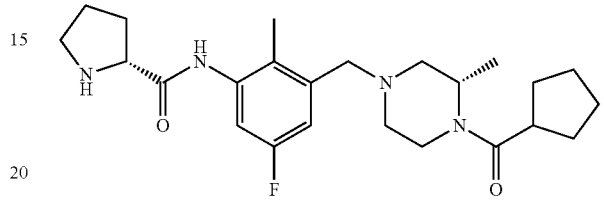

To a solution of (S)-(4-(3-amino-5-fluoro-2-methylbenzyl)-2-methylpiperazin-1-yl)(cyclopentyl)methanone (D31) (200 mg, 0.510 mmol), (R)-1-(tert-butoxycarbonyl)pyrrolidine-2-carboxylic acid (110 mg, 0.510 mmol) and HATU (194 mg, 0.510 mmol) in DCM (3 mL) was added DIEA (0.134 mL, 0.765 mmol) and the mixture was stirred at rt for overnight. LCMS indicated the reaction was completed. The mixture was evaporated and the residue was dissolved in methanol (6 mL) and purified by MDAP to give the title compound (11 mg) as a white solid. $C_{24}H_{35}FN_4O_2 \cdot C_2HF_3O_2$ 430 found 431.

Description 103

(S)-tert-butyl 4-(5-chloro-2-methyl-3-nitrobenzyl)-2-methylpiperazine-1-carboxylate (D103)

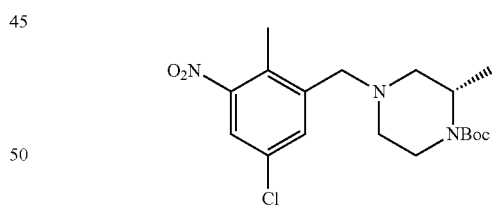

Sodium triacetoxyborohydride (5.73 g, 27.1 mmol) was added to a mixture of 5-chloro-2-methyl-3-nitrobenzaldehyde (D11) (2.7 g, 13.53 mmol), (S)-tert-butyl 2-methyl piperazine-1-carboxylate (2.84 g, 14.20 mmol), AcOH (0.387 mL, 6.76 mmol) in DCM (300 mL). After the reaction was completed, Sat. NaHCO$_3$ aqueous solution was added to the reaction mixture carefully with stirring until the pH reached around pH8 (no gas released). The organic phase was separated, concentrated and purified by column chromatography (10% EA in PE) to give the title compound as

Description 104

(S)-tert-butyl 4-(3-amino-5-chloro-2-methylbenzyl)-2-methylpiperazine-1-carboxylate (D104)

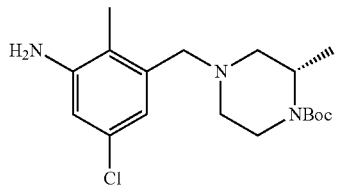 [SMILES: Cc1c(CN2CCN(C(=O)OC(C)(C)C)[C@@H](C)C2)cc(Cl)cc1[N+](=O)[O-]]

Iron (7.54 g, 135 mmol) was added in to a solution of (S)-tert-butyl 4-(5-chloro-2-methyl-3-nitrobenzyl)-2-methylpiperazine-1-carboxylate (3.7 g, 9.64 mmol) in acetic acid (20 mL) at 0° C. and stirred at this temperature for 5 min and then at rt for 3 hr. After the reaction was complete, the reaction mixture was concentrated to remove most of the solvent. The residue was taken up in DCM (100 ml) and the mixture was filtered through celite. The filterate was concentrated and the pH adjusted to about 8 by sat. NaHCO3. The mixture was extracted with DCM (30 ml×3), the organic layer was dried via Na2SO4, filtered and the filtrate was concentrated to give the title compound as brown oil. MS (ES): C, 18; H, 28; Cl, N, 3; O, 2; requires 353, found 354 (M+H$^+$).

Description 105

(S)-tert-butyl-4-(5-chloro-2-methyl-3-(6-methylnicotinamido)benzyl)-2-methylpiperazine-1-carboxylate (D105)

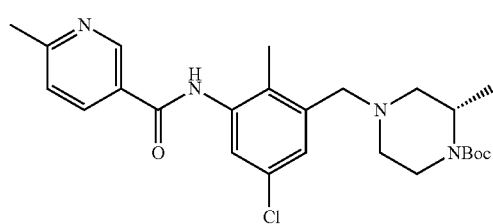

6-Methylnicotinoyl chloride (0.933 g, 4.20 mmol) was added into a solution of (S)-tert-butyl 4-(3-amino-5-chloro-2-methylbenzyl)-2-methylpiperazine-1-carboxylate (D104) (1.35 g, 3.81 mmol) in pyridine (6 mL) at RT. After the reaction was completed, the mixture was concentrated to remove most of solvent and the residue was purified via column chromatography (15% MeOH in DCM) to give the title compound (1.86 g) as brown oil. MS (ES): C, 25; H, 33; Cl, N, 4; O, 3; requires 473, found 473 (M+H$^+$).

Description 106

(S)-N-(5-chloro-2-methyl-3-((3-methylpiperazin-1-yl)methyl)phenyl)-6-methylnicotinamide (D106)

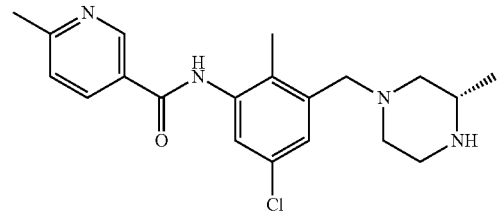

TFA (3.03 mL, 39.3 mmol) was added to a solution of (S)-tert-butyl 4-(5-chloro-2-methyl -3-(6-methylnicotinamido)benzyl)-2-methylpiperazine-1-carboxylate (D105) (1.86 g, 3.93 mmol) in DCM (10 mL) at rt. The reaction mixture was heated to 40° C. and stirred until the reaction was complete. The mixture was concentrated to remove most of solvent and the residue was purified by column chromatography (15% MeOH in DCM) to give the title compound (1.7 g) as brown oil. MS (ES): C, 20; H, 25; Cl, N, 4; O, requires 372, found 373(M+H$^+$).

Description 107

(S)-tert-butyl 4-(5-chloro-2-methyl-3-(2-methylpyrimidine-5-carboxamido)benzyl)-2-methylpiperazine-1-carboxylate (D107)

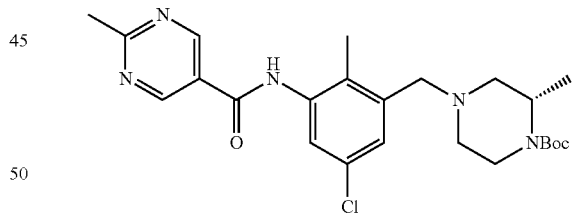

POCl3 (0.743 mL, 7.97 mmol) was added to a solution of (S)-tert-butyl 4-(3-amino-5- chloro-2-methylbenzyl)-2-methylpiperazine-1-carboxylate (D104) (1.41 g, 3.98 mmol) and 2-methylpyrimidine-5-carboxylic acid (0.550 g, 3.98 mmol) in pyridine (30 mL) at 0° C. and stirred at this temperature for 5 min. Then the reaction was stirred at rt for 3 hr. After the reaction was complete, water (2 ml) was added in batches with stirring for 2 min. The mixture was concentrated and purified by column chromatography (50% MeOH in DCM) to give the title compound (1.3 g) as brown oil. MS (ES): C, 24; H, 32; Cl, N, 5; O, 3; requires 473, found 474(M+H⁺).

Description 108

(S)-N-(5-chloro-2-methyl-3-((3-methylpiperazin-1-yl)methyl)phenyl)-2-methylpyrimidine-5-carboxamide (D108)

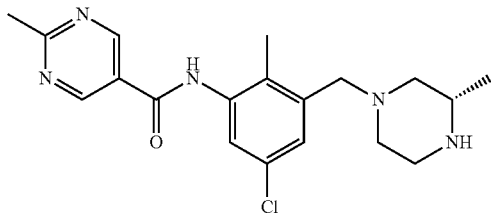

TFA (2.113 mL, 27.4 mmol) was added to a solution of (5)-tert-butyl 4-(5-chloro-2-methyl-3-(2-methylpyrimidine-5-carboxamido)benzyl)-2-methylpiperazine-1-carboxylate (D107) (1.3 g, 2.74 mmol) in DCM (50 mL) and the reaction was heated to 45° C. for 4 hr. When the reaction was complete, the mixture was concentrated, adjusted the pH8 with sat. aqueous NaHCO3 and the layers were separated. The organic layer was concentrated and purified via column chromatography (50% MeOH in DCM) to give the title compound (860 mg) as a brown oil. MS (ES): C, 19; H, 24; Cl, N, 5; O, requires 373, found 374(M+H⁺).

Example 1

3-chloro-N-(2-chloro-3-{[(3R,5S)-4-(cyclopentylcarbonyl)-3,5-dimethyl-1-piperazinyl]methyl}phenyl)benzamide, trifluoroacetic acid salt (E1)

2-chloro-3-{[(3R,5S)-4-(cyclopentylcarbonyl)-3,5-dimethyl-1-piperazinyl]methyl}aniline (60 mg, 0.171 mmol) and pyridine (0.028 mL, 0.343 mmol) were dissolved in DCM (15 mL), to this solution, 3-chlorobenzoyl chloride (36.0 mg, 0.206 mmol) was added gradually. The reaction mixture was stirred at rt for 2 hr. DCM was removed. The obtained mixture was redissolved in DMF, solid was filtered off. The filtrate was purified by MDAP to give the title compound (69 mg) as a white solid. ¹H-NMR (MeOD-d₄, 400 MHz): 7.90 (s, 1H), 7.82 (d, 1H), 7.59 (d, 1H), 7.53 (d, 1H), 7.45 (m, 2H), 7.32 (t, 1H), 4.51 (brs, 1H), 4.21 (brs, 1H), 3.81 (brs, 2H), 2.93 (m, 3H), 2.41 (brs, 2H), 1.74-1.52 (m, 8H), 1.28 (m, 6H). δF (MeOD-d₄, 376 MHz): −77.1. MS (ES): $C_{26}H_{31}Cl_2N_3O_2$ requires 487; found 488(M+H⁺).

Examples 2-9

Examples 2 to 9 were prepared using a similar procedure to that described for Example 1.

E2   N-(2-chloro-3-{[(3R,5S)-4-(cyclopentylcarbonyl)-3,5-dimethyl-1-piperazinyl]methyl}phenyl)-2-(4-chlorophenyl)acetamide, trifluoroacetic acid salt E3   N-(2-chloro-3-{[(3R,5S)-4-(cyclopentylcarbonyl)-3,5-dimethyl-1-piperazinyl]methyl}phenyl)-2-ethylbutanamide, trifluoroacetic acid salt E4   N-(2-chloro-3-{[(3R,5S)-4-(cyclopentylcarbonyl)-3,5-dimethyl-1-piperazinyl]methyl}phenyl)-8-quinolinesulfonamide, trifluoroacetic acid salt E5   (S)-N-(3-((4-(cyclopentanecarbonyl)-3-methylpiperazin-1-yl)methyl)-4-fluoro-2-methylphenyl)cyclopropanecarboxamide, trifluoroacetic acid salt E6   (S)-N-(3-((4-(cyclopentanecarbonyl)-3-methylpiperazin-1-yl)methyl)-4-fluoro-2-methylphenyl)-2-phenylacetamide, trifluoroacetic acid salt E7   N-(2-chloro-3-(((3S,5R)-4-(cyclopentanecarbonyl)-3,5-dimethylpiperazin-1-yl)methyl)phenyl)isobutyramide E8   N-(2-chloro-3-(((3S,5R)-4-(cyclopentanecarbonyl)-3,5-dimethylpiperazin-1-yl)methyl)phenyl)-3-methylbutanamide E9   (S)-3-cyano-N-(2,4-dichloro-3-((4-(cyclopentanecarbonyl)-3-methylpiperazin-1-yl)methyl)phenyl)benzamide

| Example | Structure | Characterization |
|---|---|---|
| E2 | 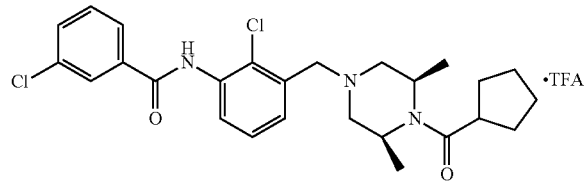 •TFA | ¹H-NMR (MeOD-d₄, 400 MHz) 7.67 (d, 1H), 7.41 (s, 1H), 7.28 (m, 5H), 4.52 (brs, 2H), 4.19 (brs, 2H), 3.68 (s, 2H), 3.15 (brs, 2H), 2.90 (m, 3H), 1.77--1.52 (m, 8H), 1.29 (s, 6H) δF (MeOD-d₄, 376 MHz): −77.4. MS (ES): $C_{27}H_{33}Cl_2N_3O_2$ requires 501; found 502(M + H⁺) |

-continued

| Example | Structure | Characterization |
|---|---|---|
| E3 | 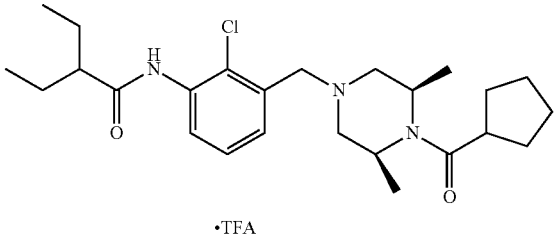 [SMILES: CCC(CC)C(=O)Nc1cccc(CN2C[C@@H](C)N(C(=O)C3CCCC3)[C@@H](C)C2)c1Cl] •TFA | ¹H-NMR (MeOD-d₄, 400 MHz): 7.46 (d, 1H), 7.33 (d, 1H), 7.21 (t, 1H), 4.42 (s, 1H), 4.10 (s, 1H), 3.54 (s, 2H), 2.93 (m, 1H), 2.67 (m, 2H), 2.27 (m, 1H), 2.17--2.10 (m, 2H), 1.84--1.46 (m, 12H), 1.30 (s, 3H), 1.18 (s, 3H), 0.91 (t, 6H). δF (MeOD-d₄, 376 MHz): −77.3, MS (ES): $C_{25}H_{38}ClN_3O_2$ requires 447; found 448(M + H⁺) |
| E4 | 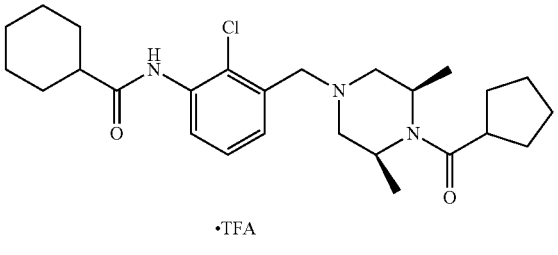 [SMILES: C[C@@H]1CN(Cc2cccc(NC(=O)C3CCCCC3)c2Cl)C[C@H](C)N1C(=O)C1CCCC1] •TFA | ¹H-NMR (MeOD-d₄, 600 MHz): 7.51 (d, 1H), 7.30 (d, 1H), 7.19 (t, 1H), 4.42 (s, 1H), 4.09 (s, 1H), 3.53 (s, 2H), 2.92 (m, 1H), 2.62 (m, 2H), 2.40 (t, 1H), 2.13 (m, 2H), 1.86--1.33 (m, 15H), 1.30--1.17 (m, 9H). δF (MeOD-d₄, 376 MHz): −77.4. MS (ES): $C_{26}H_{38}ClN_3O_2$ requires 459; found 460(M + H⁺). |
| E5 | 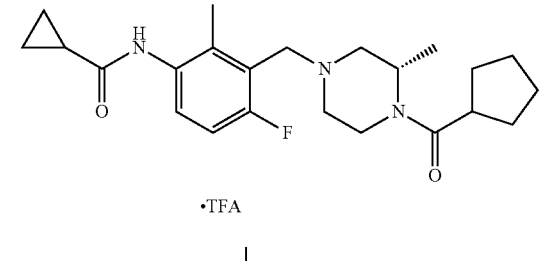 •TFA | ¹H-NMR (MeOD-d₄, 600 MHz): 0.80 (m, 2 H), 0.85 (m, 2 H), 1.18 (br. s., 2 H), 1.30 (br. s., 1 H), 1.54 (m, 3 H), 1.61 (br. s., 3 H), 1.75 (m, 4 H), 2.23 (m, 3 H), 2.94 (m, 2 H), 3.04 (m, 1 H), 3.35 (m, 3 H), 4.02 (br. s., 1 H), 4.26 (br. s., 2 H), 4.50 (br. s., 1 H), 4.85 (br. s., 1 H), 7.02 (t, 1 H), 7.30 (dd, 1 H). δF (MeOD-d₄, 376 MHz): −77.0, −115.3, −122.6. MS (ES): $C_{23}H_{32}FN_3O_2$ requires 401; found 402(M + H⁺). |
| E6 | 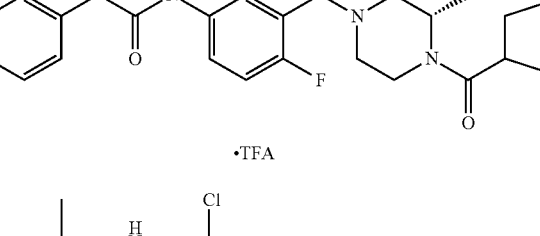 •TFA | ¹H-NMR (MeOD-d₄, 400 MHz): 1.27 (m, 3 H), 1.68 (m, 5 H), 1.84 (m, 3 H), 2.24 (s, 3 H), 3.07 (m, 3 H), 3.40 (t, 2 H), 3.49 (m, 1 H), 3.60 (s, 1 H), 3.74 (s, 2 H), 4.12 (br. s., 0.5 H), 4.36 (br. s., 0.5 H), 4.59 (br. s., 2 H), 7.13 (t, 1 H), 7.26 (m, 2 H), 7.38 (m, 5 H). δF (MeOD-d₄, 376 MHz): −76.9, −114.5, −114.6. MS (ES): $C_{27}H_{34}FN_3O_2$ requires 451; found 452(M + H⁺). |
| E7 | 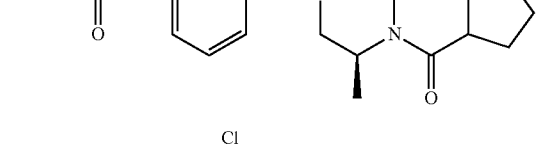 | HNMR (CDCl₃, 400 MHz): 1.26-1.33 (12H, m), 1.66-2.88 (14H, m), 3.57 (2H, s), 4.05-4.06 (1H, m), 4.62-4.63 (1H, m), 7.23-7.27 (1H, m), 7.83-7.84 (1H, m), 8.31-8.33 (1H, m). MS (ES): $C_{23}H_{34}ClN_3O_2$ requires 419; found 420(M + H⁺). |
| E8 | 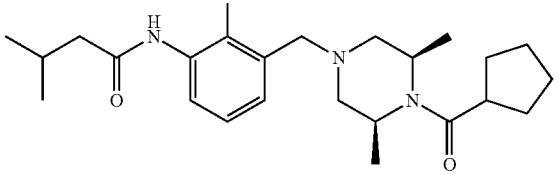 | HNMR (CDCl₃, 400 MHz): 1.20-1.97 (11H, m), 2.11-2.38 (7H, m), 3.66 (2H, s), 3.77 (2H, s), 4.19-4.22 (1H, m), 7.29-7.60 (7H, m), 9.74 (1H, s). MS (ES): $C_{24}H_{34}ClN_3O_2$ requires 433; found 434(M + H⁺). |
| E9 | 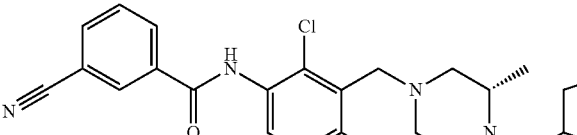 | ¹H-NMR (MeOD-d₄, 400 MHz): 0.49 (m, 5 H), 0.83 (br. s., 3 H), 0.91 (br. s., 4 H), 1.04 (br. s., 3 H), 2.23 (br. s., 3 H), 3.58 (br. s., 3 H), 6.79 (d, 1 H), 6.96 (m, 2 H), 7.18 (d, 1 H), 7.46 (d, 1 H), 7.52 (s, 1 H). δF (MeOD-d₄, 376 MHz): −77.0. MS (ES): $C_{28}H_{28}Cl_2N_4O_2$ requires 498; found 499(M + H⁺). |

Examples 10

(S)-N-(3-((4-(cyclopentanecarbonyl)-3-methylpiperazin-1-yl)methyl)-5-fluoro-2-methylphenyl)cyclopentanecarboxamide, trifluoroacetic acid salt

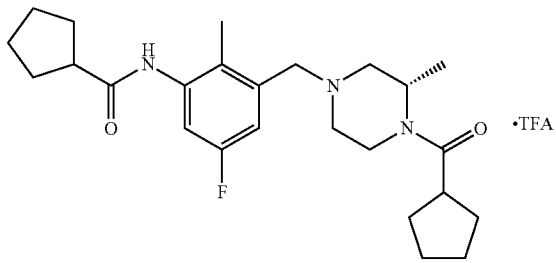 [SMILES: Cc1c(CN2CCN(C(=O)C3CCCC3)[C@@H](C)C2)cc(F)cc1NC(=O)C1CCCC1]

Cyclopentanecarbonyl chloride (38.2 mg, 0.288 mmol) was added into a solution of (S)-(4-(3-amino-5-fluoro-2-methylbenzyl)-2-methylpiperazin-1-yl)(cyclopentyl)methanone (80 mg, 0.240 mmol) and pyridine (38.0 mg, 0.480 mmol) in DCM at RT. The reaction was stirred at RT overnight. After checked by LCMS, the reaction was completed. The mixture was concentrated and purified via MDAP to afford the title compound (43 mg, 31.3% yield) as white solid. $^1$H NMR (400 MHz, MeOD-d$_4$) δ 1.16-1.42 (m, 4H), 1.55-2.09 (m, 18H), 2.12-2.20 (m, 1H), 2.22 (s, 3H), 2.72 (t, 1H), 2.78-3.08 (m, 3H), 3.34-3.41 (m, 1H), 3.41-3.53 (m, 2H), 3.83 (d, 0.5H), 4.19-4.39 (m, 1H), 4.66 (brs, 0.5H), 6.97 (d, 1H), 7.05 (d, 1H). $^{19}$F NMR (376 MHz, MeOD-d$_4$) δ −78.6, −119.0. MS (ESI): $C_{25}H_{36}FN_3O_2$ requires: 429, found 430 (M+H$^+$).

Examples 11-14

Examples 11 to 14 were prepared using a similar procedure to that described for Example 10.

E11: (S)-N-(3-((4-(cyclopentanecarbonyl)-3-methylpiperazin-1-yl)methyl)-5-fluoro-2-methylphenyl)cyclohexanecarboxamide, trifluoroacetic acid salt E12: (S)-N-(3-((4-(cyclopentanecarbonyl)-3-methylpiperazin-1-yl)methyl)-5-fluoro-2-methylphenyl)-6-(trifluoromethyl)nicotinamide, trifluoroacetic acid salt E13: (S)-N-(3-((4-(cyclopentanecarbonyl)-3-methylpiperazin-1-yl)methyl)-5-fluoro-2-methylphenyl)-2,6-difluorobenzamide, trifluoroacetic acid salt E14: (S)-N-(3-((4-(cyclopentanecarbonyl)-3-methylpiperazin-1-yl)methyl)-5-fluoro-2-methylphenyl)-2,6-dimethylbenzamide, trifluoroacetic acid salt

| Example | Structure | Characterization |
|---|---|---|
| E11 | 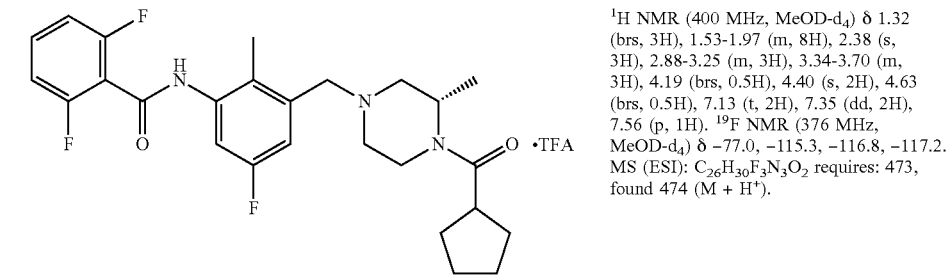 | $^1$H NMR (400 MHz, MeOD-d$_4$) δ 1.10-1.35 (m, 6H), 1.38-1.90 (m, 16H), 2.15 (s, 3H), 2.28-2.45 (m, 1H), 2.87-3.12 (m, 4H), 3.30-3.48 (m, 1H), 3.85-4.28 (m, 3H), 4.43 (brs, 1H), 7.07 (brs, 2H). $^{19}$F NMR (376 MHz, MeOD-d$_4$) δ −76.9, −119.7. MS (ESI): $C_{26}H_{38}FN_3O_2$ requires: 443, found 444 (M + H$^+$). |
| E12 | 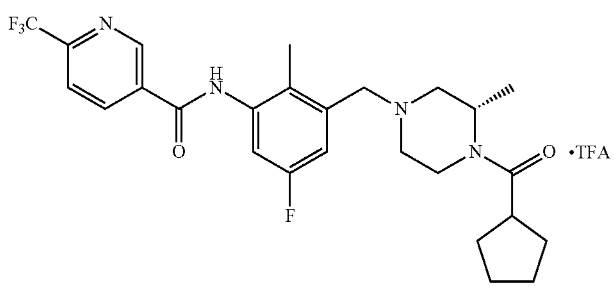 [SMILES: Cc1c(CN2CCN(C(=O)C3CCCC3)[C@@H](C)C2)cc(F)cc1NC(=O)c1ccc(C(F)(F)F)nc1] | $^1$H NMR (400 MHz, MeOD-d$_4$) δ 1.19-1.52 (m, 3H), 1.54-2.01 (m, 8H), 2.36 (s, 3H), 2.88-3.27 (m, 3H), 3.36-3.69 (m, 3H), 4.10-4.31 (m, 1H), 4.42 (s, 2H), 4.65 (brs, 1H), 7.31-7.45 (m, 2H), 8.01 (d, 1H), 8.58 (d, 1H), 9.26 (s, 1H). $^{19}$F NMR (376 MHz, MeOD-d$_4$) δ −69.6, −77.1, −116.9. MS (ESI): $C_{26}H_{30}F_4N_4O_2$ requires: 506, found 507 (M + H$^+$). |
| E13 | 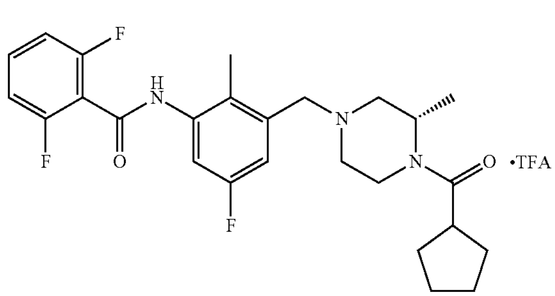 [SMILES: Cc1c(CN2CCN(C(=O)C3CCCC3)[C@@H](C)C2)cc(F)cc1NC(=O)c1c(F)cccc1F] | $^1$H NMR (400 MHz, MeOD-d$_4$) δ 1.32 (brs, 3H), 1.53-1.97 (m, 8H), 2.38 (s, 3H), 2.88-3.25 (m, 3H), 3.34-3.70 (m, 3H), 4.19 (brs, 0.5H), 4.40 (s, 2H), 4.63 (brs, 0.5H), 7.13 (t, 2H), 7.35 (dd, 2H), 7.56 (p, 1H). $^{19}$F NMR (376 MHz, MeOD-d$_4$) δ −77.0, −115.3, −116.8, −117.2. MS (ESI): $C_{26}H_{30}F_3N_3O_2$ requires: 473, found 474 (M + H$^+$). |

| Example | Structure | Characterization |
|---|---|---|
| E14 | 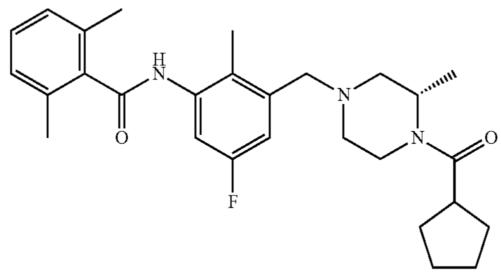 | $^1$H NMR (400 MHz, MeOD-d$_4$) δ 1.13-1.49 (m, 3H), 1.50-1.96 (m, 8H), 2.36 (s, 3H), 2.44 (s, 6H), 2.49-3.18 (m, 5H), 3.36-3.55 (m, 1H), 3.62-4.08 (m, 3H), 4.42 (brs, 1H), 7.09-7.20 (m, 3H), 7.20-7.33 (m, 2H). $^{19}$F NMR (376 MHz, MeOD-d$_4$) δ −77.0, −118.7. MS (ESI): C$_{28}$H$_{36}$FN$_3$O$_2$ requires: 465, found 466 (M + H$^+$). |

Example 15

(S)-N-(2-chloro-3-((4-(cyclopentanecarbonyl)-3-methylpiperazin-1-yl)methyl)phenyl)-3-cyanobenzamide (E15)

Example 16

(S)-N-(3-((4-(cyclopentanecarbonyl)-3-methylpiperazin-1-yl)methyl)-5-fluoro-2-methylphenyl)-6-methylnicotinamide, trifluoroacetic acid salt (E16)

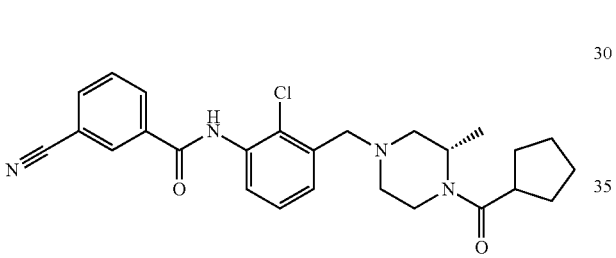

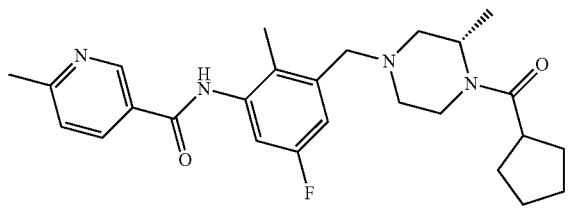

To the solution of (S)-(4-(3-amino-2-chlorobenzyl)-2-methylpiperazin-1-yl)(cyclopentyl)methanone (100 mg, 0.298 mmol) in acetonitrile (5 mL) was added the solution of 3-cyanobenzoyl chloride (54.2 mg, 0.328 mmol) at RT. After the addtion, Na2CO3 (63.1 mg, 0.595 mmol) was added. The resulted reaction mixture was stirred overnight. Then the solid was filtered off and the filtrate was purified by MDAP to afford the title compound (27 mg). $^1$H-NMR (DCM-d$_2$, 400 MHz): 1.69 (d, 2 H), 1.82 (d, 1 H), 2.04 (br. s., 2 H), 2.13 (br. s., 3 H), 2.24 (m, 2 H), 2.34 (br. s., 1 H), 2.56 (br. s., 1 H), 2.66 (d, 1 H), 3.22 (m, 1 H), 3.33 (d, 1 H), 3.44 (d, 1 H), 3.74 (br. s., 3 H), 3.84 (br. s., 1 H), 4.10 (m, 2 H), 4.29 (d, 1 H), 4.76 (m, 1 H), 5.10 (br. s., 1 H), 7.81 (t, 1 H), 7.93 (d, 1 H), 8.08 (d, 1 H), 8.17 (t, 1 H), 8.40 (d, 1 H), 8.70 (d, 1 H), 8.76 (s, 1 H). MS (ES): C$_{26}$H$_{29}$ClN$_4$O$_2$ requires 464; found 465(M+H$^+$).

To the solution of 6-methylnicotinic acid (99 mg, 0.720 mmol) and one drop of DMF in DCM (5 mL) was added oxalyl chloride (0.105 mL, 1.2 mmol) dropwise. After the addtion, the resulted mixture was stirred for another 1 hr and then the solvent was removed in vacuo. Then (S)-(4-(3-amino-5-fluoro-2-methylbenzyl)-2-methylpiperazin-1-yl)(cyclopentyl)methanone (200 mg, 0.6 mmol) and the acyl chloride was dissolved in DCM (3 mL). DIPEA (0.105 mL, 0.6 mmol) was added to the above solution. The resulted solution was stirred at rt overnight. The solvent was then removed and the residue was purified by MDAP to afford the title compound (10 mg). $^1$H-NMR (MeOD-d$_4$, 400 MHz): 1.29 (br. s., 2 H), 1.43 (br. s., 1 H), 1.64 (m, 5 H), 1.84 (br. s., 3 H), 2.34 (s, 3 H), 2.74 (s, 3 H), 3.05 (m, 3 H), 3.42 (m, 3 H), 4.18 (br. s., 0.5 H), 4.41 (br. s., 2 H), 4.65 (br. s., 0.5 H), 7.35 (d, 2 H), 7.73 (d, 1 H), 8.56 (d, 1 H), 9.11 (s, 1 H). δF (MeOD-d$_4$, 376 MHz): −77.3, −116.9. MS (ES): C$_{26}$H$_{33}$FN$_4$O$_2$ requires 452; found 453(M+H$^+$).

Examples 17

(S)-N-(3-((4-(cyclopentanecarbonyl)-3-methylpiperazin-1-yl)methyl)-5-fluoro-2-methylphenyl)picolinamide, trifluoroacetic acid salt (E17)

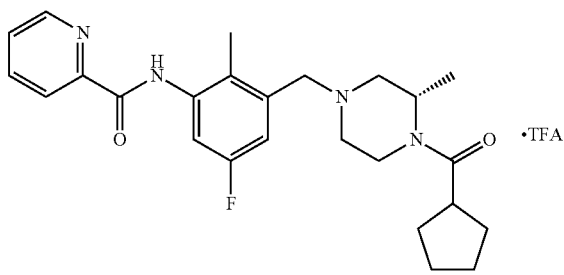 [SMILES: Cc1c(CN2CCN(C(=O)C3CCCC3)[C@@H](C)C2)cc(F)cc1NC(=O)c1ccccn1]

To a suspension of picolinic acid (35.4 mg, 0.288 mmol) in dry DCM (10 mL) under nitrogen, 1 drop of dry DMF followed with oxalyl chloride (0.084 mL, 0.96 mmol) were added. The reaction mixture was stirred at RT for 1 hr. After that, solvents were evaporated carefully to afford the acid chloride. The acid chloride was added into a solution of (S)-(4-(3-amino-5-fluoro-2-methylbenzyl)-2-methylpiperazin-1-yl)(cyclopentyl)methanone (80 mg, 0.24 mmol) and Et3N (0.067 mL, 0.48 mmol) in DCM (10 mL) at RT and stirred at this temperature overnight. After checked with LCMS, the reaction was completed. The mixture was concentrated and purified with MDAP to give the title compound (16 mg, 11.47% yield) as brown solid. $^1$H NMR (400 MHz, DMSO-$d_6$) δ 1.07-1.40 (m, 3H), 1.42-1.92 (m, 8H), 2.33 (s, 3H), 2.89-3.03 (m, 2H), 3.07-3.45 (m, 3H), 3.89-4.16 (m, 1H), 4.23-4.93 (m, 3H), 7.25 (brs, 1H), 7.68-7.77 (m, 1H), 7.84 (brs, 1H), 8.11 (t, 1H), 8.18 (d, 1H), 8.76 (d, 1H), 10.47 (s, 1H). $^{19}$F NMR (376 MHz, DMSO-$d_6$) δ −73.4, −117.1. MS (ESI) $C_{25}H_{31}FN_4O_2$ requires: 438, found 439 (M+H$^+$).

Examples 18 & 19

Examples 18 and 19 were prepared using a similar procedure to that described for Example 17.

E18: (S)-N-(3-((4-(cyclopentanecarbonyl)-3-methylpiperazin-1-yl)methyl)-5-fluoro-2-methylphenyl)nicotinamide, trifluoroacetic acid salt E19: (S)-N-(3-((4-(cyclopentanecarbonyl)-3-methylpiperazin-1-yl)methyl)-5-fluoro-2-methylphenyl)isonicotinamide, trifluoroacetic acid salt

| Example | Structure | Characterization |
|---|---|---|
| E18 | 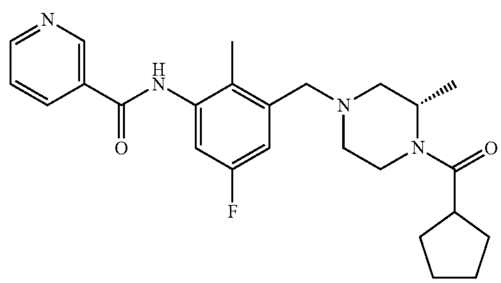 | $^1$H NMR (400 MHz, MeOD-$d_4$) δ 1.20-1.51 (m, 3H), 1.55-2.00 (m, 8H), 2.35 (s, 3H), 2.97-3.23 (m, 3H), 3.38-3.66 (m, 3H), 4.12-4.31 (m, 0.5H), 4.48 (s, 2H), 4.66 (brs, 1H), 7.38 (d, 2H), 7.68-7.87 (m, 1H), 8.59 (d, 1H), 8.85 (d, 1H), 9.21 (s, 1H). $^{19}$F NMR (376 MHz, MeOD-$d_4$) δ −77.2, −116.8. MS (ESI) $C_{25}H_{31}FN_4O_2$ requires: 438, found 439 (M + H$^+$). |
| E19 | 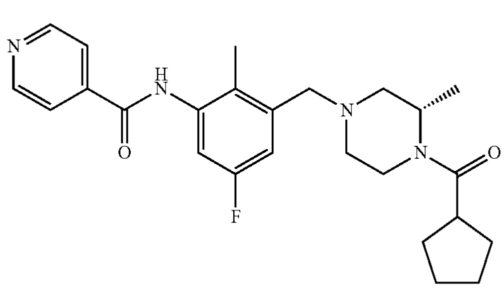 | $^1$H NMR (400 MHz, MeOD-$d_4$) δ 1.23-1.50 (m, 3H), 1.56-2.01 (m, 8H), 2.35 (s, 3H), 2.93-3.27 (m, 3H), 3.37-3.69 (m, 3H), 4.13-4.33 (m, 0.5H), 4.45 (s, 2H), 4.65 (brs, 1H), 7.38 (d, 2H), 8.10 (d, 2H), 8.87 (d, 2H). $^{19}$F NMR (376 MHz, MeOD-$d_4$) δ −78.8, −118.3. MS (ESI) $C_{25}H_{31}FN_4O_2$ requires: 438, found 439 (M + H$^+$). |

Example 20

(S)-N-(3-((4-(cyclopentanecarbonyl)-3-methylpiperazin-1-yl)methyl)-5-fluoro-2-methylphenyl)-2-methylpyrimidine-5-carboxamide (E20)

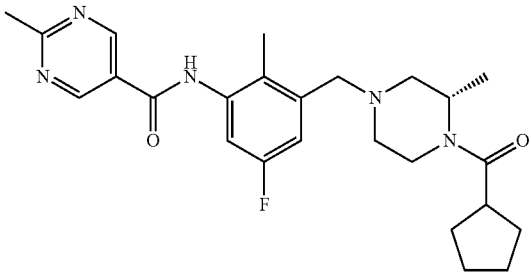 [SMILES: Cc1ncc(C(=O)Nc2cc(F)cc(CN3CCN(C(=O)C4CCCC4)[C@@H](C)C3)c2C)cn1]

Oxalyl chloride (0.084 mL, 0.960 mmol) was added into a mixture of 2-methylpyrimidine-5-carboxylic acid (43.1 mg, 0.312 mmol) and DMF (1.858 µL, 0.024 mmol) in DCM (10 mL) and the reaction was stirred for 1 hr (water bath). Then the mixture was concentrated to give the acid chloride. The acid chloride was added into a solution of (S)-(4-(3-amino-5-fluoro-2-methylbenzyl)-2-methylpiperazin-1-yl)(cyclopentyl)methanone (D31) (80 mg, 0.240 mmol) in pyridine (10mL). Then the reaction was heated to 80° C. under microwave for 1 hr. The mixture was concentrated to remove most of the solvent and the residue was purified via MDAP to give the title compound (26.7 mg) as a solid. $^1$H NMR (400 MHz, MeOD-d$_4$) δ1.15-1.41 (m, 3H), 1.54-2.18 (m, 11H), 2.22 (s, 3H), 2.73 (s, 3H), 2.75-3.10 (m, 4H), 3.35-3.55 (m, 3H), 3.84 (d, 0.5H), 4.32 (d, 1H), 4.66 (brs, 0.5H), 6.75 (d, 2H), 9.19 (s, 2H). $^{19}$F NMR (376 MHz, MeOD-d$_4$) δ −121.3. MS (ESI) $C_{25}H_{32}FN_5O_2$ requires: 453, found 454 (M+H$^+$).

Examples 21-58

Examples 21 to 58 were prepared using a similar procedure to that described for Example 17.

E21: (S)-N-(3-((4-(cyclopentanecarbonyl)-3-methylpiperazin-1-yl)methyl)-5-fluoro-2-methylphenyl)-2-methylnicotinamide E22: (S)-N-(3-((4-(cyclopentanecarbonyl)-3-methylpiperazin-1-yl)methyl)-5-fluoro-2-methylphenyl)-6-methylpicolinamide E23: (S)-N-(3-((4-(cyclopentanecarbonyl)-3-methylpiperazin-1-yl)methyl)-5-fluoro-2-methylphenyl)pyridazine-3-carboxamide E24: (S)-N-(3-((4-(cyclopentanecarbonyl)-3-methylpiperazin-1-yl)methyl)-5-fluoro-2-methylphenyl)-2,6-dimethylnicotinamide, trifluoroacetic acid salt E25: (S)-N-(3-((4-(cyclopentanecarbonyl)-3-methylpiperazin-1-yl)methyl)-5-fluoro-2-methylphenyl)-2-methylisonicotinamide, trifluoroacetic acid salt E26: (S)-N-(3-((4-(cyclopentanecarbonyl)-3-methylpiperazin-1-yl)methyl)-5-fluoro-2-methylphenyl)-2-methoxybenzamide E27: (S)-4-cyano-N-(3-((4-(cyclopentanecarbonyl)-3-methylpiperazin-1-yl)methyl)-5-fluoro-2-methylphenyl)benzamide, trifluoroacetic acid salt E28: (S)-2-cyano-N-(3-((4-(cyclopentanecarbonyl)-3-methylpiperazin-1-yl)methyl)-5-fluoro-2-methylphenyl)benzamide E29: (S)-3-chloro-N-(3-((4-(cyclopentanecarbonyl)-3-methylpiperazin-1-yl)methyl)-5-fluoro-2-methylphenyl)benzamide, trifluoroacetic acid salt E30: (S)-N-(3-((4-(cyclopentanecarbonyl)-3-methylpiperazin-1-yl)methyl)-5-fluoro-2-methylphenyl)-3,4-difluorobenzamide, trifluoroacetic acid salt E31: (S)-N-(3-((4-(cyclopentanecarbonyl)-3-methylpiperazin-1-yl)methyl)-5-fluoro-2-methylphenyl)-2,6-dimethylisonicotinamide, trifluoroacetic acid salt E32: (S)-N-(3-((4-(cyclopentanecarbonyl)-3-methylpiperazin-1-yl)methyl)-5-fluoro-2-methylphenyl)-6-methoxynicotinamide, trifluoroacetic acid salt E33: (S)-N-(3-((4-(cyclopentanecarbonyl)-3-methylpiperazin-1-yl)methyl)-5-fluoro-2-methylphenyl)-1-methyl-2-oxo-1,2-dihydropyridine-4-carboxamide E34: (S)-N-(3-((4-(cyclopentanecarbonyl)-3-methylpiperazin-1-yl)methyl)-5-fluoro-2-methylphenyl)-3-fluoro-4-methylbenzamide E35: (S)-N-(3-((4-(cyclopentanecarbonyl)-3-methylpiperazin-1-yl)methyl)-5-fluoro-2-methylphenyl)-6-methylpyridazine-3-carboxamide, trifluoroacetic acid salt E36: (S)-N-(3-((4-(cyclopentanecarbonyl)-3-methylpiperazin-1-yl)methyl)-5-fluoro-2-methylphenyl)-5-methylpyrazine-2-carboxamide E37: (S)-N-(3-((4-(cyclopentanecarbonyl)-3-methylpiperazin-1-yl)methyl)-5-fluoro-2-methylphenyl)-3-methylbenzamide, trifluoroacetic acid salt E38: (S)-N-(3-((4-(cyclopentanecarbonyl)-3-methylpiperazin-1-yl)methyl)-5-fluoro-2-methylphenyl)-2,5-dimethylbenzamide E39: (S)-N-(3-((4-(cyclopentanecarbonyl)-3-methylpiperazin-1-yl)methyl)-5-fluoro-2-methylphenyl)-2,3-difluorobenzamide, trifluoroacetic acid salt E40: (S)-N-(3-((4-(cyclopentanecarbonyl)-3-methylpiperazin-1-yl)methyl)-5-fluoro-2-methylphenyl)-2,4-difluorobenzamide E41: (S)-N-(3-((4-(cyclopentanecarbonyl)-3-methylpiperazin-1-yl)methyl)-5-fluoro-2-methylphenyl)-2,5-difluorobenzamide E42: (S)-N-(3-((4-(cyclopentanecarbonyl)-3-methylpiperazin-1-yl)methyl)-5-fluoro-2-methylphenyl)-3,5-difluorobenzamide, trifluoroacetic acid salt E43: (S)-N-(3-((4-(cyclopentanecarbonyl)-3-methylpiperazin-1-yl)methyl)-5-fluoro-2-methylphenyl)-3-fluoro-2-methylbenzamide, trifluoroacetic acid salt E44: (S)-N-(3-((4-(cyclopentanecarbonyl)-3-methylpiperazin-1-yl)methyl)-5-fluoro-2-methylphenyl)-3-fluoro-5-methylbenzamide, trifluoroacetic acid salt E45: (S)-N-(3-((4-(cyclopentanecarbonyl)-3-methylpiperazin-1-yl)methyl)-5-fluoro-2-methylphenyl)-5-fluoro-2-methylbenzamide, trifluoroacetic acid salt E46: (S)-N-(3-((4-(cyclopentanecarbonyl)-3-methylpiperazin-1-yl)methyl)-5-fluoro-2-methylphenyl)-5-fluoro-2-methylbenzamide, trifluoroacetic acid salt E47: (S)-N-(3-((4-(cyclopentanecarbonyl)-3-methylpiperazin-1-yl)methyl)-5-fluoro-2-methylphenyl)-2-fluoro-4-methylbenzamide E48: (S)-N-(3-((4-(cyclopentanecarbonyl)-3-methylpiperazin-1-yl)methyl)-5-fluoro-2-methylphenyl)-2-fluoro-5-methylbenzamide, trifluoroacetic acid salt E49: (S)-N-(3-((4-(cyclopentanecarbonyl)-3-methylpiperazin-1-yl)methyl)-5-fluoro-2-methylphenyl)-2,4-dimethylbenzamide, trifluoroacetic acid salt E50: (S)-4-cyano-N-(3-((4-(cyclopentanecarbonyl)-3-methylpiperazin-1-yl)methyl)-5-fluoro-2-methylphenyl)-2-fluorobenzamide, trifluoroacetic acid salt E51: (S)-N-(3-((4-(cyclopentanecarbonyl)-3-methylpiperazin-1-yl)methyl)-5-fluoro-2-methylphenyl)-3-(dimethylamino)benzamide E52: (S)-N-(3-((4-(cyclopentanecarbonyl)-3-methylpiperazin-1-yl)methyl)-5-fluoro-2-methylphenyl)-2,3-dimethylbenzamide E53: (S)-4-cyano-N-(3-((4-(cyclopentanecarbonyl)-3-methylpiperazin-1-yl)methyl)-5-fluoro-2-methylphenyl)-3-fluorobenzamide, trifluoroacetic acid salt E54: (S)-N-(3-((4-(cyclopentanecarbonyl)-3-methylpiperazin-1-yl)methyl)-5-fluoro-2-methylphenyl)pyrimidine-5-carboxamide E55: (S)-N-(3-((4-(cyclopentanecarbonyl)-3-methylpiperazin-1-yl)methyl)-5-fluoro-2-methylphenyl)imidazo[1,2-a]pyridine-2-carboxamide, trifluoroacetic acid salt E56: (S)-3-cyano-N-(3-((4-(cyclopentanecarbonyl)-3-methylpiperazin-1-yl)methyl)-5-fluoro-2-methylphenyl)-4-methylbenzamide, trifluoroacetic acid salt E57: (S)-N-(3-((4-(cyclopentanecarbonyl)-3-methylpiperazin-1-yl)methyl)-5-fluoro-2-methylphenyl)-6-ethylnicotinamide E58: (S)-3-cyano-N-(3-((4-(cyclopentanecarbonyl)-3-methylpiperazin-1-yl)methyl)-5-fluoro-2-methylphenyl)-4-fluorobenzamide

| Example | Structure | Characterization |
|---|---|---|
| E21 | 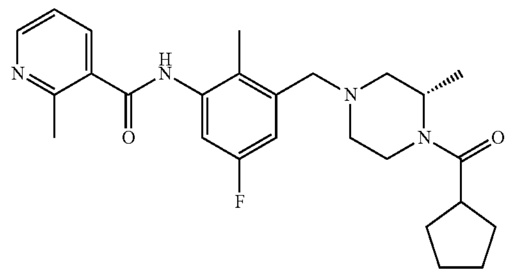 [SMILES: Cc1ncccc1C(=O)Nc1cc(F)cc(CN2CCN(C(=O)C3CCCC3)[C@@H](C)C2)c1C] | $^1$H NMR (400 MHz, MeOD-$d_4$) δ 1.14-1.43 (m, 3H), 1.53-2.09 (m, 9H), 2.10-2.25 (m, 1H), 2.29 (s, 3H), 2.65-3.13 (m, 7H), 3.37-3.58 (m, 2H), 3.77-3.94 (m, 0.5H), 4.19-4.41 (m, 1H), 4.67 (brs, 0.5H), 6.88 (d, 2H), 7.33 (d, 1H), 7.94 (s, 1H), 8.42 (s, 1H). $^{19}$F NMR (376 MHz, MeOD-$d_4$) δ −120.7. MS (ESI) $C_{26}H_{33}FN_4O_2$ requires: 452, found 453 (M + H$^+$). |
| E22 | 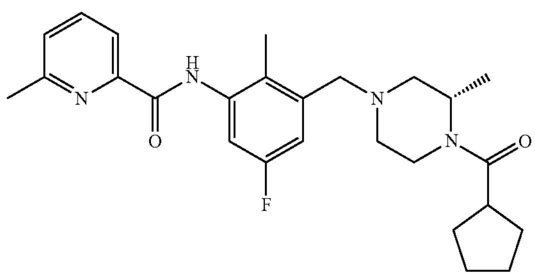 [SMILES: Cc1cccc(C(=O)Nc2cc(F)cc(CN3CCN(C(=O)C4CCCC4)[C@@H](C)C3)c2C)n1] | $^1$H NMR (400 MHz, MeOD-$d_4$) δ 1.15-1.42 (m, 3H), 1.47-2.10 (m, 9H), 2.10-2.28 (m, 1H), 2.38 (s, 3H), 2.64 (s, 3H), 2.69-3.09 (m, 4H), 3.35-3.60 (m, 3H), 3.83 (d, 0.5H), 4.22-4.40 (m, 1H), 4.67 (brs, 0.5H), 6.93 (dd, 1H), 7.49 (d, 1H), 7.81 (dd, 1H), 7.90 (t, 1H), 8.01 (d, 1H). $^{19}$F NMR (376 MHz, MeOD-$d_4$) δ −118.5. MS (ESI) $C_{26}H_{33}FN_4O_2$ requires: 452, found 453 (M + H$^+$). |
| E23 | 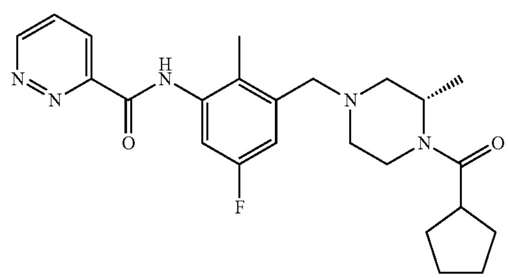 [SMILES: Cc1c(CN2CCN(C(=O)C3CCCC3)[C@@H](C)C2)cc(F)cc1NC(=O)c1cccnn1] | $^1$H NMR (400 MHz, MeOD-$d_4$) δ 1.18-1.42 (m, 3H), 1.54-2.26 (m, 10H), 2.35 (s, 3H), 2.71-3.09 (m, 4H), 3.35-3.58 (m, 3H), 3.78-3.91 (m, 0.5H), 4.23-4.39 (m, 1H), 4.67 (brs, 0.5H), 6.93 (d, 1H), 7.34-7.45 (m, 1H), 7.87-7.97 (m, 1H), 8.37 (d, 1H), 9.33 (d, 1H). $^{19}$F NMR (376 MHz, MeOD-$d_4$) δ −121.1. MS (ESI) $C_{24}H_{30}FN_5O_2$ requires: 439, found 440 (M + H$^+$). |
| E24 | 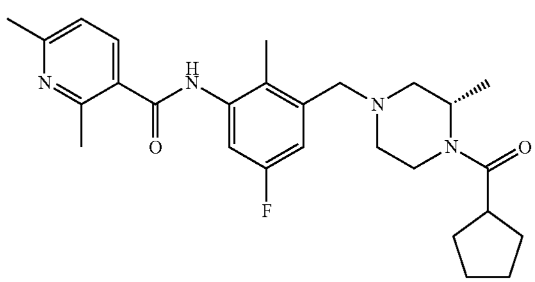 | $^1$H NMR (400 MHz, MeOD-$d_4$) δ 1.15-1.53 (m, 3H), 1.54-1.99 (m, 8H), 2.38 (s, 3H), 2.80 (s, 3H), 2.88 (s, 3H), 2.93-3.24 (m, 3H), 3.34-3.69 (m, 3H), 4.06-4.27 (m, 1H), 4.36 (s, 2H), 4.62 (brs, 1H), 7.33 (dd, 1H), 7.42-7.52 (m, 1H), 7.79 (d, 1H), 8.57 (d, 1H). $^{19}$F NMR (376 MHz, MeOD-$d_4$) δ −77.2, −116.9. MS (ESI) $C_{27}H_{35}FN_4O_2$ requires: 466, found 467 (M + H$^+$). |

| Example | Structure | Characterization |
|---|---|---|
| E25 | 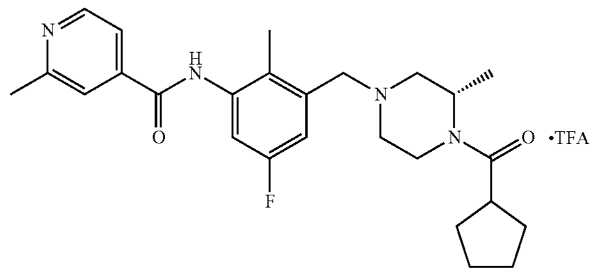 [SMILES: Cc1cc(C(=O)Nc2cc(F)cc(CN3CCN(C(=O)C4CCCC4)[C@@H](C)C3)c2C)ccn1] | $^1$H NMR (400 MHz, MeOD-d$_4$) δ 1.19-1.52 (m, 3H), 1.54-1.99 (m, 1H), 2.35 (s, 3H), 2.81 (s, 3H), 2.89-3.28 (m, 3H), 3.35-3.70 (m, 3H), 4.10-4.30 (m, 1H), 4.41 (s, 2H), 4.64 (brs, 1H), 7.37 (d, 2H), 8.09 (d, 1H), 8.17 (s, 1H), 8.80 (d, 1H). $^{19}$F NMR (376 MHz, MeOD-d$_4$) δ −77.1, −116.8. MS (ESI) C$_{26}$H$_{33}$FN$_4$O$_2$ requires: 452, found 453 (M + H$^+$). |
| E26 | 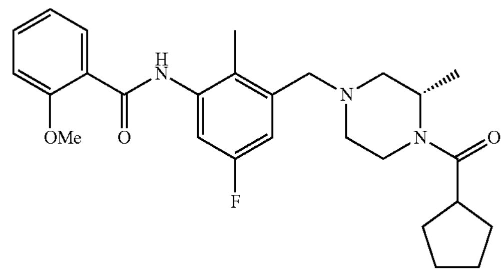 [SMILES: COc1ccccc1C(=O)Nc1cc(F)cc(CN2CCN(C(=O)C3CCCC3)[C@@H](C)C2)c1C] | $^1$H NMR (400 MHz, MeOD-d$_4$) δ 1.11-1.42 (m, 3H), 1.48-1.87 (m, 8H), 1.87-2.23 (m, 2H), 2.33 (s, 3H), 2.63-3.08 (m, 4H), 3.35-3.55 (m, 2H), 3.81 (d, 0.5H), 4.07 (s, 3H), 4.18-4.39 (m, 1H), 4.55-4.72 (m, 0.5H), 6.88 (d, 1H), 7.12 (t, 1H), 7.21 (d, 1H), 7.55 (t, 1H), 7.82 (d, 1H), 8.08 (d, 1H). $^{19}$F NMR (376 MHz, MeOD-d$_4$) δ −118.5. MS (ESI) C$_{27}$H$_{34}$FN$_3$O$_3$ requires: 467, found 468 (M + H$^+$). |
| E27 | 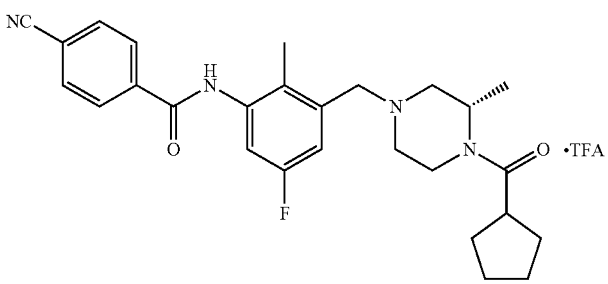 [SMILES: Cc1c(CN2CCN(C(=O)C3CCCC3)[C@@H](C)C2)cc(F)cc1NC(=O)c1ccc(C#N)cc1] | $^1$H NMR (400 MHz, MeOD-d$_4$) δ 1.20-1.51 (m, 3H), 1.56-1.99 (m, 8H), 2.33 (s, 3H), 2.93-3.26 (m, 3.5H), 3.35-3.63 (m, 3H), 4.19 (d, 0.5H), 4.41 (s, 2H), 4.65 (brs, 1H), 7.34 (d, 2H), 7.93 (d, 2H), 8.13 (d, 2H). $^{19}$F NMR (376 MHz, MeOD-d$_4$) δ −78.8, −118.4. MS (ESI) C$_{27}$H$_{31}$FN$_4$O$_2$ requires: 462, found 463 (M + H$^+$). |
| E28 | 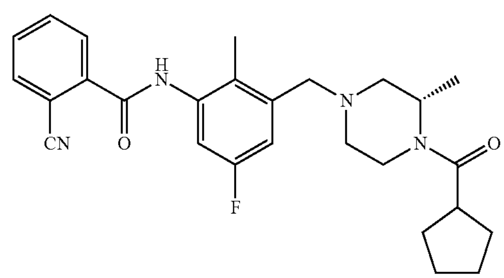 [SMILES: Cc1c(CN2CCN(C(=O)C3CCCC3)[C@@H](C)C2)cc(F)cc1NC(=O)c1ccccc1C#N] | $^1$H NMR (400 MHz, MeOD-d$_4$) δ 1.19-1.43 (m, 3H), 1.53-1.98 (m, 8H), 1.98-2.30 (m, 5H), 2.71-3.11 (m, 4H), 3.35-3.65 (m, 3H), 3.86 (d, 0.5H), 4.25-4.40 (m, 1H), 4.60 (s, 2H), 4.68 (brs, 0.5H), 6.99-7.11 (m, 1H), 7.23-7.41 (m, 1H), 7.78-7.98 (m, 3H), 8.07-8.17 (m, 1H). $^{19}$F NMR (376 MHz, MeOD-d$_4$) δ −118.8. MS (ESI) C$_{27}$H$_{31}$FN$_4$O$_2$ requires: 462, found 463 (M + H$^+$). |
| E29 | 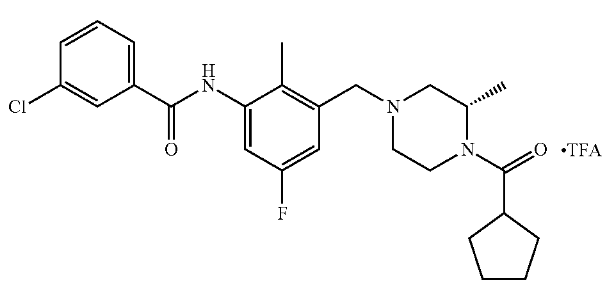 [SMILES: Cc1c(CN2CCN(C(=O)C3CCCC3)[C@@H](C)C2)cc(F)cc1NC(=O)c1cccc(Cl)c1] | $^1$H NMR (400 MHz, MeOD-d$_4$) δ 1.17-1.50 (m, 3H), 1.55-1.98 (m, 8H), 2.31 (s, 3H), 2.69-3.20 (m, 4H), 3.33-3.63 (m, 2H), 4.03-4.37 (m, 2.5H), 4.58 (brs, 0.5H), 7.28 (d, 2H), 7.54 (t, 1H), 7.64 (d, 1H), 7.92 (d, 1H), 8.00 (s, 1H). $^{19}$F NMR (376 MHz, MeOD-d$_4$) δ −77.0, −117.4. MS (ESI) C$_{26}$H$_{31}$ClFN$_3$O$_2$ requires: 471, found 472 (M + H$^+$). |

-continued

| Example | Structure | Characterization |
|---|---|---|
| E30 | 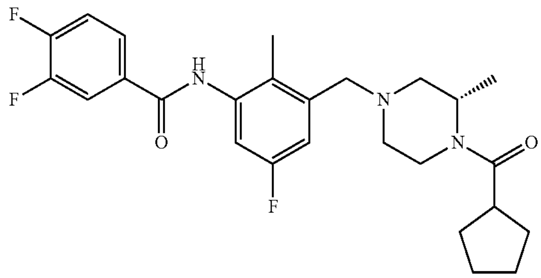 | $^1$H NMR (400 MHz, MeOD-$d_4$) δ 1.22-1.48 (m, 3H), 1.54-1.99 (m, 8H), 2.32 (s, 3H), 2.83-3.24 (m, 4H), 3.34-3.62 (m, 3H), 4.16 (d, 0.5H), 4.36 (brs, 2H), 4.62 (brs, 0.5H), 7.31 (t, 2H), 7.46 (q, 1H), 7.82-8.01 (m, 2H). $^{19}$F NMR (376 MHz, MeOD-$d_4$) δ −77.2, −117.3, −134.7 (d), −139.06 (d). MS (ESI) $C_{26}H_{30}F_3N_3O_2$ requires: 473, found 474 (M + H$^+$). |
| E31 | 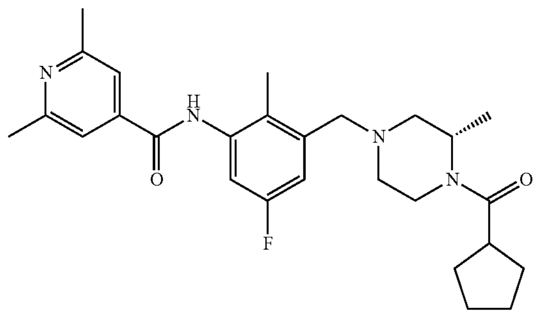 | $^1$H NMR (400 MHz, MeOD-$d_4$) δ 1.20-1.50 (m, 3H), 1.56-1.99 (m, 8H), 2.34 (s, 3H), 2.79 (s, 6H), 2.83-3.28 (m, 5H), 3.41-3.66 (m, 1H), 4.00-4.34 (m, 3H), 4.55 (brs, 1H), 7.24-7.37 (m, 2H), 8.01 (s, 2H). $^{19}$F NMR (376 MHz, MeOD-$d_4$) δ −78.6, −118.9. MS (ESI) $C_{27}H_{35}FN_4O_2$ requires: 466, found 467 (M + H$^+$). |
| E32 | 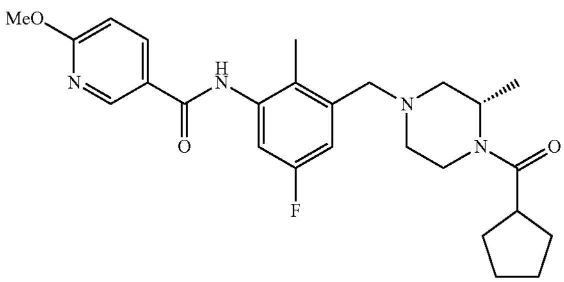 | $^1$H NMR (400 MHz, MeOD-$d_4$) δ 1.23-1.50 (m, 3H), 1.55-2.00 (m, 8H), 3.23 (s, 3H), 2.88-3.25 (m, 3.5H), 3.34-3.67 (m, 3H), 4.01 (s, 3H), 4.18 (d, 0.5H), 4.39 (brs, 2H), 4.64 (brs, 1H), 6.93 (d, 1H), 7.25-7.37 (m, 2H), 8.23 (dd, 1H), 8.81 (d, 1H). $^{19}$F NMR (376 MHz, MeOD-$d_4$) δ −77.1, −117.1. MS (ESI) $C_{26}H_{33}FN_4O_3$ requires: 468, found 469 (M + H$^+$). |
| E33 | 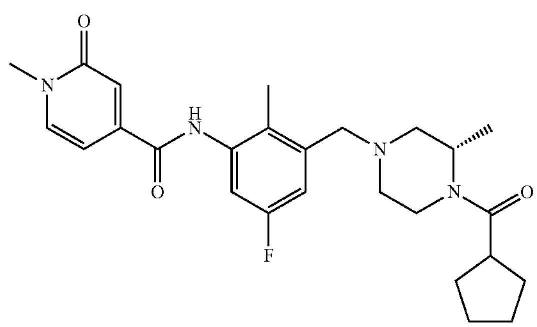 [SMILES: Cc1c(CN2CCN(C(=O)C3CCCC3)[C@@H](C)C2)cc(F)cc1NC(=O)c1ccn(C)c(=O)c1] | $^1$H NMR (400 MHz, MeOD-$d_4$) δ 1.16-1.41 (m, 3H), 1.52-1.94 (m, 8H), 1.94-2.24 (m, 2H), 2.27 (s, 3H), 2.66-3.09 (m, 3.5H), 3.35-3.57 (m, 2.5H), 3.62 (s, 3H), 3.84 (d, 0.5H), 4.21-4.37 (m, 1H), 4.49 (s, 1H), 4.67 (brs, 0.5H), 6.76 (d, 1H), 6.97-7.14 (m, 3H), 7.78 (d, 1H). $^{19}$F NMR (376 MHz, MeOD-$d_4$) δ −119.3. MS (ESI) $C_{26}H_{33}FN_4O_3$ requires: 468, found 469 (M + H$^+$). |
| E34 | 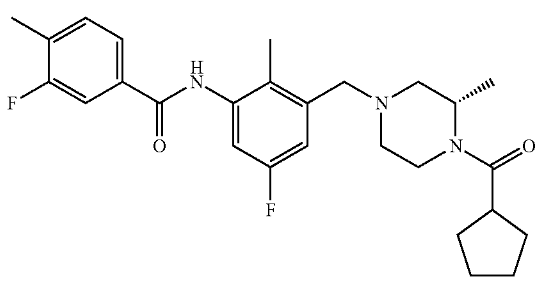 [SMILES: Cc1ccc(C(=O)Nc2cc(F)cc(CN3CCN(C(=O)C4CCCC4)[C@@H](C)C3)c2C)cc1F] | $^1$H NMR (400 MHz, MeOD-$d_4$) δ 1.16-1.45 (m, 3H), 1.54-1.98 (m, 8H), 1.98-2.28 (m, 2H), 2.30 (s, 3H), 2.37 (s, 3H), 2.70-3.12 (m, 3.5H), 3.35-3.59 (m, 2.5H), 3.86 (d, 0.5H), 4.23-4.41 (m, 1H), 4.69 (brs, 0.5H), 7.05-7.15 (m, 2H), 7.42 (t, 1H), 7.67 (d, 1H), 7.72 (d, 1H). $^{19}$F NMR (376 MHz, MeOD-$d_4$) δ −118.6, −119.5. MS (ESI) $C_{27}H_{33}F_2N_3O_2$ requires: 469, found 470 (M + H$^+$). |

| Example | Structure | Characterization |
|---|---|---|
| E35 | 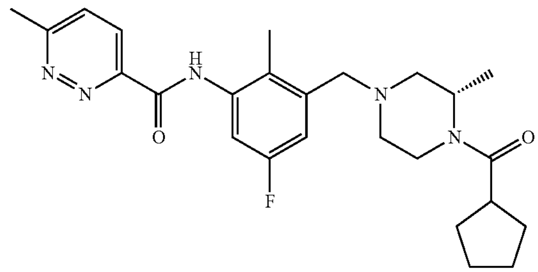 | $^1$H NMR (400 MHz, MeOD-d$_4$) δ 1.31 (brs, 3H), 1.54-1.99 (m, 8H), 2.43 (s, 3H), 2.82 (s, 3H), 2.91-3.28 (m, 4H), 3.35-3.69 (m, 2.5H), 4.19 (brs, 0.5H), 4.42 (s, 2H), 4.64 (brs, 0.5H), 4.94 (brs, 0.5H), 7.26 (d, 1H), 7.82-7.91 (m, 2H), 8.31 (d, 1H). $^{19}$F NMR (376 MHz, MeOD-d$_4$) δ −77.2, −116.4. MS (ESI) C$_{25}$H$_{32}$FN$_5$O$_2$ requires: 453, found 454 (M + H$^+$). |
| E36 | 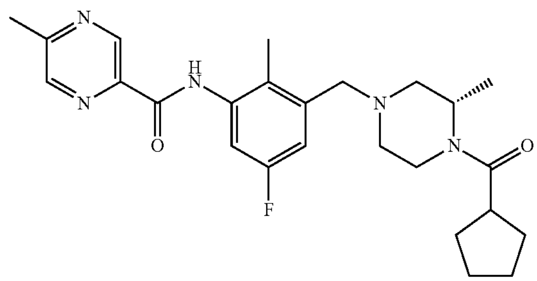 [SMILES: Cc1cnc(C(=O)Nc2cc(F)cc(CN3CCN(C(=O)C4CCCC4)[C@@H](C)C3)c2C)cn1] | $^1$H NMR (400 MHz, MeOD-d$_4$) δ 1.16-1.40 (m, 4H), 1.50-1.94 (m, 9H), 1.94-2.29 (m, 3H), 2.36 (s, 3H), 2.68 (s, 3H), 2.70-3.10 (m, 4H), 3.35-3.60 (m, 3H), 3.84 (d, 0.5H), 4.20-4.37 (m, 1H), 4.50 (d, 1.5H), 7.00 (d, 1H), 7.63 (d, 1H), 8.65 (s, 1H), 9.21 (s, 1H). $^{19}$F NMR (376 MHz, MeOD-d$_4$) δ −118.7. MS (ESI) C$_{25}$H$_{32}$FN$_5$O$_2$ requires: 453, found 454 (M + H$^+$). |
| E37 | 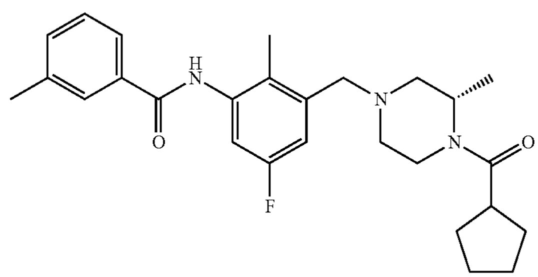 | $^1$H NMR (400 MHz, MeOD-d$_4$) δ 1.17-1.44 (m, 3H), 1.53-1.95 (m, 8H), 1.95-2.26 (m, 3H), 2.28 (s, 3H), 2.44 (s, 3H), 2.65-3.09 (m, 3H), 3.35-3.60 (m, 3H), 3.84 (d, 0.5H), 4.22-4.38 (m, 1H), 4.67 (brs, 0.5H), 7.04 (dd, 2H), 7.39 (d, 2H), 7.72-7.78 (m, 1H), 7.79 (s, 1H). $^{19}$F NMR (376 MHz, MeOD-d$_4$) δ −76.9, −119.8. MS (ESI) C$_{27}$H$_{34}$FN$_3$O$_2$ requires: 451, found 452 (M + H$^+$). |
| E38 | 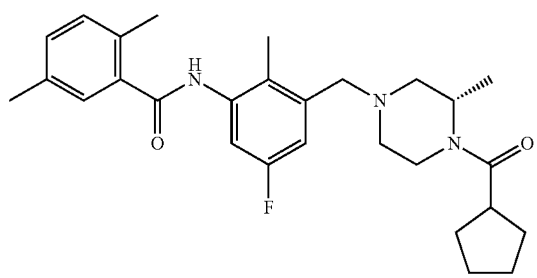 [SMILES: Cc1ccc(C)c(C(=O)Nc2cc(F)cc(CN3CCN(C(=O)C4CCCC4)[C@@H](C)C3)c2C)c1] | $^1$H NMR (400 MHz, MeOD-d$_4$) δ 1.16-1.42 (m, 3H), 1.54-1.94 (m, 8H), 1.94-2.27 (m, 2H), 2.32 (s, 3H), 2.37 (s, 3H), 2.45 (s, 3H), 2.65-3.08 (m, 4H), 3.33-3.59 (m, 3H), 3.84 (d, 0.5H), 4.20-4.38 (m, 1H), 4.67 (brs, 0.5H), 7.05 (d, 1H), 7.10-7.24 (m, 3H), 7.37 (s, 1H). $^{19}$F NMR (376 MHz, MeOD-d$_4$) δ −119.4. MS (ESI) C$_{28}$H$_{36}$FN$_3$O$_2$ requires: 465, found 466 (M + H$^+$). |
| E39 | 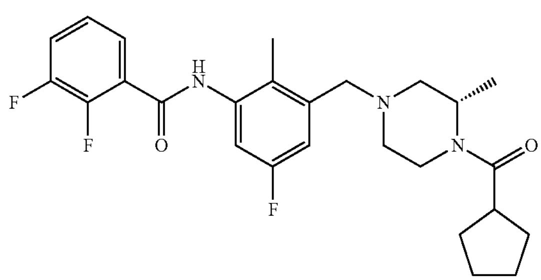 | $^1$H NMR (400 MHz, MeOD-d$_4$) δ 1.18-1.50 (m, 3H), 1.54-2.01 (m, 8H), 2.36 (s, 3H), 2.56-3.25 (m, 5H), 3.41-3.63 (m, 1H), 4.11 (brs, 2.5H), 4.53 (brs, 1.5H), 7.22 (d, 1H), 7.27-7.37 (m, 1H), 7.41 (d, 1H), 7.45-7.55 (m, 1H), 7.60 (t, 1H). $^{19}$F NMR (376 MHz, MeOD-d$_4$) δ −77.2, −117.4, −139.8 (d), −141.8 (d). MS (ESI) C$_{26}$H$_{30}$F$_3$N$_3$O$_2$ requires: 473, found 474 (M + H$^+$). |

-continued

| Example | Structure | Characterization |
|---|---|---|
| E40 | (structure) | $^1$H NMR (400 MHz, MeOD-d$_4$) δ 1.15-1.44 (m, 3H), 1.51-1.94 (m, 8H), 1.94-2.28 (m, 2H), 2.32 (s, 3H), 2.67-3.09 (m, 4H), 3.34-3.60 (m, 2.5H), 3.84 (d, 0.5H), 4.21-4.39 (m, 1H), 4.40-4.72 (m, 1H), 7.04 (dd, 1H), 7.07-7.20 (m, 2H), 7.30 (d, 1H), 7.85-7.98 (m, 1H). $^{19}$F NMR (376 MHz, MeOD-d$_4$) δ −106.6 (d), −110.7 (d), −119.2. MS (ESI) C$_{26}$H$_{30}$F$_3$N$_3$O$_2$ requires: 473, found 474 (M + H$^+$). |
| E41 | (structure) | $^1$H NMR (400 MHz, MeOD-d$_4$) δ 1.16-1.42 (m, 3H), 1.54-1.96 (m, 8H), 1.96-2.26 (m, 2H), 2.32 (s, 3H), 2.67-3.10 (m, 3.5H), 3.34-3.44 (m, 0.5H), 3.44-3.59 (m, 2H), 3.84 (d, 0.5H), 4.20-4.41 (m, 1H), 4.67 (brs, 0.5H), 7.00-7.10 (m, 1H), 7.25-7.39 (m, 3H), 7.50-7.61 (m, 1H). $^{19}$F NMR (376 MHz, MeOD-d$_4$) δ −119.2, −119.7 (d), −121.2 (d). MS (ESI) C$_{26}$H$_{30}$F$_3$N$_3$O$_2$ requires: 473, found 474 (M + H$^+$). |
| E42 | (structure) ·TFA | $^1$H NMR (400 MHz, MeOD-d$_4$) δ 1.21-1.48 (m, 3H), 1.55-1.98 (m, 8H), 2.31 (s, 3H), 2.59-3.27 (m, 5H), 3.42-3.60 (m, 1H), 4.16 (brs, 1.5H), 4.55 (brs, 1.5H), 4.82-4.97 (m, 0.5H), 7.20-7.30 (m, 3H), 7.56-7.63 (m, 2H). $^{19}$F NMR (376 MHz, MeOD-d$_4$) δ −77.15, −77.18, −110.2, −117.6. MS (ESI) C$_{26}$H$_{30}$F$_3$N$_2$O$_2$ requires: 473, found 474 (M + H$^+$). |
| E43 | (structure) ·TFA | $^1$H NMR (400 MHz, MeOD-d$_4$) δ 1.20-1.49 (m, 3H), 1.56-1.98 (m, 8H), 2.37 (s, 3H), 2.40 (d, 3H), 2.90-3.25 (m, 3.5H), 3.34-3.64 (m, 3H), 4.19 (brs, 0.5H), 4.37 (s, 2H), 4.52-4.73 (m, 1H), 7.22 (t, 1H), 7.26-7.46 (m, 4H). $^{19}$F NMR (376 MHz, MeOD-d$_4$) δ −77.2, −117.0, −117.5. MS (ESI) C$_{27}$H$_{33}$F$_2$N$_3$O$_2$ requires: 469, found 470 (M + H$^+$). |
| E44 | (structure) ·TFA | $^1$H NMR (400 MHz, MeOD-d$_4$) δ 1.20-1.51 (m, 3H), 1.55-2.01 (m, 8H), 2.32 (s, 3H), 2.46 (s, 3H), 2.79-3.19 (m, 3.5H), 3.34-3.65 (m, 2H), 4.05-4.39 (m, 3H), 4.49-4.68 (m, 1H), 4.82-5.03 (m, 0.5H), 7.21 (d, 1H), 7.24-7.32 (m, 2H), 7.50 (d, 1H), 7.64 (s, 1H). $^{19}$F NMR (376 MHz, MeOD-d$_4$) δ −77.2, −115.1, −117.4. MS (ESI) C$_{27}$H$_{33}$F$_2$N$_3$O$_2$ requires: 469, found 470 (M + H$^+$). |

| Example | Structure | Characterization |
|---|---|---|
| E45 | 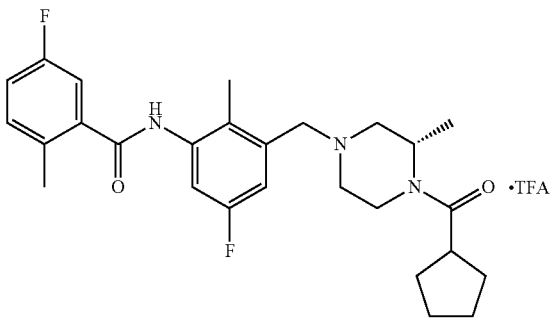 [SMILES: Cc1ccc(F)cc1C(=O)Nc1cc(F)cc(CN2CCN(C(=O)C3CCCC3)[C@@H](C)C2)c1C] | $^1$H NMR (400 MHz, MeOD-d$_4$) δ 1.20-1.49 (m, 3H), 1.55-1.99 (m, 8H), 2.36 (s, 3H), 2.47 (s, 3H), 2.75-3.22 (m, 3.5H), 3.35-3.63 (m, 2H), 4.04-4.40 (m, 3H), 4.44-4.69 (m, 2H), 4.83-5.05 (m, 0.5H), 7.16 (td, 1H), 7.27 (dd, 1H), 7.30-7.39 (m, 3H). $^{19}$F NMR (376 MHz, MeOD-d$_4$) δ −77.2, −117.2, −119.0. MS (ESI) C$_{27}$H$_{33}$F$_2$N$_3$O$_2$ requires: 469, found 470 (M + H$^+$). |
| E46 | 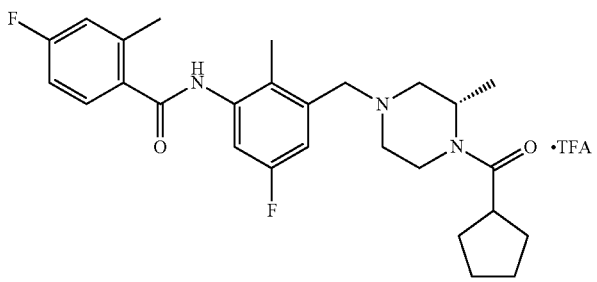 [SMILES: Cc1cc(F)ccc1C(=O)Nc1cc(F)cc(CN2CCN(C(=O)C3CCCC3)[C@@H](C)C2)c1C] | $^1$H NMR (400 MHz, MeOD-d$_4$) δ 1.18-1.50 (m, 3H), 1.54-1.98 (m, 8H), 2.36 (s, 3H), 2.52 (s, 3H), 2.82-3.23 (m, 3.5H), 3.32-3.67 (m, 3H), 4.15 (brs, 0.5H), 4.31 (s, 2H), 4.63 (brs, 1H), 7.01-7.13 (m, 2H), 7.28 (dd, 1H), 7.31-7.39 (m, 1H), 7.63 (dd, 1H). $^{19}$F NMR (376 MHz, MeOD-d$_4$) δ −77.2, −112.5, −117.3. MS (ESI) C$_{27}$H$_{33}$F$_2$N$_3$O$_2$ requires: 469, found 470 (M + H$^+$). |
| E47 | 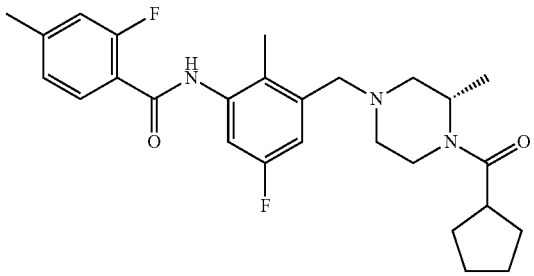 [SMILES: Cc1ccc(C(=O)Nc2cc(F)cc(CN3CCN(C(=O)C4CCCC4)[C@@H](C)C3)c2C)c(F)c1] | $^1$H NMR (400 MHz, MeOD-d$_4$) δ 1.17-1.43 (m, 3H), 1.51-1.94 (m, 8H), 1.94-2.28 (m, 2H), 2.31 (s, 3H), 2.43 (s, 3H), 2.67-3.08 (m, 3.5H), 3.32-3.43 (m, 0.5H), 3.43-3.58 (m, 2H), 3.83 (d, 0.5H), 4.22-4.37 (m, 1H), 4.49 (brs, 0.5H), 4.67 (brs, 1H), 7.02 (dd, 1H), 7.11 (d, 1H), 7.16 (d, 1H), 7.33 (d, 1H), 7.76 (t, 1H). $^{19}$F NMR (376 MHz, MeOD-d$_4$) δ −116.0, −119.2. MS (ESI) C$_{27}$H$_{33}$F$_2$N$_3$O$_2$ requires: 469, found 470 (M + H$^+$). |
| E48 | 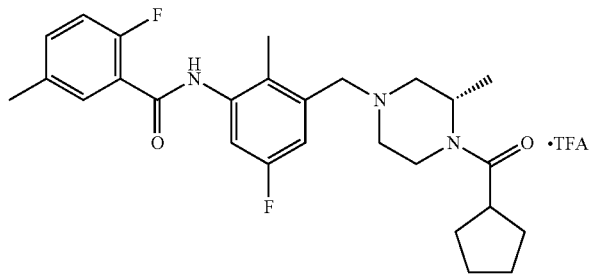 [SMILES: Cc1ccc(F)c(C(=O)Nc2cc(F)cc(CN3CCN(C(=O)C4CCCC4)[C@@H](C)C3)c2C)c1] | $^1$H NMR (400 MHz, MeOD-d$_4$) δ 1.17-1.50 (m, 3H), 1.55-2.01 (m, 8H), 2.35 (s, 3H), 2.40 (s, 3H), 2.46-2.93 (m, 2H), 2.96-3.27 (m, 4H), 3.48 (brs, 1H), 3.81-4.22 (m, 2.5H), 4.49 (brs, 0.5H), 7.09-7.26 (m, 2H), 7.34-7.48 (m, 2H), 7.61-7.72 (m, 1H). $^{19}$F NMR (376 MHz, MeOD-d$_4$) δ −77.0, −118.7, −120.8. MS (ESI) C$_{27}$H$_{33}$F$_2$N$_3$O$_2$ requires: 469, found 470 (M + H$^+$). |
| E49 | 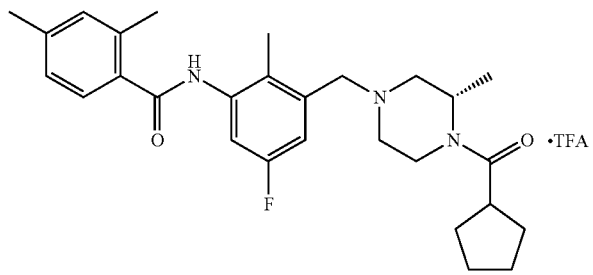 [SMILES: Cc1ccc(C(=O)Nc2cc(F)cc(CN3CCN(C(=O)C4CCCC4)[C@@H](C)C3)c2C)c(C)c1] | $^1$H NMR (400 MHz, MeOD-d$_4$) δ 1.21-1.50 (m, 3H), 1.56-2.00 (m, 8H), 2.36 (s, 3H), 2.37 (s, 3H), 2.48 (s, 3H), 2.74-3.24 (m, 4H), 3.36-3.66 (m, 2H), 4.14 (brs, 0.5H), 4.29 (s, 2H), 4.59 (brs, 1H), 7.10-7.18 (m, 2H), 7.27 (d, 1H), 7.33 (d, 1H), 7.48 (d, 1H). $^{19}$F NMR (376 MHz, MeOD-d$_4$) δ −77.1, −117.3. MS (ESI) C$_{28}$H$_{36}$FN$_3$O$_2$ requires: 465, found 466 (M + H$^+$). |

| Example | Structure | Characterization |
|---|---|---|
| E50 | 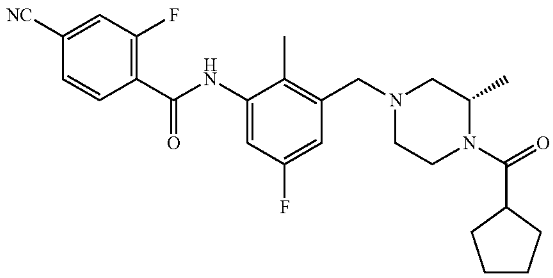 | ¹H NMR (400 MHz, MeOD-d₄) δ 1.33 (brs, 3H), 1.55-1.98 (m, 8H), 2.37 (s, 3H), 2.97-3.30 (m, 3H), 3.37-3.70 (m, 3H), 4.21 (brs, 0.5H), 4.46 (s, 2H), 4.64 (brs, 0.5H), 7.34 (dd, 1H), 7.45-7.53 (m, 1H), 7.75 (dd, 21H), 7.98 (t, 1H). ¹⁹F NMR (376 MHz, MeOD-d₄) δ −77.2, −113.0, −116.6. MS (ESI) C₂₇H₃₀F₂N₄O₂ requires: 480, found 481 (M + H⁺). |
| E51 | 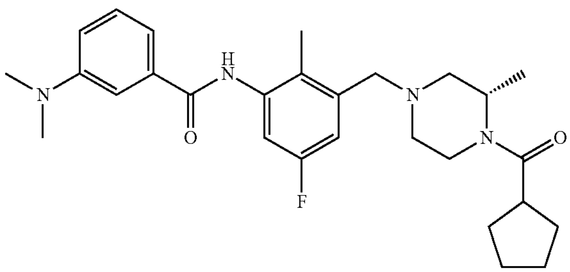 [SMILES: Cc1c(CN2CCN(C(=O)C3CCCC3)[C@@H](C)C2)cc(F)cc1NC(=O)c1cccc(N(C)C)c1] | ¹H NMR (400 MHz, MeOD-d₄) δ 1.17-1.43 (m, 3H), 1.54-1.93 (m, 8H), 1.95-2.26 (m, 2H), 2.29 (s, 3H), 2.69-2.80 (m, 1H), 2.85 (d, 1H), 3.01 (s, 7H), 3.34-3.43 (m, 0.5H), 3.45-3.57 (m, 2H), 3.84 (d, 0.5H), 4.21-4.38 (m, 1H), 4.50 (s, 1H), 4.67 (brs, 1H), 6.98 (dd, 1H), 7.05 (dd, 1H), 7.11 (dd, 1H), 7.23-7.37 (m, 3H). ¹⁹F NMR (376 MHz, MeOD-d₄) δ −119.6. MS (ESI) C₂₈H₃₇FN₄O₂ requires: 480, found 481 (M + H⁺). |
| E52 | 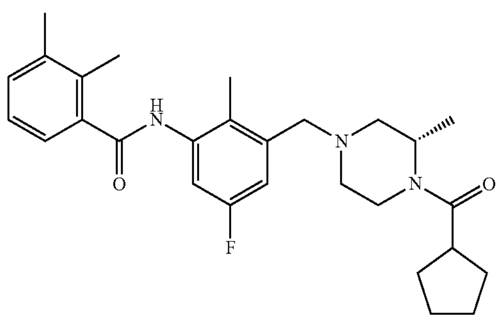 [SMILES: Cc1cccc(C(=O)Nc2cc(F)cc(CN3CCN(C(=O)C4CCCC4)[C@@H](C)C3)c2C)c1C] | ¹H NMR (400 MHz, MeOD-d₄) δ 1.16-1.41 (m, 3H), 1.53-1.95 (m, 8H), 1.95-2.26 (m, 2H), 2.32 (s, 3H), 2.35 (s, 3H), 2.40 (s, 3H), 2.68-3.08 (m, 3.5H), 3.34-3.44 (m, 0.5H), 3.44-3.60 (m, 2H), 3.84 (d, 0.5H), 4.23-4.39 (d, 1H), 4.74 (brs, 0.5H), 7.01-7.10 (m, 1H), 7.14-7.24 (m, 2H), 7.28 (d, 1H), 7.35 (d, 1H). ¹⁹F NMR (376 MHz, MeOD-d₄) δ −119.5. MS (ESI) C₂₈H₃₆FN₃O₂ requires: 465, found 466 (M + H⁺). |
| E53 | 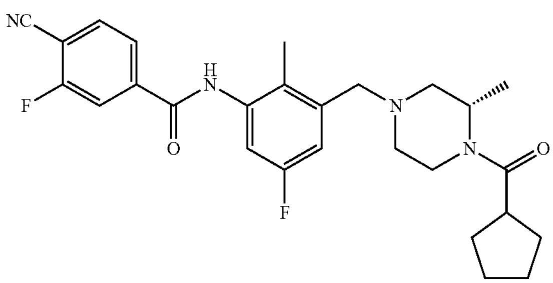 | ¹H NMR (400 MHz, MeOD-d₄) δ 1.18-1.50 (m, 3H), 1.53-1.97 (m, 8H), 2.32 (s, 3H), 2.70-3.20 (m, 4H), 3.34-3.42 (m, 1H), 3.44-3.62 (m, 1H), 4.04-4.39 (m, 3H), 4.62 (brs, 1H), 7.30 (d, 2H), 7.91-8.00 (m, 3H). ¹⁹F NMR (376 MHz, MeOD-d₄) δ −77.2, −108.5, 117.2. MS (ESI) C₂₇H₃₀F₂N₄O₂ requires: 480, found 481 (M + H⁺). |
| E54 | 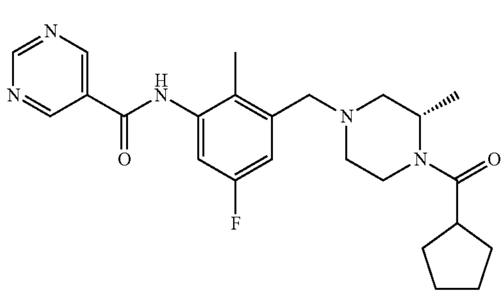 [SMILES: Cc1c(CN2CCN(C(=O)C3CCCC3)[C@@H](C)C2)cc(F)cc1NC(=O)c1cncnc1] | ¹H NMR (400 MHz, MeOD-d₄) δ 1.17-1.43 (m, 3H), 1.50-1.96 (m, 8H), 1.96-2.28 (m, 2H), 2.31 (s, 3H), 2.68-3.09 (m, 3.5H), 3.34-3.45 (m, 0.5H), 3.45-3.61 (m, 2H), 3.85 (d, 0.5H), 4.23-4.38 (m, 1H), 4.49 (s, 1H), 4.68 (brs, 0.5H), 7.13 (ddd, 2H), 9.29 (s, 2H), 9.33 (s, 1H). ¹⁹F NMR (376 MHz, MeOD-d₄) δ −119.2. MS (ESI) C₂₄H₃₀FN₅O₂ requires: 439, found 440 (M + H⁺). |

| Example | Structure | Characterization |
|---|---|---|
| E55 | 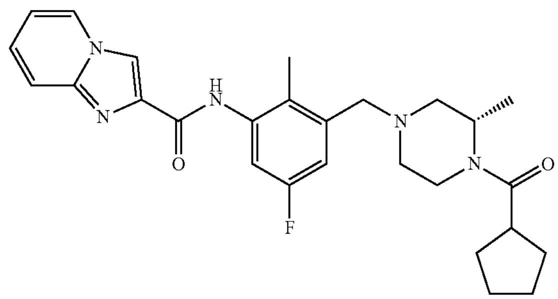 | $^1$H NMR (400 MHz, MeOD-d$_4$) δ 1.16-1.52 (m, 3H), 1.54-1.98 (m, 8H), 2.42 (s, 3H), 2.96-3.28 (m, 3H), 3.35-3.72 (m, 3H), 4.21 (brs, 1H), 4.44 (s, 2H), 4.68 (brs, 1H), 7.18-7.34 (m, 2H), 7.62-7.82 (m, 3H), 8.56-8.71 (m, 2H). $^{19}$F NMR (376 MHz, MeOD-d$_4$) δ −77.2, −77.3, −116.5. MS (ESI) C$_{27}$H$_{32}$FN$_5$O$_2$ requires: 477, found 478 (M + H$^+$). |
| E56 | 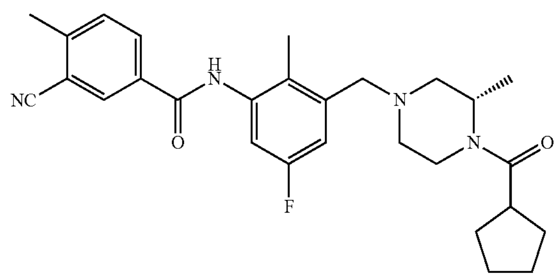 | $^1$H NMR (400 MHz, MeOD-d$_4$) δ 1.18-1.52 (m, 3H), 1.52-1.99 (m, 8H), 2.32 (s, 3H), 2.63 (s, 3H), 2.95-3.26 (m, 4H), 3.35-3.67 (m, 3H), 4.20 (brs, 1H), 4.40 (s, 2H), 4.65 (s, 1H), 7.32 (dq, 2H), 7.61 (d, 1H), 8.15 (dd, 1H), 8.28 (d, 1H). $^{19}$F NMR (376 MHz, MeOD-d$_4$) δ −77.2, −117.0. MS (ESI) C$_{28}$H$_{33}$FN$_4$O$_2$ requires: 476, found 477 (M + H$^+$). |
| E57 | 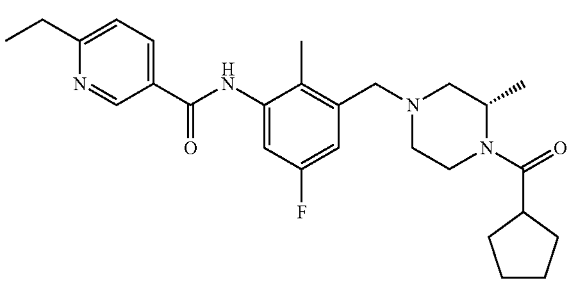 [SMILES: CCc1ccc(C(=O)Nc2cc(F)cc(CN3CCN(C(=O)C4CCCC4)[C@@H](C)C3)c2C)cn1] | $^1$H NMR (400 MHz, MeOD-d$_4$) δ 1.16-1.43 (m, 6H), 1.54-1.95 (m, 8H), 1.95-2.27 (m, 2H), 2.29 (s, 3H), 2.68-3.10 (m, 5.5H), 3.34-3.44 (m, 0.5H), 3.44-3.59 (m, 2H), 3.84 (d, 0.5H), 4.20-4.39 (m, 1H), 4.67 (brs, 0.5H), 7.10 (dd, 2H), 7.47 (d, 1H), 8.29 (dd, 1H), 9.02 (s, 1H). $^{19}$F NMR (376 MHz, MeOD-d$_4$) δ −119.4. MS (ESI) C$_{27}$H$_{35}$FN$_4$O$_2$ requires: 466, found 467 (M + H$^+$). |
| E58 | 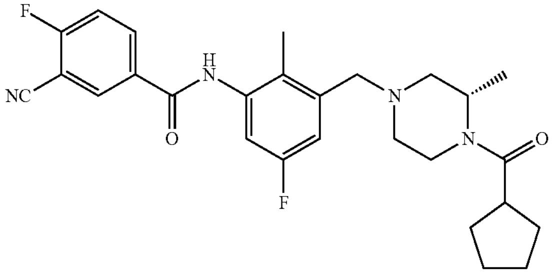 [SMILES: Cc1c(CN2CCN(C(=O)C3CCCC3)[C@@H](C)C2)cc(F)cc1NC(=O)c1ccc(F)c(C#N)c1] | $^1$H NMR (400 MHz, MeOD-d$_4$) δ 1.15-1.43 (m, 3H), 1.53-1.90 (m, 8H), 1.90-2.25 (m, 2H), 2.29 (s, 3H), 2.68-3.11 (m, 3.5H), 3.33-3.46 (m, 0.5H), 3.46-3.60 (m, 2H), 3.85 (d, 0.5H), 4.22-4.39 (m, 1H), 4.59 (s, 0.5H), 4.67 (brs, 0.5H), 7.04-7.15 (m, 2H), 7.54 (t, 1H), 8.29-8.36 (m, 1H), 8.39 (dd, 1H). $^{19}$F NMR (376 MHz, MeOD-d$_4$) δ −107.6, −121.7. MS (ESI) C$_{27}$H$_{30}$F$_2$N$_4$O$_2$ requires: 480, found 481 (M + H$^+$). |

Example 59

(S)-N-(2,4-dichloro-3-((4-(cyclopentanecarbonyl)-3-methylpiperazin-1-yl)methyl)phenyl)-6-methylnicotinamide (E59)

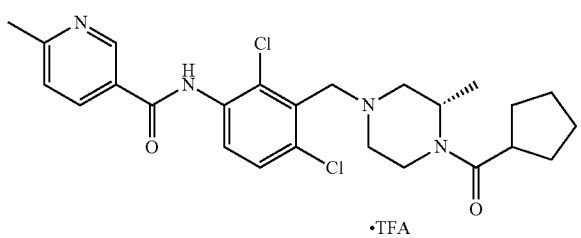 [SMILES: Cc1ccc(C(=O)Nc2ccc(Cl)c(CN3CCN(C(=O)C4CCCC4)[C@@H](C)C3)c2Cl)cn1]

·TFA

Oxalyl dichloride (34.3 mg, 0.270 mmol) was added into a suspension of 6-methylnicotinic acid (37.0 mg, 0.270 mmol) and cat. DMF (0.1 mL) in DCM (2 mL) at 0° C. and the reaction was stirred for 1 hr. Then the mixture was concentrated to give the acyl chloride. Then the acyl chloride was added into a solution of (S)-(4-(3-amino-2,6-dichlorobenzyl)-2-methylpiperazin-1-yl)(cyclopentyl)methanone (100 mg, 0.270 mmol) in pyridine (3 mL). The reaction was stirred at rt overnight. The mixture was purified by MDAP to afford the title compound (8 mg). $^1$H-NMR (MeOD-d$_4$, 400 MHz): 1.34 (br. s., 3H), 1.67 (m, 6 H), 1.84 (m, 3 H), 2.77 (br. s., 3 H), 3.04 (dt, 2 H), 3.19 (br. s., 1 H), 3.40 (br. s., 2 H), 4.48 (d, 3 H), 7.62 (d, 1 H), 7.80 (m, 2 H), 8.62 (m, 1 H), 9.14 (br. s., 1 H). δF (MeOD-d$_4$, 376 MHz): −77.0, −114.0. MS (ES): $C_{25}H_{30}Cl_2N_4O_2$ requires 488; found 489(M+H$^+$).

Example 60

(S)-N-(2-chloro-3-((4-(cyclopentanecarbonyl)-3-methylpiperazin-1-yl)methyl)phenyl)-6-methylnicotinamide, trifluoroacetic acid salt (E60)

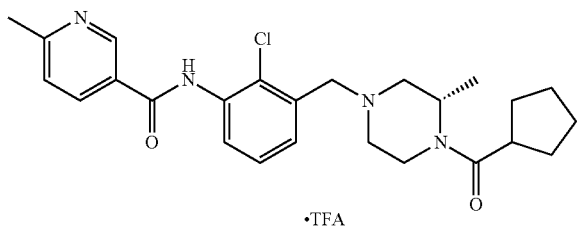 [SMILES: Cc1ccc(C(=O)Nc2cccc(CN3CCN(C(=O)C4CCCC4)[C@@H](C)C3)c2Cl)cn1]

·TFA

To solution of 6-methylnicotinic acid (1.5 g, 10.94 mmol) in DCM (40 mL) with a few drops of DMF was added oxalyl chloride (1.596 mL, 18.23 mmol) dropwise. The resulted mixture was stirred at rt for another 2 hr. The solvent was removed to afford 6-methylnicotinoyl chloride, HCl (1.8 g), which was used directly for the following reactions. The mixture of (S)-(4-(3-amino-2-chlorobenzyl)-2-methylpiperazin-1-yl)(cyclopentyl)methanone (150 mg, 0 447 mmol), 6-methylnicotinoyl chloride, Hydrochloride (94 mg, 0.491 mmol), and DIPEA (0.156 mL, 0.893 mmol) in DCM (3 mL) was stirred at rt overnight. The mixture was purified by MDAP to afford the title compound (45 mg). $^1$H-NMR (MeOD-d$_4$, 400 MHz): 1.31 (br. s., 3 H), 1.66 (m, 6 H), 1.85 (m, 3 H), 2.77 (s, 3 H), 3.04 (m, 1 H), 3.49 (d, 1 H), 3.57 (d, 2 H), 4.22 (br. s., 0.5 H), 4.61 (m, 2.5 H), 7.55 (t, 1 H), 7.68 (d, 1 H), 7.84 (d, 1 H), 7.79 (d, 1 H), 8.63 (dd, 1 H), 9.14 (s, 1 H). δF (MeOD-d$_4$, 376 MHz): −77.2. MS (ES): $C_{25}H_{31}ClN_4O_2$ requires 454; found 455(M+H$^+$).

Example 61

(S)-N-(2-chloro-3-((4-(cyclopentanecarbonyl)-3-methylpiperazin-1-yl)methyl)-5-fluorophenyl)-6-methylnicotinamide, trifluoroacetic acid salt (E61)

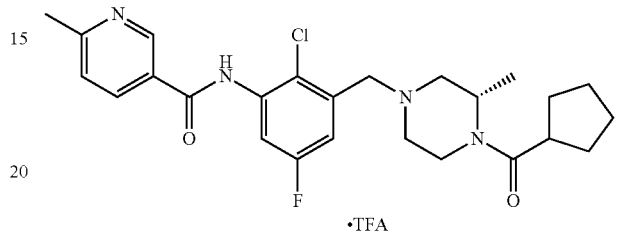

·TFA

To the solution of 6-methylnicotinic acid (2 g, 14.58 mmol) in DCM (50 mL) with a few drops of DMF was added oxalyl chloride (2.55 mL, 29.2 mmol) dropwise at 0° C. using ice water bath under stirring. After the addtion, the resulted reaction mixture was stirred for another 3 hr. Then the solvent was removed by rotavapor to afford 6-methylnicotinoyl chloride, hydrochloride (3.1 g), which was used directly without further purification. To the mixture of (S)-(4-(3-amino-2-chloro-5-fluorobenzyl)-2-methylpiperazin-1-yl)(cyclopentyl)methanone (200 mg, 0 565 mmol) and K2CO3 (156 mg, 1.130 mmol) in acetonitrile (3 mL) was added 6-methylnicotinoyl chloride, hydrochloride (119 mg, 0.622 mmol) at rt. The resulted reaction mixture was stirred overnight. The solid was filtered off and the filtrate was purified by MDAP to afford the title compound (99 mg). $^1$H-NMR (MeOD-d$_4$, 400 MHz): 1.36 (br. s., 3 H), 1.69 (m, 5 H), 1.84 (m, 3 H), 2.78 (s, 3 H), 3.04 (dt, 2 H), 3.18 (dd, 1 H), 3.39 (d, 1 H), 3.48 (d, 1 H), 4.48 (m, 2 H), 7.48 (dd, 1 H), 7.80 (m, 2 H), 8.65 (dd, 1 H), 9.14 (m, 1 H). δF (MeOD-d$_4$, 376 MHz): −77.3, −113.9. MS (ES): $C_{25}H_{30}ClFN_4O_2$ requires 472; found 473(M+H$^+$).

Example 62

(S)-N-(5-chloro-3-((4-(cyclopentanecarbonyl)-3-methylpiperazin-1-yl)methyl)-2-methylphenyl)-6-methylnicotinamide (E62)

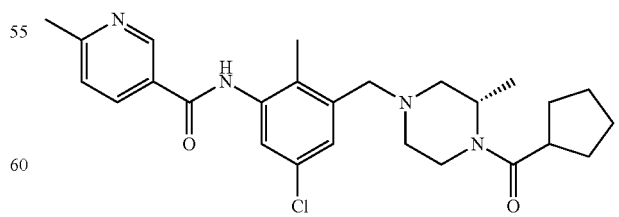

To the solution of 6-methylnicotinic acid (2 g, 14.58 mmol) in DCM (50 mL) with a few drops of DMF was added oxalyl chloride (2.55 mL, 29.2 mmol) dropwise at 0° C. using ice water bath under stirring. After the addition, the resulted reaction mixture was stirred for another 3 hr. Then the solvent was removed by rotavapor to afford 6-methylnicotinoyl chloride, hydrochloride (3.1 g), which was used directly without further purification. To the mixture of (S)-(4-(3-amino-5-chloro-2-methylbenzyl)-2-methylpiperazin-1-yl)(cyclopentyl)methanone (200mg, 0.572 mmol) and K2CO3 (158 mg, 1.143 mmol) in acetonitrile (3 mL) was added 6-methylnicotinoyl chloride, Hydrochloride (121 mg, 0.629 mmol) at rt. The resulted reaction mixture was stirred overnight. The solid was filtered off and the filtrate was purified by MDAP to afford the title compound (62 mg). $^1$H-NMR (MeOD-d$_4$, 400 MHz): 1.23 (d, 2 H), 1.35 (d, 1 H), 1.62 (d, 2 H), 1.70 (br. s., 3 H), 1.80 (br. s., 3 H), 2.07 (m, 1 H), 2.20 (m, 1 H), 2.31 (m, 3 H), 2.62 (m, 3 H), 2.72 (m, 1 H), 2.84 (d, 1 H), 3.02 (d, 1 H), 3.50 (d, 3 H), 3.84 (m, 0.5 H), 4.30 (br. s., 1 H), 4.74 (m, 0.5 H), 7.30 (m, 1 H), 7.36 (d, 1 H), 7.46 (d, 1 H), 8.26 (dd, 1 H), 9.00 (m, 1 H). MS (ES): $C_{26}H_{33}ClN_4O_2$ requires 468; found 469(M+H$^+$).

Example 63

(S)-N-(5-fluoro-3-((4-(3-fluorobenzoyl)-3-methylpiperazin-1-yl)methyl)-2-methylphenyl)-6-methylnicotinamide (E63)

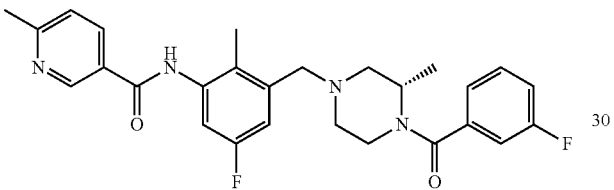

To a solution of 6-methylnicotinic acid (76 mg, 0.556 mmol), HOBT (102 mg, 0.668 mmol) and EDC (128 mg, 0.668 mmol) in THF (8 mL) was added (S)-(4-(3-amino-5-fluoro-2-methylbenzyl)-2-methylpiperazin-1-yl)(3-fluorophenyl)methanone (200 mg, 0.556 mmol) in one charge. The reaction mixture was stirred at rt overnight. The residue was purified by MDAP. The solvent was freeze dried to give the title compound (75 mg). $^1$H-NMR (MeOD-d$_4$, 400 MHz): 1.30 (m, 4 H), 2.24 (br. s., 4 H), 2.58 (s, 5 H), 3.26 (br. s., 3 H), 4.51 (br. s., 2 H), 4.93 (br. s., 3 H), 7.24 (br. s., 4 H), 7.31 (br. s., 3 H), 7.51 (m, 3 H), 8.26 (d, 1 H), 9.04 (s, 1 H), 10.13 (br. s., 1 H). δF (MeOD-d$_4$, 376 MHz): –110.9, –178.3. MS (ES): $C_{27}H_{28}F_2N_4O_2$ requires 478; found 479 (M+H$^+$).

Example 64

N-(1-((S)-4-(cyclopentanecarbonyl)-3-methylpiperazin-1-yl)-2,3-dihydro-1H-inden-4-yl)-6-methylnicotinamide (E64)

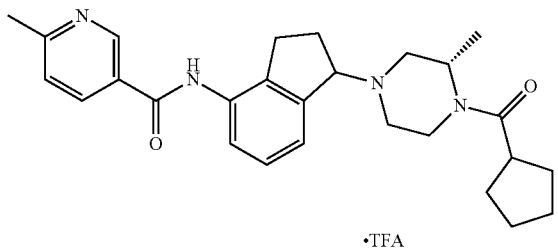 [SMILES: Cc1ccc(C(=O)Nc2cccc3c2CCC3N2CCN(C(=O)C3CCCC3)[C@@H](C)C2)cn1]

To the solution of ((2S)-4-(4-amino-2,3-dihydro-1H-inden-1-yl)-2-methylpiperazin-1-yl)(cyclopentyl)methanone (100 mg, 0.305 mmol) and 6-methylnicotinic acid (41.9 mg, 0 305 mmol) in DMF (10 mL) was added DIEA (0.107 mL, 0.611 mmol), HOBt (56.1 mg, 0.366 mmol) and then EDC (70.2 mg, 0.366 mmol). The resulted mixture was stirred at RT overnight. The reaction was quenched with methanol (10 mL), and concentrated. The residue was purified by MDAP to afford the title compound (29 mg). $^1$H-NMR (MeOD-d$_4$, 400 MHz): 1.35 (m, 4 H), 1.62 (br. s., 3 H), 1.70 (br. s., 3 H), 1.82 (m, 4 H), 2.60 (m, 2 H), 2.76 (m, 3 H), 2.98 (m, 4 H), 3.17 (m, 3 H), 3.40 (m, 1 H), 3.57 (br. s., 1 H), 3.67 (m, 1 H), 4.21 (br. s., 0.5 H), 4.67 (br. s., 0.5 H), 5.10 (m, 1 H), 7.46 (m, 1 H), 7.59 (d, 2 H), 7.86 (d, 1 H), 8.72 (d, 1 H), 9.17 (s, 1 H). δF (MeOD-d$_4$, 376 MHz): –77.2. MS (ES): $C_{27}H_{34}N_4O_2$ requires 446; found 447(M+H$^+$).

Example 65

N-(3-((S)-4-(cyclopentanecarbonyl)-3-methylpiperazin-1-yl)-2,3-dihydro-1H-inden-5-yl)-6-methylnicotinamide, trifluoroacetic acid salt (E65)

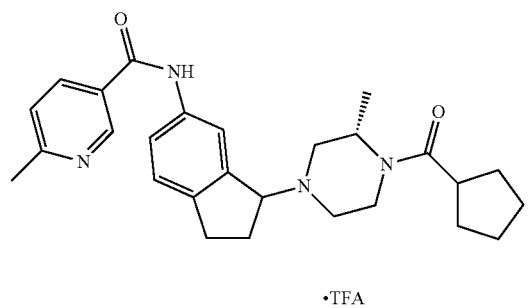 [SMILES: Cc1ccc(C(=O)Nc2ccc3c(c2)C(N2CCN(C(=O)C4CCCC4)[C@@H](C)C2)CC3)cn1]

To the solution of ((2S)-4-(6-amino-2,3-dihydro-1H-inden-1-yl)-2-methylpiperazin-1-yl)(cyclopentyl)methanone (150 mg, 0.458 mmol) and 6-methylnicotinic acid (126 mg, 0.916 mmol) in DMF (10 mL) was added DIPEA (0.160 mL, 0.916 mmol), 1H-benzo[d][1,2,3]triazol-1-ol hydrate (140 mg, 0.916 mmol) and then N1-((ethylimino)methylene)-N3,N3-dimethylpropane-1,3-diamine hydrochloride (176 mg, 0.916 mmol). The resulted mixture was stirred at RT for 4 hr. The reaction mixture was quenched with methanol (10 mL), and concentrated. The residue was purified by MDAP to afford the title compound (85 mg). $^1$H-NMR (DMSO-d$_6$, 400 MHz): 1.20 (dd, 2 H), 1.35 (m, 1 H), 1.51 (br. s., 6 H), 1.71 (m, 3 H), 2.57 (m, 4 H), 2.94 (m, 6 H), 3.43 (br. s., 2 H), 4.10 (br. s., 0.5 H), 4.51 (br. s., 1 H), 4.79 (br. s., 0.5H), 5.06 (m, 1 H), 7.39 (d, 1 H), 7.50 (d, 1 H), 7.64 (m, 1 H), 8.20 (br. s., 1 H), 8.28 (d, 1 H), 9.04 (s, 1 H), 10.54 (br. s., 1 H). δF (MeOD-d$_4$, 376 MHz): –74.3. MS (ES): $C_{27}H_{34}N_4O_2$ requires 446; found 447(M+H$^+$).

Example 66

(S)-3-cyano-N-(3-((4-(cyclopentanecarbonyl)-3-methylpiperazin-1-yl)methyl)-5-fluoro-2-methylphenyl)benzamide (E66)

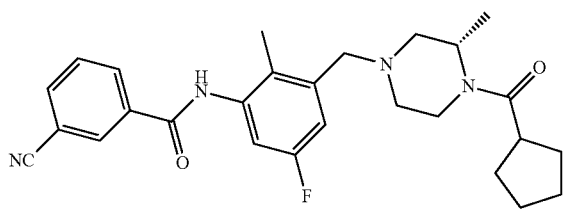 [SMILES: Cc1c(CN2CCN(C(=O)C3CCCC3)[C@@H](C)C2)cc(F)cc1NC(=O)c1cccc(C#N)c1]

The mixture of (S)-(4-(3-amino-5-fluoro-2-methylbenzyl)-2-methylpiperazin-1-yl)(cyclopentyl) methanone (100 mg, 0.3 mmol), HATU (125 mg, 0.33 mmol), 3-cyanobenzoic acid (48.5 mg, 0.33 mmol)and DIPEA (116 mg, 0.9 mmol) in DCM (2 mL) and DMF (2 mL) was stirred at rt overnight. After most of the solvent was removed, the residue was purified by MDAP to afford the title compound (8 mg). $^1$H-NMR (MeOD-$d_4$, 400 MHz): 1.25 (m, 2 H), 1.35 (m, 1 H), 1.65 (m, 6 H), 1.81 (m, 3 H), 1.91 (br. s., 1 H), 2.07 (m, 1 H), 2.20 (m, 1 H), 2.29 (s, 3 H), 2.75 (m, 1 H), 2.86 (d, 1 H), 3.00 (m, 2 H), 3.39 (m, 1 H), 3.51 (m, 2 H), 3.85 (d, 0.5 H), 4.33 (m, 1 H), 4.67 (br. s., 0.5 H), 7.10 (m, 2 H), 7.73 (t, 1 H), 7.97 (d, 1 H), 8.26 (d, 1 H), 8.33 (s, 1 H). δF (MeOD-$d_4$, 376 MHz): −119.4. MS (ES): $C_{27}H_{31}FN_4O_2$ requires 462; found 463(M+H$^+$).

Example 67

N-(3-(((S)-4-(cyclopentanecarbonyl)-3-methylpiperazin-1-yl)methyl)-4-fluoro-2-methylphenyl)bicyclo[3.1.0]hexane-6-carboxamide, trifluoroacetic acid salt (E67)

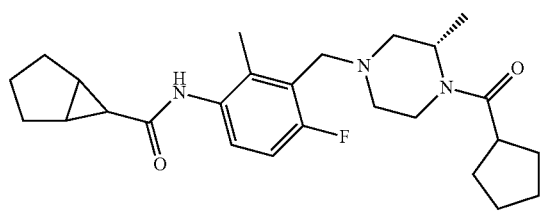

·TFA

The mixture of (S)-(4-(3-amino-6-fluoro-2-methylbenzyl)-2-methylpiperazin-1-yl)(cyclopentyl)methanone (200 mg, 0.6 mmol), HATU (251 mg, 0.66 mmol), bicyclo[3.1.0]hexane-6-carboxylic acid (76 mg, 0.6 mmol) and DIPEA (233 mg, 1.799 mmol) in DCM (3 mL) and DMF (3 mL) was stirred at rt overnight. The mixture was purified by MDAP to afford the title compound (137 mg). $^1$H-NMR (MeOD-$d_4$, 400 MHz):1.24 (m, 3 H), 1.41 (m., 1 H), 1.67 (m, 7 H), 1.87 (m, 9 H), 2.33 (s, 3 H), 3.04 (m, 3 H), 3.45 (t, 3 H), 4.14 (br. s., 0.5 H), 4.42 (m., 2 H), 4.62 (br. s., 0.5 H), 7.12 (t, 1 H), 7.40 (dd, 1 H). δF (MeOD-$d_4$, 376 MHz): −77.6, −116.5. MS (ES): $C_{26}H_{36}FN_3O_2$ requires 441; found 442(M+H$^+$).

Examples 68-108

Examples 68-108 were prepared using a similar procedure to that described for Example 67.

E 68: N-(2-chloro-3-{[(3R,5S)-4-(cyclopentylcarbonyl)-3,5-dimethyl-1-piperazinyl]methyl}phenyl)-2-[4-(ethylsulfonyl)phenyl]acetamide, trifluoroacetic acid salt E69: N-(2-chloro-3-{[(3R,5S)-4-(cyclopentylcarbonyl)-3,5-dimethyl-1-piperazinyl]methyl}phenyl)-2,6-difluorobenzamide E70: N-(3-(((S)-4-(cyclopentanecarbonyl)-3-methylpiperazin-1-yl)methyl)-4-fluoro-2-methylphenyl)-2,2-dimethylcyclopropanecarboxamide, trifluoroacetic acid salt E71: (S)-N-(3-((4-(cyclopentanecarbonyl)-3-methylpiperazin-1-yl)methyl)-4-fluoro-2-methylphenyl)-1-fluorocyclopentanecarboxamide, trifluoroacetic acid salt E72: (S)-N-(3-((4-(cyclopentanecarbonyl)-3-methylpiperazin-1-yl)methyl)-4-fluoro-2-methylphenyl)-3-phenylpropanamide, trifluoroacetic acid salt E73: (S)-N-(3-((4-(cyclopentanecarbonyl)-3-methylpiperazin-1-yl)methyl)-4-fluoro-2-methylphenyl)-1-phenylcyclopropanecarboxamide, trifluoroacetic acid salt E74: (S)-N-(3-((4-(cyclopentanecarbonyl)-3-methylpiperazin-1-yl)methyl)-4-fluoro-2-methylphenyl)-2-(2-fluorophenyl)acetamide, trifluoroacetic acid salt E75: (S)-N-(3-((4-(cyclopentanecarbonyl)-3-methylpiperazin-1-yl)methyl)-4-fluoro-2-methylphenyl)-2-(3-methoxyphenyl)acetamide, trifluoroacetic acid salt E76: (S)-N-(3-(((S)-4-(cyclopentanecarbonyl)-3-methylpiperazin-1-yl)methyl)-4-fluoro-2-methylphenyl)-2-methoxy-2-phenylacetamide, trifluoroacetic acid salt E77: (S)-N-(3-(((S)-4-(cyclopentanecarbonyl)-3-methylpiperazin-1-yl)methyl)-4-fluoro-2-methylphenyl)-2-phenylpropanamide, trifluoroacetic acid salt E78: N-(3-(((S)-4-(cyclopentanecarbonyl)-3-methylpiperazin-1-yl)methyl)-4-fluoro-2-methylphenyl)-2-fluoro-2-phenylacetamide, trifluoroacetic acid salt E79: trans-N-(3-(((S)-4-(cyclopentanecarbonyl)-3-methylpiperazin-1-yl)methyl)-4-fluoro-2-methylphenyl)-2-phenylcyclopropanecarboxamide, trifluoroacetic acid salt E80: (R)-N-(3-(((S)-4-(cyclopentanecarbonyl)-3-methylpiperazin-1-yl)methyl)-4-fluoro-2-methylphenyl)-2-methoxy-2-phenylacetamide, trifluoroacetic acid salt E81: (S)-N-(3-((4-(cyclopentanecarbonyl)-3-methylpiperazin-1-yl)methyl)-5-fluoro-2-methylphenyl)-3-(3-fluorophenyl)propanamide, trifluoroacetic acid salt E82: (S)-N-(3-((4-(cyclopentanecarbonyl)-3-methylpiperazin-1-yl)methyl)-5-fluoro-2-methylphenyl)-2,3-dihydro-1H-indene-2-carboxamide, trifluoroacetic acid salt E83: (S)-N-(3-((4-(cyclopentanecarbonyl)-3-methylpiperazin-1-yl)methyl)-5-fluoro-2-methylphenyl)-1-methyl-1H-pyrazole-4-carboxamide E84: (S)-N-(3-((4-(cyclopentanecarbonyl)-3-methylpiperazin-1-yl)methyl)-5-fluoro-2-methylphenyl)-1H-indole-2-carboxamide, trifluoroacetic acid salt E85: (R)-N-(3-(((S)-4-(cyclopentanecarbonyl)-3-methylpiperazin-1-yl)methyl)-4-fluoro-2-methylphenyl)-2-phenylpropanamide E86: N-(3-(((S)-4-(cyclopentanecarbonyl)-3-methylpiperazin-1-yl)methyl)-4-fluoro-2-methylphenyl)-3-oxabicyclo[3.1.0]hexane-6-carboxamide, trifluoroacetic acid salt E87: (S,Z)-N-(3-((4-(cyclopentanecarbonyl)-3-methylpiperazin-1-yl)methyl)-4-fluoro-2-methylphenyl)-2-fluoro-3-phenylacrylamide, trifluoroacetic acid salt E88: (S)-N-(3-((4-(cyclopentanecarbonyl)-3-methylpiperazin-1-yl)methyl)-5-fluoro-2-methylphenyl)-3-phenylpropanamide, trifluoroacetic acid salt E89: (S)-N-(3-((4-(cyclopentanecarbonyl)-3-methylpiperazin-1-yl)methyl)-5-fluoro-2-methylphenyl)-2-(2-fluorophenyl)acetamide, trifluoroacetic acid salt E90: (1 S,2S)-N-(3-(((S)-4-(cyclopentanecarbonyl)-3-methylpiperazin-1-yl)methyl)-5-fluoro-2-methylphenyl)-2-phenylcyclopropanecarboxamide, trifluoroacetic acid salt E91: (S)-N-(3-((4-(cyclopentanecarbonyl)-3-methylpiperazin-1-yl)methyl)-5-fluoro-2-methylphenyl)-2-cyclopropylacetamide E92: (1S,2S)-N-(2-chloro-3-(((S)-4-(cyclopentanecarbonyl)-3-methylpiperazin-1-yl)methyl)phenyl)-2-phenylcyclopropanecarboxamide, trifluoroacetic acid salt E93: (S)-N-(2-chloro-3-((4-(cyclopentanecarbonyl)-3-methylpiperazin-1-yl)methyl)phenyl)-3-phenylpropanamide, trifluoroacetic acid salt E94: N-(2-chloro-3-(((S)-4-(cyclopentanecarbonyl)-3-methylpiperazin-1-yl)methyl)phenyl)bicyclo[3.1.0]hexane-6-carboxamide E95: (S)-N-(3-((4-(cyclopentanecarbonyl)-3-methylpiperazin-1-yl)methyl)-5-fluoro-2-methylphenyl)-3-(3-methoxyphenyl)propanamide, trifluoroacetic acid salt E96: (S)-N-(3-((4-(cyclopentanecarbonyl)-3-methylpiperazin-1-yl)methyl)-5-fluoro-2-methylphenyl)-3-(4-methoxyphenyl)propanamide, trifluoroacetic acid salt E97: (S)-N-(3-((4-(cyclopentanecarbonyl)-3-methylpiperazin-1-yl)methyl)-5-fluoro-2-methylphenyl)-3-(2-methoxyphenyl)propanamide, trifluoroacetic acid salt E98: (S)-N-(3-((4-(cyclopentanecarbonyl)-3-methylpiperazin-1-yl)methyl)-5-fluoro-2-methylphenyl)-3-(4-fluorophenyl)propanamide, trifluoroacetic acid salt E99: (S)-N-(3-((4-(cyclopentanecarbonyl)-3-methylpiperazin-1-yl)methyl)-5-fluoro-2-methylphenyl)-3,3-difluorocyclobutanecarboxamide, trifluoroacetic acid salt E100: (S)-N-(3-((4-(cyclopentanecarbonyl)-3-methylpiperazin-1-yl)methyl)-5-fluoro-2-methylphenyl)cyclopentanecarboxamide, trifluoroacetic acid salt E101: N-(3-(((S)-4-(cyclopentanecarbonyl)-3-methylpiperazin-1-yl)methyl)-5-fluoro-2-methylphenyl)bicyclo[3.1.0]hexane-6-carboxamide E102: (S)-N-(3-((4-(cyclopentanecarbonyl)-3-methylpiperazin-1-yl)methyl)-5-fluoro-2-methylphenyl)-2-phenoxyacetamide, trifluoroacetic acid salt E103: (S)-N-(3-((4-(cyclopentanecarbonyl)-3-methylpiperazin-1-yl)methyl)-5-fluoro-2-methylphenyl)-4-methylbenzamide E104: (S)-N-(3-((4-(cyclopentanecarbonyl)-3-methylpiperazin-1-yl)methyl)-5-fluoro-2-methylphenyl)benzamide, trifluoroacetic acid salt E105: (S)-N-(3-((4-(cyclopentanecarbonyl)-3-methylpiperazin-1-yl)methyl)-5-fluoro-2-methylphenyl)-3-(2-fluorophenyl)propanamide, trifluoroacetic acid salt E106: (S)-3-acetyl-N-(3-((4-(cyclopentanecarbonyl)-3-methylpiperazin-1-yl)methyl)-5-fluoro-2-methylphenyl)benzamide E107: (S)-N-(3-((4-(cyclopentanecarbonyl)-3-methylpiperazin-1-yl)methyl)-5-fluoro-2-methylphenyl)-3-(methoxymethyl)benzamide E108: N-(3-(((S)-4-(cyclopentanecarbonyl)-3-methylpiperazin-1-yl)methyl)-5-fluoro-2-methylphenyl)-3-fluorocyclopentanecarboxamide, formic acid salt

| Example | Structure | Characterization |
|---|---|---|
| E68 | 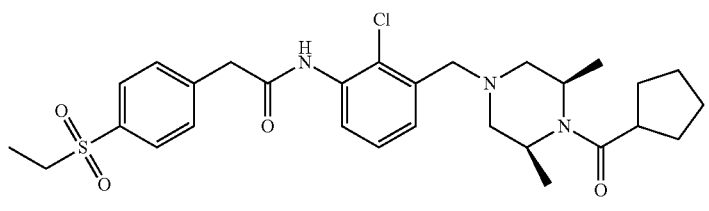 •TFA | $^1$H-NMR (MeOD-d$_4$, 400 MHz) 7.79 (m, 2H), 7.69 (d, 1H, J = 7.6 Hz), 7.57 (d, 2H, J = 7.6 Hz), 7.45 (d, 1H, J = 6.0 Hz), 733 (t, 1H, J = 7.8 Hz), 4.57-4.37 (m, 4H), 3.84 (s, 2H), 3.25 (brs, 2H), 3.09 (m, 3H), 2.91 (m, 2H), 1.76--1.51 (m, 8H), 1.30 (s, 6H), 1.11 (t, 3H, J = 7.4 Hz). δF (MeOD-d$_4$, 376 MHz): −77.3. MS (ES): C$_{29}$H$_{38}$ClN$_3$O$_4$S requires 559; found 560 (M + H$^+$). |
| E69 | 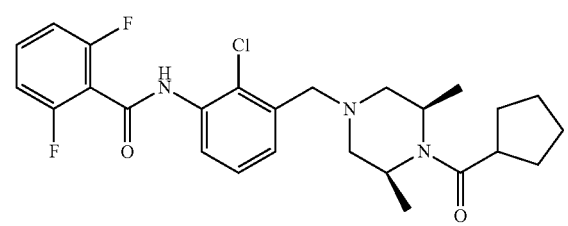 •TFA | $^1$H-NMR (MeOD-d$_4$, 400 MHz)7.76 (d, 1H), 7.45 (m, 3H), 7.01 (m, 2H), 4.55 (brs, 2H), 4.24 (brs, 2H), 3.17 (m, 3H), 2.92 (m, 2H), 1.77--1.52 (m, 8H), 1.31 (m, 6H). δF (MeOD-d$_4$, 376 MHz): −77.1, −115.0, −116.3. MS (ES): C$_{26}$H$_{30}$ClF$_2$N$_3$O$_2$ requires 489; found 490(M + H$^+$). |
| E70 | 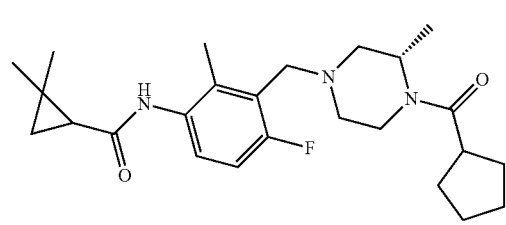 •TFA | $^1$H-NMR (MeOD-d$_4$, 400 MHz): 0.87 (dd, 1 H), 1.13 (t, 1 H), 1.24 (m, 6 H), 1.29 (br. s., 2 H), 1.41 (m, 1 H), 1.65 (m, 3 H), 1.73 (dd, 3 H), 1.85 (m, 3 H), 2.34 (s, 3 H), 3.09 (m, 3 H), 3.47 (t, 3 H), 4.16 (m, 0.5 H), 4.44 (br. s., 2 H), 4.64 (br. s., 1 H), 4.96 (m., 0.5 H), 7.14 (t, 1 H), 7.38 (dd, 1 H). δF (MeOD-d$_4$, 376 MHz): −77.1, −114.8. MS (ES): C$_{25}$H$_{36}$FN$_3$O$_2$ requires 429; found 430(M + H$^+$). |

| Example | Structure | Characterization |
|---|---|---|
| E71 | 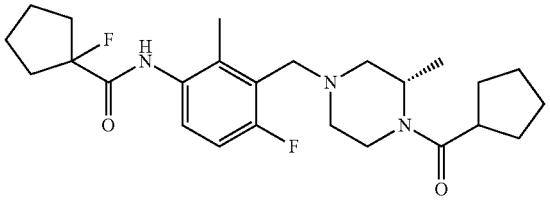 ·TFA | ¹H-NMR (MeOD-d₄, 400 MHz): 1.29 (br. s., 3 H), 1.64 (m, 3 H), 1.72 (br. s., 2 H), 1.94 (m, 10 H), 2.14 (m, 4 H), 2.28 (dd, 1 H), 2.34 (s, 3 H), 3.03 (m, 2 H), 3.16 (m, 1 H), 3.46 (m, 3 H), 4.14 (m, 0.5 H), 4.40 (br. s., 2 H), 4.61 (br. s., 0.5 H), 7.17 (t, 1 H), 7.42 (dd, 1 H). δF (MeOD-d₄, 376 MHz): −77.1, −114.3, −150.6. MS (ES): $C_{25}H_{35}F_2N_3O_2$ requires 447; found 448(M + H⁺). |
| E72 | 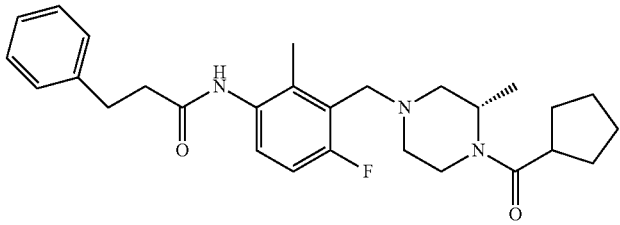 ·TFA | ¹H-NMR (MeOD-d₄, 400 MHz): 1.27 (br. s., 2 H), 1.40 (br. s., 1 H), 1.64 (m, 3 H), 1.72 (br. s., 2 H), 1.84 (d, 3 H), 2.15 (s, 3 H), 2.75 (m, 2 H), 3.09 (m, 4 H), 3.36 (br. s., 1 H), 3.48 (m, 1 H), 4.12 (m, 0.5 H), 4.30 (br. s., 2 H), 4.58 (br. s., 0.5 H), 7.09 (t, 1 H), 7.20 (m, 1 H), 7.28 (m, 4 H). δF (MeOD-d₄, 376 MHz): −77.0, −114.8. MS (ES): $C_{28}H_{36}FN_3O_2$ requires 465; found 466(M + H⁺). |
| E73 | 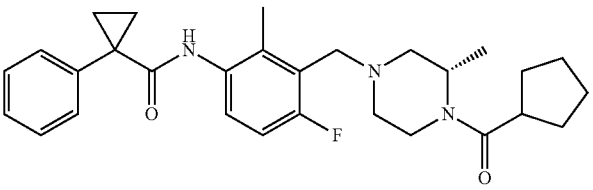 ·TFA | ¹H-NMR (MeOD-d₄, 400 MHz): 1.24 (m, 4 H), 1.37 (br. s., 1 H), 1.62 (m, 5 H), 1.83 (br. s., 5 H), 2.14 (s, 3 H), 3.02 (br. s., 2 H), 4.23 (m, 2.5 H), 4.55 (br. s., 0.5 H), 7.08 (t, 1 H), 7.42 (m, 4 H), 7.57 (d, 2 H). δF (MeOD-d₄, 376 MHz): −77.2. MS (ES): $C_{29}H_{36}F_2N_3O_2$ requires 447; found 448(M + H⁺). |
| E74 | 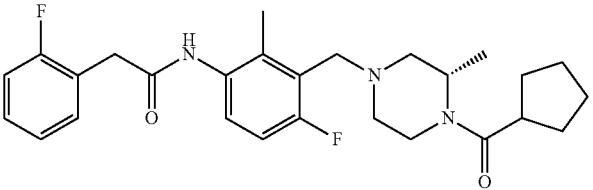 ·TFA | ¹H-NMR (MeOD-d₄, 400 MHz): 1.39 (br. s., 3 H), 1.71 (br. s., 8 H), 2.32 (s, 3 H), 3.07 (m, 3 H), 3.46 (d, 3 H), 3.82 (s, 2 H), 4.12 (m, 0.5 H), 4.37 (br. s., 2 H), 4.60 (br. s., 0.5 H), 7.14 (m, 3 H), 7.32 (m, 1 H), 7.41 (m, 2 H). δF (MeOD-d₄, 376 MHz): −77.3, −119.1. MS (ES): $C_{27}H_{33}F_2N_3O_2$ requires 469; found 470(M + H⁺). |
| E75 | 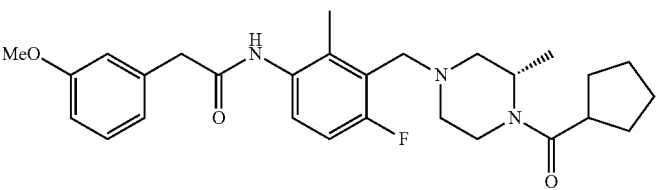 ·TFA | ¹H-NMR (MeOD-d₄, 400 MHz): 1.27 (br. s., 3 H), 1.63 (m, 5 H), 1.84 (m, 3 H), 2.24 (s, 3 H), 3.03 (m, 3 H), 3.45 (t, 2 H), 3.70 (m, 2 H), 3.79 (m, 3 H), 4.13 (m, 0.5H), 4.42 (br. s., 2 H), 4.64 (m, 0.5H), 6.84 (m, 1 H), 6.98 (m, 2 H), 7.14 (t, 1 H), 7.26 (m, 1 H), 7.41 (dd, 1 H). δF (MeOD-d₄, 376 MHz): −79.4, −116.7. MS (ES): $C_{28}H_{36}FN_3O_3$ requires 481; found 482(M + H⁺). |
| E76 | 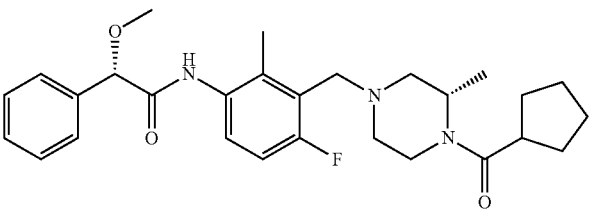 ·TFA | ¹H-NMR (MeOD-d₄, 400 MHz): 1.14 (d, 2 H), 1.26 (d, 1 H), 1.72 (m, 8 H), 1.93 (m, 1 H), 2.03 (br. s., 1 H), 2.19 (m, 4 H), 2.72 (m, 2 H), 2.98 (br. s., 1 H), 3.51 (m, 5 H), 3.79 (d, 0.5 H), 4.25 (br. s., 1 H), 4.63 (br. s., 0.5 H), 4.83 (s, 1 H), 6.91 (t, 1 H), 7.20 (dd, 1 H), 7.38 (m, 3 H), 7.54 (d, 2 H). δF (MeOD-d₄, 376 MHz): −77.3, −114.7. MS (ES): $C_{28}H_{36}FN_3O_3$ requires 481; found 482(M + H⁺). |

| Example | Structure | Characterization |
|---|---|---|
| E77 | 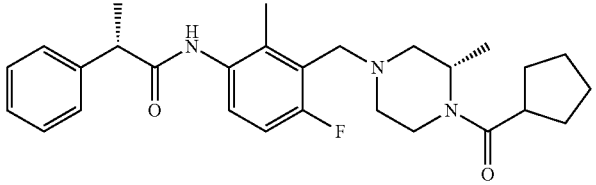 ·TFA | ¹H-NMR (MeOD-d₄, 400 MHz): 1.03 (d, 2 H), 1.16 (d, 1 H), 1.44 (d, 3 H), 1.68 (d, 9 H), 2.08 (m, 4 H), 2.58 (m, 2 H), 2.88 (br. s., 1 H), 3.39 (m, 2 H), 3.78 (q, 1 H), 4.15 (br. s., 0.5H), 4.53 (m, 0.5 H), 6.80 (t, 1 H), 7.03 (dd, 1 H), 7.16 (m, 1 H), 7.25 (t, 2 H), 7.34 (d, 2 H). δF (MeOD-d₄, 376 MHz): −77.3, −114.7. MS (ES): $C_{28}H_{36}FN_3O_2$ requires 465; found 466(M + H⁺). |
| E78 | 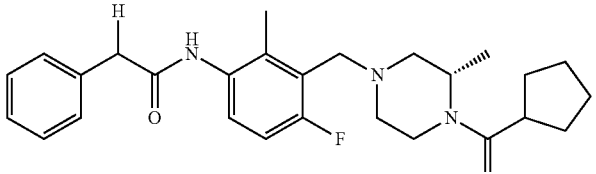 ·TFA | ¹H-NMR (MeOD-d₄, 400 MHz): 1.04 (d, 2 H), 1.18 (m, 1 H), 1.64 (m, 9 H), 2.09 (m, 4 H), 2.64 (m, 3 H), 2.87 (m, 1 H), 3.39 (m, 2 H), 3.67 (br. s., 0.5 H), 4.15 (br. s., 1 H), 4.53 (br. s., 0.5 H), 6.78 (t, 1 H), 6.98 (m, 1 H), 7.24 (m, 0.5 H), 7.32 (m, 3 H), 7.35 (m, 0.5 H), 7.52 (d, 2 H). δF (MeOD-d₄, 376 MHz): −76.9, −122.7, −168.8, −177.8, −177.9. MS (ES): $C_{27}H_{33}F_2N_3O_2$ requires 469; found 470(M + H⁺). |
| E79 | 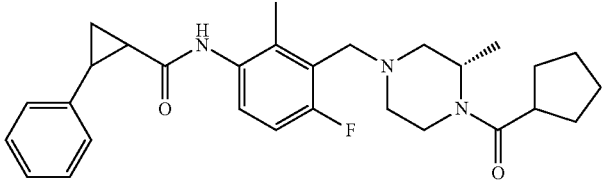 ·TFA | ¹H-NMR (MeOD-d₄, 400 MHz): 1.29 (br. s., 2 H), 1.40 (ddd, 2 H), 1.62 (m, 6 H), 1.85 (m, 3 H), 2.15 (m, 1 H), 2.36 (s, 3 H), 2.48 (m, 1 H), 3.09 (m, 3 H), 3.46 (t, 3 H), 4.17 (d, 0.5 H), 4.44 (br. s., 2 H), 4.63 (br. s., 0.5 H), 7.18 (m, 4 H), 7.30 (m, 2 H), 7.46 (dd, 1 H). δF (MeOD-d₄, 376 MHz): −77.6, −114.7. MS (ES): $C_{29}H_{36}FN_3O_2$ requires 477; found 478(M + H⁺). |
| E80 | 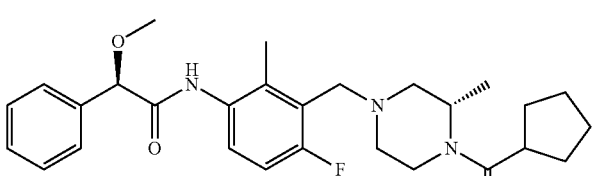 ·TFA | ¹H-NMR (MeOD-d₄, 400 MHz): 1.14 (d, 2 H), 1.26 (d, 1 H), 1.79 (m, 9 H), 2.21 (m, 4 H), 2.97 (m, 4 H), 3.49 (m, 5 H), 3.79 (d, 0.5 H), 4.27 (m, 1 H), 4.63 (br. s., 0.5 H), 4.83 (s, 1 H), 6.91 (t, 1 H), 7.20 (dd, 1 H), 7.38 (m, 3 H), 7.54 (m, 2 H). δF (MeOD-d₄, 376 MHz): −77.0, −114.0. MS (ES): $C_{28}H_{36}FN_3O_3$ requires 481; found 482(M + H⁺). |
| E81 | 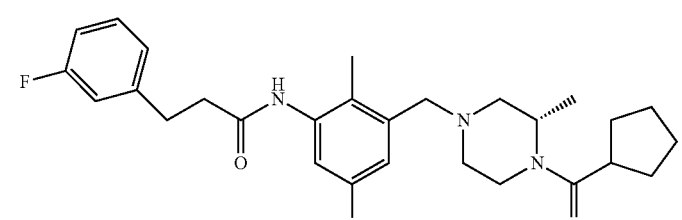 ·TFA | ¹H-NMR (MeOD-d₄, 400 MHz): 1.20 (d, 2 H), 1.33 (d, 1 H), 1.65 (m, 5 H), 1.79 (d, 2 H), 2.07 (s, 3 H), 1.95 (m, 1 H), 2.17 (m, 1 H), 2.74 (m, 4 H), 2.90 (t, 1 H), 3.03 (m, 3 H), 3.37 (m, 1 H), 3.42 (br. s., 2 H), 3.80 (br. s., 0.5 H), 4.28 (br. s., 1 H), 4.64 (br. s., 0.5 H), 6.97 (m, 4 H), 7.09 (d, 1 H), 7.28 (m, 1 H). δF (MeOD-d₄, 376 MHz): 76.9, 115.6. MS (ES): $C_{28}H_{35}F_2N_3O_2$ requires 483; found 484(M + H⁺). |
| E82 | 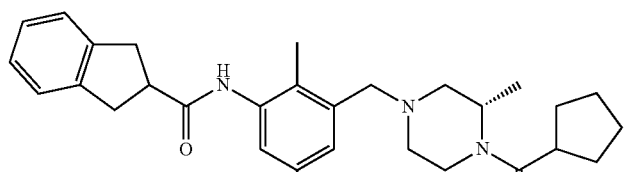 ·TFA | ¹H-NMR (MeOD-d₄, 400 MHz): 1.22 (d, 2 H), 1.34 (d, 1 H), 1.62 (br. s., 2 H), 1.69 (br. s., 3 H), 1.79 (d, 3 H), 1.90 (br. s., 1 H), 2.03 (br. s., 1 H), 2.13 (br. s., 1 H), 2.25 (s, 3 H), 2.68 (br. s., 1 H), 2.81 (br. s., 1 H), 2.99 (br. s., 1 H), 3.25 (m, 4 H), 3.50 (m, 3 H), 3.81 (br. s., 0.5 H), 4.29 (br. s., 1 H), 4.65 (br. s., 0.5 H), 6.97 (d, 1 H), 7.12 (m, 3 H), 7.20 (d, 2 H). δF (MeOD-d₄, 376 MHz): 77.3, 117.1. MS (ES): $C_{29}H_{36}FN_3O_2$ requires 477; found 478(M + H⁺). |

| Example | Structure | Characterization |
|---|---|---|
| E83 | 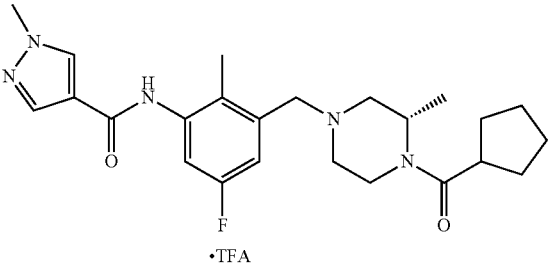 [SMILES: Cc1c(CN2CCN(C(=O)C3CCCC3)[C@@H](C)C2)cc(F)cc1NC(=O)c1cnn(C)c1] ·TFA | $^1$H-NMR (MeOD-d$_4$, 400 MHz): 1.05 (d, 1 H), 1.23 (d, 2 H), 1.36 (d, 1 H), 1.66 (br. s., 6 H), 1.79 (br. s., 3 H), 2.04 (s, 2 H), 2.26 (s, 3 H), 2.75 (m, 1 H), 2.85 (d, 1 H), 3.02 (d, 2 H), 3.50 (m, 2 H), 3.84 (d, 0.5 H), 3.95 (s, 3 H), 4.30 (br. s., 1 H), 4.66 (br. s., 0.5 H), 7.01 (m, 2 H), 7.99 (br. s., 1 H), 8.16 (s, 1 H). δF (MeOD-d$_4$, 376 MHz): −119.6. MS (ES): C$_{24}$H$_{32}$FN$_5$O$_2$ requires 441; found 442(M + H$^+$). |
| E84 | 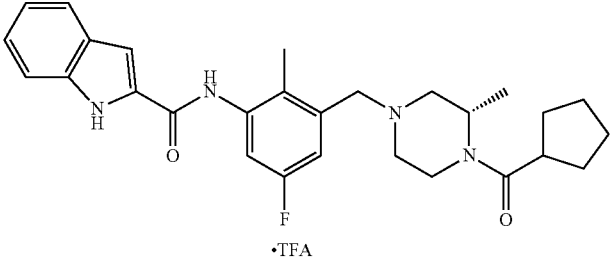 [SMILES: Cc1c(CN2CCN(C(=O)C3CCCC3)[C@@H](C)C2)cc(F)cc1NC(=O)c1cc2ccccc2[nH]1] ·TFA | $^1$H-NMR (MeOD-d$_4$, 400 MHz): 1.25 (m, 2 H), 1.36 (m, 1 H), 1.71 (m, 9 H), 2.03 (br. s., 1 H), 2.19 (br. s., 1 H), 2.32 (s, 3 H), 2.74 (br. s., 1 H), 2.85 (d, 1 H), 3.00 (br. s., 1 H), 3.50 (br. s., 2 H), 3.81 (br. s., 0.5 H), 4.30 (br. s., 1 H), 4.49 (br. s., 1 H), 4.66 (br. s., 0.5 H), 7.08 (m, 2 H), 7.17 (d, 1 H), 7.25 (m, 2 H), 7.47 (d, 1H), 7.65 (d, 1 H). δF (MeOD-d$_4$, 376 MHz): −76.9, −119.5. MS (ES): C$_{28}$H$_{38}$FN$_4$O$_2$ requires 476; found 477(M + H$^+$). |
| E85 | 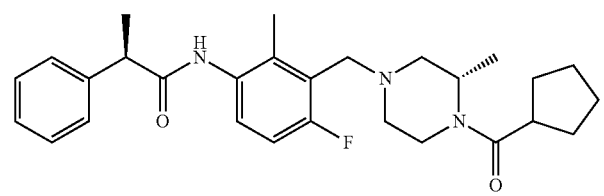 [SMILES: Cc1c(NC(=O)[C@H](C)c2ccccc2)ccc(F)c1CN1CCN(C(=O)C2CCCC2)[C@@H](C)C1] | $^1$H-NMR (MeOD-d$_4$, 400 MHz): 1.11 (d, 2 H), 1.24 (d, 1 H), 1.53 (d, 3 H), 1.68 (m, 8 H), 1.94 (m, 2 H), 2.14 (m, 4 H), 2.65 (t, 1 H), 2.74 (d, 1 H), 2.83 (t, 0.5 H), 2.97 (dt, 1 H), 3.22 (t, 0.5 H), 3.46 (m, 2 H), 3.75 (d, 0.5 H), 3.88 (q, 1 H), 4.26 (m, 1 H), 4.62 (br. s., 0.5 H), 6.88 (t, 1 H), 7.13 (m, 1 H), 7.25 (m, 1 H), 7.33 (t, 2 H), 7.43 (d, 2 H). δF (MeOD-d$_4$, 376 MHz): −120.7. MS (ES): C$_{28}$H$_{36}$FN$_3$O$_2$ requires 465; found 466(M + H$^+$). |
| E86 | 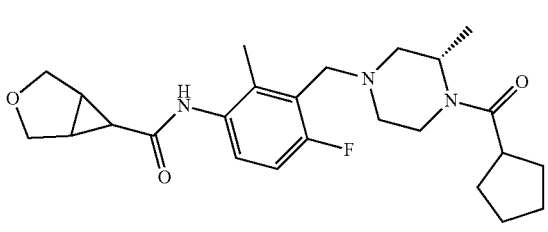 ·TFA | $^1$H-NMR (MeOD-d$_4$, 400 MHz): 1.15 (d, 2 H), 1.28 (d, 1 H), 1.65 (m, 5 H), 1.80 (m, 4 H), 1.93 (m, 1 H), 2.06 (m, 1 H), 2.20 (m, 3 H), 2.35 (m, 3 H), 2.69 (m, 1 H), 2.79 (d, 1 H), 2.87 (t, 0.5 H), 3.01 (m, 1 H), 3.28 (m, 0.5 H), 3.52 (m, 2 H), 3.79 (m, 2.5 H), 3.96 (d, 2 H), 4.28 (m, 1 H), 4.65 (br. s., 0.5 H), 6.91 (t, 1 H), 7.23 (m, 1 H). δF (MeOD-d$_4$, 376 MHz): −77.1, −114.2. MS (ES): C$_{25}$H$_{34}$FN$_3$O$_3$ requires 443; found 444(M + H$^+$). |
| E87 | 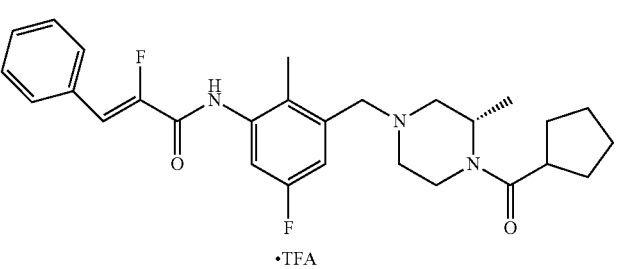 [SMILES: Cc1c(CN2CCN(C(=O)C3CCCC3)[C@@H](C)C2)cc(F)cc1NC(=O)/C(F)=C/c1ccccc1] ·TFA | $^1$H-NMR (MeOD-d$_4$, 400 MHz): 1.17 (d, 2 H), 1.29 (d, 1 H), 1.62 (m, 2 H), 1.70 (br. s., 5 H), 2.05 (br. s., 2 H), 2.20 (m, 1 H), 2.34 (s, 3 H), 2.73 (d, 1 H), 2.83 (d, 3 H), 3.00 (m, 1 H), 3.52 (m, 2 H), 3.81 (d, 0.5 H), 4.28 (m, 1 H), 4.65 (br. s., 0.5 H), 6.85 (m, 2 H), 7.04 (dd, 1 H), 7.31 (m, 1 H), 7.39 (m, 2 H), 7.66 (d, 2 H). δF (MeOD-d$_4$, 376 MHz): −77.2, −129.2. MS (ES): C$_{28}$H$_{33}$F$_2$N$_3$O$_2$ requires 481; found 482(M + H$^+$). |

| Example | Structure | Characterization |
|---|---|---|
| E88 | 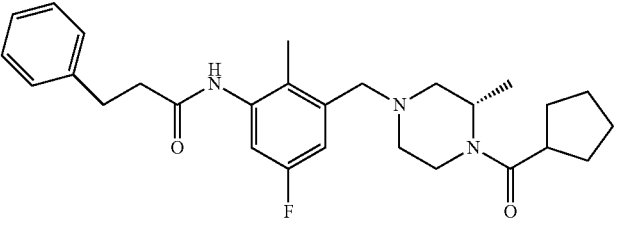 ·TFA | $^1$H-NMR (MeOD-d$_4$, 400 MHz): 1.21 (d, 2 H), 1.34 (d, 1 H), 1.64 (m, 6 H), 1.79 (m, 2 H), 2.04 (s, 4 H), 2.16 (m, 1 H), 2.71 (m, 3 H), 2.81 (d, 1 H), 3.02 (m, 3 H), 3.43 (br. s., 2 H), 3.81 (br. s., 0.5 H), 4.28 (br. s., 1 H), 4.65 (br. s., 0.5 H), 6.95 (m, 2 H), 7.21 (m, 1 H), 7.29 (m, 4 H). δF (MeOD-d$_4$, 376 MHz): −77.2, −117.3. MS (ES): C$_{28}$H$_{36}$FN$_3$O$_2$ requires 465; found 466(M + H$^+$). |
| E89 | 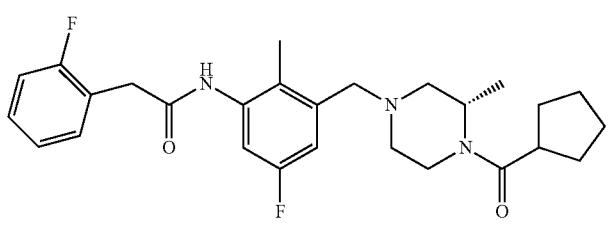 ·TFA | $^1$H-NMR (MeOD-d$_4$, 400 MHz): 1.21 (d, 2 H), 1.34 (d, 1 H), 1.64 (m, 5 H), 1.78 (m, 3 H), 1.96 (br. s., 1 H), 2.04 (d, 1 H), 2.16 (m, 4 H), 2.71 (t, 1 H), 2.82 (d, 1 H), 3.00 (m, 1 H), 3.44 (m, 2 H), 3.80 (d, 0.5 H), 4.28 (br. s., 1 H), 4.65 (br. s., 0.5 H), 6.96 (d, 1 H), 7.08 (m, 2 H), 7.15 (m, 1 H), 7.30 (m, 1 H), 7.41 (m, 1 H). δF (MeOD-d$_4$, 376 MHz): −77.2, −116.9, −118.9. MS (ES): C$_{27}$H$_{33}$F$_2$N$_3$O$_2$ requires 469; found 470(M + H$^+$). |
| E90 | 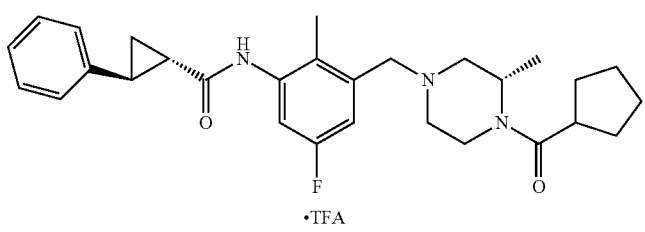 [SMILES: Cc1c(CN2CCN(C(=O)C3CCCC3)[C@@H](C)C2)cc(F)cc1NC(=O)[C@H]1C[C@@H]1c1ccccc1] ·TFA | $^1$H-NMR (MeOD-d$_4$, 400 MHz): 1.21 (d, 2 H), 1.35 (br. s., 2 H), 1.61 (br. s., 6 H), 1.79 (m, 2 H), 2.03 (br. s., 1 H), 2.17 (m, 2 H), 2.25 (s, 3 H), 2.48 (br. s., 1 H), 2.70 (d, 1 H), 2.82 (d, 1 H),2.98 (m, 1 H), 3.46 (br. s., 2 H), 3.81 (br. s., 0.5 H), 4.29 (br. s., 1 H), 4.65 (br. s., 0.5 H), 6.96 (d, 1 H), 7.17 (m, 4 H), 7.28 (t, 2 H). δF (MeOD-d$_4$, 376 MHz): −77.2, −117.1. MS (ES): C$_{29}$H$_{36}$FN$_3$O$_2$ requires 477; found 478(M + H$^+$). |
| E91 | 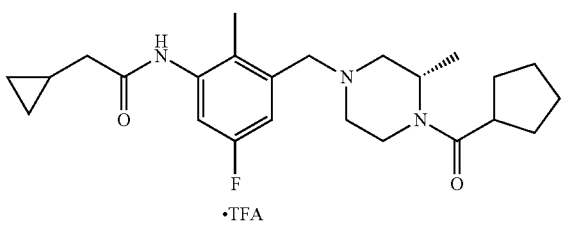 [SMILES: Cc1c(CN2CCN(C(=O)C3CCCC3)[C@@H](C)C2)cc(F)cc1NC(=O)CC1CC1] ·TFA | $^1$H-NMR (MeOD-d$_4$, 400 MHz): 0.29 (d, 2 H), 0.61 (d, 2 H), 1.15 (m, 1 H), 1.22 (d, 2 H), 1.34 (d, 1 H), 1.64 (m, 5 H), 1.84 (m, 3 H), 2.00 (m, 1 H), 2.17 (m, 1 H), 2.23 (m, 3 H), 2.31 (d, 2 H), 2.72 (m, 1 H), 2.82 (d, 1 H), 2.99 (m, 1.5 H), 3.43 (m, 2.5 H), 3.83 (d, 0.5 H), 4.31 (m, 1 H), 4.66 (br. s., 0.5 H), 6.98 (d, 1 H), 7.12 (d, 1 H). δF (MeOD-d$_4$, 376 MHz): −119.4. MS (ES): C$_{24}$H$_{34}$FN$_3$O$_2$ requires 415; found 416(M + H$^+$). |
| E92 | 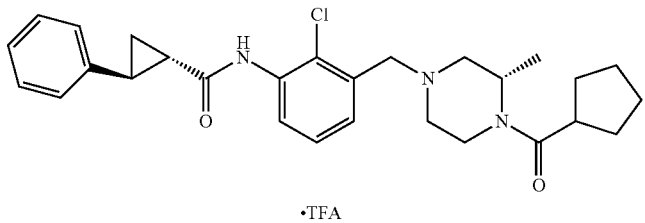 [SMILES: C[C@H]1CN(Cc2cccc(NC(=O)[C@H]3C[C@@H]3c3ccccc3)c2Cl)CCN1C(=O)C1CCCC1] ·TFA | $^1$H-NMR (MeOD-d$_4$, 400 MHz): 1.29 (br. s., 2 H), 1.42 (m, 2 H), 1.62 (m, 7 H), 1.83 (br. s., 3 H), 2.24 (br. s., 1 H), 2.51 (dt, 1 H), 3.03 (d, 2 H), 3.14 (br. s., 2 H), 3.45 (br. s., 3 H), 4.16 (m, 0.5 H), 4.43 (m, 2 H), 4.62 (br. s., 1 H), 4.98 (m, 0.5 H), 7.19 (m, 3 H), 7.29 (m, 2 H), 7.48 (m, 2 H), 7.87 (d, 1 H). δF (MeOD-d$_4$, 376 MHz): −77.2. MS (ES): C$_{28}$H$_{34}$ClN$_3$O$_2$ requires 479; found 480(M + H$^+$). |
| E93 | 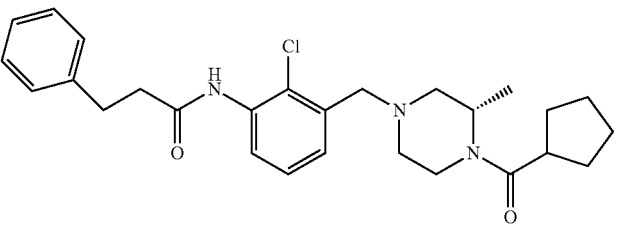 ·TFA | $^1$H-NMR (MeOD-d$_4$, 400 MHz): 1.28 (br. s., 2 H), 1.43 (m, 1 H), 1.64 (m, 6 H), 1.83 (br. s., 3 H), 2.78 (m, 2 H), 3.03 (t, 5 H), 4.16 (br. s., 0.5H), 4.38 (m, 2 H), 4.60 (br. s., 1 H), 4.99 (br. s., 0.5H), 7.19 (m, 1 H), 7.28 (m, 4 H), 7.43 (t, 1 H), 7.50 (d, 1 H), 7.69 (d, 1 H). δF (MeOD-d$_4$, 376 MHz): −77.2. MS (ES): C$_{27}$H$_{34}$ClN$_3$O$_2$ requires 467; found 468(M + H$^+$). |

| Example | Structure | Characterization |
|---|---|---|
| E94 | 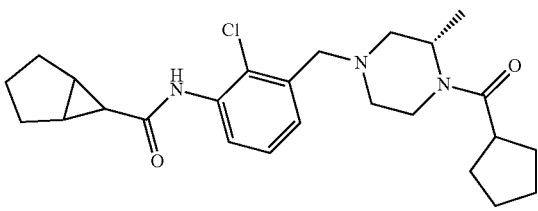 •TFA | ¹H-NMR (MeOD-d₄, 400 MHz): 1.25 (d, 3 H), 1.38 (d, 2 H), 1.66 (m, 6 H), 1.85 (m, 11 H), 2.11 (br. s., 1 H), 2.23 (m, 1 H), 2.75 (m, 1 H), 2.86 (br. s., 1 H), 3.02 (d, 2 H), 3.39 (br. s., 0.5 H), 3.61 (m, 2 H), 3.83 (br. s., 0.5 H), 4.30 (br. s., 1 H), 4.66 (br. s., 1 H), 7.27 (t, 1 H), 7.35 (d, 1 H), 7.66 (d, 1 H). MS (ES): $C_{25}H_{34}ClN_3O_2$ requires 443; found 444(M + H⁺). |
| E95 | 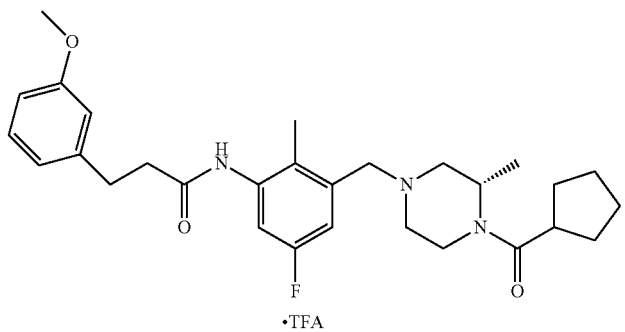 [SMILES: COc1cccc(CCC(=O)Nc2cc(F)cc(CN3CCN(C(=O)C4CCCC4)[C@@H](C)C3)c2C)c1] •TFA | ¹H-NMR (MeOD-d₄, 400 MHz): 1.21 (d, 2 H), 1.33 (m, 2 H), 1.61 (br. s., 2 H), 1.70 (br. s., 6 H), 2.07 (d, 3 H), 2.72 (t, 3 H), 2.99 (t, 4 H), 3.43 (br. s., 2 H), 3.77 (s, 3.5 H), 4.29 (m, 1 J), 4.65 (br. s., 0.5 H), 6.76 (d, 1 H), 6.85 (m, 2 H), 6.96 (m, 2 H), 7.19 (t, 1 H). δF (MeOD-d₄, 376 MHz): −77.2, −118.2. MS (ES): $C_{29}H_{38}FN_3O_3$ requires 495; found 496(M + H⁺). |
| E96 | 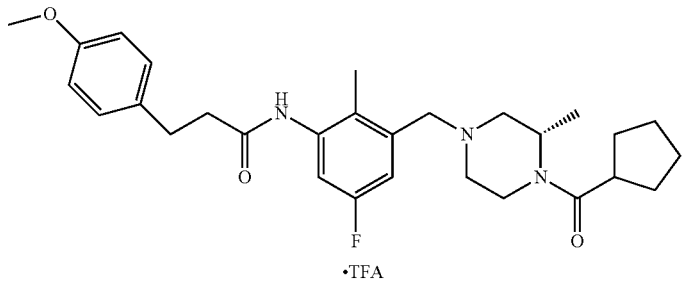 [SMILES: COc1ccc(CCC(=O)Nc2cc(F)cc(CN3CCN(C(=O)C4CCCC4)[C@@H](C)C3)c2C)cc1] •TFA | ¹H-NMR (MeOD-d₄, 400 MHz): 1.29 (br. s., 3 H), 1.64 (m, 2 H), 1.72 (br. s., 3 H), 1.84 (dd, 3 H), 2.10 (s, 3 H), 2.72 (m, 2 H), 2.97 (t, 3 H), 3.03 (m, 2 H), 3.41 (br. s., 1 H), 3.76 (s, 3 H), 4.15 (m, 0.5 H), 4.31 (d, 2 H), 4.59 (br. s., 0.5 H), 6.85 (d, 2 H), 7.18 (m, 4 H). δF (MeOD-d₄, 376 MHz): −77.2, −117.3. MS (ES): $C_{29}H_{38}FN_3O_3$ requires 495; found 496(M + H⁺). |
| E97 | 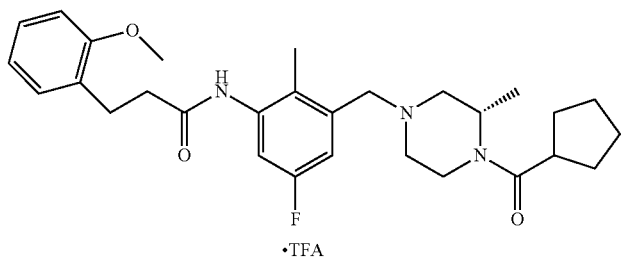 [SMILES: COc1ccccc1CCC(=O)Nc1cc(F)cc(CN2CCN(C(=O)C3CCCC3)[C@@H](C)C2)c1C] •TFA | ¹H-NMR (MeOD-d₄, 400 MHz): 1.27 (br. s., 3 H), 1.64 (m, 2 H), 1.72 (br. s., 3 H), 1.83 (m, 3 H), 2.13 (s, 3 H), 2.72 (t, 2 H), 3.02 (t, 4 H), 3.51 (br. s., 0.5 H), 3.85 (s, 3 H), 4.23 (br. s., 2 H), 4.58 (br. s., 0.5 H), 6.86 (t, 1 H), 6.95 (d, 1 H), 7.18 (m, 4 H). δF (MeOD-d₄, 376 MHz): −77.1, −117.6. MS (ES): $C_{29}H_{38}FN_3O_3$ requires 495; found 496(M + H⁺). |
| E98 | 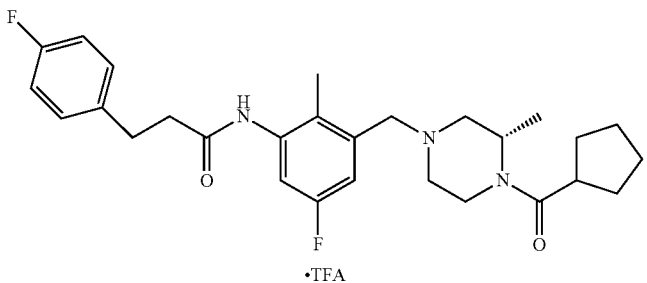 [SMILES: Cc1c(CN2CCN(C(=O)C3CCCC3)[C@@H](C)C2)cc(F)cc1NC(=O)CCc1ccc(F)cc1] •TFA | ¹H-NMR (MeOD-d₄, 400 MHz): 1.27 (br. s., 2 H), 1.39 (br. s., 1 H), 1.64 (br. s., 4 H), 1.83 (br. s., 4 H), 2.10 (s, 3 H), 2.75 (m, 2 H), 3.03 (m, 5 H), 3.52 (br. s., 1 H), 4.13 (br. s., 0.5 H), 4.27 (br. s., 2 H), 4.59 (br. s., 0.5 H), 7.02 (t, 2 H), 7.18 (t, 2 H), 7.29 (dd, 2 H). δF (MeOD-d₄, 376 MHz): −77.1, −117.4, −119.2. MS (ES): $C_{28}H_{32}F_2N_3O_2$ requires 483; found 484(M + H⁺). |

| Example | Structure | Characterization |
|---|---|---|
| E99 | 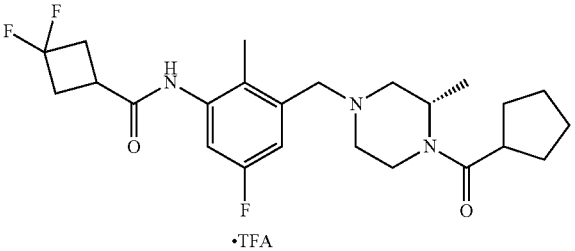 [SMILES: Cc1c(CN2CCN(C(=O)C3CCCC3)[C@@H](C)C2)cc(F)cc1NC(=O)C1CC(F)(F)C1] •TFA | ¹H-NMR (MeOD-d₄, 400 MHz): 1.28 (br. s., 2 H), 1.41 (br. s., 1 H), 1.65 (m, 3 H), 1.72 (br. s., 2 H), 1.84 (m, 3 H), 2.27 (s, 3 H), 2.86 (m, 5 H), 3.03 (m, 2 H), 3.20 (m, 2 H), 3.40 (m, 2 H), 4.15 (br. s., 0.5 H), 4.35 (br. s., 2 H), 4.62 (br. s., 0.5 H), 7.25 (m, 1 H), 7.33 (d, 1 H). δF (MeOD-d₄, 376 MHz): −77.0, −83.7, −84.2, −98.7, −99.2, −117.1. MS (ES): $C_{24}H_{32}F_3N_3O_2$ requires 451; found 452(M + H⁺). |
| E100 | 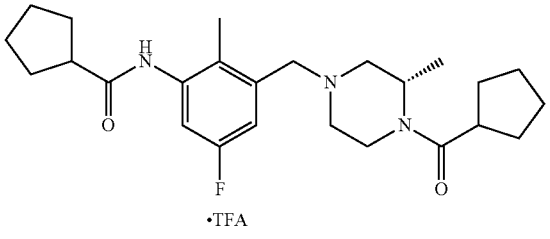 [SMILES: Cc1c(CN2CCN(C(=O)C3CCCC3)[C@@H](C)C2)cc(F)cc1NC(=O)C1CCCC1] •TFA | ¹H-NMR (MeOD-d₄, 400 MHz): 1.28 (br. s., 2 H), 1.40 (br. s., 1 H), 1.68 (m, 7 H), 1.83 (m, 8 H), 2.01 (m, 2 H), 2.26 (s, 3 H), 2.92 (quin, 1 H), 3.04 (dt, 2 H), 3.15 (br. s., 1 H), 3.37 (d, 1 H), 3.44 (d, 1 H), 3.54 (br. s., 0.5 H), 4.15 (br. s., 0.5 H), 4.36 (br. s., 2 H), 4.62 (br. s., 1 H), 7.25 (t, 2 H). δF (MeOD-d₄, 376 MHz): −77.7, −117.3. MS (ES): $C_{25}H_{36}FN_3O_2$ requires 429; found 430(M + H⁺). |
| E101 | 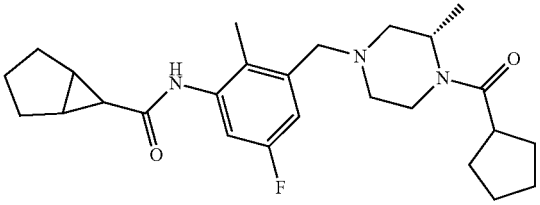 [SMILES: Cc1c(CN2CCN(C(=O)C3CCCC3)[C@@H](C)C2)cc(F)cc1NC(=O)C1C2CCCC21] | ¹H-NMR (MeOD-d₄, 400 MHz): 1.22 (d, 3 H), 1.34 (d, 1 H), 1.62 (m, 3 H), 1.69 (br. s., 5 H), 1.86 (m, 10 H), 2.00 (m, 1 H), 2.16 (d, 1 H), 2.24 (s, 3 H), 2.72 (m, 1 H), 2.82 (d, 1 H), 2.98 (m, 2 H), 3.43 (m, 3 H), 3.83 (d, 0.5 H), 4.29 (br. s., 1 H), 4.66 (br. s., 0.5 H), 6.94 (d, 1 H), 7.12 (d, 1 H). δF (MeOD-d₄, 376 MHz): −119.6. MS (ES): $C_{26}H_{36}FN_3O_2$ requires 441; found 442(M + H⁺). |
| E102 | 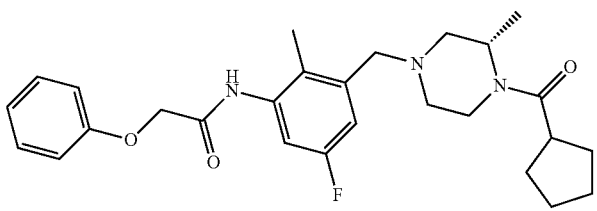 •TFA | ¹H-NMR (MeOD-d₄, 400 MHz): 1.27 (br. s., 2 H), 1.37 (br. s., 1 H), 1.64 (m, 3 H), 1.72 (br. s., 3 H), 1.83 (br. s., 4 H), 2.22 (s, 3 H), 3.04 (m, 3 H), 3.48 (br. s., 1 H), 4.23 (br. s., 3 H), 4.57 (br. s., 1 H), 7.05 (m, 3 H), 7.21 (d, 1 H), 7.34 (m, 2 H), 7.41 (d, 1 H). δF (MeOD-d₄, 376 MHz): −77.3, −117.2. MS (ES): $C_{27}H_{34}FN_3O_3$ requires 467; found 468(M + H⁺). |
| E103 | 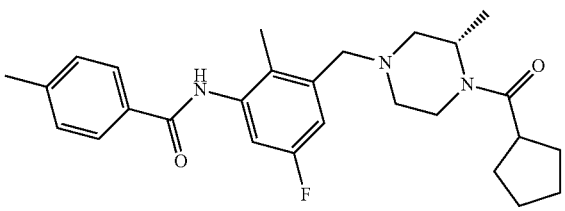 [SMILES: Cc1ccc(C(=O)Nc2cc(F)cc(CN3CCN(C(=O)C4CCCC4)[C@@H](C)C3)c2C)cc1] | ¹H-NMR (MeOD-d₄, 400 MHz): 1.24 (d, 2 H), 1.36 (d, 1 H), 1.65 (m, 6 H), 1.81 (m, 3 H), 2.02 (m, 1 H), 2.20 (m, 1 H), 2.28 (s, 3 H), 2.44 (m, 3 H), 2.77 (m, 1 H), 2.86 (d, 1 H), 3.01 (m, 2 H), 3.36 (m, 1 H), 3.50 (m, 2 H), 3.85 (d, 0.5 H), 4.32 (m, 1 H), 4.67 (br. s., 0.5 H), 7.09 (m, 2 H), 7.34 (m, 2 H), 7.87 (m, 2 H). δF (MeOD-d₄, 376 MHz): −119.6. MS (ES): $C_{27}H_{34}FN_3O_2$ requires 451; found 452(M + H⁺). |
| E104 | 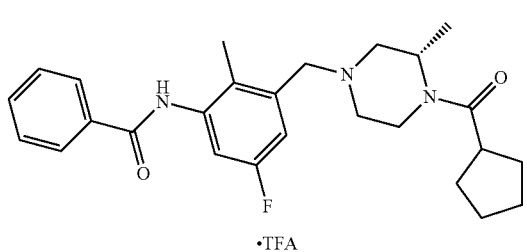 [SMILES: Cc1c(CN2CCN(C(=O)C3CCCC3)[C@@H](C)C2)cc(F)cc1NC(=O)c1ccccc1] •TFA | ¹H-NMR (MeOD-d₄, 400 MHz): 1.30 (br. s., 2 H), 1.43 (br. s., 1 H), 1.65 (m, 3 H), 1.72 (br. s., 3 H), 1.85 (m, 3 H), 2.33 (s, 3 H), 3.06 (m, 3 H), 3.41 (d, 1 H), 3.48 (d, 1 H), 3.57 (br. s., 1 H), 4.17 (br. s., 0.5 H), 4.41 (br. s., 2 H), 4.64 (br. s., 0.5 H), 7.32 (d, 2 H), 7.55 (m, 2 H), 7.63 (m, 1 H), 7.99 (d, 2 H). δF (MeOD-d₄, 376 MHz): −77.1, −117.1. MS (ES): $C_{28}H_{32}FN_3O_2$ requires 437; found 438(M + H⁺). |

| Example | Structure | Characterization |
|---|---|---|
| E105 | 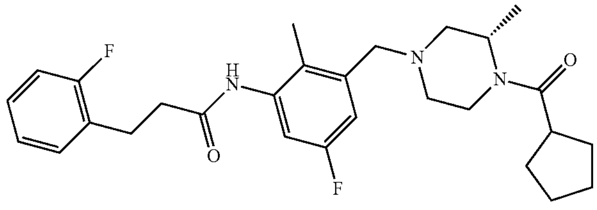 | $^1$H-NMR (MeOD-d$_4$, 400 MHz): 1.27 (br. s., 2 H), 1.40 (br. s., 1 H), 1.65 (m, 3 H), 1.72 (br. s., 2 H), 1.84 (m, 3 H), 2.13 (s, 3 H), 2.77 (t, 2 H), 3.06 (m, 5 H), 3.35 (d, 1 H), 3.43 (d, 1 H), 3.48 (br. s., 1 H), 4.15 (br. s., 0.5 H), 4.33 (br. s., 2 H), 4.62 (br. s., 0.5 H), 7.09 (m, 2 H), 7.22 (m, 3 H), 7.30 (q, 1 H). δF (MeOD-d$_4$, 376 MHz): −77.1, −117.3, −120.5. MS (ES): C$_{28}$H$_{35}$F$_2$N$_3$O$_2$ requires 483; found 484(M + H$^+$). |
| E106 | 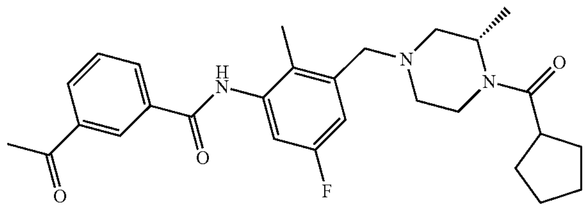 [SMILES: CC(=O)c1cccc(C(=O)Nc2cc(F)cc(CN3CCN(C(=O)C4CCCC4)[C@@H](C)C3)c2C)c1] | $^1$H-NMR (MeOD-d$_4$, 400 MHz): 1.30 (m, 4 H), 1.61 (d, 3 H), 1.70 (br. s., 3 H), 1.80 (br. s., 3 H), 2.07 (m, 1 H), 2.20 (m, 1 H), 2.30 (s, 3 H), 2.67 (s, 3 H), 2.75 (m, 1 H), 2.86 (m, 1 H), 3.01 (m, 2 H), 3.38 (t, 1 H), 3.51 (d, 2 H), 3.84 (m, 0.5 H), 4.32 (m, 1 H), 4.67 (m, 0.5 H), 7.10 (m, 2 H), 7.67 (t, 1 H), 8.21 (m, 2 H), 8.58 (s, 1 H). δF (MeOD-d$_4$, 376 MHz): −115.9. MS (ES): C$_{28}$H$_{34}$FN$_3$O$_3$ requires 479; found 480(M + H$^+$). |
| E107 | 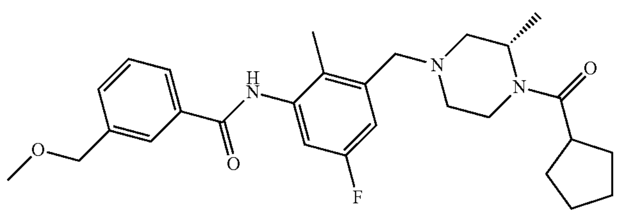 [SMILES: COCc1cccc(C(=O)Nc2cc(F)cc(CN3CCN(C(=O)C4CCCC4)[C@@H](C)C3)c2C)c1] | $^1$H-NMR (MeOD-d$_4$, 400 MHz): 1.23 (d, 2 H), 1.29 (br. s., 1 H), 1.35 (d, 2 H), 1.61 (m, 3 H), 1.70 (br. s., 4 H), 1.80 (br. s., 3 H), 1.91 (m, 1 H), 2.03 (m, 1 H), 2.18 (m, 1 H), 2.28 (s, 4 H), 2.73 (m, 1 H), 2.84 (d, 1 H), 3.00 (m, 2 H), 3.40 (m, 4 H), 3.49 (br. s., 3 H), 3.82 (d, 0.5 H), 4.33 (m, 1 H), 4.54 (s, 3 H), 4.66 (br. s., 0.5 H), 7.09 (m, 3 H), 7.50 (t, 1 H), 7.57 (d, 1 H), 7.90 (d, 1 H), 7.95 (s, 1 H). δF (MeOD-d$_4$, 376 MHz): −119.3. MS (ES): C$_{28}$H$_{36}$FN$_3$O$_3$ requires 481; found 482(M + H$^+$). |
| E108 | 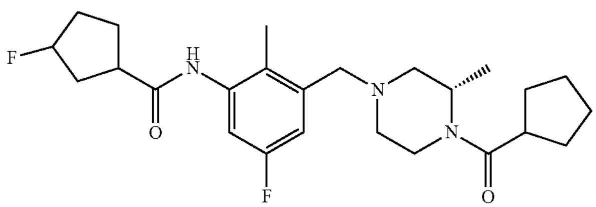 [SMILES: Cc1c(CN2CCN(C(=O)C3CCCC3)[C@@H](C)C2)cc(F)cc1NC(=O)C1CCC(F)C1] | $^1$H-NMR (MeOD-d$_4$, 400 MHz): 1.3 (m, 3 H), 1.5-2 (m, 8H), 2.1 (m, 3H), 2.5 (s, 3H), 2.65 (m, 1H), 2.8-3.1 (m, 4H), 3.3 (s, 3H), 3.5-4.1 (m, 3H), 4.5 (m, 1H), 4.6 (m, 2H), 5.1 (m, 1H), 7.1 (m, 2H), δF (MeOD-d$_4$, 376 MHz): −121, −75.9, −74. MS (ES): C$_{25}$H$_{35}$F$_2$N$_3$O$_2$ requires 447; found 448 (M + H$^+$). |

Examples 109

(S)-N-(3-((4-(cyclopentanecarbonyl)-3-methylpiperazin-1-yl)methyl)-5-fluoro-2-methylphenyl)-2-fluorobenzamide, trifluoroacetic acid salt (E109)

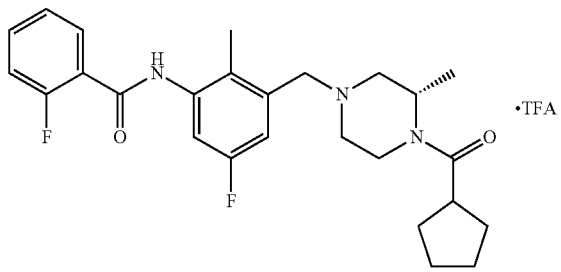 [SMILES: Cc1c(CN2CCN(C(=O)C3CCCC3)[C@@H](C)C2)cc(F)cc1NC(=O)c1ccccc1F]

(S)-(4-(3-amino-5-fluoro-2-methylbenzyl)-2-methylpiperazin-1-yl)(cyclopentyl)methanone (80 mg, 0.24 mmol) was added into a mixture of 2-fluorobenzoic acid (33.6 mg, 0.24 mmol), HATU (109 mg, 0.288 mmol) and DIPEA (93 mg, 0.720 mmol) in DMF (5 mL) at rt. The reaction was stirred at RT overnight. After checked by LCMS, the reaction was completed. The mixture was subjected to MDAP to afford the title compound (34 mg, 23.64% yield) as white solid. $^1$H NMR (400 MHz, MeOD-d$_4$) δ 1.18-1.54 (m, 4H), 1.54-2.01 (m, 8H), 2.38 (s, 3H), 2.92-3.28 (m, 3H), 3.36-3.67 (m, 3H), 4.10-4.30 (m, 0.5H), 4.43 (s, 2H), 4.65 (brs, 1H), 7.27-7.40 (m, 3H), 7.51 (d, 1H), 7.62 (dd, 1H), 7.87 (t, 1H). $^{19}$F NMR (376 MHz, MeOD-d$_4$) δ −77.2, −115.5, −116.8. MS (ESI) C$_{26}$H$_{31}$F$_2$N$_3$O$_2$ requires: 455, found 456 (M+H$^+$).

Examples 110-124

Examples 110-124 were prepared using a similar procedure to that described for Example 109.

E110: (S)-N-(3-((4-(cyclopentanecarbonyl)-3-methylpiperazin-1-yl)methyl)-5-fluoro-2-methylphenyl)-4-fluorobenzamide, trifluoroacetic acid salt E111: (S)-N-(3-((4-(cyclopentanecarbonyl)-3-methylpiperazin-1-yl)methyl)-5-fluoro-2-methylphenyl)-3-fluorobenzamide, trifluoroacetic acid salt

103

E112: (S)-N-(3-((4-(cyclopentanecarbonyl)-3-methylpiperazin-1-yl)methyl)-5-fluoro-2-methylphenyl)-3-methoxybenzamide, trifluoroacetic acid salt
E113: N-(3-(((S)-4-(cyclopentanecarbonyl)-3-methylpiperazin-1-yl)methyl)-5-fluoro-2-methylphenyl)tetrahydrofuran-3-carboxamide, trifluoroacetic acid salt
E114: (S)-4-chloro-N-(3-((4-(cyclopentanecarbonyl)-3-methylpiperazin-1-yl)methyl)-5-fluoro-2-methylphenyl)-3-fluorobenzamide, trifluoroacetic acid salt
E115: N-(3-(((S)-4-(cyclopentanecarbonyl)-3-methylpiperazin-1-yl)methyl)-5-fluoro-2-methylphenyl)tetrahydro-2H-pyran-3-carboxamide, trifluoroacetic acid salt
E116: (R)-N-(3-(((S)-4-(cyclopentanecarbonyl)-3-methylpiperazin-1-yl)methyl)-5-fluoro-2-methylphenyl)tetrahydrofuran-3-carboxamide
E117: (S)-N-(3-((4-(cyclopentanecarbonyl)-3-methylpiperazin-1-yl)methyl)-5-fluoro-2-methylphenyl)tetrahydro-2H-pyran-4-carboxamide
E118: (S)-N-(3-((4-(cyclopentanecarbonyl)-3-methylpiperazin-1-yl)methyl)-5-fluoro-2-methylphenyl)-2-methylbenzamide

104

E119: (S)-4-chloro-N-(3-((4-(cyclopentanecarbonyl)-3-methylpiperazin-1-yl)methyl)-5-fluoro-2-methylphenyl)benzamide
E120: (S)-2-chloro-N-(3-((4-(cyclopentanecarbonyl)-3-methylpiperazin-1-yl)methyl)-5-fluoro-2-methylphenyl)benzamide
E121: (S)-N-(3-((4-(cyclopentanecarbonyl)-3-methylpiperazin-1-yl)methyl)-5-fluoro-2-methylphenyl)-4-methoxybenzamide
E122: (S)-N-(3-((4-(cyclopentanecarbonyl)-3-methylpiperazin-1-yl)methyl)-5-fluoro-2-methylphenyl)-4-fluoro-3-methylbenzamide
E123: (S)-N-(3-((4-(cyclopentanecarbonyl)-3-methylpiperazin-1-yl)methyl)-5-fluoro-2-methylphenyl)-2-methylthiazole-5-carboxamide, trifluoroacetic acid salt
E124: (S)-N-(3-((4-(cyclopentanecarbonyl)-3-methylpiperazin-1-yl)methyl)-5-fluoro-2-methylphenyl)-3-(difluoromethyl)benzamide, trifluoroacetic acid salt

| Example | Structure | Characterization |
|---|---|---|
| E110 | 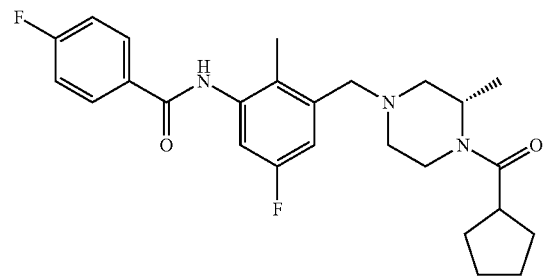 | $^1$H NMR (400 MHz, MeOD-d$_4$) δ 1.20-1.52 (m, 4H), 1.53-2.00 (m, 9H), 2.32 (s, 3H), 2.80-3.26 (m, 4H), 3.35-3.61 (m, 3H), 4.11-4.24 (m, 0.5H), 4.24-4.49 (m, 2H), 4.53-4.70 (m, 1H), 7.23-7.35 (m, 4H), 8.00-8.10 (m, 2H). $^{19}$F NMR (376 MHz, MeOD-d$_4$) δ −77.2, −109.4, −117.2. MS (ESI) C$_{26}$H$_{31}$F$_2$N$_3$O$_2$ requires: 455, found 456 (M + H$^+$). |
| E111 | 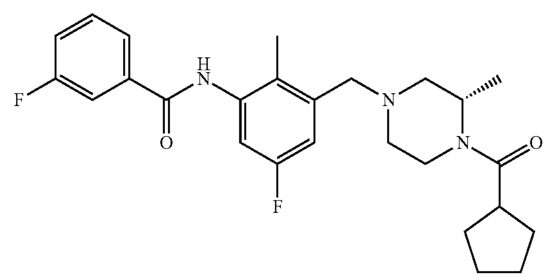 | $^1$H NMR (400 MHz, MeOD-d$_4$) δ 1.16-1.42 (m, 4H), 1.52-1.88 (m, 13H), 1.86-2.27 (m, 3H), 2.28 (s, 4H), 2.67-3.10 (m, 5H), 3.32-3.44 (m, 1H), 3.43-3.58 (m, 3H), 3.84 (d, 1H), 4.21-4.39 (m, 1H), 4.67 (s, 1H), 7.06 (t, 3H), 7.33 (d, 1H), 7.54 (q, 2H), 7.70 (d, 1H), 7.81 (d, 1H). $^{19}$F NMR (376 MHz, MeOD-d$_4$) δ −76.9, −114.4, −119.6. MS (ESI) C$_{26}$H$_{31}$F$_2$N$_3$O$_2$ requires: 455, found 456 (M + H$^+$). |
| E112 | 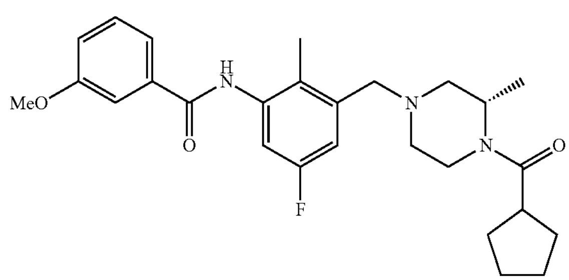 | $^1$H NMR (400 MHz, MeOD-d$_4$) δ 1.22-1.52 (m, 3H), 1.56-2.00 (m, 8H), 2.32 (s, 3H), 2.83-3.26 (m, 3H), 3.34-3.63 (m, 3H), 3.88 (s, 3H), 4.07-4.26 (m, 0.5H), 4.36 (s, 2H), 4.62 (brs, 1H), 7.18 (dd, 1H), 7.26-7.36 (m, 2H), 7.45 (t, 1H), 7.50-7.59 (m, 2H). $^{19}$F NMR (376 MHz, MeOD-d$_4$) δ −74.9, −76.7, −78.6, −118.8. MS (ESI) C$_{27}$H$_{34}$FN$_3$O$_3$ requires: 467, found 468 (M + H$^+$). |
| E113 | 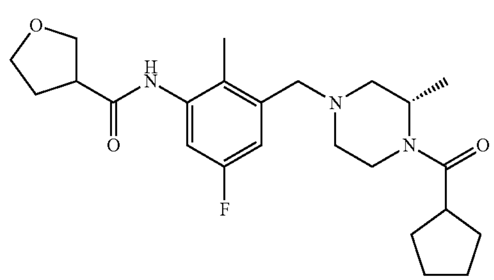 | $^1$H NMR (400 MHz, MeOD-d$_4$) δ 1.18-1.42 (m, 4H), 1.55-2.11 (m, 8H), 2.11-2.28 (m, 5H), 2.67-2.90 (m, 2H), 2.90-3.08 (m, 2H), 3.22-3.31 (m, 3H), 3.35-3.57 (m, 2H), 3.79-3.89 (m, 1H), 3.89-3.98 (m, 2H), 4.05 (t, 1H), 4.23-4.38 (m, 1H), 4.66 (brs, 0.5H), 7.00 (d, 1H), 7.11 (dd, 1H). $^{19}$F NMR (376 MHz, MeOD-d$_4$) δ −76.9, −119.5. MS (ESI) C$_{24}$H$_{34}$FN$_3$O$_3$ requires: 431, found 432 (M + H$^+$). |

| Example | Structure | Characterization |
|---|---|---|
| E114 | 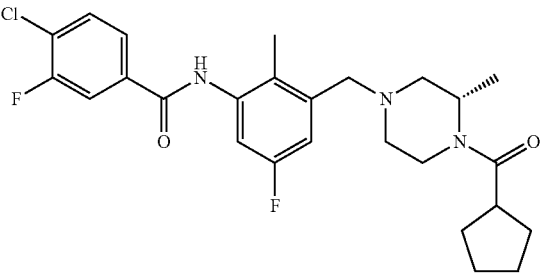 •TFA | $^1$H NMR (400 MHz, MeOD-d$_4$) δ 1.20-1.49 (m, 3H), 1.55-1.99 (m, 8H), 2.32 (s, 3H), 2.68-3.20 (m, 4H), 3.37-3.60 (m, 2H), 4.05-4.44 (m, 3H), 4.58 (brs, 1H), 7.29 (d, 2H), 7.68 (t, 1H), 7.82 (d, 1H), 7.87 (d, 1H). $^{19}$F NMR (376 MHz, MeOD-d$_4$) δ −73.7, −75.6, −77.2, −116.3, −117.3. MS (ESI) C$_{26}$H$_{30}$ClF$_2$N$_3$O$_2$ requires: 489, found 490 (M + H$^+$). |
| E115 | 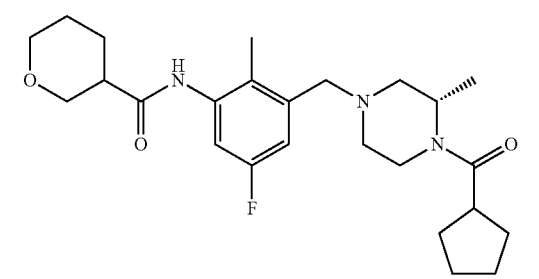 [SMILES: Cc1c(CN2CCN(C(=O)C3CCCC3)[C@@H](C)C2)cc(F)cc1NC(=O)C1CCOCC1] •TFA | $^1$H NMR (400 MHz, MeOD-d$_4$) δ 1.28 (dd, 3H), 1.52-2.19 (m, 13H), 2.22 (s, 3H), 2.66-3.09 (m, 4H), 3.33-3.55 (m, 4H), 3.63 (t, 1H), 3.86 (dd, 2H), 4.04 (dd, 1H), 4.29 (s, 1H), 4.65 (s, 1H), 6.97 (d, 1H), 7.07 (d, 1H). $^{19}$F NMR (376 MHz, MeOD-d$_4$) δ −73.8, −75.6, −77.0, −119.6. MS (ESI) C$_{25}$H$_{36}$FN$_3$O$_3$ requires: 445, found 446 (M + H$^+$). |
| E116 | 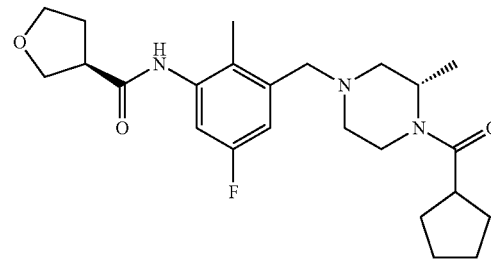 | $^1$H NMR (400 MHz, MeOD-d$_4$) δ 1.16-1.45 (m, 3H), 1.53-2.19 (m, 10H), 2.17-2.36 (m, 6H), 2.64-3.15 (m, 4H), 3.42-3.62 (m, 3H), 3.79-4.16 (m, 5H), 4.23-4.39 (m, 1H), 4.67 (brs, 0.5H), 6.97 (d, 1H), 7.08 (d, 1H). $^{19}$F NMR (376 MHz, MeOD-d$_4$) δ −119.6. MS (ESI) C$_{24}$H$_{34}$FN$_3$O$_3$ requires: 431, found 432 (M + H$^+$). |
| E117 | 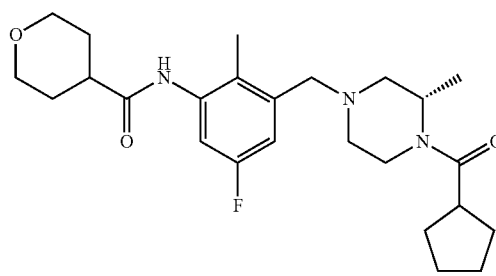 | $^1$H NMR (400 MHz, MeOD-d$_4$) δ 1.13-1.41 (m, 3H), 1.51-1.93 (m, 11H), 1.96-2.19 (m, 2H), 2.22 (s, 3H), 2.66-3.08 (m, 5H), 3.35-3.59 (m, 5H), 3.84 (d, 0.5H), 4.02 (d, 2H), 4.18-4.38 (m, 1H), 4.66 (brs, 0.5H), 6.98 (d, 1H), 7.05 (d, 1H). $^{19}$F NMR (376 MHz, MeOD-d$_4$) δ −119.6. MS (ESI) C$_{25}$H$_{36}$FN$_3$O$_3$ requires: 445, found 446 (M + H$^+$). |
| E118 | 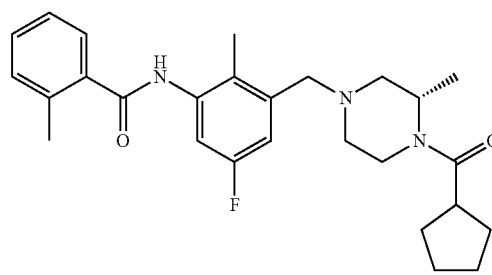 | $^1$H NMR (400 MHz, MeOD-d$_4$) δ 1.16-1.48 (m, 3H), 1.51-1.94 (m, 8H), 1.94-2.28 (m, 2H), 2.32 (s, 3H), 2.50 (s, 3H), 2.68-3.11 (m, 4H), 3.35-3.61 (m, 2H), 3.84 (d, 0.5H), 4.23-4.40 (m, 1H), 4.56-4.72 (m, 1H), 7.06 (d, 1H), 7.17 (d, 1H), 7.31 (d, 2H), 7.39 (t, 1H), 7.55 (d, 1H). $^{19}$F NMR (376 MHz, MeOD-d$_4$) δ −120.9. MS (ESI) C$_{27}$H$_{34}$FN$_3$O$_2$ requires: 451, found 452 (M + H$^+$). |

| Example | Structure | Characterization |
|---------|-----------|------------------|
| E119 | 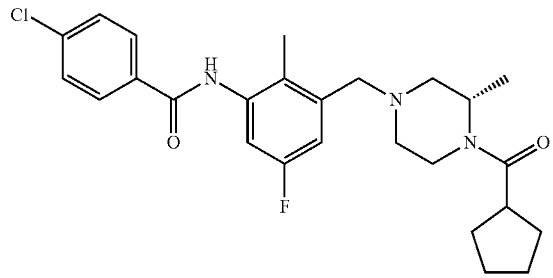 [SMILES: Cc1c(CN2CCN(C(=O)C3CCCC3)[C@@H](C)C2)cc(F)cc1NC(=O)c1ccc(Cl)cc1] | $^1$H NMR (400 MHz, MeOD-d$_4$) δ 1.16-1.43 (m, 3H), 1.54-1.94 (m, 8H), 1.94-2.25 (m, 2H), 2.28 (s, 3H), 2.67-3.09 (m, 4H), 3.33-3.57 (m, 3H), 3.84 (d, 1H), 4.24-4.39 (m, 1H), 4.57-4.73 (m, 2H), 7.08 (t, 2H), 7.54 (d, 2H), 7.96 (d, 2H). $^{19}$F NMR (376 MHz, MeOD-d$_4$) δ −120.9. MS (ESI) C$_{26}$H$_{31}$ClFN$_3$O$_2$ requires: 471, found 472 (M + H$^+$). |
| E120 | 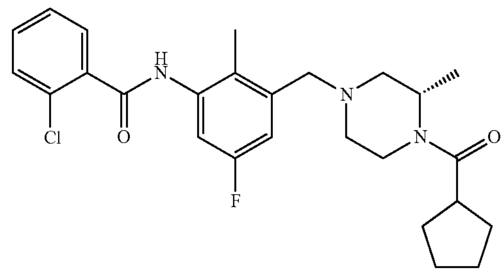 | $^1$H NMR (400 MHz, MeOD-d$_4$) δ 1.16-1.41 (m, 3H), 1.52-1.94 (m, 8H), 1.94-2.27 (m, 2H), 2.34 (s, 3H), 2.66-3.11 (m, 4H), 3.33-3.59 (m, 3H), 3.84 (d, 0.5H), 4.23-4.38 (m, 1H), 4.60 (s, 1H), 4.67 (brs, 0.5H), 7.07 (d, 1H), 7.20 (dd, 1H), 7.41-7.57 (m, 3H), 7.63 (d, 1H). $^{19}$F NMR (376 MHz, MeOD-d$_4$) δ −119.3. MS (ESI) C$_{26}$H$_{31}$ClFN$_3$O$_2$ requires: 471, found 472 (M + H$^+$). |
| E121 | 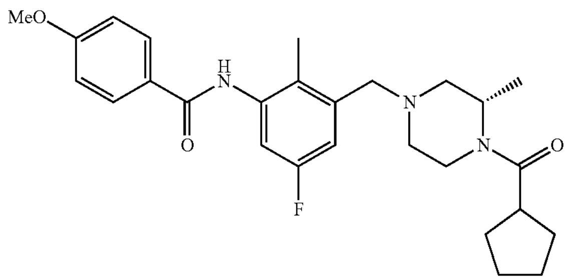 [SMILES: COc1ccc(C(=O)Nc2cc(F)cc(CN3CCN(C(=O)C4CCCC4)[C@@H](C)C3)c2C)cc1] | $^1$H NMR (400 MHz, MeOD-d$_4$) δ 1.20-1.41 (m, 3H), 1.54-1.94 (m, 8H), 1.94-2.26 (m, 2H), 2.28 (s, 3H), 2.68-3.10 (m, 4H), 3.35-3.56 (m, 3H), 3.80-3.86 (m, 0.5H), 3.88 (s, 3H), 4.24-4.38 (m, 1H), 4.62 (s, 1H), 4.67 (brs, 0.5H), 7.01-7.13 (m, 4H), 7.95 (d, 2H). $^{19}$F NMR (376 MHz, MeOD-d$_4$) δ −119.6. MS (ESI) C$_{27}$H$_{34}$FN$_3$O$_3$ requires: 467, found 468 (M + H$^+$). |
| E122 | 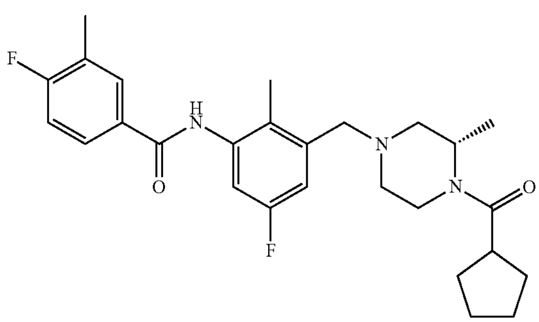 [SMILES: Cc1cc(C(=O)Nc2cc(F)cc(CN3CCN(C(=O)C4CCCC4)[C@@H](C)C3)c2C)ccc1F] | $^1$H NMR (400 MHz, MeOD-d$_4$) δ 1.15-1.43 (m, 3H), 1.55-1.94 (m, 8H), 1.94-2.26 (m, 2H), 2.28 (s, 3H), 2.36 (s, 3H), 2.69-2.82 (m, 1H), 2.85 (d, 1H), 2.91-3.10 (m, 1.5H), 3.33-3.45 (m, 0.5H), 3.45-3.59 (m, 2H), 3.84 (d, 0.5H), 4.23-4.37 (m, 1H), 4.49 (s, 1H), 4.67 (brs, 0.5H), 7.07 (t, 2H), 7.17 (t, 1H), 7.80-7.86 (m, 1H), 7.89 (d, 1H). $^{19}$F NMR (376 MHz, MeOD-d$_4$) δ −114.2, −119.5. MS (ESI) C$_{27}$H$_{33}$F$_2$N$_3$O$_2$ requires: 469, found 470 (M + H$^+$). |
| E123 | ·TFA | $^1$H NMR (400 MHz, MeOD-d$_4$) δ 1.19-1.46 (m, 3H), 1.54-1.98 (m, 8H), 2.31 (s, 3H), 2.77 (s, 3H), 2.81-3.15 (m, 4H), 3.48 (brs, 1H), 4.07-4.36 (m, 3H), 4.58 (brs, 1H), 7.21-7.32 (m, 2H), 8.32 (s, 1H). $^{19}$F NMR (376 MHz, MeOD-d$_4$) δ −73.9, −75.8, −77.3, −117.2. MS (ESI) C$_{24}$H$_{31}$FN$_4$O$_2$S requires: 458, found 459 (M + H$^+$). |

| Example | Structure | Characterization |
|---|---|---|
| E124 | 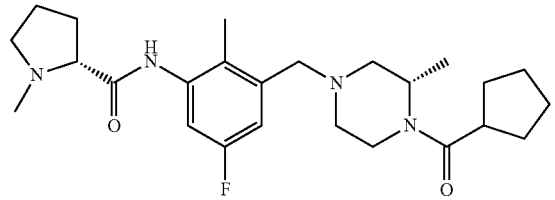 ·TFA | $^1$H NMR (400 MHz, MeOD-d$_4$) δ 1.16-1.51 (m, 3H), 1.51-2.00 (m, 8H), 2.32 (s, 3H), 2.43-2.94 (m, 2H), 2.98-3.29 (m, 3.5H), 3.48 (brs, 1H), 4.02 (brs, 2.5H), 4.49 (brs, 1H), 6.88 (t, 1H), 7.16-7.32 (m, 2H), 7.64-7.86 (m, 2H), 8.09-8.25 (m, 2H). $^{19}$F NMR (376 MHz, MeOD-d$_4$) δ −77.0, −112.6, −118.3. MS (ESI) C$_{27}$H$_{32}$F$_3$N$_3$O$_2$ requires: 487, found 488 (M + H$^+$). |

Examples 125

(R)-N-(3-(((S)-4-(cyclopentanecarbonyl)-3-methyl-piperazin-1-yl)methyl)-5-fluoro-2-methylphenyl)-1-methylpyrrolidine-2-carboxamide (E125)

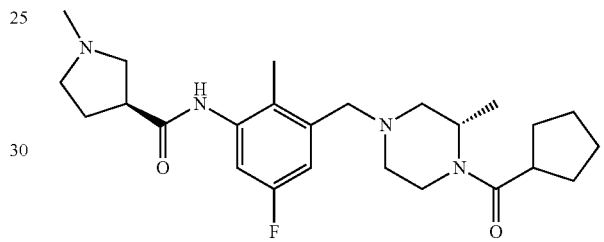

To a solution of (R)-N-(3-(((S)-4-(cyclopentanecarbonyl)-3-methylpiperazin-1-yl)methyl)-5-fluoro-2-methylphenyl)pyrrolidine-2-carboxamide (129 mg, 0.3 mmol) and formaldehyde (48.6 mg, 0.599 mmol) in DCM (30 mL) was added AcOH (8.58 µL, 0.15 mmol). After stirring at rt for half an hour, sodium triacetoxyborohydride (95 mg, 0.449 mmol) was added and the mixture was stirred at rt overnight. The mixture was quenched with water, washed with sat. NaHCO3 solution, the organic layer was dried and evaporated, the residue was purified by MDAP to give the title compound (28 mg) as a white solid. $^1$H-NMR (MeOD-d$_4$, 400 MHz): 1.22 (d, 2 H), 1.35 (d, 1 H), 1.88 (m, 13 H), 2.16 (dd, 1 H), 2.26 (s, 3 H), 2.33 (m, 1 H), 2.49 (m, 4 H), 2.73 (m, 1 H), 2.82 (d, 1 H), 3.03 (m, 3 H), 3.24 (m, 1 H), 3.46 (m, 2 H), 3.81 (br. s., 0.5 H), 4.29 (br. s., 1 H), 4.66 (br. s., 0.5 H), 6.93 (dd, 1 H), 7.50 (dd, 1 H). δF (MeOD-d$_4$, 376 MHz): −118.9. MS (ES): C$_{25}$H$_{37}$FN$_4$O$_2$ requires 444; found 445(M+H$^+$).

Examples 126

(S)-N-(3-(((S)-4-(cyclopentanecarbonyl)-3-methyl-piperazin-1-yl)methyl)-5-fluoro-2-methylphenyl)-1-methylpyrrolidine-3-carboxamide (E126)

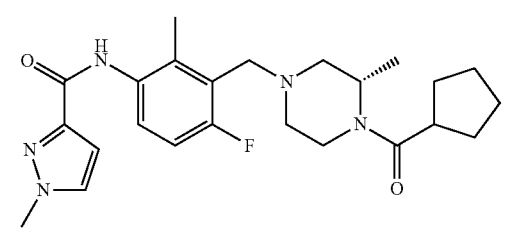 [SMILES: Cc1c(NC(=O)c2ccn(C)n2)ccc(F)c1CN1CCN(C(=O)C2CCCC2)[C@@H](C)C1]

Example 126 was prepared using a similar procedure to that described for E125. $^1$H-NMR (MeOD-d$_4$, 400 MHz): 1.22 (d, 2 H), 1.31 (m, 1 H), 1.61 (m, 2 H), 1.70 (br. s., 3 H), 2.04 (m, 1 H), 2.16 (m, 2 H), 2.25 (m, 4 H), 2.42 (s, 3 H), 2.73 (m, 5 H), 2.94 (t, 1 H), 3.00 (br. s., 1 H), 3.19 (quin, 1 H), 3.47 (d, 2H), 3.83 (d, 0.5 H), 4.29 (br. s., 1 H), 4.66 (br. s., 0.5 H), 6.96 (d, 1 H), 7.18 (d, 1 H). δF (MeOD-d$_4$, 376 MHz): −119.5. MS (ES): C$_{25}$H$_{37}$FN$_4$O$_2$ requires 444; found 445(M+H$^+$).

Example 127

(S)-N-(3-((4-(cyclopentanecarbonyl)-3-methylpiper-azin-1-yl)methyl)-4-fluoro-2-methylphenyl)-1-methyl-1H-pyrazole-3-carboxamide, Trifluoroacetic acid salt (E127)

The mixture of 1-methyl-1H-pyrazole-3-carboxylic acid (30.3 mg, 0.24 mmol),(S)-(4-(3-amino-6-fluoro-2-methyl-benzyl)-2-methylpiperazin-1-yl)(cyclopentyl)methanone (80 mg, 0.24 mmol), EDC (55.2 mg, 0.288 mmol), HOBT (44.1 mg, 0.288 mmol), in DMF (4 mL) was stirred at rt overnight. The mixture was purified by MDAP to give the title compound (50 mg). ¹H-NMR (MeOD-d₄, 400 MHz): 1.20 (d, 1 H), 1.33 (d, 2 H), 1.63 (m, 9 H), 1.75 (m, 2H), 2.30 (d, 3 H), 2.97(m,2H), 3.15 (s. 1 H), 3.37 (m, 3 H), 3.91 (s, 1 H), 4.08 (s., 1 H), 4.33 (br. s., 2 H), 4.52 (br.s. 1 H), 4.90 (br. s., 0.5 H),6.71 (d, 2 H), 7.09 (d, 3 H), 7.49 (d, 4 H),7.60 (d, 2 H). δF (MeOD-d₄, 376 MHz): −77.1, −114.6. MS (ES): $C_{24}H_{32}FN_5O_2$ requires 441; found 442(M+H⁺).

Examples 128-137

Examples 128-137 were prepared using a similar procedure to that described for Example 127.

E128: (S)-N-(3-((4-(cyclopentanecarbonyl)-3-methylpiperazin-1-yl)methyl)-4-fluoro-2-methylphenyl)-6-methylnicotinamide, trifluoroacetic acid salt E129: (S)-N-(3-((4-(cyclopentanecarbonyl)-3-methylpiperazin-1-yl)methyl)-4-fluoro-2-methylphenyl)-2-oxo-1,2-dihydropyridine-3-carboxamide, trifluoroacetic acid salt E130: (S)-N-(3-((4-(cyclopentanecarbonyl)-3-methylpiperazin-1-yl)methyl)-5-fluoro-2-methylphenyl)-1-methyl-1H-pyrazole-3-carboxamide, trifluoroacetic acid salt E131: (S)-N-(3-((4-(cyclopentanecarbonyl)-3-methylpiperazin-1-yl)methyl)-5-fluoro-2-methylphenyl)thiazole-5-carboxamide, trifluoroacetic acid salt E132: (S)-N-(3-((4-(cyclopentanecarbonyl)-3-methylpiperazin-1-yl)methyl)-5-fluoro-2-methylphenyl)-5-methyloxazole-4-carboxamide, trifluoroacetic acid salt E133: (S)-N-(3-((4-(cyclopentanecarbonyl)-3-methylpiperazin-1-yl)methyl)-5-fluoro-2-methylphenyl)thiazole-4-carboxamide E134: (S)-N-(3-((4-(cyclopentanecarbonyl)-3-methylpiperazin-1-yl)methyl)-5-fluoro-2-methylphenyl)oxazole-4-carboxamide, trifluoroacetic acid salt E135: (S)-N-(3-((4-(cyclopentanecarbonyl)-3-methylpiperazin-1-yl)methyl)-5-fluoro-2-methylphenyl)-3-(1H-pyrazol-1-yl)propanamide, trifluoroacetic acid salt E136: (S)-N-(2-chloro-3-((4-(cyclopentanecarbonyl)-3-methylpiperazin-1-yl)methyl)phenyl)-1H-pyrazole-5-carboxamide, trifluoroacetic acid salt E137: (S)-N-(2-chloro-3-((4-(cyclopentanecarbonyl)-3-methylpiperazin-1-yl)methyl)phenyl)-2-(3-chlorophenyl)acetamide

| Example | Structure | Characterization |
|---|---|---|
| E128 | 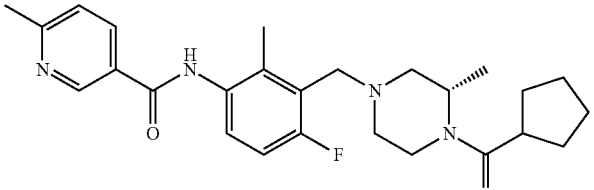 •TFA | ¹H-NMR (MeOD-d₄, 400 MHz): 1.17 (d, 2 H), 1.29 (d, 1 H), 1.86 (m, 9 H), 2.04 (d, 1 H), 2.23 (m, 1 H), 2.37 (s, 3 H), 2.61 (s, 3 H), 2.82 (m, 3 H), 2.99 (m, 1 H), 3.55 (m, 2 H), 3.81 (d, 0.5 H), 4.27 (br. s., 1 H), 4.65 (br. s., 0.5 H), 6.93 (t, 1 H), 7.17 (dd, 1 H), 7.41 (d, 1 H), 8.28 (dd, 1 H), 9.01 (d, 1 H). δF (MeOD-d₄, 376 MHz): −78.7, −115.1. MS (ES): $C_{26}H_{33}FN_4O_2$ requires 452; found 453(M + H⁺). |
| E129 | 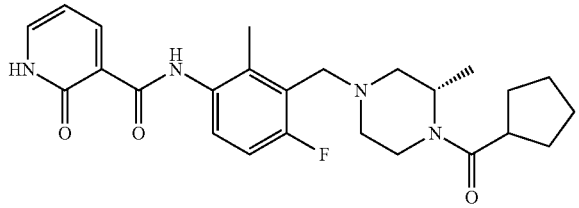 •TFA | ¹H-NMR (MeOD-d₄, 400 MHz): 1.17 (d, 2 H), 1.29 (d, 1 H), 1.77 (m, 11 H), 2.21 (m, 1 H), 2.51 (s, 3 H), 2.76 (m, 3 H), 2.99 (br. s., 1 H), 3.53 (m, 2 H), 3.81 (d, 0.5 H), 4.28 (br. s., 1 H), 4.65 (br. s., 0.5 H), 6.51 (dd, 1 H), 6.93 (t, 1 H), 8.00 (m, 2 H), 8.27 (d, 1 H). δF (MeOD-d₄, 376 MHz): −77.1, −115.9. MS (ES): $C_{25}H_{31}FN_4O_3$ requires 454; found 455(M + H⁺). |
| E130 | 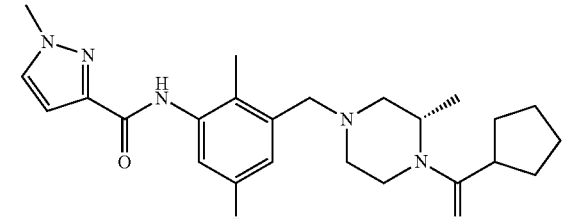 •TFA | ¹H-NMR (MeOD-d₄, 400 MHz): 1.29 (br. s., 2 H), 1.40 (m, 1 H), 1.65 (m, 5 H), 1.89 (m, 4 H), 2.36 (s, 3 H), 3.05 (m, 2 H), 3.13 (m, 1 H), 3.36 (br. s., 1 H), 3.46 (m, 2 H), 4.01 (s, 3 H), 4.18 (br. s., 1 H), 4.35 (m, 2 H), 4.62 (br. s., 1 H), 6.83 (d, 1 H), 7.24 (m, 1 H), 7.61 (dd, 1 H), 7.72 (m, 1 H). δF (MeOD-d₄, 376 MHz): −77.1, −114.6. MS (ES): $C_{24}H_{32}FN_5O_2$ requires 441; found 442(M + H⁺). |
| E131 | 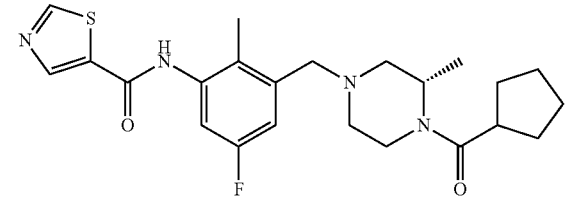 •TFA | ¹H-NMR (MeOD-d₄, 400 MHz): 1.29 (br. s., 2 H), 1.42 (br. s., 1 H), 1.65 (br. s., 5 H), 1.84 (br. s., 4 H), 2.33 (s, 3 H), 3.04 (d, 3 H), 3.38 (br. s., 4 H), 4.17 (br. s., 0.5 H), 4.40 (br. s., 2 H), 4.63 (br. s., 0.5 H), 7.33 (m, 2 H), 8.61 (s, 1 H), 9.24 (s, 1 H). δF (MeOD-d₄, 376 MHz): −78.8, −118.5. MS (ES): $C_{23}H_{29}FN_4O_2S$ requires 444; found 445(M + H⁺). |

| Example | Structure | Characterization |
|---|---|---|
| E132 | (structure) ·TFA | ¹H-NMR (MeOD-d₄, 400 MHz): 1.24 (d, 2 H), 1.36 (d, 1 H), 1.70 (br. s., 8 H), 2.04 (m, 1 H), 2.14 (m, 1 H), 2.23 (s, 3 H), 2.48 (s, 3 H), 2.76 (d, 1 H), 2.86 (br. s., 1 H), 3.01 (m, 2 H), 3.46 (m, 3 H), 3.82 (br. s., 0.5 H), 4.30 (br. s., 1 H), 4.66 (br. s., 0.5 H), 6.83 (br. s., 2 H), 8.13 (s, 1 H). δF (MeOD-d₄, 376 MHz): −77.2, −116.7. MS (ES): $C_{34}H_{31}FN_4O_3$ requires 442; found 443(M + H⁺). |
| E133 | (structure) | ¹H-NMR (MeOD-d₄, 400 MHz): 1.40 (m, 2 H), 1.52 (m, 1 H), 1.87 (m, 9 H), 2.18 (m, 1 H), 2.37 (m, 1 H), 2.90 (m, 1 H), 3.00 (d, 1 H), 3.16 (m, 2 H), 3.50 (m, 1 H), 3.65 (d, 2 H), 3.99 (d, 0.5 H), 4.48 (m, 1 H), 4.85 (m, 0.5 H), 4.95 (s, 2 H), 7.12 (d, 1 H), 7.83 (d, 1 H), 8.56 (br. s., 1 H), 9.25 (br. s., 1 H). δF (MeOD-d₄, 376 MHz): −120.5. MS (ES): $C_{23}H_{29}FN_4O_2S$ requires 444; found 445(M + H⁺). |
| E134 | (structure) ·TFA | ¹H-NMR (MeOD-d₄, 400 MHz): 1.23 (d, 2 H), 1.36 (d, 1 H), 1.62 (d, 3 H), 1.70 (m, 3 H), 1.79 (m, 3 H), 2.04 (d, 1 H), 2.16 (m, 1 H), 2.31 (s, 3 H), 2.73 (d, 1 H), 2.85 (d, 1 H), 3.03 (m, 1 H), 3.37 (br. s., 1 H), 3.48 (m, 2 H), 3.82 (br. s., 0.5 H), 4.30 (br. s., 1 H), 4.67 (br. s., 0.5 H), 6.98 (d, 1 H), 7.37 (br. s., 1 H), 8.29 (s, 1 H), 8.53 (s, 1 H). δF (MeOD-d₄, 376 MHz): −77.1, −116.6. MS (ES): $C_{23}H_{29}FN_4O_3$ requires 428; found 429(M + H⁺). |
| E135 | (structure) ·TFA | ¹H-NMR (MeOD-d₄, 400 MHz): 1.20 (d, 2 H), 1.33 (d, 1 H), 1.69 (m, 6 H), 1.80 (d, 3 H), 2.04 (m, 1 H), 2.66 (br. s., 1 H), 2.81 (d, 1 H), 2.97 (t, 3 H), 3.43 (s, 2 H), 3.81 (br. s., 0.5 H), 4.28 (br. s., 1 H), 4.53 (m, 2 H), 4.65 (m, 0.5 H), 6.28 (s, 1 H), 6.99 (d, 1 H), 6.94 (d, 1 H), 7.51 (s, 1 H), 7.64 (s, 1 H). δF (MeOD-d₄, 376 MHz): −78.9, −118.5. MS (ES): $C_{25}H_{34}FN_5O_2$ requires 455; found 456(M + H⁺). |
| E136 | (structure) ·TFA | ¹H-NMR (MeOD-d₄, 400 MHz): 1.25 (m, 2 H), 1.38 (m, 1 H), 1.70 (br. s., 8 H), 2.12 (br. s., 1 H), 2.24 (br. s., 1 H), 2.79 (br. s., 1 H), 2.91 (br. s., 1 H), 3.03 (br. s., 2 H), 3.63 (m, 2 H), 3.86 (br. s., 0.5 H), 4.31 (br. s., 1 H), 4.67 (br. s., 0.5 H), 6.78 (m, 1 H), 7.30 (m, 2 H), 7.61 (m, 1 H), 8.22 (m, 1 H). δF (MeOD-d₄, 376 MHz): −77.2. MS (ES): $C_{22}H_{28}ClN_5O_2$ requires 429; found 430(M + H⁺). |
| E137 | (structure) | HNMR (DMSO-d₆, 400 MHz): 1.20-1.97 (11H, m), 2.11-3.28 (7H, m), 3.66 (2H, s), 3.77 (2H, s), 4.19-4.22 (1H, m), 7.29-7.60 (7H, m), 9.74 (1H, s). MS (ES): $C_{26}H_{31}Cl_2N_4O_3$ requires 487; found 488(M + H⁺). |

Example 138

(S)-N-(3-((4-(2,2-dimethylbutanoyl)-3-methylpiperazin-1-yl)methyl)-5-fluoro-2-methylphenyl)-6-methylnicotinamide (E138)

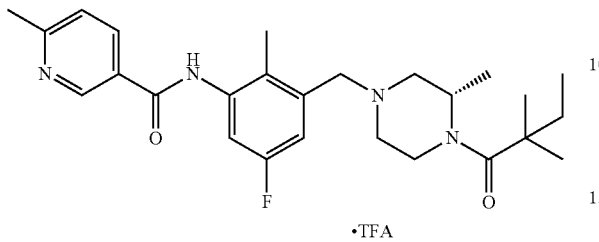

To a solution of (S)-N-(5-fluoro-2-methyl-3-((3-methylpiperazin-1-yl)methyl)phenyl)-6-methylnicotinamide (100 mg, 0 281 mmol) and 2,2-dimethylbutanoyl chloride (0.038 mL, 0.281 mmol) in DCM (5 mL) was added DIPEA (0.049 mL, 0.281 mmol). The mixture was stirred at rt for 3 hr. The mixture was washed with sat. NaHCO3 solution and brine, the organic layer was dried, evaporated and purified by MDAP to give the title compound (20 mg). $^1$H-NMR (MeOD-d$_4$, 400 MHz): 0.89 (t, 3 H), 1.26 (d, 6 H), 1.34 (d, 3 H), 1.68 (m, 2 H), 2.34 (s, 3 H), 2.72 (s, 3 H), 2.97 (br. s., 1 H), 3.10 (br. s., 1 H), 3.42 (d, 2 H), 4.33 (br. s., 2 H), 4.44 (d, 1 H), 4.90 (br. s., 1 H), 7.32 (m, 2 H), 7.67 (d, 1 H), 8.50 (dd, 1 H), 9.09 (d, 1 H). δF (MeOD-d$_4$, 376 MHz): −77.4, −117.2. MS (ES): C$_{26}$H$_{35}$FN$_4$O$_2$ requires 454; found 455 (M+H$^+$).

Example 139

(S)-N-(3-((4-(2-cyclopropylacetyl)-3-methylpiperazin-1-yl)methyl)-5-fluoro-2-methylphenyl)-6-methylnicotinamide (E139)

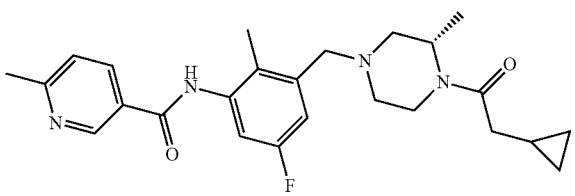 [SMILES: Cc1ccc(C(=O)Nc2cc(F)cc(CN3CCN(C(=O)CC4CC4)[C@@H](C)C3)c2C)cn1]

The mixture of (S)-N-(5-fluoro-2-methyl-3-((3-methylpiperazin-1-yl)methyl)phenyl)-6-methylnicotinamide (100 mg, 0.281 mmol), 2-cyclopropylacetic acid (30.9 mg, 0.309 mmol), HATU (117 mg, 0.309 mmol) and DIPEA (0.098 mL, 0.561 mmol) in DCM (3 mL) was stirred at rt overnight. The mixture was purified by MDAP to afford the title compound (33 mg). $^1$H-NMR (MeOD-d$_4$, 400 MHz): 0.19 (br. s., 2 H), 0.53 (d, 2 H), 1.00 (d, 1 H), 1.27 (m, 2 H), 1.34 (m, 2 H), 2.07 (m, 1 H), 2.25 (m, 6 H), 2.44 (dd, 1 H), 2.63 (s, 3 H), 2.75 (d, 1 H), 2.84 (br. s., 1 H), 2.99 (m, 1 H), 3.40 (t, 1 H), 3.51 (m, 2 H), 3.72 (d, 0.5 H), 4.15 (br. s., 0.5 H), 4.33 (br. s., 0.5 H), 4.69 (br. s., 0.5 H), 7.12 (d, 1 H), 7.08 (d, 1 H), 7.47 (d, 1 H), 8.27 (d, 1 H), 9.00 (s, 1 H). δF (MeOD-d$_4$, 376 MHz): −119.4. MS (ES): C$_{25}$H$_{31}$FN$_4$O$_2$ requires 438; found 439(M+H$^+$).

Example 140

(S)-N-(3-((4-(3,3-difluorocyclobutanecarbonyl)-3-methylpiperazin-1-yl)methyl)-5-fluoro-2-methylphenyl)-6-methylnicotinamide, trifluoroacetic acid salt (E140)

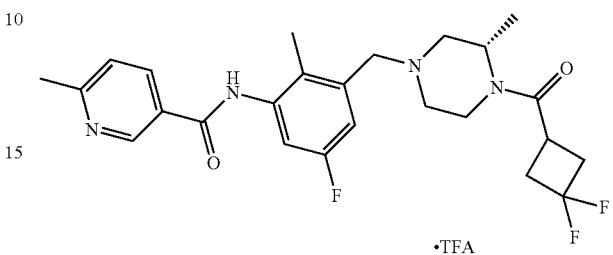

The mixture of (S)-N-(5-fluoro-2-methyl-3-((3-methylpiperazin-1-yl)methyl)phenyl)-6-methylnicotinamide (100 mg, 0.281 mmol), 3,3-difluorocyclobutanecarboxylic acid (42.0 mg, 0.309 mmol), HATU (117 mg, 0.309 mmol) and DIPEA (0.098 mL, 0.561 mmol) in DCM (3 mL) was stirred at rt overnight. The mixture was purified by MDAP to afford the title compound (73 mg). $^1$H-NMR (MeOD-d$_4$, 400 MHz): 1.32 (br. s., 3 H), 2.34 (s, 3 H), 2.87 (m, 7 H), 3.19 (br. s., 2 H), 3.27 (d, 1 H), 3.39 (d, 1 H), 3.47 (d, 1 H), 3.57 (br. s., 1 H), 3.91 (br. s., 0.5 H), 4.40 (br. s., 2 H), 4.59 (br. s., 0.5 H), 7.35 (m, 2 H), 7.81 (d, 1 H), 8.66 (d, 1 H), 9.15 (s, 1 H). δF (MeOD-d$_4$, 376 MHz): −77.2, −84.2, −84.7, −97.5, −98.1, −116.9. MS (ES): C$_{25}$H$_{29}$F$_3$N$_4$O$_2$ requires 474; found 475(M+H$^+$).

Examples 141-162

Examples 141-162 were prepared using a similar procedure to that described for Example 140.

E141: (S)-N-(5-fluoro-2-methyl-3-((3-methyl-4-(4,4,4-trifluorobutanoyl)piperazin-1-yl)methyl)phenyl)-6-methylnicotinamide E142: (S)-N-(3-((4-(cyclohexanecarbonyl)-3-methylpiperazin-1-yl)methyl)-5-fluoro-2-methylphenyl)-6-methylnicotinamide, trifluoroacetic acid salt E143: (S)-N-(3-((4-(3,3-dimethylbutanoyl)-3-methylpiperazin-1-yl)methyl)-5-fluoro-2-methylphenyl)-6-methylnicotinamide, trifluoroacetic acid salt E144: (S)-N-(5-fluoro-2-methyl-3-((3-methyl-4-(3,3,3-trifluoropropanoyl)piperazin-1-yl)methyl)phenyl)-6-methylnicotinamide, trifluoroacetic acid salt E145: (S)-N-(5-fluoro-2-methyl-3-((3-methyl-4-(spiro[3.3]heptane-2-carbonyl)piperazin-1-yl)methyl)phenyl)-6-methylnicotinamide E146: (S)-N-(3-((4-butyryl-3-methylpiperazin-1-yl)methyl)-5-fluoro-2-methylphenyl)-6-methylnicotinamide E147: N-(5-fluoro-2-methyl-3-(((3S)-3-methyl-4-(2-methylbutanoyepiperazin-1-yl)methyl)phenyl)-6-methylnicotinamide E148: (S)-N-(3-((4-(2-ethylbutanoyl)-3-methylpiperazin-1-yl)methyl)-5-fluoro-2-methylphenyl)-6-methylnicotinamide E149: (S)-N-(3-((4-(cyclobutanecarbonyl)-3-methylpiperazin-1-yl)methyl)-5-fluoro-2-methylphenyl)-6-methylnicotinamide E150: (S)-N-(5-fluoro-2-methyl-3-((3-methyl-4-pivaloylpiperazin-1-yl)methyl)phenyl)-6-methylnicotinamide
E151: N-(3-(((3S)-4-((1S,4R)-bicyclo[2.2.1]heptane-2-carbonyl)-3-methylpiperazin-1-yl)methyl)-5-fluoro-2-methylphenyl)-6-methylnicotinamide
E152: (S)-N-(5-fluoro-3-((4-(3-fluorocyclobutanecarbonyl)-3-methylpiperazin-1-yl)methyl)-2-methylphenyl)-6-methylnicotinamide formate
E153: (S)-N-(3-((4-benzoyl-3-methylpiperazin-1-yl)methyl)-5-fluoro-2-methylphenyl)-6-methylnicotinamide
E154: (S)-N-(5-fluoro-3-((4-(3-methoxycyclobutanecarbonyl)-3-methylpiperazin-1-yl)methyl)-2-methylphenyl)-6-methylnicotinamide
E155: (S)-N-(5-fluoro-3-((4-(3-(fluoromethyl)cyclobutanecarbonyl)-3-methylpiperazin-1-yl)methyl)-2-methylphenyl)-6-methylnicotinamide
E156: N-(5-fluoro-3-(((3S)-4-(2-methoxypropanoyl)-3-methylpiperazin-1-yl)methyl)-2-methylphenyl)-6-methylnicotinamide
E157: (S)-N-(5-fluoro-2-methyl-3-((3-methyl-4-(1-methyl-1H-pyrrole-2-carbonyl)piperazin-1-yl)methyl)phenyl)-6-methylnicotinamide
E158: (S)-N-(5-fluoro-2-methyl-3-((3-methyl-4-(thiazole-2-carbonyl)piperazin-1-yl)methyl)phenyl)-6-methylnicotinamide
E159: (S)-N-(5-fluoro-2-methyl-3-((3-methyl-4-(thiazole-5-carbonyl)piperazin-1-yl)methyl)phenyl)-6-methylnicotinamide
E160: (S)-N-(5-fluoro-3-((4-(furan-2-carbonyl)-3-methylpiperazin-1-yl)methyl)-2-methylphenyl)-6-methylnicotinamide
E161: (S)-N-(5-fluoro-2-methyl-3-((3-methyl-4-(oxazole-5-carbonyl)piperazin-1-yl)methyl)phenyl)-6-methylnicotinamide
E162: (S)-N-(5-fluoro-2-methyl-3-((3-methyl-4-(1-methyl-1H-pyrrole-3-carbonyl)piperazin-1-yl)methyl)phenyl)-6-methylnicotinamide

| Example | Structure | Characterization |
|---|---|---|
| E141 | ·TFA | $^1$H-NMR (MeOD-d$_4$, 400 MHz): 1.26 (m, 2 H), 1.36 (d, 1 H), 2.11 (d, 1 H), 2.20 (d, 1 H), 2.28 (m, 4 H), 2.50 (m, 2 H), 2.58 (br. s., 1 H), 2.63 (m, 4 H), 2.73 (m, 2 H), 2.86 (d, 1 H), 2.99 (br. s., 1 H), 3.41 (m, 1 H), 3.52 (m, 2 H), 3.70 (d, 1 H), 4.15 (br. s., 0.5 H), 4.30 (br. s., 0.5 H), 4.65 (br. s., 0.5 H), 7.12 (d, 1 H), 7.08 (d, 1 H), 7.47 (d, 1 H), 8.27 (d, 1 H), 9.00 (s, 1 H). δF (MeOD-d$_4$, 376 MHz): −68.1, −119.4. MS (ES): C$_{24}$H$_{28}$F$_4$N$_4$O$_2$ requires 480; found 481(M + H$^+$). |
| E142 | ·TFA | $^1$H-NMR (MeOD-d$_4$, 400 MHz): 1.34 (m, 6 H), 1.50 (d, 1 H), 1.72 (d, 2 H), 1.79 (br. s., 2 H), 2.33 (m, 3 H), 2.62 (m, 1 H), 2.75 (s, 3 H), 3.07 (m, 2 H), 3.39 (d, 1 H), 3.47 (d, 2 H), 4.13 (br. s., 0.5 H), 4.40 (br. s., 2 H), 4.60 (br. s., 0.5 H), 7.35 (d, 2 H), 7.74 (d, 1 H), 8.57 (d, 1 H), 9.12 (s, 1 H). δF (MeOD-d$_4$, 376 MHz): −77.2, −116.9. MS (ES): C$_{27}$H$_{35}$FN$_4$O$_2$ requires 466; found 467(M + H$^+$). |
| E143 | ·TFA | $^1$H-NMR (MeOD-d$_4$, 400 MHz): 1.06 (s, 9 H), 1.32 (br. s., 3 H), 2.25 (d, 1 H), 2.34 (m, 3 H), 2.45 (d, 1 H) 2.77 (s, 3 H), 3.20 (br. s., 2 H), 3.41 (d, 1 H), 3.49 (d, 1 H), 4.21 (br. s., 0.5 H), 4.43 (br. s., 2 H), 4.61 (br. s., 0.5 H), 7.36 (d, 2 H), 7.79 (d, 1 H), 8.63 (d, 1 H), 9.13 (m, 1 H). δF (MeOD-d$_4$, 376 MHz): −77.2, −116.9. MS (ES): C$_{26}$H$_{35}$FN$_4$O$_2$ requires 454; found 455(M + H$^+$). |
| E144 | ·TFA | $^1$H-NMR (MeOD-d$_4$, 400 MHz): 1.33 (br. s., 3 H), 2.34 (s, 3 H), 2.80 (m, 3 H), 3.17 (br. s., 2 H), 3.42 (m, 2 H), 3.55 (br. s., 3 H), 3.98 (br. s., 0.5 H), 4.37 (br. s., 2 H), 4.61 (br. s., 0.5 H), 7.34 (dd, 2 H), 7.83 (d, 1 H), 8.68 (d, 1 H), 9.15 (s, 1 H). δF (MeOD-d$_4$, 376 MHz): −64.2, −77.2, −117.0. MS (ES): C$_{23}$H$_{26}$F$_4$N$_4$O$_2$ requires 466: found 467(M + H$^+$). |

-continued

| Example | Structure | Characterization |
|---|---|---|
| E145 | 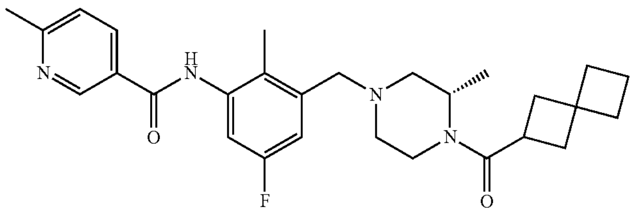 [SMILES: Cc1ccc(C(=O)Nc2cc(F)cc(CN3CCN(C(=O)C4CC5(CCC5)C4)[C@@H](C)C3)c2C)cn1] | ¹H-NMR (MeOD-d₄, 400 MHz): 1.22 (m, 2 H), 1.31 (m, 2 H), 1.82 (d, 2 H), 1.90 (m, 2 H), 2.01 (d, 1 H), 2.08 (br. s., 2 H), 2.21 (m, 5 H), 2.28 (br. s., 3 H), 2.63 (br. s., 3 H), 2.72 (d, 1 H), 2.83 (br. s., 1 H), 3.18 (m, 1 H), 3.51 (m, 2.5 H), 4.12 (m, 1 H), 4.61 (br. s., 0.5 H), 7.11 (d, 1 H), 7.07 (d, 1 H), 7.46 (d, 1 H), 8.26 (d, 1 H), 9.00 (br. s., 1 H). δF (MeOD-d₄, 376 MHz): −119.4. MS (ES): $C_{28}H_{35}FN_4O_2$ requires 478; found 479(M + H⁺). |
| E146 | 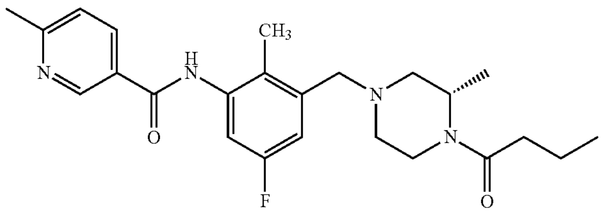 [SMILES: CCCC(=O)N1CCN(Cc2cc(F)cc(NC(=O)c3ccc(C)nc3)c2C)C[C@@H]1C] | δH (MeOD-d₄, 400 MHz): 0.93-0.97 (m, 3H), 1.21-1.23 (m, 2H), 1.32-1.34 (m, 1H), 1.57-1.64 (m, 2H), 1.98-2.06 (m, 1H), 2.09-2.18 (m, 1H), 2.23-2.29 (m, 3H), 2.31-2.35 (m, 1H), 2.38-2.48 (m, 1H), 2.617 (s, 3H), 2.70-2.75 (m, 1H), 2.82-2.85 (m, 1H), 2.91-2.99 (m, 0.5H), 3.36-3.41 (m, 0.5H), 3.49-3.50 (m, 2H), 3.69-3.74 (m, 0.5H), 4.10-4.18 (s, 0.5H), 4.27-4.35 (m, 0.5H), 4.61-4.69 (s, 0.5H), 7.04-7.11 (m, 2H), 7.45 (d, 1H), 8.24-8.26 (m, 1H), 8.98 (d, 1H). δF (MeOD-d₄, 376 MHz): −120.223, MS (ES): $C_{24}H_{31}FN_4O_2$ requires 426; found 427 (M + H⁺). |
| E147 | 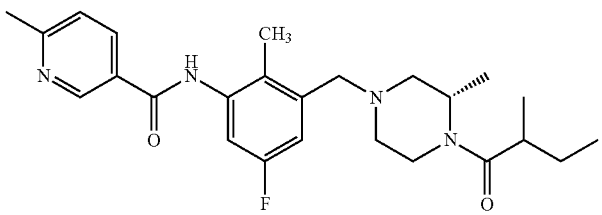 [SMILES: CCC(C)C(=O)N1CCN(Cc2cc(F)cc(NC(=O)c3ccc(C)nc3)c2C)C[C@@H]1C] | δH (MeOD-d₄, 400 MHz): 0.82-0.90 (m, 3H), 1.00-1.10 (m, 3H), 1.21-1.23 (m, 2H), 1.34-1.41 (m, 2H), 1.63-1.66 (m, 1H), 2.04-2.08 (m, 1H), 2.17-2.18 (m, 1H), 2.27 (s, 3H), 2.61 (s, 3H), 2.70-2.75 (m, 2H), 2.84-2.89 (m, 1H), 2.93-2.97 (m, 0.5H), 3.34-3.49 (m, 0.5H), 3.49-3.50 (m, 2H), 3.81-3.88 (m, 0.5H), 4.21-4.29 (s, 0.5H), 4.34-4.41 (m, 0.5H), 4.67-4.76 (s, 0.5H), 7.05-7.11 (m, 2H), 7.45 (d, 1H), 8.24-8.26 (m, 1H), 8.98 (d, 1H). δF (MeOD-d₄, 376 MHz): −120.208, MS (ES): $C_{25}H_{33}FN_4O_2$ requires 440; found 441 (M + H⁺) |
| E148 | 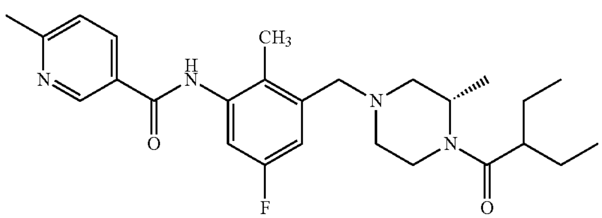 [SMILES: CCC(CC)C(=O)N1CCN(Cc2cc(F)cc(NC(=O)c3ccc(C)nc3)c2C)C[C@@H]1C] | δH (MeOD-d₄, 400 MHz): 0.80-0.85 (m, 3H), 0.85-0.92 (m, 3H), 1.23-1.25 (m, 2H), 1.34-1.36 (m, 1H), 1.43-1.60 (m, 4H), 1.96-2.11 (m, 1H), 2.15-2.23 (m, 1H), 2.27 (s, 3H), 2.65 (s, 3H), 2.66-2.72 (m, 1H), 2.72-2.76 (m, 1H), 2.85-2.88 (m, 1H), 2.93-3.11 (m, 0.5H), 3.34-3.49 (m, 0.5H), 3.49-3.50 (m, 2H), 3.91-3.98 (m, 0.5H), 4.42-4.47 (m, 1H), 4.75-4.83 (s, 0.5H), 7.05-7.11 (m, 2H), 7.45 (d, 1H), 8.24-8.27 (m, 1H), 8.98 (d, 1H). δF (MeOD-d₄, 376 MHz): −119.888, MS (ES): $C_{26}H_{35}FN_4O_2$ requires 454; found 455 (M + H⁺) |
| E149 | 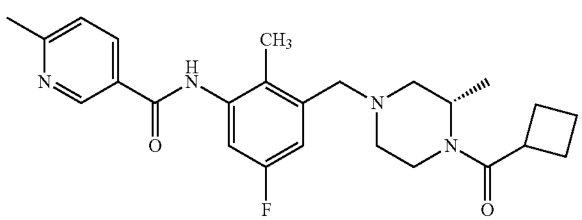 [SMILES: Cc1ccc(C(=O)Nc2cc(F)cc(CN3CCN(C(=O)C4CCC4)[C@@H](C)C3)c2C)cn1] | δH (MeOD-d₄, 400 MHz): 1.20-1.31 (m, 3H), 1.80-1.82 (m, 1H), 1.95-2.02 (m, 2H), 2.10-2.19 (m, 4H), 2.20-2.21 (m, 0.5H), 2.23-2.29 (m, 3H), 2.30-2.35 (m, 0.5H), 2.618 (s, 3H), 2.69-2.72 (m, 1H), 2.78-2.81 (m, 1H), 2.91-2.97 (m, 0.5H), 3.44-3.47 (m, 1H), 3.47-3.48 (m, 0.5H), 3.48-3.52 (m, 2H), 3.52-3.55 (m, 0.5H), 3.98-4.05(m, 0.5H), 4.21-4.29 (m, 0.5H), 4.57-4.68 (m, 0.5H),7.04-7.11 (m, 2H), 7.45 (d, 1H), 8.24-8.26 (m, 1H), 8.98 (d, 1H). δF (MeOD-d₄, 376 MHz): −119.893 MS (ES): $C_{25}H_{31}FN_4O_2$ requires 438; found 439 (M + H⁺). |
| E150 | 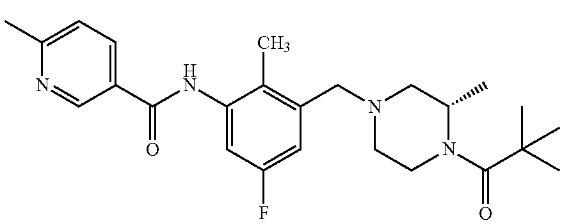 [SMILES: Cc1ccc(C(=O)Nc2cc(F)cc(CN3CCN(C(=O)C(C)(C)C)[C@@H](C)C3)c2C)cn1] | δH (MeOD-d₄, 400 MHz): 1.20-1.30 (m, 13H), 2.03-2.06 (m, 1H), 2.17-2.21 (m, 1H), 2.275 (s, 3H), 2.618 (s, 3H), 2.70-2.73 (m, 1H), 2.81-2.84 (m, 1H), 3.486 (s, 2H), 4.12-4.18 (m, 1H), 4.585-4.587 (m, 1H), 7.04-7.11 (m, 2H), 7.45 (d, 1H), 8.24-8.27 (m, 1H), 8.98 (d, 1H). δF (MeOD-d₄, 376 MHz): −119.904, MS (ES): $C_{25}H_{33}FN_4O_2$ requires 440; found 441 (M + H⁺). |

| Example | Structure | Characterization |
|---|---|---|
| E151 | 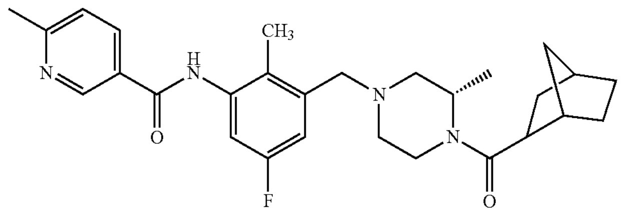 [SMILES: Cc1ccc(C(=O)Nc2cc(F)cc(CN3CCN(C(=O)C4CC5CCC4C5)[C@@H](C)C3)c2C)cn1] | δH (MeOD-d$_4$, 400 MHz): 1.18-1.29 (m, 3H), 1.31-1.38 (m, 4H), 1.45-1.54 (m, 3H), 1.61-1.89 (m, 1H), 1.98-2.03 (m, 1H), 2.11-2.16 (m, 1H), 2.22-2.23 (m, 1H), 2.278 (s, 3H), 2.34-2.37 (m, 0.5H), 2.48-2.52 (m, 1H), 2.618 (s, 3H), 2.71-2.76 (m, 1H), 2.77-2.91 (m, 1H), 2.96-3.11 (m, 1H), 3.38-3.41 (m, 0.5H), 3.48-3.49 (m, 2H), 3.76-3.91 (m, 0.5H), 4.23-4.38 (m, 1H), 4.58-4.72 (m, 0.5H), 7.05-7.11 (m, 2H), 7.45 (d, 1H), 8.24-8.26 (m, 1H), 8.982 (s, 1H). δF (MeOD-d$_4$, 376 MHz): −119.886, MS (ES): C$_{28}$H$_{35}$FN$_4$O$_2$ requires 478; found 479 (M + H$^+$) |
| E152 | 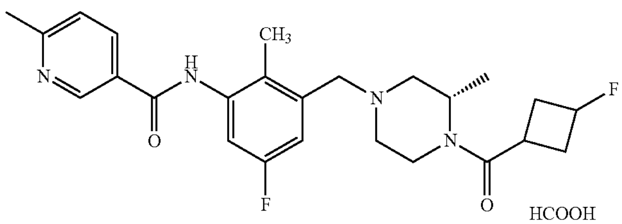 [SMILES: Cc1ccc(C(=O)Nc2cc(F)cc(CN3CCN(C(=O)C4CC(F)C4)[C@@H](C)C3)c2C)cn1 ; "HCOOH"] | δH (MeOD-d$_4$, 400 MHz): 1.22-1.38 (m, 3H), 2.01-2.11 (m, 1H), 2.18-2.21 (m, 1H), 2.27 (s, 3H), 2.32-2.38 (m, 1H), 2.41-2.59 (m, 3H), 2.62 (s, 3H), 2.71-2.74 (m, 1H), 2.80-2.86 (m, 2H), 2.89-2.98 (m, 0.5H), 3.41-3.47 (m, 0.5H), 3.50-3.54 (m, 2H), 3.57-3.61 (m, 0.5H), 3.97-4.08 (m, 0.5H), 4.27-4.30 (m, 0.5H), 4.61-4.63 (m, 0.5H), 4.96-5.00 (m, 1H), 7.05-7.12 (m, 2H), 7.46 (d, 1H), 8.24-8.27 (m, 1H), 8.98 (s, 1H). δF (MeOD-d$_4$, 376 MHz): −73.969, −75.848, −119.368. MS (ES): C$_{25}$H$_{30}$F$_2$N$_4$O$_2$ requires 456; found 457 (M + H$^+$) |
| E153 | 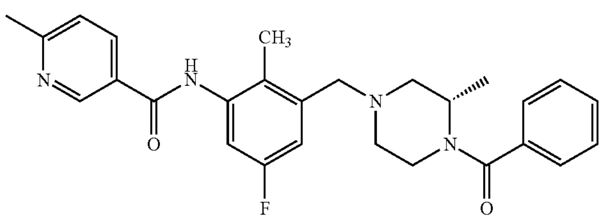 [SMILES: Cc1ccc(C(=O)Nc2cc(F)cc(CN3CCN(C(=O)c4ccccc4)[C@@H](C)C3)c2C)cn1] | δH (MeOD-d$_4$, 400 MHz): 1.26-1.34 (m, 3H), 2.11-2.14 (m, 1H), 2.27-2.30 (m, 4H), 2.620 (s, 3H), 2.69-2.92 (m, 2H), 3.28-3.29 (m, 2H), 3.32-3.34 (m, 0.5H), 3.523 (s, 2H), 4.581 (s, 0.5H), 7.05-7.11 (m, 2H), 7.35-7.39 (m, 2H), 7.43-7.46 (m, 4H), 8.24-8.26 (m, 1H), 8.98 (d, 1H). δF (MeOD-d$_4$, 376 MHz): −119.372, MS (ES): C$_{27}$H$_{29}$FN$_4$O$_2$ requires 460; found 461 (M + H$^+$). |
| E154 | 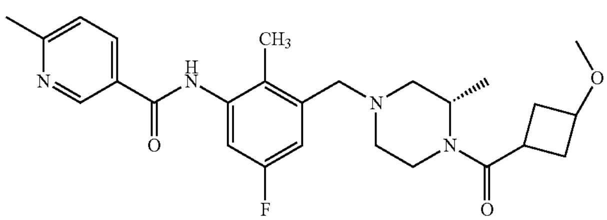 [SMILES: COC1CC(C(=O)N2CCN(Cc3cc(F)cc(NC(=O)c4ccc(C)nc4)c3C)C[C@@H]2C)C1] | δH (MeOD-d$_4$, 400 MHz): 1.21-1.32 (m, 3H), 1.98-2.18 (m, 4H), 2.270 (s, 3H), 2.43-2.49 (m, 2H), 2.618 (s, 3H), 2.70-2.72 (m, 1H), 2.82-2.86 (m, 2H), 2.86-2.90 (m, 0.5H), 3.211 (s, 3H), 3.48-3.58 (m, 2H). 3.59-3.62 (m, 0.5H), 3.80-3.85 (m, 1H), 4.03-4.11 (m, 0.5H), 4.25-4.32 (m, 0.5H), 4.56-4.63 (m, 1H), 7.05-7.11 (m, 2H), 7.46 (d, 1H), 8.24-8.26 (m, 1H), 8.98 (d, 1H). δF (MeOD-d$_4$, 376 MHz): −119.425, MS (ES): C$_{26}$H$_{33}$FN$_4$O$_3$ requires 468; found 469 (M + H$^+$). |
| E155 | 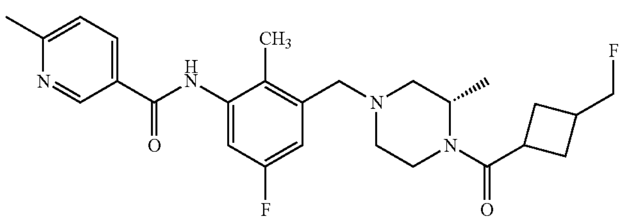 [SMILES: Cc1ccc(C(=O)Nc2cc(F)cc(CN3CCN(C(=O)C4CC(CF)C4)[C@@H](C)C3)c2C)cn1] | δH (MeOD-d$_4$, 400 MHz): 1.21-1.37 (m, 3H), 1.62-1.85 (m, 1H), 1.87-2.13 (m, 4H), 2.15-2.25 (m, 2H), 2.278 (s, 3H), 2.619 (s, 3H), 2.71-2.86 (m, 2H), 2.98-3.04 (m, 0.5H), 3.42-3.48 (m, 2H), 3.49-3.50 (m, 2H), 3.81-3.87 (m, 0.5H), 4.29-4.38 (m, 1H), 4.58-4.69 (m, 1H), 5.10-5.24 (m, 1H), 7.05-7.11 (m, 2H), 7.45 (d, 1H), 8.24-8.27 (m, 1H), 8.983 (s, 1H). δF (MeOD-d$_4$, 376 MHz): −119.396, −224.889, −224.972. MS (ES): C$_{26}$H$_{32}$F$_2$N$_4$O$_2$ requires 470: found 471 (M + H$^+$) |
| E156 | 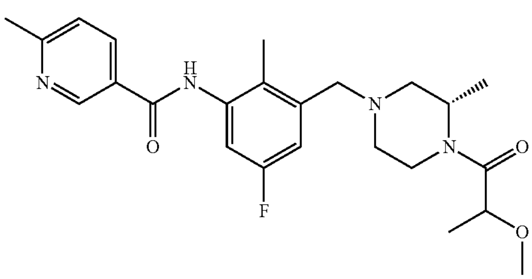 | δH (MeOD-d$_4$, 400 MHz): 1.31-1.34 (m, 3H), 1.36-1.39 (m, 3H), 2.01-2.12 (m, 1H), 2.19-2.25 (m, 1H), 2.282 (s, 3H), 2.623 (s, 3H), 2.74-2.76 (m, 1H), 2.83-2.88 (m, 1H), 3.02-3.05 (m, 0.5H), 3.27-3.47 (m, 3H), 3.50-3.54 (m, 2H), 3.86-3.90 (m, 0.5H), 4.20-4.31 (m, 2H), 4.58-4.68 (m, 1H), 7.06-7.11 (m, 2H), 7.46 (d, 1H), 8.24-8.27 (m, 1H), 8.988 (s, 1H). δF (MeOD-d$_4$, 376 MHz): −119.403, MS (ES): C$_{24}$H$_{31}$FN$_4$O$_3$ requires 442; found 443 (M + H$^+$). |

| Example | Structure | Characterization |
|---|---|---|
| E157 | 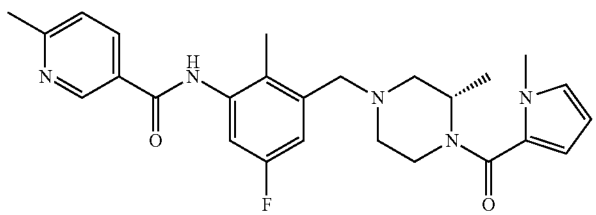 [SMILES: Cc1ccc(C(=O)Nc2cc(F)cc(CN3CCN(C(=O)c4cccn4C)[C@@H](C)C3)c2C)cn1] | δH (MeOD-d₄, 400 MHz): 1.36-1.37 (m, 3H), 2.10-2.11 (m, 0.5H), 2.12-2.14 (m, 2H), 2.25-2.26 (m, 0.5H), 2.288 (s, 3H), 2.622 (s, 3H), 2.73-2.76 (m, 1H), 2.84-2.86 (m, 1H), 3.522 (s, 2H), 3.695 (s, 3H), 4.16-4.20 (m, 1H), 4.643 (s, 1H), 6.05-6.06 (m, 1H), 6.32-6.33 (m, 1H), 6.78-6.79 (m, 1H), 7.06-7.12 (m, 2H), 7.46 (d, 1H), 8.24-8.27 (m, 1H), 8.991 (s, 1H). δF (MeOD-d₄, 376 MHz): −119.399 MS (ES): $C_{26}H_{30}FN_5O_2$ requires 463; found 464 (M + H⁺). |
| E158 | 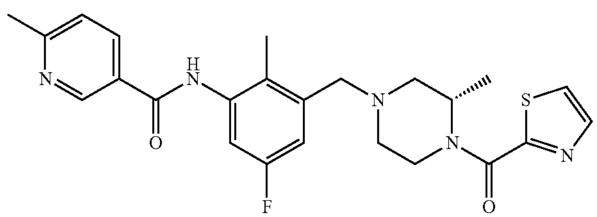 [SMILES: Cc1ccc(C(=O)Nc2cc(F)cc(CN3CCN(C(=O)c4nccs4)[C@@H](C)C3)c2C)cn1] | δH (MeOD-d₄, 400 MHz): 1.45 (m, 4H), 2.15 (m, 1H), 2.29 (m, 4H), 2.62 (s, 3H), 2.75 (m, 2H), 3.55 (m, 3H), 4.56 (m, 1H), 7.11 (m, 2H), 7.44 (m, 1H), 7.8 (m, 1H), 7.95 (m, 1H), 8.25 (m, 1H), 9.05 (s, 1H). δF (MeOD-d₄, 376 MHz): −119 MS (ES): $C_{24}H_{26}FN_5O_2S$ requires 467; found 468 (M + H⁺). |
| E159 | 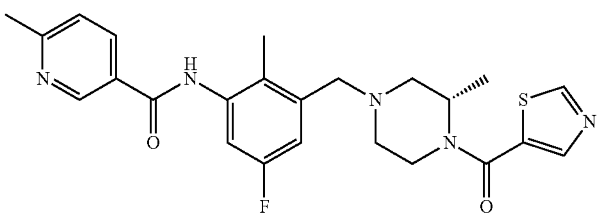 [SMILES: Cc1ccc(C(=O)Nc2cc(F)cc(CN3CCN(C(=O)c4cncs4)[C@@H](C)C3)c2C)cn1] | δH (MeOD-d₄, 400 MHz): 1.40 (m, 4H), 2.15 (m, 1H), 2.29 (m, 4H), 2.62 (s, 3H), 2.85 (m, 2H), 3.45 (m, 3H), 4.16 (m, 1H), 4.56 (m, 1H), 7.09 (m, 2H), 7.46 (m, 1H), 8.10 (m, 1H), 8.25 (m, 1H), 9.15 (m, 2H). δF (MeOD-d₄, 376 MHz): −119 MS (ES): $C_{24}H_{26}FN_5O_2S$ requires 467; found 468 (M + H⁺). |
| E160 | 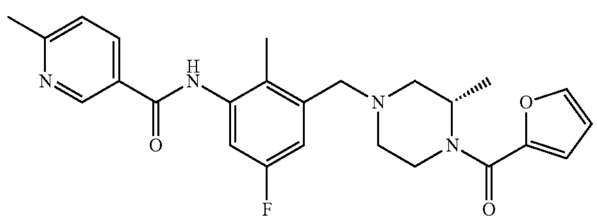 [SMILES: Cc1ccc(C(=O)Nc2cc(F)cc(CN3CCN(C(=O)c4ccco4)[C@@H](C)C3)c2C)cn1] | δH (MeOD-d₄, 400 MHz): 1.40 (m, 3H), 2.15 (m, 1H), 2.29 (m, 4H), 2.62 (s, 3H), 2.75 (m, 1H), 2.90 (m, 1H), 3.50 (m, 3H), 4.30 (m, 1H), 4.65 (m, 1H), 6.50 (m, 1H), 6.98 (m, 1H), 7.10 (m, 2H), 7.47 (m, 1H), 7.65 (m, 1H), 8.25 (m, 1H), 8.98 (m, 1H).. δF (MeOD-d₄, 400 MHz): −119 MS (ES): $C_{25}H_{27}FN_4O_3$ requires 450; found 451 (M + H⁺). |
| E161 | 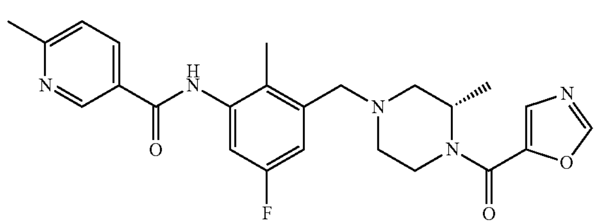 [SMILES: Cc1ccc(C(=O)Nc2cc(F)cc(CN3CCN(C(=O)c4cnco4)[C@@H](C)C3)c2C)cn1] | δH (MeOD-d₄, 400 MHz): 1.35-1.50 (m, 3H), 2.11-2.18 (m, 1H), 2.293 (s, 3H), 2.31-2.32 (m, 1H), 2.623 (s, 3H), 2.77-2.80 (m, 1H), 2.89-2.92 (m, 1H), 3.45-3.47 (m, 1H), 3.537 (s, 2H), 4.204 (s, 1H), 4.56-4.61 (m, 1H), 7.06-7.12 (m, 2H), 7.46 (d, 1H), 7.626 (s, 1H), 8.24-8.32 (m, 2H), 8.992 (s, 1H). δF (MeOD-d₄, 376 MHz): −119.368, MS (ES): $C_{24}H_{26}FN_5O_3$ requires 451; found 452 (M + H⁺). |
| E162 | 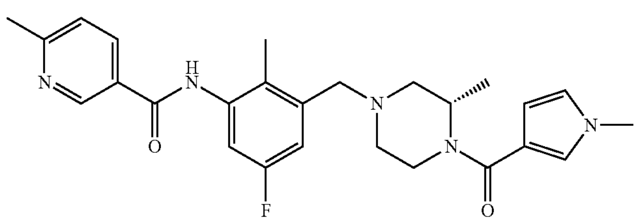 | δH (MeOD-d₄, 400 MHz): 1.35-1.36 (m, 3H), 2.05-2.12 (m, 1H), 2.22-2.28 (m, 4H), 2.621 (s, 3H), 2.71-2.85 (m, 2H), 3.35-3.38 (m, 1H), 3.509 (s, 2H), 3.667 (s, 3H), 4.24-4.27 (m, 1H), 4.675 (s, 1H), 6.25-6.26 (m, 1H), 6.65-6.66 (m, 1H), 7.02-7.11 (m, 3H), 7.45 (d, 1H), 8.24-8.27 (m, 1H), 8.988 (s, 1H). δF (MeOD-d₄, 376 MHz): −120.211, MS (ES): $C_{26}H_{30}FN_5O_2$ requires 463.2; found 464.2 (M + H⁺). |

Example 163

(S)-N-(3-((4-(2-cyclobutylacetyl)-3-methylpiperazin-1-yl)methyl)-5-fluoro-2-methylphenyl)-6-methylnicotinamide (E163)

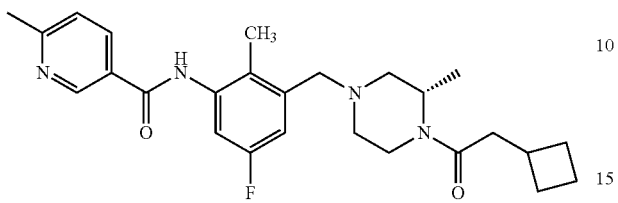

To a solution of 2-cyclobutylacetic acid (25.6 mg, 0.224 mmol) in $CH_2Cl_2$ (2 mL) was added HATU (85 mg, 0.224 mmol), N-ethyl-N-isopropylpropan-2-amine (87 mg, 0.673 mmol), after 30 mins, (S)-N-(5-fluoro-2-methyl-3-((3-methylpiperazin-1-yl)methyl)phenyl)-6-methylnicotinamide (80 mg, 0.224 mmol) was added. Then the reaction mixture was stirred for 15 hr at RT. Then water was added, and the solution was extracted with $CH_2Cl_2$ (20 mL×2). The combined organic layers were dried over $MgSO_4$ and condensed. The obtained mixture was purified by MDAP to afford the title compound (24.5 mg) as a white solid. δH (MeOD-$d_4$, 400 MHz): 1.20-1.33 (m, 3H), 1.69-1.76 (m, 2H), 1.82-1.90 (m, 2H), 1.98-2.01 (m, 0.5H), 2.05-2.16 (m, 3H), 2.19-2.21 (m, 0.5H), 2.272 (s, 3H), 2.41-2.48 (m, 2H), 2.56-2.61 (m, 3H), 2.62-2.65 (m, 1H), 2.68-2.74 (m, 1H), 2.82-2.84 (m, 1H), 2.89-2.92 (m, 0.5H), 3.38-3.41 (m, 0.5H), 3.48-3.49 (m, 2H), 3.65-3.79 (m, 0.5H), 4.12-4.35 (m, 1H), 4.58-4.69 (m, 0.5H), 7.04-7.11 (m, 2H), 7.45 (d, 1H), 8.24-8.26 (m, 1H), 8.98 (d, 1H). δF (MeOD-$d_4$, 376 MHz): −119.885, MS (ES): $C_{26}H_{33}FN_4O_2$ requires 452; found 453 (M+H$^+$).

Example 164

(S)-N-(3-((4-(3,3-dimethylcyclobutanecarbonyl)-3-methylpiperazin-1-yl)methyl)-5-fluoro-2-methylphenyl)-6-methylnicotinamide (E164)

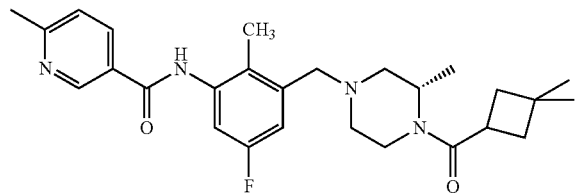

To a solution of 3,3-dimethylcyclobutanecarboxylic acid (21.58 mg, 0.168 mmol) in $CH_2Cl_2$ (2 mL) was added HATU (64.0 mg, 0.168 mmol), N-ethyl-N-isopropylpropan-2-amine (65.3 mg, 0.505 mmol), after 30 mins, (S)-N-(5-fluoro-2-methyl-3-((3-methylpiperazin-1-yl)methyl)phenyl)-6-methylnicotinamide (60 mg, 0.168 mmol) was added. Then the reaction mixture was stirred for 15 hr at RT. Then water was added, and the solution was extracted with $CH_2Cl_2$ (20 mL×2). The combined organic layers were dried over $MgSO_4$ and condensed. The obtained mixture was purified by MDAP to give the title compound (20.2 mg) as a white solid. δH (MeOD-$d_4$, 400 MHz): 1.05-1.07 (m, 3H), 1.14-1.22 (m, 5H), 1.27-1.36 (m, 1H), 1.18-1.97 (m, 2H), 2.00-2.10 (m, 2H), 2.144 (s, 3H), 2.15-2.18 (m, 1H), 2.272 (s, 3H), 2.621 (s, 3H), 2.69-2.72 (m, 1H), 2.79-2.84 (m, 1H), 2.95-2.98 (m, 0.5H), 3.48-3.55 (m, 2H), 3.993 (s, 0.5H), 4.25-4.28 (m, 0.5H), 4.615 (s, 0.5H), 7.05-7.11 (m, 2H), 7.46 (d, 1H), 8.25-8.27 (m, 1H), 8.987 (s, 1H). δF (MeOD-$d_4$, 376 MHz): −119.415, MS (ES): $C_{27}H_{35}FN_4O_2$ requires 466; found 467 (M+H$^+$).

Example 165

(S)-N-(3-((4-(3-(difluoromethyl)cyclobutanecarbonyl)-3-methylpiperazin-1-yl)methyl)-5-fluoro-2-methylphenyl)-6-methylnicotinamide (E165)

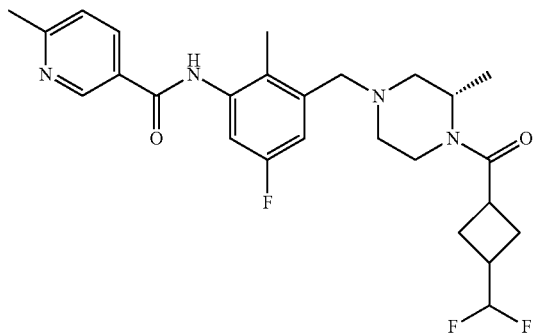 [SMILES: Cc1ccc(C(=O)Nc2cc(F)cc(CN3CCN(C(=O)C4CC(C(F)F)C4)[C@@H](C)C3)c2C)cn1]

To a solution of 3-(difluoromethyl)cyclobutanecarboxylic acid (21.06 mg, 0.140 mmol) in $CH_2Cl_2$ (2 mL) was added HATU (53.3 mg, 0.140 mmol), N-ethyl-N-isopropylpropan-2-amine (54.4 mg, 0.421 mmol), after 30 mins, (S)-N-(5-fluoro-2-methyl-3-((3-methylpiperazin-1-yl)methyl)phenyl)-6-methylnicotinamide (50 mg, 0.140 mmol) was added. Then the reaction mixture was stirred for 15 hr at RT. Then water was added, and the solution was extracted with $CH_2Cl_2$ (20 mL×2). The combined organic layers were dried over $MgSO_4$ and condensed. The obtained mixture was purified by MDAP to give the title compound (8.4 mg) as a white solid. δH (MeOD-$d_4$, 400 MHz): 1.22-1.25 (m, 2H), 1.27-1.31 (m, 1H), 1.99-2.02 (m, 1H), 2.15-2.21 (m, 2H), 2.26-2.31 (m, 3H), 2.33-2.37 (m, 2H), 2.39-2.48 (m, 1H), 2.617 (s, 3H), 2.70-2.73 (m, 1H), 2.81-2.89 (m, 1H), 2.95-2.98 (m, 0.5H), 3.45-3.48 (m, 0.5H), 3.48-3.49 (m, 1H), 3.49-3.52 (m, 2H), 3.87-3.95 (m, 0.5H), 4.26-4.30 (m, 0.5H), 4.62-4.75 (m, 2H), 5.78-6.16 (m, 1H), 7.04-7.11 (m, 2H), 7.45 (d, J=8 Hz, 1H), 8.24-8.26 (m, 1H), 8.979 (s, 1H). δF (MeOD-$d_4$, 376 MHz): −119.396, 125.983, 126.066. MS (ES): $C_{26}H_{31}F_3N_4O_2$ requires 488; found 489 (M+H$^+$).

Example 166

N-(5-fluoro-3-(((3S)-4-(3-fluorocyclopentanecarbonyl)-3-methylpiperazin-1-yl)methyl)-2-methylphenyl)-6-methylnicotinamide (E166)

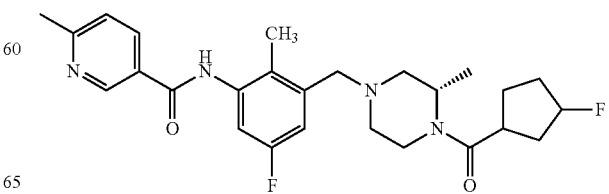

To a solution of 3-fluorocyclopentanecarboxylic acid (29.7 mg, 0.224 mmol) in $CH_2Cl_2$ (2 mL) was added HATU (85 mg, 0 224 mmol), N-ethyl-N-isopropylpropan-2-amine (87 mg, 0.673 mmol), after 30 mins, (S)-N-(5-fluoro-2-methyl-3-((3-methylpiperazin-1-yl)methyl)phenyl)-6-methylnicotinamide (80 mg, 0.224 mmol) was added. Then the reaction mixture was stirred for 15 hr at RT. Then water was added, and the solution was extracted with $CH_2Cl_2$ (20 mL×2). The combined organic layers were dried over $MgSO_4$ and condensed. The obtained mixture was purified MDAP to give the title compound (28.2 mg) as a white solid. δH (MeOD-$d_4$, 400 MHz): 1.22-1.36 (m, 3H), 1.68-1.70 (m, 1H), 1.82-1.85 (m, 1H), 1.86-2.08 (m, 4H), 2.16-2.23 (m, 2H), 2.28 (s, 3H), 2.621 (s, 3H), 2.71-2.76 (m, 1H), 2.83-2.86 (m, 1H), 2.96-3.04 (m, 0.5H), 3.06-3.08 (m, 1H), 3.36-3.39 (m, 0.5H), 3.49-3.51 (m, 2H), 3.77-3.80 (m, 0.5H), 4.21-4.38 (m, 1H), 4.66-4.67 (m, 0.5H), 5.02-5.16 (m, 1H), 7.05-7.12 (m, 2H), 7.46 (d, J=8 Hz, 1H), 8.24-8.27 (m, 1H), 8.98 (d, J=2 Hz, 1H). δF (MeOD-$d_4$, 376 MHz): −119.398, −169.974. MS (ES): $C_{26}H_{32}F_2N_4O_2$ requires 470; found 471 (M+H$^+$).

Example 167

(S)-N-(5-fluoro-3-((4-(3-fluoro-3-methylcyclobutanecarbonyl)-3-methylpiperazin-1-yl)methyl)-2-methylphenyl)-6-methylnicotinamide (E167)

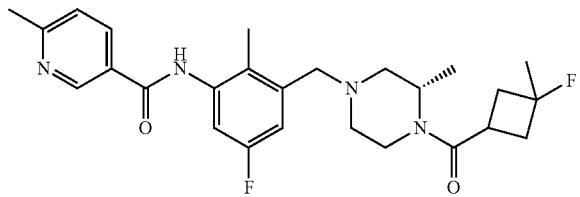 [SMILES: Cc1ccc(C(=O)Nc2cc(F)cc(CN3CCN(C(=O)C4CC(C)(F)C4)[C@@H](C)C3)c2C)cn1]

The mixture of 3-fluoro-3-methylcyclobutanecarboxylic acid (20.39 mg, 0.154 mmol), (S)-N-(5-fluoro-2-methyl-3-((3-methylpiperazin-1-yl)methyl)phenyl)-6-methylnicotinamide (55 mg, 0.154 mmol), DIEA (0.054 mL, 0.309 mmol) and HATU (58.7 mg, 0.154 mmol) was stirred at 20° C. for 16 hr. The reaction mixture was added water and extracted with DCM. The organic layer was dried over Na2SO4, filtered and concentrated. The residue was purified by MDAP to afford the title compound (10 mg). δH (MeOD-$d_4$, 400 MHz): 9.02 (d, J=1.8 Hz, 1H), 8.29 (dd, J=2.4, 8.2 Hz, 1H), 7.49 (d, J=8.0 Hz, 1H), 7.18-7.06 (m, 2H), 4.70-4.55 (m, 1H), 4.37-3.94 (m, 1H), 3.58-3.40 (m, 3H), 3.06-2.70 (m, 3H), 2.68-2.35 (m, 7H), 2.31 (s, 3H), 2.24-2.17 (m, 1H), 2.10-1.98 (m, 1H), 1.48-1.38 (m, 3H), 1.36-1.24 (m, 3H).

Example 168

N-(3-(((3S)-4-(2-cyclopropyl-2-fluoroacetyl)-3-methylpiperazin-1-yl)methyl)-5-fluoro-2-methylphenyl)-6-methylnicotinamide (E168)

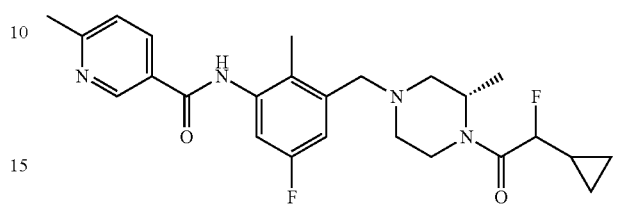

The mixture of (S)-N-(5-fluoro-2-methyl-3-((3-methylpiperazin-1-yl)methyl)phenyl)-6-methylnicotinamide (70 mg, 0.196 mmol), 2-cyclopropyl-2-fluoroacetic acid (23.19 mg, 0.196 mmol), HATU (74.7 mg, 0.196 mmol) and N-ethyl-N- isopropylpropan-2-amine (0.069 mL, 0.393 mmol) was stirred at 20° C. for 16 hr. The reaction mixture was added water and extracted with DCM.

The organic layer was dried over Na2SO4, filtered and concentrated. The residue was purified by MDAP to afford the title compound (10 mg). δH (MeOD-$d_4$, 400 MHz): 9.02 (s, 1H), 8.29 (dd, J=2.3, 8.0 Hz, 1H), 7.49 (d, J=8.0 Hz, 1H), 7.13 (ddd, J=2.8, 9.5, 12.1 Hz, 2H), 4.71-4.36 (m, 2H), 4.34-4.01 (m, 2H), 3.55 (s, 2H), 3.12-2.70 (m, 3H), 2.65 (s, 3H), 2.39-1.96 (m, 6H), 1.72 (br. s., 1H), 1.48-1.14 (m, 4H), 0.90 (br. s., 1H).

Example169

N-(3-(((3S)-4-(2-cyclopropylpropanoyl)-3-methylpiperazin-1-yl)methyl)-5-fluoro-2-methylphenyl)-6-methylnicotinamide (E169)

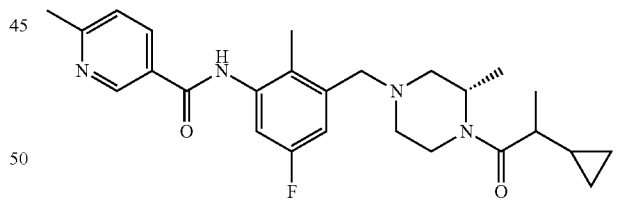

The mixture of 2-cyclopropylpropanoic acid (D33) (17.61 mg, 0.154 mmol), (S)-N-(5-fluoro-2-methyl-3-((3-methylpiperazin-1-yl)methyl)phenyl)-6-methylnicotinamide (55 mg, 0.154 mmol), DIEA (0.054 mL, 0.309 mmol)and HATU (58.7 mg, 0.154 mmol) was stirred at 20° C. for 16 hr. The reaction mixture was added water and extracted with DCM. The organic layer was dried over Na2SO4, filtered and concentrated. The residue was purified by MDAP to afford the title compound (12 mg). δH (MeOD-$d_4$, 400 MHz): 9.02 (s, 1H), 8.29 (dd, J=2.1, 7.9 Hz, 1H), 7.49 (d, J=8.0 Hz, 1H), 7.18-7.06 (m, 2H), 4.64-3.69 (m, 1H), 3.53 (d, J=5.0 Hz, 2H), 3.06-2.71 (m, 3H), 2.65 (s, 3H), 2.36-1.91 (m, 7H), 1.46-1.12 (m, 6H), 1.00 (d, J=14.6 Hz, 1H), 0.61-0.36 (m, 2H), 0.17 (d, J=12.0 Hz, 2H).

Example 170

N-(3-(((3S)-4-(2-cyclobutylpropanoyl)-3-methylpiperazin-1-yl)methyl)-5-fluoro-2-methylphenyl)-6-methylnicotinamide (E170)

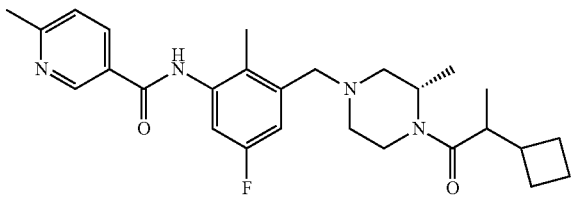 [SMILES: Cc1ccc(C(=O)Nc2cc(F)cc(CN3CCN(C(=O)C(C)C4CCC4)[C@@H](C)C3)c2C)cn1]

The mixture of 2-cyclobutylpropanoic acid (19.78 mg, 0.154 mmol), (S)-N-(5-fluoro-2-methyl-3-((3-methylpiperazin-1-yl)methyl)phenyl)-6-methylnicotinamide (55 mg, 0.154 mmol), DIEA (0.054 mL, 0.309 mmol) and HATU (58.7 mg, 0.154 mmol) was stirred at 20° C. for 16 hr. The reaction mixture was added water and extracted with DCM. The organic layer was dried over Na2SO4, filtered and concentrated. The residue was purified by MDAP to afford the title compound (20 mg). δH (MeOD-d$_4$, 400 MHz): 7.41-7.32 (m, 2H), 7.28-7.20 (m, 3H), 5.31-5.24 (m, 5H), 4.24 (td, J=4.1, 13.9 Hz, 2H), 3.71-3.57 (m, 4H), 3.03 (s, 6H), 2.19-1.91 (m, 5H), 1.31 (d, J=6.5 Hz, 7H).

Example 171

N-(3-(((S)-4-(cyclopentanecarbonyl)-3-methylpiperazin-1-yl)methyl)-5-fluoro-2-methylphenyl)-2-fluorocyclopentanecarboxamide hydrochloride (E171)

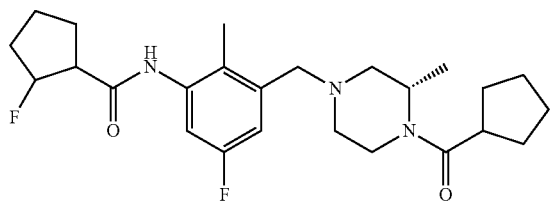

To a solution of 2-fluorocyclopentanecarboxylic acid (39.6 mg, 0.3 mmol) in DCM (2 mL) was added HATU (114 mg, 0.3 mmol) and Et3N (3 eq). The reaction mixture was stirred at rt for 3 h. To this mixture was added rt (S)-(4-(3-amino-5-fluoro-2-methylbenzyl)-2-methylpiperazin-1-yl)(cyclopentyl)methanone (1 eq). This mixture was stirred at rt for 18 hr. This crude was purified by MDAP to afford the title compound (19 mg) as white solid. δH (CDCl3-d$_1$, 400 MHz): 1.26 (m, 2H), 1.42 (m, 1H), 1.75 (m, 8H), 2.02 (m, 2H), 2.26 (s, 3H), 2.56 (m, 2H), 2.67 (m, 2H), 3.30 (m, 2H), 3.50 (m, 4H), 4.25 (m, 1H), 4.47 (m, 2H), 4.65 (m, 1H), 5.00 (m, 1H), 6.78 (m, 1H), 7.27 (m, 2H). δF (MeOD-d$_4$, 376 MHz): −70.5, −111.3. MS (ES): C, 25; H, 35; F, 2; N, 3; O, 2; requires 447; found 428(M−F$^+$).

Example 172

(S)-N-(5-fluoro-2-methyl-3-((3-methyl-4-(3-methylcyclobutanecarbonyl)piperazin-1-yl)methyl)phenyl)-6-methylnicotinamide (E172)

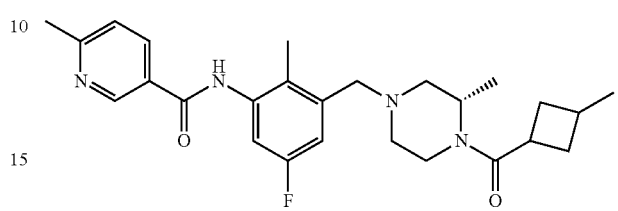

To a solution of (S)-N-(5-fluoro-2-methyl-3-((3-methylpiperazin-1-yl)methyl)phenyl)-6-methylnicotinamide (100 mg, 0.281 mmol), 3-methylcyclobutanecarboxylic acid (32.0 mg, 0.281 mmol) and HATU (107 mg, 0.281 mmol) in DCM (1 mL) stirred under nitrogen at 0° C. was added DIEA (0.098 mL, 0.561 mmol), then the reaction mixture was stirred at RT for 15 hr. Removed the solvent, and the residue was purified by MDAP to give the title compound (40 mg) as a white oil. δH (CDCl3-d$_1$, 400 MHz): 1.18 (m, 7H), 1.89 (m, 3H), 2.15 (m, 2H), 2.22 (m, 4H), 2.61 (m, 1H), 2.64 (s, 3H), 2.75 (m, 1H), 3.00 (m, 1H), 3.20 (m, 1H), 3.50 (m, 3H), 4.50 (m, 1H), 6.88 (d, 1H), 7.29 (d, 1H), 7.67 (d, 1H), 7.76 (s, 1H), 8.10 (dd, 2 Hz, 1H), 8.98 (d, 1H). δF (MeOD-d$_4$, 376 MHz): −118 MS (ES): C, 25; H, 35; F, 2; N, 3; O, 2; requires 452; found 453 (M+1$^+$).

Example 173

(S)-3-cyano-N-(5-fluoro-3-((4-(3-fluorobenzoyl)-3-methylpiperazin-1-yl)methyl)-2-methylphenyl)benzamide (E173)

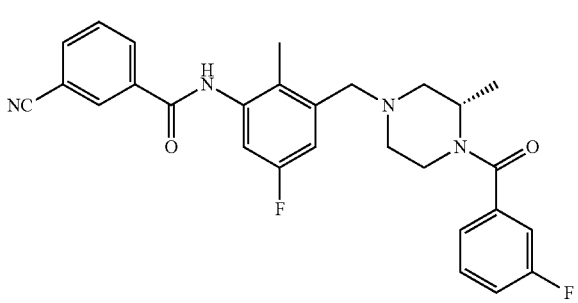 [SMILES: Cc1c(CN2CCN(C(=O)c3cccc(F)c3)[C@@H](C)C2)cc(F)cc1NC(=O)c1cccc(C#N)c1]

(S)-3-cyano-N-(5-fluoro-2-methyl-3-((3-methylpiperazin-1-yl)methyl)phenyl)benzamide (200 mg, 0.546 mmol) was added into a solution of 3-fluorobenzoic acid (76 mg, 0.546 mmol). HATU (311 mg, 0.819 mmol) and DIPEA (0.286 mL, 1.637 mmol) in DMF (8 mL) at RT. The reaction was stirred at RT overnight. After checked by LCMS, the reaction was completed. The mixture was concentrated and the residue was subjected to MDAP to give the title compound (47 mg, 0.091 mmol, 16.75% yield) as white solid. $^1$H NMR (400 MHz, MeOD-d$_4$) δ 1.37 (d, 3H), 2.07-2.21 (m, 1H), 2.29 (s, 3H), 2.32 (s, 0.5H), 2.66-2.93 (m, 2H), 3.54 (s, 2H), 4.49 (s, 0.5H), 7.05-7.17 (m, 3H), 7.17-7.25 (m, 2H), 7.44-7.53 (m, 1H), 7.72 (t, 1H), 7.96 (d, 1H), 8.25 (d, 1H), 8.32 (s, 1H). $^{19}$F NMR (376 MHz, MeOD-d$_4$) δ −113.7, −119.3. MS (ESI) C$_{28}$H$_{26}$F$_2$N$_4$O$_2$ requires: 488, found 489 (M+H$^+$).

Examples 174

(S)-3-cyano-N-(3-((4-(2-cyclopropylacetyl)-3-methylpiperazin-1-yl)methyl)-5-fluoro-2-methylphenyl)benzamide, trifluoroacetic acid salt (E174)

Examples 174 was prepared using a similar procedure to that described for Example 173. $^1$H NMR (400 MHz, MeOD-d$_4$) δ 0.13-0.25 (m, 2H), 0.50-0.63 (m, 2H), 1.01 (tq, 1H), 1.35 (brs, 3H), 2.26-2.50 (m, 5H), 2.89-3.27 (m, 3H), 3.35-3.69 (m, 3H), 4.04 (brs, 0.5H), 4.38 (s, 2H), 4.44-4.70 (m, 1H), 4.89-5.07 (m, 0.5H), 7.33 (d, 2H), 7.75 (t, 1H), 7.98 (d, 1H), 8.27 (d, 1H), 8.33 (s, 1H). $^{19}$F NMR (376 MHz, MeOD-d$_4$) δ −73.5, −75.4, −77.3, −117.0. MS (ESI) C$_{26}$H$_{29}$FN$_4$O$_2$ requires: 448, found 449 (M+H$^+$).

Example 175

(S)-3-cyano-N-(3-((4-(3,3-difluorocyclobutanecarbonyl)-3-methylpiperazin-1-yl)methyl)-5-fluoro-2-methylphenyl)benzamide, trifluoroacetic acid salt (E175)

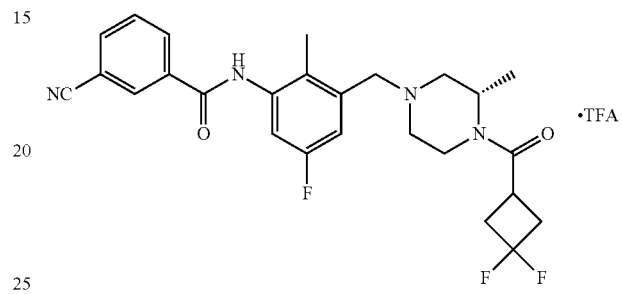

HATU (311 mg, 0.819 mmol) was added into a mixture of 3,3-difluorocyclobutanecarboxylic acid (74.3 mg, 0.546 mmol), (S)-3-cyano-N-(5-fluoro-2-methyl-3-((3-methylpiperazin-1-yl)methyl)phenyl)benzamide (200 mg, 0.546 mmol) and DIPEA (212 mg, 1.637 mmol) in N,N-Dimethylformamide (DMF) (5 mL) at RT. The reaction was stirred at RT overnight. The mixture was subjected to MDAP to afford the title compound as white solid. $^1$H NMR (400 MHz, MeOD-d$_4$) δ 1.24-1.45 (m, 3H), 2.32 (s, 3H), 2.67-3.18 (m, 7H), 3.37 (s, 1H), 3.20-3.41 (m, 1H), 3.86 (brs, 1H), 4.13-4.42 (m, 3H), 4.55 (brs, 1H), 7.24-7.35 (m, 2H), 7.74 (t, 1H), 7.98 (d, 1H), 8.27 (d, 1H), 8.33 (s, 1H). $^{19}$F NMR (376 MHz, MeOD-d$_4$) δ −73.8, −75.7, −77.0, −84.24 (dd), −98.34 (dd), −121.1. MS (ESI) C$_{26}$H$_{27}$F$_3$N$_4$O$_2$ requires: 484, found 485 (M+H$^+$).

Examples 176-178

Examples 176-178 were prepared using a similar procedure to that described for Example 175.

E176: 3-cyano-N-(5-fluoro-3-(((3S)-4-(3-fluorocyclopentanecarbonyl)-3-methylpiperazin-1-yl)methyl)-2-methylphenyl)benzamide, trifluoroacetic acid salt E177: (S)-N-(3-((4-benzoyl-3-methylpiperazin-1-yl)methyl)-5-fluoro-2-methylphenyl)-3-cyanobenzamide E178: (S)-3-cyano-N-(3-((4-(2-cyclobutylacetyl)-3-methylpiperazin-1-yl)methyl)-5-fluoro-2-methylphenyl)benzamide, trifluoroacetic acid salt

| Example | Structure | Characterization |
|---|---|---|
| E176 | 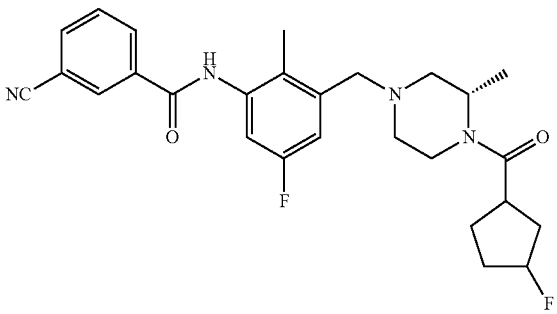 | ¹H NMR (400 MHz, MeOD-d₄) δ 1.16-1.44 (m, 3H), 1.65-2.41 (m, 11H), 2.70-3.16 (m, 3.5H), 3.35-3.46 (m, 0.5H), 3.53 (s, 2H), 3.80 (d, 0.5H), 4.16-4.40 (m, 1H), 5.01-5.07 (m, 0.5H), 5.14-5.22 (m, 0.5H), 7.04-7.16 (m, 2H), 7.72 (t, 1H), 7.95 (d, 1H), 8.26 (d, 1H), 8.32 (s, 1H). ¹⁹F NMR (376 MHz, MeOD-d₄) δ −76.9, −119.2, −170.0−−170.4 (m). MS (ESI) $C_{27}H_{30}F_2N_4O_2$ requires: 480, found 481 (M + H⁺). ·TFA |
| E177 | 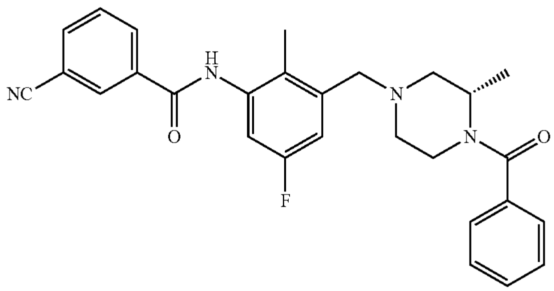 [SMILES: Cc1c(CN2CCN(C(=O)c3ccccc3)[C@@H](C)C2)cc(F)cc1NC(=O)c1cccc(C#N)c1] | ¹H NMR (400 MHz, MeOD-d₄) δ 1.36 (d, 3H), 2.07-2.20 (m, 1H), 2.29 (s, 3H), 2.31 (s, 1H), 2.78 (d, 2H), 3.53 (s, 2H), 4.50 (brs, 1H), 7.09 (t, 2H), 7.32-7.53 (m, 5H), 7.72 (t, 1H), 7.95 (d, 1H), 8.25 (d, 1H), 8.32 (s, 1H). ¹⁹F NMR (376 MHz, MeOD-d₄) δ −119.3. MS (ESI) $C_{28}H_{27}FN_4O_2$ requires: 470, found 471 (M + H⁺). |
| E178 | 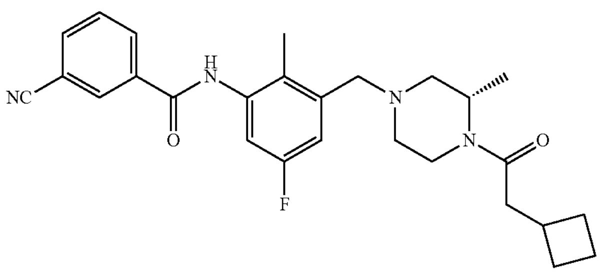 | ¹H NMR (400 MHz, MeOD-d₄) δ 1.21-1.49 (m, 3H), 1.65-1.99 (m, 4H), 2.06-2.22 (m, 2H), 2.34 (s, 3H), 2.45-2.75 (m, 3H), 2.86 (s, 1H), 2.99 (s, 1H), 3.03-3.29 (m, 2H), 3.37-3.68 (m, 2.5H), 4.12 (brs, 0.5H), 4.40-4.53 (m, 2H), 7.35 (d, 2H), 7.75 (t, 1H), 7.98 (d, 1H), 8.27 (d, 1H), 8.33 (s, 1H). ¹⁹F NMR (376 MHz, MeOD-d₄) δ −73.3, −75.2, −77.4, −116.8. MS (ESI) $C_{27}H_{31}FN_4O_2$ requires: 462, found 463 (M + H⁺). ·TFA |

Example 179

(S)-3-cyano-N-(3-((4-(cyclohexanecarbonyl)-3-methylpiperazin-1-yl)methyl)-5-fluoro-2-methylphenyl)benzamide (E179)

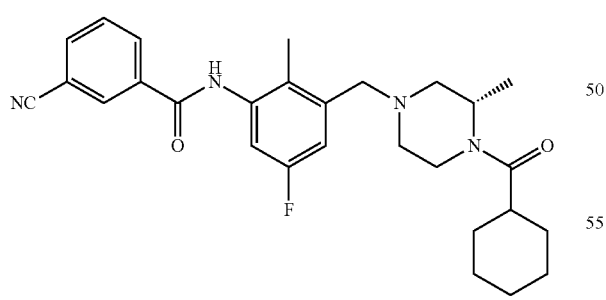

Cyclohexanecarbonyl chloride (84 mg, 0.573 mmol) was added into a mixture of (S)-3-cyano-N-(5-fluoro-2-methyl-3-((3-methylpiperazin-1-yl)methyl)phenyl)benzamide (150 mg, 0.409 mmol) in Pyridine (4 mL) at RT. The reaction was stirred at RT overnight. After checked by LCMS, the reaction was completed. The mixture was subjected to MDAP to afford the title compound (14 mg, 0.028 mmol, 6.82% yield) as white solid. ¹H NMR (400 MHz, MeOD-d₄) δ 1.13-1.60 (m, 8H), 1.60-1.86 (m, 5H), 1.92-2.26 (m, 2H), 2.29 (s, 3H), 2.53-3.02 (m, 3.5H), 3.34-3.45 (m, 0.5H), 3.45-3.58 (m, 2H), 3.79 (d, 0.5H), 4.16-4.37 (m, 1H), 4.67 (brs, 0.5H), 7.10 (ddd, 2H), 7.72 (t, 1H), 7.95 (d, 1H), 8.25 (d, 1H), 8.32 (s, 1H). ¹⁹F NMR (376 MHz, MeOD-d₄) δ −119.2. MS (ESI) $C_{28}H_{33}FN_4O_2$ requires: 476, found 477 (M+H⁺).

Example 180

(S)-N-(2-chloro-3-((4-(cyclohexanecarbonyl)-3-methylpiperazin-1-yl)methyl)phenyl)-3-cyanobenzamide (E180)

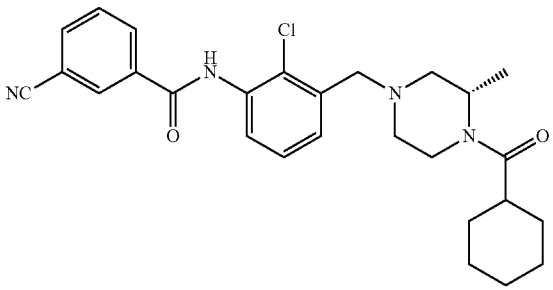 [SMILES: C[C@H]1CN(Cc2cccc(NC(=O)c3cccc(C#N)c3)c2Cl)CCN1C(=O)C1CCCCC1]

Cyclohexanecarboxylic acid (31.3 mg, 0.244 mmol) was added into a mixture of (S)-N-(2-chloro-3-((3-methylpiperazin-1-yl)methyl)phenyl)-3-cyanobenzamide (90 mg, 0.244 mmol), HATU (139 mg, 0.366 mmol) and DIPEA (0.128 mL, 0.732 mmol) in DMF (6 mL) at RT and stirred overnight. After checked by LCMS, the reaction was completed. The mixture was concentrated and the residue was subjected to MDAP to afford the title compound (29 mg, 0.058 mmol, 23.57% yield) as white solid. $^1$H NMR (400 MHz, MeOD-d$_4$) δ 1.16-1.61 (m, 9H), 1.61-1.86 (m, 5H), 1.99-2.39 (m, 2H), 2.53-3.05 (m, 3.5H), 3.36-3.48 (m, 0.5H), 3.60-3.72 (m, 2H), 3.81 (d, 0.5H), 4.23 (brs, 0.5H), 4.32 (d, 0.5H), 4.67 (brs, 0.5H), 7.37 (t, 1H), 7.50 (d, 1H), 7.64 (d, 1H), 7.74 (t, 1H), 7.97 (d, 1H), 8.27 (d, 1H), 8.33 (s, 1H). MS (ESI) C$_{27}$H$_{31}$ClN$_4$O$_2$ requires: 478, found 479 (M+H$^+$).

Examples 181-183

Examples 181-183 were prepared using a similar procedure to that described for Example 180.
E181: (S)-N-(3-((4-benzoyl-3-methylpiperazin-1-yl)methyl)-2-chlorophenyl)-3-cyanobenzamide
E182: (S)-N-(2-chloro-3-((4-(3-fluorobenzoyl)-3-methylpiperazin-1-yl)methyl)phenyl)-3-cyanobenzamide
E183: (S)-N-(2-chloro-3-((4-(3,3-difluorocyclobutanecarbonyl)-3-methylpiperazin-1-yl)methyl)phenyl)-3-cyanobenzamide, trifluoroacetic acid salt Example 184

(S)-N-(5-chloro-3-((4-(2-cyclopropylacetyl)-3-methylpiperazin-1-yl)methyl)-2-methylphenyl)-6-methylnicotinamide, trifluoroacetic acid salt (E184)

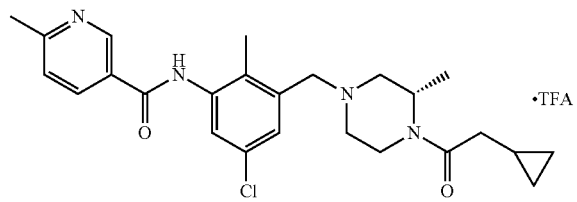

DIPEA (0.211 mL, 1.207 mmol) was added into a mixture of 2-cyclopropylacetic acid (40.3 mg, 0.402 mmol), (S)-N-(5-chloro-2-methyl-3-((3-methylpiperazin-1-yl)methyl)phenyl)-6-methylnicotinamide (150 mg, 0.402 mmol) and HATU (214 mg, 0.563 mmol) in DMF (6 mL) at RT. The reaction was stirred at RT overnight. After the reaction was completed, the mixture was subjected to MDAP to give the title compound (115 mg) as white solid. 1H NMR (400 MHz, MeOD-d4) δ 0.0 (m, 2 H), 0.4 (m, 2 H), 0.8 (m, 1 H), 1.2 (m, 3 H), 2.2 (m, 5 H), 2.6 (s, 3 H), 2.7 (m, 1 H), 2.8 (m,

| Example | Structure | Characterization |
|---|---|---|
| E181 | 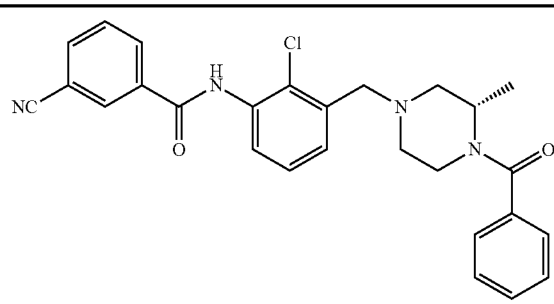 | $^1$H NMR (400 MHz, MeOD-d$_4$) δ 1.39 (s, 3H), 2.09-2.28 (m, 1H), 2.28-2.42 (m, 1H), 2.56-3.06 (m, 2H), 3.36-3.58 (m, 1H), 3.67 (s, 2H), 3.79-4.70 (m, 2H), 7.31-7.43 (m, 3H), 7.43-7.54 (m, 4H), 7.63 (d, 1H), 7.72 (t, 1H), 7.96 (d, 1H), 8.25 (d, 1H), 8.32 (s, 1H). MS (ESI) C$_{27}$H$_{25}$ClN$_4$O$_2$ requires: 472, found 473 (M + H$^+$). |
| E182 | 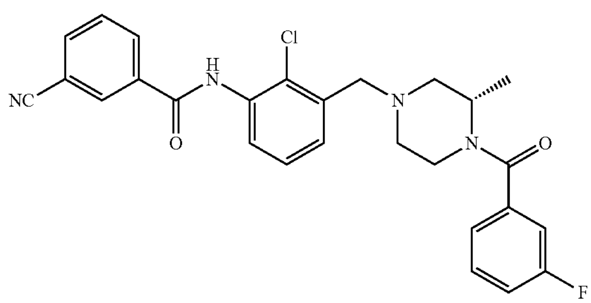 [SMILES: C[C@H]1CN(Cc2cccc(NC(=O)c3cccc(C#N)c3)c2Cl)CCN1C(=O)c1cccc(F)c1] | $^1$H NMR (400 MHz, MeOD-d$_4$) δ 1.39 (d, 3H), 2.12-2.27 (m, 1H), 2.37 (d, 1H), 2.83 (d, 2H), 3.35-3.60 (m, 1H), 3.61-3.77 (m, 2H), 3.77-4.72 (m, 2H), 7.12-7.25 (m, 3H), 7.37 (t, 1H), 7.45-7.53 (m, 2H), 7.64 (d, 1H), 7.73 (t, 1H), 7.97 (d, 1H), 8.26 (d, 1H), 8.33 (s, 1H). $^{19}$F NMR (376 MHz, MeOD-d$_4$) δ −113.6. MS (ESI) C$_{27}$H$_{24}$ClFN$_4$O$_2$ requires: 490, found 491 (M + H$^+$). |
| E183 | 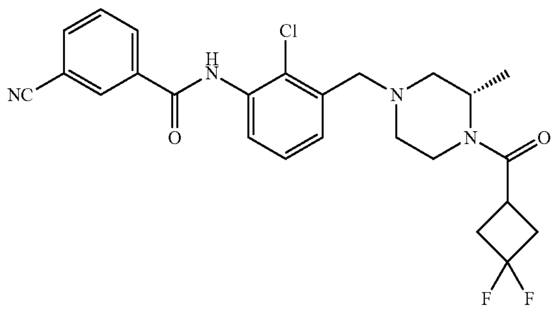 | $^1$H NMR (400 MHz, MeOD-d$_4$) δ 1.13-1.41 (m, 3H), 2.58-3.18 (m, 7H), 3.23-3.55 (m, 3H), 3.82 (d, 1H), 4.20-4.59 (m, 3H), 7.44 (t, 1H), 7.54 (d, 1H), 7.63-7.73 (m, 2H), 7.90 (d, 1H), 8.18 (d, 1H), 8.24 (s, 1H). $^{19}$F NMR (376 MHz, MeOD-d$_4$) δ −77.0, −84.2 (dd), −98.4 (dd). MS (ESI) C$_{25}$H$_{25}$ClF$_2$N$_4$O$_2$ requires: 486, found 487 (M + H$^+$). |

1 H), 2.9 (m, 1.5 H), 3.3 (m, 2.5 H), 3.9 (m, 0.5 H), 4.3 (s, 2 H), 4.5 (m, 0.5 H), 7.4 (dd, 2 H), 7.7 (d, 1 H), 8.6 (dd, 1 H), 9.0 (d, 1 H). 19F NMR (376 MHz, MeOD-d4) δ −77.2. MS (ESI) C, 25; H, 31; Cl, N, 4; O, 2; requires: 454, found 455 (M+H+).

Example 185

N-(5-fluoro-2-methyl-3-(((S)-3-methyl-4-((cis)-3-methylcyclobutanecarbonyl)piperazin-1-yl)methyl)phenyl)-6-methylnicotinamide (E185)

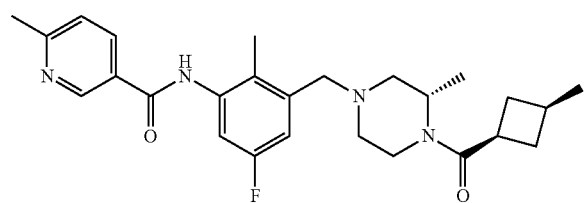

To a solution of (S)-N-(5-fluoro-2-methyl-3-((3-methylpiperazin-1-yl)methyl)phenyl)-6-methylnicotinamide (D50) (120 mg, 0.337 mmol), 3-methylcyclobutanecarboxylic acid (38.4 mg, 0.337 mmol) and HATU (128mg, 0.337 mmol) in DCM (2 mL) stirred under nitrogen at 0° C. was added DIEA (0.118 mL, 0.673 mmol), then the reaction mixture was stirred at RT for 15 hr. The solvent was removed and the residue was purified by SFC to give the title compound (100 mg). 1H NMR (400 MHz, MeOD-d4) δ ppm 1.03 (d, 3 H), 1.19-1.40 (m, 4 H), 1.69-1.92 (m, 2 H), 1.94-2.07 (m, 1 H), 2.18 (d, 1 H), 2.22-2.41 (m, 6 H), 2.63 (s, 3 H), 2.72 (d, 1 H), 2.77-2.89 (m, 1 H), 2.96 (t, 0.5 H), 3.07-3.24 (m, 1 H), 3.43-3.55 (m, 2 H), 3.59 (d, 0.5 H), 4.05 (brs, 0.5 H), 4.27 (d, 0.5 H), 4.62 (brs, 0.5 H), 7.09 (dd, 2 H), 7.46 (d, 1 H), 8.26 (d, 1 H), 9.00 (s, 1 H). 19F NMR (376 MHz, MeOD-d4) δ ppm −119.5. MS (ESI): C, 26; H, 33; FN, 4; O, 2; requires: 452, found 453 (M+H+).

Example 186

N-(5-fluoro-2-methyl-3-(((S)-3-methyl-4-((trans)-3-methylcyclobutanecarbonyl)piperazin-1-yl)methyl)phenyl)-6-methylnicotinamide (E186)

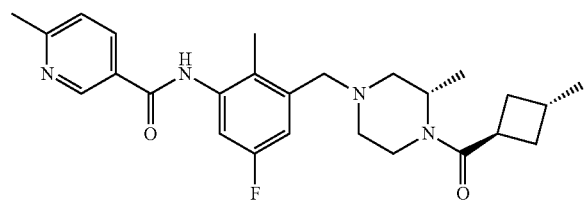

To a solution of (S)-N-(5-fluoro-2-methyl-3-((3-methylpiperazin-1-yl)methyl)phenyl)-6-methylnicotinamide (D50) (120 mg, 0.337 mmol), 3-methylcyclobutanecarboxylic acid (38.4 mg, 0.337 mmol) and HATU (128 mg, 0.337 mmol) in DCM (2 mL) stirred under nitrogen at 0° C. was added DIEA (0.118 mL, 0.673 mmol), then the reaction mixture was stirred at RT for 15 hr. Removed the solvent and the residue was purified by SFC to give the title compound (89 mg). 1H NMR (400 MHz, MeOD-d4) δ ppm 1.11-1.20 (m, 3 H), 1.24 (d, 2 H), 1.32 (d, 2 H), 1.73-1.94 (m, 2 H), 1.96-2.09 (m, 1 H), 2.19 (dd, 1 H), 2.29 (s, 3 H), 2.31-2.52 (m, 3 H), 2.63 (s, 3 H), 2.72 (d, 1 H), 2.77-2.89 (m, 1 H), 2.97 (t, 0.5 H), 3.33-3.43 (m, 0.5 H), 3.44-3.57 (m, 2.5 H), 3.94 (brs, 0.5 H), 4.30 (d, 0.5 H), 4.65 (brs, 0.5 H), 7.09 (dd, 2 H), 7.46 (d, 1 H), 8.26 (d, 1 H), 9.00 (s, 1 H). 19F NMR (376 MHz, MeOD-d4) δ ppm −119.5. MS (ESI): C, 26; H, 33; FN, 4; O, 2; requires: 452, found 453 (M+H+).

Example 187

(S)-N-(5-chloro-3-((4-(cyclopentanecarbonyl)-3-methylpiperazin-1-yl)methyl)-2-methylphenyl)-2-methylisonicotinamide (E187)

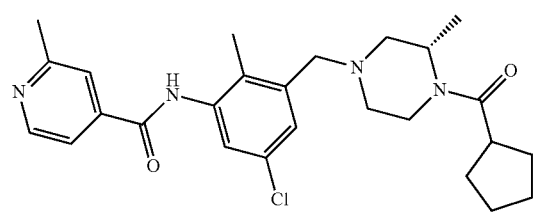 [SMILES: Cc1cc(C(=O)Nc2cc(Cl)cc(CN3CCN(C(=O)C4CCCC4)[C@@H](C)C3)c2C)ccn1]

Oxalyl chloride (0.080 mL, 0.915 mmol) was added into a solution of 2-methylisonicotinic acid (86 mg, 0.629 mmol) and cat. DMF in DCM (15 mL) at 0° C. After the reaction was stirred at this temperature for 1 hr, the mixture was concentrated (water bath at RT) to give the acyl chloride. Then the acyl chloride was added into a solution of (S)-(4-(3-amino-5-chloro-2-methylbenzyl)-2-methylpiperazin-1-yl)(cyclopentyl)methanone (200 mg, 0.572 mmol) (D27) in pyridine (6 mL). The reaction was stirred at RT overnight. After the reaction was completed, the mixture was concentrated and the residue was subjected to MDAP to give the title compound (88 mg) as white solid. 1H NMR (400 MHz, MeOD-d4) δ 1.2 (m, 3 H), 1.4-1.8 (m, 8 H), 1.8-2.0 (m, 1 H), 2.0-2.2 (m, 1 H), 2.2 (s, 3 H), 2.5 (s, 3 H), 2.6 (m, 1 H), 2.9 (m, 1.5 H), 3.0 (m, 2H), 3.3 (m, 0.5 H), 3.4 (m, 2 H), 3.7 (m, 0.5 H), 4.2 (m, 1 H), 4.6 (m, 0.5 H), 7.2 (dd, 2 H), 7.6 (d, 1 H), 7.7 (s, 1 H), 8.5 (d, 1 H). MS (ESI) C, 26; H, 33; Cl, N, 4; O, 2; requires: 468, found 469 (M+H+).

Example 188

N-(5-chloro-2-methyl-3-(((S)-3-methyl-4-((trans)-3-methylcyclobutanecarbonyl)piperazin-1-yl)methyl)phenyl)-6-methylnicotinamide (E188)

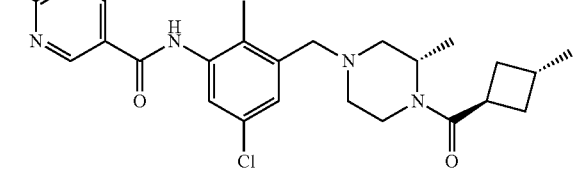

To a solution of (1R,3R)-3-methylcyclobutanecarboxylic acid (40.3 mg, 0.353 mmol) in DCM (5 mL), oxalyl dichloride (52.1 mg, 0.41 mmol) solution in DCM (1 mL) was added, the reaction mixture was stirred for 1.5 hr under N2. Solvent was removed and then re-dissolved with DCM (5 mL), added to a solution of (S)-N-(5-chloro-2-methyl-3-((3-methylpiperazin-1-yl)methyl)phenyl)-6-methylnicotinamide (D106) (85 mg, 0.228 mmol) and Et3N (0.127 mL, 0.912 mmol) in DCM (5 mL), the reaction mixture was stirred overnight. Solvent was removed and the residual was purified with MDAP to give the title compound (35.3 mg) as white solid. $^1$H NMR (400 MHz, MeOD-d$_4$) δ ppm 1.16 (t, 3 H), 1.23 (d, 2 H), 1.27-1.39 (m, 3 H), 1.73-1.93 (m, 2 H), 1.95-2.09 (m, 1 H), 2.18 (dd, 1 H), 2.30 (s, 3 H), 2.33-2.53 (m, 3 H), 2.64 (s, 3 H), 2.68-2.75 (m, 1 H), 2.76-2.88 (m, 1 H), 2.97 (t, 0.5 H), 3.44-3.56 (m, 2 H), 3.94 (brs, 0.5 H), 4.31 (d, 0.5 H), 4.65 (brs, 0.5 H), 7.30 (s, 1 H), 7.35 (d, 1 H), 7.48 (d, 1 H), 8.27 (dd, 1 H), 9.00 (s, 1 H). MS (ESI): $C_{26}H_{33}ClN_4O_2$ requires: 468, found 469 (M+H$^+$).

Example 189

N-(5-chloro-2-methyl-3-(((S)-3-methyl-4-((cis)-3-methylcyclobutanecarbonyl)piperazin-1-yl)methyl)phenyl)-6-methylnicotinamide (E189)

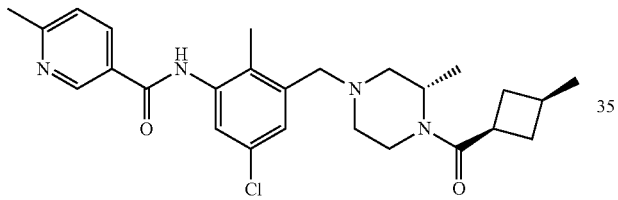

To a solution of (1 s,3 s)-3-methylcyclobutanecarboxylic acid (40.3 mg, 0.353 mmol) in DCM (5 mL), oxalyl chloride (0.036 mL, 0.41 mmol) solution in DCM (1 mL) was added, the reaction mixture was stirred for 1.5 hr under N2. Solvent was removed and then re-dissolved with DCM (5 mL), added to a solution of (S)-N-(5-chloro-2-methyl -3-((3-methylpiperazin-1-yl)methyl)phenyl)-6-methylnicotinamide (D106) (85 mg, 0.228 mmol) and Et3N (0.127 mL, 0.912 mmol) in DCM (5 mL), the reaction mixture was stirred overnight. Solvent was removed and the residual was purified with MDAP to give the title compound (37.1 mg) as white solid. $^1$H NMR (400 MHz, MeOD-d$_4$) δ ppm 1.03 (d, 3 H), 1.22 (d, 2 H), 1.31 (d, 2 H), 1.66-1.91 (m, 2 H), 1.93-2.08 (m, 1 H), 2.17 (d, 1 H), 2.21-2.42 (m, 6 H), 2.63 (s, 3 H), 2.71 (d, 1 H), 2.82 (t, 1 H), 2.89-3.03 (m, 0.5 H), 3.08-3.25 (m, 1 H), 3.42-3.56 (m, 2 H), 3.59 (d, 0.5 H), 4.05 (brs, 0.5 H), 4.27 (d, 0.5 H), 4.62 (brs, 0.5 H), 7.30 (s, 1 H), 7.35 (d, 1 H), 7.47 (d, 1 H), 8.27 (dd, 1 H), 9.00 (s, 1 H). MS (ESI): $C_{26}H_{33}ClN_4O_2$ requires: 468, found 469 (M+H$^+$).

Example 190

N-(5-chloro-2-methyl-3-(((S)-3-methyl-4-((cis)-3-methylcyclobutanecarbonyl)piperazin-1-yl)methyl)phenyl)-2-methylpyrimidine-5-carboxamide, trifluoroacetic acid salt (E190)

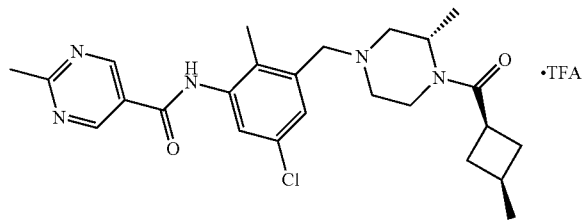 [SMILES: Cc1ncc(C(=O)Nc2cc(Cl)cc(CN3CCN(C(=O)[C@H]4C[C@@H](C)C4)[C@@H](C)C3)c2C)cn1]

DIPEA (0.187 mL, 1.070 mmol) was added into a solution of (S)-N-(5-chloro-2-methyl-3-((3-methylpiperazin-1-yl)methyl)phenyl)-2-methylpyrimidine-5-carboxamide (D108) (200 mg, 0.535 mmol), (1 s,3 s)-3-methylcyclobutanecarboxylic acid (0.043 mL, 0.562 mmol) and HATU (285 mg, 0.749 mmol) in DMF (6 mL) at RT and then the reaction was stirred at RT overnight. After the reaction was completed, the mixture was subjected to MDAP to give the title compound (112 mg) as white solid. 1H NMR (400 MHz, MeOD-d4) δ 1.8 (m, 3 H), 2.0 (m, 3 H), 2.6 (m, 2 H), 2.9-3.2 (m, 6 H), 3.5 (s, 3 H), 3.6-4.2 (m, 5.5 H), 4.5 (m, 0.5 H), 4.8-5.5 (m, 4 H), 8.4 (s, 2 H), 10.0 (s, 2 H), 11.1 (s, 1 H). 19F NMR (376 MHz, MeOD-d4) δ −73. MS (ESI) C, 25; H, 32; Cl, N, 5; O, 2; requires: 469, found 470 (M+H+).

Example 191

N-(5-chloro-2-methyl-3-(((S)-3-methyl-4-((trans)-3-methylcyclobutanecarbonyl)piperazin-1-yl)methyl)phenyl)-2-methylpyrimidine-5-carboxamide, trifluoroacetic acid salt (E191)

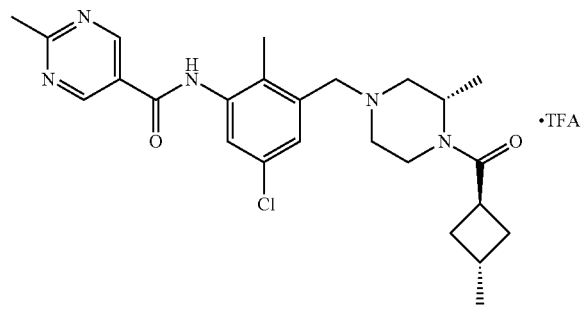 [SMILES: Cc1ncc(C(=O)Nc2cc(Cl)cc(CN3CCN(C(=O)[C@H]4C[C@H](C)C4)[C@@H](C)C3)c2C)cn1]

DIPEA (0.280 mL, 1.605 mmol) was added into a solution of (S)-N-(5-chloro-2-methyl -3-((3-methylpiperazin-1-yl)methyl)phenyl)-2-methylpyrimidine-5-carboxamide (D108) (300 mg, 0.802 mmol), (1r,3r)-3-methylcyclobutanecarboxylic acid (96 mg, 0.843 mmol) and HATU (427 mg, 1.123 mmol) in DMF(6 mL) at RT and the reaction was stirred at RT overnight. After the reaction was completed, the mixture was subjected to MDAP to give the title compound (107 mg) as white solid. 1H NMR (400 MHz, MeOD-d4) δ 1.9 (m, 3 H), 2.1 (m, 3 H), 2.6 (m, 2 H), 2.9-3.2 (m, 6 H), 3.5 (s, 3 H), 3.6-4.3 (m, 5.5 H) , 4.5 (m, 0.5 H), 4.8-5.4 (m, 3 H), 5.6 (m, 1 H), 8.4 (s, 2 H), 10.0 (s, 2 H), 11.1 (s, 1 H). 19F NMR (376 MHz, MeOD-d4) δ −74. MS (ESI) C, 25; H, 32; Cl, N, 5; O, 2; requires: 469, found 470 (M+H+).

Example 192

(S)-N-(5-chloro-3-((4-(cyclopentanecarbonyl)-3-methylpiperazin-1-yl)methyl)-2-methylphenyl)-2-methylpyrimidine-5-carboxamide (E192)

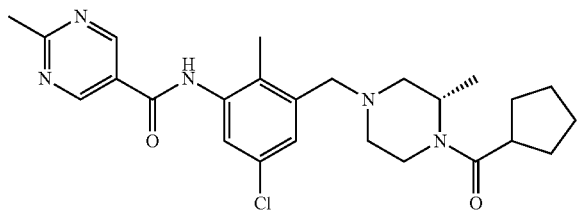 [SMILES: Cc1ncc(C(=O)Nc2cc(Cl)cc(CN3CCN(C(=O)C4CCCC4)[C@@H](C)C3)c2C)cn1]

To a solution of (S)-N-(5-chloro-2-methyl-3-((3-methylpiperazin-1-yl)methyl)phenyl)-2-methylpyrimidine-5-carboxamide (D108) (5 g, 13.37 mmol) and Et₃N (7.46 mL, 53.5 mmol) in DCM (100 mL) was added drop-wise cyclopentanecarbonyl chloride (2.128 g, 16.05 mmol). After addition the reaction mixture was stirred at 0° C. for 10 min until LCMS showed that the reaction was completed. 150 mL of water was added, the organic phase was separated, dried over Na₂SO₄ and evaporated to leave the crude product, which was purified by column chromatography (silica gel, 200-300 mesh, PE:EA=1:2) to afford the title compound (3.5 g) as white solid. LCMS: [M+H⁺]=470.0 HNMR (DMSO-d6, 400 MHz): 10.26 (1H, s); 9.17 (2H, s); 7.41 (1H, d); 7.27 (1H, d); 4.55 (0.5H, br); 4.19-4.22 (1H, m); 3.74-3.77 (0.5H, m); 3.41-3.49 (2H, m); 3.14-3.18 (0.5H, m), 2.89-2.93 (1H, m); 2.52-2.80 (5H, m), 2.23 (3H, s); 1.45-2.14 (10H, m); 1.10-1.35 (3H, m).

Example 193

(S)-N-(5-chloro-3-((4-(cyclopentanecarbonyl)-3-methylpiperazin-1-yl)methyl)-2-methylphenyl)-3-cyanobenzamide, trifluoroacetic acid salt (E193)

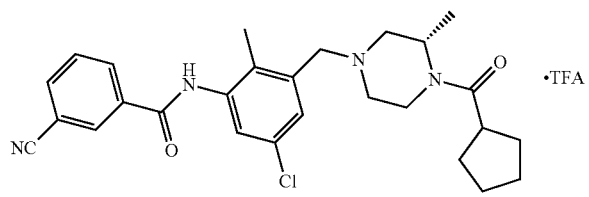 [SMILES: Cc1c(CN2CCN(C(=O)C3CCCC3)[C@@H](C)C2)cc(Cl)cc1NC(=O)c1cccc(C#N)c1]

Oxalyl chloride (0.068 mL, 0.772 mmol) was added dropwise to a solution of 3-cyanobenzoic acid (101 mg, 0.686 mmol) in DCM (10 mL) and the reaction mixture was stirred at 40° C. for 2 hr. The mixture was concentrated to give the acyl chloride which was added to a solution of (S)-(4-(3-amino-5-chloro-2-methylbenzyl)-2-methylpiperazin-1-yl)(cyclopentyl)methanone (150 mg, 0.429 mmol) (D27) in pyridine (2 mL). The reaction mixture was stirred at RT overnight. Water was added and the mixture was extracted with EtOAc. The organic layer was dried over MgSO₄, filtered and concentrated. The residue was purified by MDAP to give the title compound (88 mg) as white solid. ¹H NMR (400 MHz, MeOD-d4) δ 1.27-1.53 (m, 3 H) 1.56-2.00 (m, 9 H) 2.37 (s, 3 H) 2.97-3.30 (m, 3 H) 3.42-3.72 (m, 3 H) 4.24 (d, J=12.35 Hz, 0.5 H) 4.45-4.57 (m, 2 H) 4.69 (br. s., 0.5 H) 7.57-7.61 (m, 1 H) 7.64 (d, J=2.08 Hz, 1 H) 7.77 (t, J=7.83 Hz, 1 H) 8.01 (d, J=7.70 Hz, 1 H) 8.30 (d, J=7.95 Hz, 1 H) 8.36 (s, 1 H). MS (ESI) C₂₇H₃₁ClN₄O₂ requires: 478, found 479 (M+H⁺).

Biological Data

As stated above, the compounds according to Formula I are RORγ modulators, and are useful in the treatment of diseases mediated by RORγ. The biological activities of the compounds according to Formula I can be determined using any suitable assay for determining the activity of a candidate compound as a RORγ modulator, as well as tissue and in vivo models.

Dual Fluorescence Energy Transfer (FRET) Assay

This assay is based on the knowledge that nuclear receptors interact with cofactors (transcription factors) in a ligand dependent manner. RORγ is a typical nuclear receptor in that it has an AF2 domain in the ligand binding domain (LBD) which interacts with co-activators. The sites of interaction have been mapped to the LXXLL (SEQ ID NO. 1) motifs in the co-activator SRC1(2) sequences. Short peptide sequences containing the LXXLL (SEQ ID NO. 1) motif mimic the behavior of full-length co-activator.

The assay measures ligand-mediated interaction of the co-activator peptide with the purified bacterial-expressed RORγ ligand binding domain (RORγ-LBD) to indirectly assess ligand binding. RORγ has a basal level of interaction with the co-activator SRC1(2) in the absence of ligand, thus it is possible to find ligands that inhibit or enhance the RORγ/SRC1(2) interaction.

Materials

Generation of RORγ-LBD Bacterial Expression Plasmid

Human RORγ Ligand Binding Domain (RORγ-LBD) was expressed in E.coli strain BL21(DE3) as an amino-terminal polyhistidine tagged fusion protein. DNA encoding this recombinant protein was sub-cloned into a modified pET21a expression vector (Novagen). A modified polyhistidine tag (MKKHHHHHHLVPRGS) (SEQ ID NO. 2) was fused in frame to residues 263-518 of the human RORγ sequence.

Protein Purification

Approximately 50 g E. coli cell pellet was resuspended in 300 mL of lysis buffer (30 mM imidazole pH 7.0 and 150 mM NaCl). Cells were lysed by sonication and cell debris was removed by centrifugation for 30 minutes at 20,000 g at 4° C. The cleared supernatant was filtered through a 0.45 uM cellulose acetate membrane filter. The clarified lysate was loaded onto a column (XK-26) packed with ProBond Nickel Chelating resin (Invitrogen), pre-equilibrated with 30 mM imidazole pH 7.0 and 150 mM NaCl. After washing to baseline absorbance with the equilibration buffer, the column was developed with a gradient from 30 to 500 mM imidazole pH 7.0. Column fractions containing the RORγ-LBD protein were pooled and concentrated to a volume of 5 mls. The concentrated protein was loaded onto a Superdex 200 column pre-equilibrated with 20 mM Tris-Cl pH 7.2 and 200 mM NaCl. The fractions containing the desired RORγ-LBD protein were pooled together.

Protein Biotinylation

Purified RORγ-LBD was buffer exchanged by exhaustive dialysis [3 changes of at least 20 volumes (>8000x)] against PBS [100mM NaPhosphate, pH 8 and 150mM NaCl]. The concentration of RORγ-LBD was approximately 30uM in PBS. Five-fold molar excess of NHS-LC-Biotin (Pierce) was added in a minimal volume of PBS. This solution was incubated with occasional gentle mixing for 60 minutes at ambient RT. The modified RORγ-LBD was dialyzed against 2 buffer changes—TBS pH 8.0 containing 5mM DTT, 2mM EDTA and 2% sucrose—each at least 20 times of the volume. The modified protein was distributed into aliquots, frozen on dry ice and stored at −80° C. The biotinylated RORγ-LBD was subjected to mass spectrometric analysis to reveal the extent of modification by the biotinylation reagent. In general, approximately 95% of the protein had at least a single site of biotinylation and the overall extent of biotinylation followed a normal distribution of multiple sites ranged from one to five. A biotinylated peptide corresponding to amino acid 676 to 700 (CPSSHSSLTERH-KILHRLLQEGSPS) (SEQ ID NO. 3) of the co-activator steroid receptor coactivator SRC1(2) was generated using similar method.

Assay

Preparation of Europium labeled SRC1(2) peptide: biotinylated SRC1(2) solution was prepared by adding an appropriate amount of biotinylated SRC 1(2) from the 100 uM stock solution to a buffer containing 10 mM of freshly added DTT from solid to give a final concentration of 40 nM. An appropriate amount of Europium labeled Streptavidin was then added to the biotinylated SRC1(2) solution in a tube to give a final concentration of 10 nM. The tube was inverted gently and incubated for 15 minutes at room temperature. Twenty-fold excess biotin from the 10 mM stock solution was added and the tube was inverted gently and incubated for 10 minutes at room temperature.

Preparation of APC labeled RORγ-LBD: biotinylated RORγ-LBD solution was prepared by adding an appropriate amount of biotinylated RORγ-LBD from the stock solution to a buffer containing 10 mM of freshly added DTT from solid to give a final concentration of 40 nM. An appropriate amount of APC labeled Streptavidin was then added to the biotinylated RORγ-LBD solution in a tube to give a final concentration of 20 nM. The tube was inverted gently and incubated for 15 minutes at room temperature. Twenty-fold excess biotin from the 10 mM stock solution was then added and the tube was inverted gently and incubated for 10 minutes at room temperature.

Equal volumes of the above-described Europium labeled SRC1(2) peptide and the APC labeled RORγ-LBD were gently mixed together to give 20 nM RORγ-LBD, 10 nM APC-Strepavidin, 20 nM SRC1(2) and 5 nM Europium-Streptavidin. The reaction mixtures were incubated for 5 minutes. Using a Thermo Combi Multidrop 384 stacker unit, 25 ul of the reaction mixtures per well was added to the 384-well assay plates containing 1 ul of test compound per well in 100% DMSO. The plates were incubated for lhr and then read on ViewLux in Lance mode for EU/APC.

Jurkat Cell Luciferase Assay

RORγ is known to bind to a CNS (conserved non-coding sequences) enhancer element in the IL17 promoter. In this assay, RORγ activity is indirectly assessed using a luciferase reporter construct which contains the human IL17 promoter having the RORγ-specific CNS enhancer element. Inhibition of RORγ activity by a compound will result in a decrease in luciferase activity of Jurkat cells transfected with the reporter construct.

Materials

Jurkat Cell Line

For the luciferase reporter plasmid, the 3 Kb human IL17 promoter containing the RORγ-specific CNS enhancer element was PCR amplified from human genomic DNA and cloned into a pGL4-Luc2/hygro reporter plasmid sequencially as XhoI-HindIII (1.1 Kb) and KpnI-XhoI (1.9 Kb) fragments. For the 1.1 Kb fragment, PCR was used to amplify human IL17 proximal promoter region from genomic DNA of 293T cells using primers as follows: forward primer, 5'-CTCGAGTAGAGCAGGACAGGGAG-GAA-3' (SEQ ID NO. 4) (XhoI site is underlined) and reverse primer, 5'-AAGCTTGGATGGATGAGTTTGT-GCCT-3' SEQ ID NO. 5) (HindIII site is underlined). The 1.1 kb DNA bands were excised, purified, and inserted into pMD19-T Simple Vector (Takara). After DNA sequencing confirmation, the 1.1 kb DNA was digested with XhoI and HindIII and inserted into XhoI/HindIII sites of pGL4.31 [luc2P/GAL4UAS/Hygro] (Promega) to generate the pIL17-lkb-luc reporter construct. For the 1.9 Kb fragment, PCR was used to amplify human IL17 promoter region from genomic DNA using primers as follows: forward primer, 5'-GGTACCTGCCCTGCTCTATCCTGAGT-3' (SEQ ID NO. 6) (KpnI site is underlined) and reverse primer, 5'-CTC-GAGTGGTGAGTGCTGAGAGATGG-3' (SEQ ID NO. 7)(XhoI site is underlined). The resulting 1.9 kb DNA bands were excised, gel purified, and cloned into a pMD19-T Simple Vector (Takara). DNA sequencing analysis revealed that there were three point mutations but none of which affected RORγ binding. The 1.9 kb DNA fragment was released by double digestion with KpnI and XhoI and inserted into pIL17-lkb-luc to generate the luciferase reporter plasmid "pIL17-3kb-CNS-luc." To overexpress RORγt, the full-length cDNA of human RORγt identical to the published sequence $NM_{13}$ 001001523 was cloned into pcDNA3.1 at the KpnI-NotI cloning sites to generate the RORγt overexpression plasmid "CDNA3.1DhRORγ49-8".

The luciferase reporter plasmid and the RORγt overexpression plasmid were transfected into Jurkat cell line and a stable clone was identified. The stable clone was grown in 10% dialyzed FBS in RPMI (1640) with 800 ug/ml geneticin and 400 ug/ml hygromecin.

Assay

Compounds were dissolved in DMSO at three concentrations, 10 mM, 400 uM and 16 uM, and were dispensed into 384-wells assay plate at 40 nl, 12.5 nl, 5 nl respectively. The volume was adjusted with pure DMSO to a give a final uniform volume of 40 nl Jurkat cells described above were counted and centrifuged. The growth medium was discarded and the cells were resuspended with assay medium (phenol red free RPMI) at 1E-6/ml. Cells were added to each of the compounds in the assay plates. Cells were either untreated or treated with CD3 microbeads (Miltenyi Biotec) at 1 ul beads per 500,000 cells. Cells were culture overnight and luciferase assay (Promega) was performed. Data were collected by ViewLux (using luciferase greiner 384 setting).

Th17 Cell Differentiation Assay

ELISA

Mouse CD4+cells were purified using the CD4+ T Cell Isolation II Kit according to manufacturer's instructions (Miltenyi Biotec). 96 well plates were pre-coated with anti-mCD3 antibody. Un-coated wells were used as controls. CD4+ Cells were resuspended in RPMI 1640 complete medium and were added to the 96-well plates. Cytokine cocktail and the compound were then added to the wells. Antibodies and cytokines (all from R&D Systems) used in the assay were selected from the following: anti-mCD3; anti-mCD28; anti-mIFNγ; anti-mIL4; mIL-6; mIL-23; mIL-1β; hTGF-β1. The culture was incubated at 37° C. for 3 days and supernatants were collected for ELISA. The IL-17 ELISAs were performed according to manufacturer's instructions (R&D Systems). The results were analyzed using Prism software with non-linear regression to determine pIC50.

Intracellular Staining

The Th17 differentiation culture described above was maintained for 5 days and cells were analyzed by IL-17 and IFN-γ intracellular staining according to manufacturer's instructions (BD Biosciences).

Assay Data

The data described below represents a mean pIC50 value of multiple test results if the test was performed more than once. It is understood that the data illustrated below may have reasonable variation depending on the specific conditions and procedures used by the person conducting the testing.

All exemplified compounds except Examples 9, 16, 26, 30, 37, 59, 83-85, 93, 94, 102, 118, 129, 130, 142, 154, 156, 158, 160, 161, 165, and 167-169 were tested in the dual FRET assay described above. All tested compounds were found to have a pIC50 between 5 and 8. For instance, the compounds of Examples 20, 66, 184, 185, 186, 187, 188, 189, 190, 191, 192 and 193 had a pIC50 of approximately 7, 7.4, 6.7, 7.1, 7.1, 6.9, 7.2, 7.3, 6.8, 6.6, 6.7 and 7.2, respectively.

All exemplified compounds except Examples 9, 12, 14, 20-26, 28, 38-62, 64, 68, 69, 82, 83, 106, 107, 111, 115-120, 122-124, 126, 138, 141-145, 152, 157-162, 164, 166-170 and 172-192 were tested in the Jurkat cell luciferase assay described above. All tested compounds except Example 36 were found to have a pIC50 between 5 and 9. For instance, Example 66 and Example 193 had a mean pIC50 of approximately 8.3 and 8.6. Example 36 was tested once and found to have a pIC50 below 5, the detection limit of the assay.

All exemplified compounds except Examples 2-4, 7, 8, 11, 12, 14, 15, 26, 28, 48-50, 52-54, 64, 65, 68, 69, 75, 81, 86, 87, 94, 95, 105, 114-117, 122, 126, 132, 134-136, 143, 144, 146, 154, 156, 158-162, 177 and 179 were tested in the Th17 cell differentiation assay described above. All tested compounds except Example 129 were found to have a pIC50 greater than 5. For instance, the compounds of Examples 20, 66, 184, 185, 186, 187, 188, 189, 190, 191, 192 and 193 had a mean pIC50 of approximately 7.5, 9.1, 7.08, 7.68, 7.43, 8.5, 8.06, 8.29, 7.89, 7.58, 8.1 and 8.3, respectively. Example 129 was tested once and found to have a pIC50 below 5, the detection limit of the assay.

EAE Studies

Experimental Autoimmune Encephalomyelitis (EAE) is an animal model of multiple sclerosis. The ability of a test compound to ameliorate EAE was measured in the EAE studies. Wild-type mice of the C57BL/6 (B6) strain were obtained from Shanghai Laboratory Animal Resource Center and were maintained under pathogen-free conditions. EAE was induced by intravenous injections of 100 ng of pertussis toxin (List Biological Laboratories) and subcutaneous immunization with an emulsion composed of $MOG_{35-55}$ peptide (300 mg/mouse) in PBS and an equal volume of complete Freund's adjuvant containing 5 mg/ml heat-killed Mycobacterium tuberculosis H37Ra (Difco Laboratories) on day 0, followed by another intravenous injections of 100 ng of pertussis toxin on day 2 as described previously (Wang et al. (2006) *J. Clin. Invest.* 116: 2434-2441). For treatment of EAE, each compound or vehicle PBS was given orally from day 0 at various doses selected from 3, 10, 30 and 100 mg/kg twice a day. Mice were scored for disease severity daily using a EAE scoring system (Wang et al. (2006) *J. Clin. Invest.* 116: 2434-2441): 0, no overt signs of disease; 1, limp tail or hind limb weakness but not both; 2, limptail and paraparesis (weakness, incomplete paralysis of one or two hind limbs); 3, paraplegia (complete paralysis of two hind limbs); 4, paraplegia with forelimb weakness or paralysis; and 5, moribund state or death. Clinical score data can be expressed as means±S.E.M.

Results

Examples 20, 62, 175, 184 and 190-192 were tested in the EAE study at one or more of the following doses: 3, 10, 30 or 100 mg/kg. Examples 20, 175, 184 and 192 were shown to delay EAE onset and lower clinical score starting at 3, 10 or 30 mg/kg. Examples 62, 190 and 191 were shown to delay EAE onset at 30 mg/kg.

In Vitro Percutaneous Studies

The in vitro percutaneous study is aimed to predict the level of percutaneous penetration obtained for a compound in a topical formulation for psoriasis. This assay coupled with the intrinsic potency of the compound are used to predict the likelihood of success of a compound to engage the target. The higher the ratio of the percutaneous penetration to the intrinsic potency, the higher the ratio of local skin concentration to the intrinsic potency and therefore the higher the chance of a compound to engage the target in a topical formulation.

The compounds were manufactured in a modified aqueous cream at pH=6.

Aqueous Cream Composition

| Ingredients | % w/w |
| --- | --- |
| Cetostearyl alcohol | 7.2 |
| Cetomacrogol 1000 | 1.8 |
| White soft paraffin | 15.0 |
| Liquid paraffin | 6.0 |
| Water | 57.0 |
| Na2HPO4 | 0.6 |
| Citric Acid | 0.2 |
| Propylene Glycol | 10.0 |
| Methyl paraben | 0.1 |
| Caffeine | 0.1 |
| API#1 | 1.0 |
| API#2 | 1.0 |
| API#3 | 1.0 |

The study was conducted with dermatomed abdominal human skin sourced from three skin donors using 2 cm2 Franz diffusion cells. The receiving fluid consisted of Bovine serum albumin (4% w/v) in 0.1% w/v sodium azide in Phospate Buffer Saline and was heated at 37° C. in order to obtain 32° C. at the skin surface. The cream formulation was applied on the donor side at a 10 mg dose, i.e. 5 mg/cm². The samples taken at the following time points: t=0, 3, 6, 9 and 24 h. The receiver samples were then assayed using a method based upon protein precipitation with acetonitrile followed by LC/MS/MS analysis. The percutaneous flux (in ng/cm²/hr) was determined using the individual API (in a multiple composition) that had permeated into the receiver compartment over 24 hrs per cm².

Results

As shown in the Table below, Examples 66, 163 and 164 were tested in the in vitro percutaneous study and showed an average percutaneous penetration over 24 hr superior to 1ng/cm²/hr. Of the three compounds tested, Example 66 had the highest ratio of percutaneous penetration (Flux) to intrinsic potency (Th17 cell differentiation assay IC50) and thus the best chance to engage the target in a topical formulation.

| Compound | Flux over 24 hrs (ng/cm²/hr) | Th17 cell differentiation assay pIC50 | Th17 cell differentiation assay IC50 (ng/mL) | Flux (ng/cm2/hr)/ IC50 (ng/mL) |
|---|---|---|---|---|
| Example 163 | 7.73 | 7.6 | 11.4 | 0.68 |
| Example 164 | 3.12 | 7.7 | 9.3 | 0.33 |
| Example 66 | 3.43 | 9.1 | 0.4 | 9.3 |

CIA Studies

Collagen-induced arthritis (CIA) is an animal model of rheumatoid arthritis. CIA can be induced in 8-week old male DBA/1 mice via an initial intradermal (i.d.) injection of an emulsion consisting of bovine type II collagen in CFA. Mice are intraperitoneally (i.p.) injected with bovine type II collagen 21 days later to boost the immune system, resulting in chronic inflammation in both the hind and the front paws. Each compound is given to the mice at 100 mg/kg twice a day starting from day 20 after the first immunization. Mice are examined for onset and severity of disease in a blinded manner. Arthritis symptoms can be graded by the following scoring system: grade 0, normal appearance; grade 1, slight erythema/ edema (1-3 digits); grade 2, erythema/ edema in more than 3 digits or mild swelling in ankle/wrist joint; grade 3, erythema/ edema in entire paw; grade 4, massive erythema/edema of entire paw extending into proximal joints, ankylosis, loss of function. Each limb is graded, giving a maximum possible score of 16 per mouse. Clinical score data can be expressed as means±s.e.m. Foot volume of the mice can be determined using a YLS-7B foot volume measuring instrument (Shandong Academy of Medical Science).

Methods of Use

The compounds of Formula (I) are modulators of RORγ and can be useful in the treatment of diseases mediated by RORγ, particularly autoimmune or inflammatory diseases. Examples of the inflammatory or autoimmune diseases of the invention include multiple sclerosis, rheumatoid arthritis, psoriasis, Crohn's disease, inflammatory bowel disease, Sjorgen's syndrome, optic neuritis, chronic obstructive pulmonary disease, asthma, type I diabetes, neuromyelitis optica, Myasthenia Gavis, uveitis, Guillain-Barre syndrome, psoriatic arthritis, Gaves' disease and allergy. Accordingly, in another aspect the invention is directed to methods of treating autoimmune and inflammatory diseases mediated by RORγ.

In a further aspect, the present invention also provides a compound of Formula (I), or a pharmaceutically acceptable salt or solvate thereof, for use in therapy.

In a further aspect, the present invention also provides a compound of Formula (I), or a pharmaceutically acceptable salt or solvate thereof, for use in the treatment of inflammatory and autoimmune diseases mediated by RORγ.

In a further aspect, the present invention provides a compound of Formula (I), or a pharmaceutically acceptable salt thereof, for use in the treatment of multiple sclerosis.

In a further aspect, the present invention provides (S)-N-(5-chloro-3-((4-(2-cyclopropylacetyl)-3-methylpiperazin-1-yl)methyl)-2-methylphenyl)-6-methylnicotinamide (E184), or a pharmaceutically acceptable salt thereof, for use in the treatment of multiple sclerosis.

In a further aspect, the present invention provides a compound of Formula (I), or a pharmaceutically acceptable salt thereof, for use in the treatment of psoriasis.

In a further aspect, the present invention provides (S)-3-cyano-N-(3-((4-(cyclopentanecarbonyl)-3-methylpiperazin-1-yl)methyl)-5-fluoro-2-methylphenyl)benzamide (E66), or a pharmaceutically acceptable salt thereof, for use in the treatment of psoriasis.

In a further aspect, the present invention is directed to a method of treatment of an inflammatory or autoimmune disease mediated by RORγ, which comprises administering to a human in need thereof, a therapeutically effective amount of a compound of Formula (I), or a pharmaceutically acceptable salt thereof.

In yet a further aspect, the present invention is directed to a method of treating multiple sclerosis, which comprises administering to a human in need thereof, a therapeutically effective amount of a compound of Formula (I), or a pharmaceutically acceptable salt thereof.

In yet a further aspect, the present invention is directed to a method of treating multiple sclerosis, which comprises administering to a human in need thereof, a therapeutically effective amount of (S)-N-(5-chloro-3-((4-(2-cyclopropylacetyl)-3-methylpiperazin-1-yl)methyl)-2-methylphenyl)-6-methylnicotinamide (E184), or a pharmaceutically acceptable salt thereof.

In yet a further aspect, the present invention is directed to a method of treating psoriasis, which comprises administering to a human in need thereof, a therapeutically effective amount of a compound of Formula (I), or a pharmaceutically acceptable salt thereof.

In yet a further aspect, the present invention is directed to a method of treating psoriasis, which comprises administering to a human in need thereof, a therapeutically effective amount of (S)-3-cyano-N-(3-((4-(cyclopentanecarbonyl)-3-methylpiperazin-1-yl)methyl)-5-fluoro-2-methylphenyl)benzamide (E66), or a pharmaceutically acceptable salt thereof.

In a further aspect, the present invention is directed to the use of a compound of Formula (I), or a pharmaceutically acceptable salt thereof, in the manufacture of a medicament for use in the treatment of an inflammatory or autoimmune disease mediated by RORγ.

In a yet further aspect, the present invention is directed to the use of a compound of Formula (I), or a pharmaceutically acceptable salt thereof, in the manufacture of a medicament for use in the treatment of multiple sclerosis.

In a yet further aspect, the present invention is directed to the use of a compound of Formula (I), or a pharmaceutically acceptable salt thereof, in the manufacture of a medicament for use in the treatment of psoriasis.

As used herein, "treat" in reference to a condition means: (1) to ameliorate or prevent the condition or one or more of the biological manifestations of the condition, (2) to interfere with (a) one or more points in the biological cascade that leads to or is responsible for the condition or (b) one or more of the biological manifestations of the condition, (3) to alleviate one or more of the symptoms or effects associated with the condition, or (4) to slow the progression of the condition or one or more of the biological manifestations of the condition.

As indicated above, "treatment" of a condition includes prevention of the condition. The skilled artisan will appreciate that "prevention" is not an absolute term. In medicine, "prevention" is understood to refer to the prophylactic administration of a drug to substantially diminish the likelihood or severity of a condition or biological manifestation thereof, or to delay the onset of such condition or biological manifestation thereof.

The compounds of the invention may be administered by any suitable route of administration, including both systemic administration and topical administration. Systemic administration includes oral administration, parenteral administration, transdermal administration, rectal administration, and administration by inhalation. Parenteral administration refers to routes of administration other than enteral, transdermal, or by inhalation, and is typically by injection or infusion. Parenteral administration includes intravenous, intramuscular, and subcutaneous injection or infusion. Inhalation refers to administration into the human lungs whether inhaled through the mouth or through the nasal passages. Topical administration includes application to the skin as well as intraocular, otic, intravaginal, and intranasal administration.

The compounds of the invention may be administered once or according to a dosing regimen wherein a number of doses are administered at varying intervals of time for a given period of time. For example, doses may be administered one, two, three, or four times per day. Doses may be administered until the desired therapeutic effect is achieved or indefinitely to maintain the desired therapeutic effect. Suitable dosing regimens for a compound of the invention depend on the pharmacokinetic properties of that compound, such as absorption, distribution, and half-life, which can be determined by the skilled artisan. In addition, suitable dosing regimens, including the duration such regimens are administered, for a compound of the invention depend on the condition being treated, the severity of the condition being treated, the age and physical condition of the individual being treated, the medical history of the individual to be treated, the nature of concurrent therapy, the desired therapeutic effect, and like factors within the knowledge and expertise of the skilled artisan. It will be further understood by such skilled artisans that suitable dosing regimens may require adjustment given an individual's response to the dosing regimen or over time as individual needs change.

Typical daily dosages may vary depending upon the particular route of administration chosen. Typical daily dosages for oral administration range from 0.1 mg to 1000 mg. Typical daily dosages for topical administration range from about 0.001% to about 10% w/w (weight percent) and preferably from about 0.01% to about 1% w/w.

Additionally, the compounds of the invention may be administered as prodrugs. As used herein, a "prodrug" of a compound of the invention is a functional derivative of the compound which, upon administration to an individual, eventually liberates the compound of the invention in vivo. Administration of a compound of the invention as a prodrug may enable the skilled artisan to do one or more of the following: (a) modify the onset of the compound in vivo; (b) modify the duration of action of the compound in vivo; (c) modify the transportation or distribution of the compound in vivo; (d) modify the solubility of the compound in vivo; and (e) overcome or overcome a side effect or other difficulty encountered with the compound. Typical functional derivatives used to prepare prodrugs include modifications of the compound that are chemically or enzymatically cleaved in vivo. Such modifications, which include the preparation of phosphates, amides, esters, thioesters, carbonates, and carbamates, are well known to those skilled in the art.

Compositions

The compounds of the invention will normally, but not necessarily, be formulated into pharmaceutical compositions prior to administration to an individual. Accordingly, in another aspect the invention is directed to pharmaceutical compositions comprising a compound of the invention and one or more pharmaceutically-acceptable excipient.

The pharmaceutical compositions of the invention may be prepared and packaged in bulk form wherein a safe and effective amount of a compound of the invention can be extracted and then given to the individual such as with powders or syrups. Alternatively, the pharmaceutical compositions of the invention may be prepared and packaged in unit dosage form wherein each physically discrete unit contains a safe and effective amount of a compound of the invention. When prepared in unit dosage form, the pharmaceutical compositions of the invention typically contain from 0.1 mg to 1000 mg.

The pharmaceutical compositions of the invention typically contain one compound of the invention. However, in certain embodiments, the pharmaceutical compositions of the invention contain more than one compound of the invention. For example, in certain embodiments the pharmaceutical compositions of the invention contain two compounds of the invention. In addition, the pharmaceutical compositions of the invention may optionally further comprise one or more additional pharmaceutically active compounds.

As used herein, "pharmaceutically-acceptable excipient" means a pharmaceutically acceptable material, composition or vehicle involved in giving form or consistency to the pharmaceutical composition. Each excipient must be compatible with the other ingredients of the pharmaceutical composition when commingled such that interactions which would substantially reduce the efficacy of the compound of the invention when administered to an individual and interactions which would result in pharmaceutical compositions that are not pharmaceutically acceptable are avoided. In addition, each excipient must of course be of sufficiently high purity to render it pharmaceutically-acceptable.

The compound of the invention and the pharmaceutically-acceptable excipient or excipients will typically be formulated into a dosage form adapted for administration to the individual by the desired route of administration. For example, dosage forms include those adapted for (1) oral administration such as tablets, capsules, caplets, pills, troches, powders, syrups, elixers, suspensions, solutions, emulsions, sachets, and cachets; (2) parenteral administration such as sterile solutions, suspensions, and powders for reconstitution; (3) transdermal administration such as transdermal patches; (4) rectal administration such as suppositories; (5) inhalation such as dry powders, aerosols, suspensions, and solutions; and (6) topical administration such as creams, ointments, lotions, solutions, pastes, sprays, foams, and gels.

Suitable pharmaceutically-acceptable excipients will vary depending upon the particular dosage form chosen. In addition, suitable pharmaceutically-acceptable excipients may be chosen for a particular function that they may serve in the composition. For example, certain pharmaceutically-acceptable excipients may be chosen for their ability to facilitate the production of uniform dosage forms. Certain pharmaceutically-acceptable excipients may be chosen for their ability to facilitate the production of stable dosage forms. Certain pharmaceutically-acceptable excipients may be chosen for their ability to facilitate the carrying or transporting of the compound or compounds of the invention once administered to the individual from one organ, or portion of the body, to another organ, or portion of the body. Certain pharmaceutically-acceptable excipients may be chosen for their ability to enhance compliance.

Suitable pharmaceutically-acceptable excipients include the following types of excipients: Diluents, fillers, binders, disintegrants, lubricants, glidants, granulating agents, coating agents, wetting agents, solvents, co-solvents, suspending agents, emulsifiers, sweeteners, flavoring agents, flavor masking agents, coloring agents, anticaking agents, hemectants, chelating agents, plasticizers, viscosity increasing agents, antioxidants, preservatives, stabilizers, surfactants, and buffering agents. The skilled artisan will appreciate that certain pharmaceutically-acceptable excipients may serve more than one function and may serve alternative functions depending on how much of the excipient is present in the formulation and what other ingredients are present in the formulation.

Skilled artisans possess the knowledge and skill in the art to enable them to select suitable pharmaceutically-acceptable excipients in appropriate amounts for use in the invention. In addition, there are a number of resources that are available to the skilled artisan which describe pharmaceutically-acceptable excipients and may be useful in selecting suitable pharmaceutically-acceptable excipients. Examples include Remington's Pharmaceutical Sciences (Mack Publishing Company), *The Handbook of Pharmaceutical Additives* (Gower Publishing Limited), and *The Handbook of Pharmaceutical Excipients* (the American Pharmaceutical Association and the Pharmaceutical Press).

The pharmaceutical compositions of the invention are prepared using techniques and methods known to those skilled in the art. Some of the methods commonly used in the art are described in *Remington's Pharmaceutical Sciences* (Mack Publishing Company).

In one aspect, the invention is directed to a solid oral dosage form such as a tablet or capsule comprising a safe and effective amount of a compound of the invention and a diluent or filler. Suitable diluents and fillers include lactose, sucrose, dextrose, mannitol, sorbitol, starch (e.g. corn starch, potato starch, and pre-gelatinized starch), cellulose and its derivatives (e.g. microcrystalline cellulose), calcium sulfate, and dibasic calcium phosphate. The oral solid dosage form may further comprise a binder. Suitable binders include starch (e.g. corn starch, potato starch, and pre-gelatinized starch), gelatin, acacia, sodium alginate, alginic acid, tragacanth, guar gum, povidone, and cellulose and its derivatives (e.g. microcrystalline cellulose). The oral solid dosage form may further comprise a disintegrant. Suitable disintegrants include crospovidone, sodium starch glycolate, croscarmelose, alginic acid, and sodium carboxymethyl cellulose. The oral solid dosage form may further comprise a lubricant. Suitable lubricants include stearic acid, magnesuim stearate, calcium stearate, and talc.

The invention claimed is:

1. A compound of Formula I or a pharmaceutically acceptable salt thereof

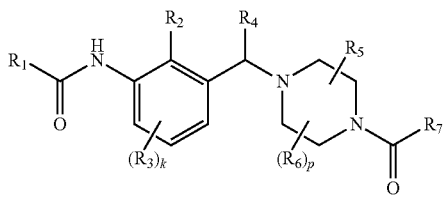

Formula I wherein:

$R_1$ is selected from the group consisting of:

$C_1$-$C_6$ alkyl;

methyl substituted with i) $C_3$-$C_5$ cycloalkyl; ii) phenoxy; or iii) a phenyl and a second substituent selected from the group consisting of: methyl, halo and methoxy;

ethyl substituted with i) phenyl, said phenyl is optionally substituted with halo or methoxy, or ii) heteroary;

benzyl, wherein the phenyl group of said benzyl is optionally substituted with halo, methoxy or $SO_2CH_2CH_3$;

$C_2$ alkenyl optionally substituted with one F and one phenyl;

$C_3$-$C_7$ cycloalkyl, said cycloalkyl is optionally substituted with one or two substituents selected from the group consisting of phenyl, methyl and F; or said cycloalkyl is optionally fused to a phenyl ring;

heterocycloalkyl optionally substituted with one or two $C_1$-$C_3$ alkyl;

heteroaryl optionally substituted with one to two substituents selected from the group consisting of: $C_1$-$C_3$ alkyl, $C_1$-$C_3$ alkoxy and $CF_3$; and phenyl substituted with one to three substituents selected from the group consisting of:
  i) halo;
  ii) CN;
  iii) $C_1$-$C_3$ alkyl optionally substituted with one to three F;
  iv) $C_1$-$C_3$ alkoxy;
  v) $(CH_2)_nNR^aR^b$;
  vi) $C(O)CH_3$; and
  vii) $CH_2OCH_3$;

$R_2$ is methyl;

$R_3$ is halo or methyl;

R₄ is H or methyl;
R₅ is $C_1$-$C_3$ alkyl;
R₆ is $C_1$-$C_3$ alkyl;
R₇ is selected from the group consisting of:
  $C_1$-$C_7$ alkyl optionally substituted with one or more substituents selected from the group consisting of halo, $C_3$-$C_5$ cycloalkyl and $CF_3$; and
  $C_3$-$C_7$ cycloalkyl optionally substituted with one or two substituents selected from the group consisting of F, $CH_2F$, $CHF_2$, methyl and methoxy;
each k is 0 or 1 each p is 0 or 1; each n is 0, 1 or 2;
each $R^a$ is H or $C_1$-$C_3$ alkyl; and each is $R^b$ is H or $C_1$-$C_3$alkyl.

2. The compound or salt according to claim 1, wherein $R_1$ is heteroaryl substituted with $C_1$-$C_3$ alkyl.

3. The compound or salt according to claim 1, wherein $R_1$ pyridinyl substituted with methyl.

4. The compound or salt according to claim 1, wherein k is 1 and $R_3$ is Cl or F.

5. The compound or salt according to claim 1, wherein $R_4$ is H.

6. The compound or salt according to claim 1, wherein $R_5$ is methyl.

7. The compound or salt according to claim 1, wherein p is 0.

8. The compound or salt according to claim 1, wherein $R_7$ is $C_3$-$C_6$ cycloalkyl optionally substituted with one or two F or methyl.

9. The compound or salt according to claim 8, wherein $R_7$ is cyclobutyl substituted with methyl or two F.

10. The compound or salt according to claim 8, wherein $R_7$ is cyclopentyl.

11. The compound or salt according to claim 1, wherein $R_7$ is methyl substituted with cyclopropyl.

12. The compound or salt according to claim 1 wherein the compound is selected from:
  (S)-N-(3-((4-(cyclopentanecarbonyl)-3-methylpiperazin-1-yl)methyl)-5-fluoro-2-methylphenyl)-2-methylpyrimidine-5-carboxamide;
  (S)-N-(5-chloro-3-((4-(cyclopentanecarbonyl)-3-methylpiperazin-1-yl)methyl)-2-methylphenyl)-6-methylnicotinamide;
  (S)-3-cyano-N-(3-((4-(3,3-difluorocyclobutanecarbonyl)-3-methylpiperazin-1-yl)methyl)-5-fluoro-2-methylphenyl)benzamide;
  (S)-N-(5-chloro-3-((4-(2cyclopropylacetyl)-3-methylpiperazin-1-yl)methyl)-2-methylphenyl)-6-methylnicotinamide;
  N-(5-fluoro-2-methyl-3-(((S)-3-methyl-4-((cis)-3-methylcyclobutanecarbonyl)piperazin-1-yl)methyl)phenyl)-6-methylnicotinamide;
  N-(5-fluoro-2-methyl-3-(((S)-3-methyl-4-((trans)-3-methylcyclobutanecarbonyl)piperazin-1-yl)methyl)phenyl)-6-methylnicotinamide;
  N-(5-chloro-2-methyl-3-(((S)-3-methyl-4-((trans)-3-methylcyclobutanecarbonyl)piperazin-1-yl)methyl)phenyl)-6-methylnicotinamide;
  N-(5-chloro-2-methyl-3-(((S)-3-methyl-4-((cis)-3-methylcyclobutanecarbonyl)piperazin-1-yl)methyl)phenyl)-6-methylnicotinamide;
  N-(5-chloro-2-methyl-3-(((S)-3-methyl-4-((cis)-3-methylcyclobutanecarbonyl)piperazin-1-yl)methyl)phenyl)-2-methylpyrimidine-5-carboxamide;
  N-(5-chloro-2-methyl-3-(((S)-3-methyl-4-((trans)-3-methylcyclobutanecarbonyl)piperazin-1-yl)methyl)phenyl)-2-methylpyrimidine-5-carboxamide; and
  (S)-N-(5-chloro-3-((4-(cyclopentanecarbonyl)-3methyl-piperazin-1-yl)methyl)-2methylphenyl)-2-methylpyrimidine-5-carboxamide.

13. The compound according to claim 1 which is (S)-N-(5-chloro-3((4-(cyclopentanecarbonyl)-3-methylpiperazin-1-yl)methyl)-2-methylphenyl)-6-methylnicotinamide; or a pharmaceutically acceptable salt thereof.

14. The compound according to claim 1 which is (S)-3-cyano-N-(3-((4-(cyclopentanecarbonyl)-3-methylpiperazin-1-yl)methyl)-5-fluoro-2-methylphenyl)benzamide; or a pharmaceutically acceptable salt thereof.

15. The compound according to claim 1 which is N-(5-chloro-2-methyl-3-(((S)-3-methyl-4-((cis)-3-methylcyclobutanecarbonyl)piperazin-1-yl)methyl)phenyl)-6-methylnicotinamide; or a pharmaceutically acceptable salt thereof.

16. A. pharmaceutical composition comprising the compound or pharmaceutically acceptable salt according to claim 1 and a pharmaceutically acceptable excipient.

17. A pharmaceutical composition comprising the compound or pharmaceutically acceptable salt according to claim 13 and a pharmaceutically acceptable excipient.

18. A pharmaceutical composition comprising the compound or pharmaceutically acceptable salt according to claim 14 and a pharmaceutically acceptable excipient.

19. A pharmaceutical composition comprising the compound or pharmaceutically acceptable salt according to claim 15 and a pharmaceutically acceptable excipient.

* * * * *

SEQUENCE LISTING

```
<160> NUMBER OF SEQ ID NOS: 7

<210> SEQ ID NO 1
<211> LENGTH: 5
<212> TYPE: PRT
<213> ORGANISM: Artificial Sequence
<220> FEATURE:
<223> OTHER INFORMATION: motif
<220> FEATURE:
<221> NAME/KEY: VARIANT
<222> LOCATION: 2, 3
<223> OTHER INFORMATION: Xaa = Any Amino Acid

<400> SEQUENCE: 1

Leu Xaa Xaa Leu Leu
 1               5

<210> SEQ ID NO 2
<211> LENGTH: 15
<212> TYPE: PRT
<213> ORGANISM: Artificial Sequence
<220> FEATURE:
<223> OTHER INFORMATION: Modified polyhistidine tag

<400> SEQUENCE: 2

Met Lys Lys His His His His His His Leu Val Pro Arg Gly Ser
 1               5                  10                  15

<210> SEQ ID NO 3
<211> LENGTH: 25
<212> TYPE: PRT
<213> ORGANISM: Artificial Sequence
<220> FEATURE:
<223> OTHER INFORMATION: Biotinylated peptide

<400> SEQUENCE: 3

Cys Pro Ser Ser His Ser Ser Leu Thr Glu Arg His Lys Ile Leu His
 1               5                  10                  15

Arg Leu Leu Gln Glu Gly Ser Pro Ser
                20                  25

<210> SEQ ID NO 4
```

```
<211> LENGTH: 26
<212> TYPE: DNA
<213> ORGANISM: Artificial Sequence
<220> FEATURE:
<223> OTHER INFORMATION: Forward primer

<400> SEQUENCE: 4
ctcgagtaga gcaggacagg gaggaa                                          26

<210> SEQ ID NO 5
<211> LENGTH: 26
<212> TYPE: DNA
<213> ORGANISM: Artificial Sequence
<220> FEATURE:
<223> OTHER INFORMATION: Reverse primer

<400> SEQUENCE: 5
aagcttggat ggatgagttt gtgcct                                          26

<210> SEQ ID NO 6
<211> LENGTH: 26
<212> TYPE: DNA
<213> ORGANISM: Artificial Sequence
<220> FEATURE:
<223> OTHER INFORMATION: Forward primer

<400> SEQUENCE: 6
ggtacctgcc ctgctctatc ctgagt                                          26

<210> SEQ ID NO 7
<211> LENGTH: 26
<212> TYPE: DNA
<213> ORGANISM: Artificial Sequence
<220> FEATURE:
<223> OTHER INFORMATION: Reverse primer

<400> SEQUENCE: 7
ctcgagtggt gagtgctgag agatgg                                          26
```